US009278926B2

(12) United States Patent
Kato

(10) Patent No.: US 9,278,926 B2
(45) Date of Patent: *Mar. 8, 2016

(54) AROMATIC AMINE DERIVATIVE, AND ORGANIC ELECTROLUMINESCENT ELEMENT COMPRISING SAME

(75) Inventor: Tomoki Kato, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 874 days.

This patent is subject to a terminal disclaimer.

(21) Appl. No.: 13/509,681

(22) PCT Filed: Nov. 16, 2010

(86) PCT No.: PCT/JP2010/070403
§ 371 (c)(1),
(2), (4) Date: May 14, 2012

(87) PCT Pub. No.: WO2011/059099
PCT Pub. Date: May 19, 2011

(65) Prior Publication Data
US 2012/0248426 A1 Oct. 4, 2012

(30) Foreign Application Priority Data
Nov. 16, 2009 (JP) .................. 2009-261263

(51) Int. Cl.
| H01L 51/54 | (2006.01) |
| C07D 333/76 | (2006.01) |
| C07D 209/86 | (2006.01) |
| C07D 409/12 | (2006.01) |
| C07D 307/91 | (2006.01) |
| C07D 407/12 | (2006.01) |
| C07D 487/22 | (2006.01) |
| C09B 57/00 | (2006.01) |
| C09K 11/06 | (2006.01) |
| H05B 33/10 | (2006.01) |

(52) U.S. Cl.
CPC ............ *C07D 209/86* (2013.01); *C07D 307/91* (2013.01); *C07D 333/76* (2013.01); *C07D 487/22* (2013.01); *C09B 57/00* (2013.01); *C09B 57/008* (2013.01); *C09K 11/06* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01)

(58) Field of Classification Search
CPC .. C07D 209/86; C07D 307/91; C07D 333/76; C07D 487/22; C09B 57/00; C09B 57/008; C09K 11/06; C09K 2211/1007; C09K 2211/1011; C09K 2211/1014; C09K 2211/1029; C09K 2211/1088; C09K 2211/1092; H05B 33/10; H05B 33/14; H01L 51/50

See application file for complete search history.

(56) References Cited

U.S. PATENT DOCUMENTS

| 6,515,182 | B2 | 2/2003 | Hosokawa et al. | |
| 6,657,084 | B2 | 12/2003 | Hosokawa et al. | |
| 7,081,550 | B2 | 7/2006 | Hosokawa et al. | |
| 7,375,250 | B2 | 5/2008 | Saitoh et al. | |
| 8,129,038 | B2 * | 3/2012 | Yabunouchi et al. | 428/690 |
| 8,703,304 | B2 * | 4/2014 | Yabunouchi | 428/690 |
| 2002/0057050 | A1 * | 5/2002 | Shi | 313/504 |
| 2002/0137969 | A1 | 9/2002 | Hosokawa et al. | |
| 2003/0018218 | A1 | 1/2003 | Hosokawa et al. | |
| 2004/0054232 | A1 | 3/2004 | Hosokawa et al. | |
| 2005/0067951 | A1 | 3/2005 | Richter et al. | |
| 2005/0221124 | A1 * | 10/2005 | Hwang et al. | 428/690 |
| 2006/0125378 | A1 | 6/2006 | Saitoh et al. | |
| 2006/0186799 | A1 | 8/2006 | Hosokawa et al. | |
| 2007/0228941 | A1 | 10/2007 | Abe et al. | |
| 2007/0231503 | A1 | 10/2007 | Hwang et al. | |
| 2007/0278938 | A1 * | 12/2007 | Yabunouchi et al. | 313/504 |
| 2008/0017853 | A1 | 1/2008 | Egawa et al. | |
| 2008/0124572 | A1 * | 5/2008 | Mizuki et al. | 428/690 |
| 2009/0017330 | A1 * | 1/2009 | Iwakuma et al. | 428/690 |

(Continued)

FOREIGN PATENT DOCUMENTS

| EP | 2 202 283 A1 | 6/2010 |
| JP | 2002 080433 | 3/2002 |

(Continued)

OTHER PUBLICATIONS

Extended Search Report issued Oct. 10, 2013 in European Patent Application No. 10830055.9.

(Continued)

*Primary Examiner* — Dawn L. Garrett
(74) *Attorney, Agent, or Firm* — Oblon, McClelland, Maier & Neustadt, L.L.P.

(57) ABSTRACT

Provided is an aromatic amine derivative represented by the formula $N(Ar^A)(Ar^B)(Ar^C)$ as an organic EL device material capable of reducing the driving voltage of an organic EL device, and improving its luminous efficiency and device lifetime. $Ar^A$ represents the formula (II-1) or (II-2). $L^a$ represents an arylene group or the like, $Ar^a$ represents an aryl group or the like, and n represents 2 or 3. $Ar^B$ represents the formula (III). $L^b$ represents a single bond or the like, $R^1$ and $R^2$ each represent an alkyl group or the like, o and p each represent 0 to 3 or the like, X represents an oxygen atom or the like, and $R^3$, $R^4$ and $R^5$ each represent an alkyl group or the like. $Ar^C$ represents an aryl group, a heteroaryl group, or the formula (II-1), (II-2), or (III).

15 Claims, No Drawings

(56) References Cited

U.S. PATENT DOCUMENTS

| | | |
|---|---|---|
| 2009/0200926 A1 | 8/2009 | Lee et al. |
| 2009/0230846 A1 | 9/2009 | Yabe et al. |
| 2010/0001635 A1 | 1/2010 | Lee et al. |
| 2010/0001636 A1* | 1/2010 | Yabunouchi ............ 313/504 |
| 2010/0019657 A1 | 1/2010 | Eum et al. |
| 2010/0019659 A1 | 1/2010 | Morishita |
| 2010/0033081 A1 | 2/2010 | Yamada et al. |
| 2010/0096981 A1* | 4/2010 | Seo et al. ............ 313/504 |
| 2011/0297924 A1 | 12/2011 | Yabunouchi et al. |
| 2012/0074395 A1* | 3/2012 | Yabunouchi et al. ....... 257/40 |
| 2012/0146014 A1 | 6/2012 | Kato |
| 2014/0061602 A1* | 3/2014 | Kato et al. ............ 257/40 |
| 2014/0061630 A1* | 3/2014 | Yabunouchi ............ 257/40 |
| 2014/0084270 A1* | 3/2014 | Kato et al. ............ 257/40 |

FOREIGN PATENT DOCUMENTS

| | | |
|---|---|---|
| JP | 2002 083685 | 3/2002 |
| JP | 2005 015419 | 1/2005 |
| JP | 2005 516059 | 6/2005 |
| JP | 2006 352088 | 12/2006 |
| JP | 2007 291064 | 11/2007 |
| JP | 2007 318101 | 12/2007 |
| JP | 2008 019238 | 1/2008 |
| JP | 2008 081490 | 4/2008 |
| JP | 2008 133225 | 6/2008 |
| JP | 2009 021335 | 1/2009 |
| JP | 2009-123976 | 6/2009 |
| JP | 2009 185024 | 8/2009 |
| JP | 2009 215281 | 9/2009 |
| JP | 2009 246354 | 10/2009 |
| JP | 2009 249385 | 10/2009 |
| JP | 2010 222268 | 10/2010 |
| KR | 10 2010 073543 | 7/2010 |
| WO | WO 2004/020372 A1 | 3/2004 |
| WO | 2007 043484 | 4/2007 |
| WO | 2008 120626 | 10/2008 |
| WO | 2009 011327 | 1/2009 |
| WO | 2009 066778 | 5/2009 |
| WO | 2010 041872 | 4/2010 |
| WO | 2010 044130 | 4/2010 |
| WO | 2010 114017 | 10/2010 |
| WO | WO 2010/114017 | * 10/2010 |

OTHER PUBLICATIONS

U.S. Appl. No. 13/979,075, filed Jul. 17, 2013, Kato.

Okumoto, K., "New Hole-transporting Amorphous Molecular Materials with High Glass-transition Temperatures for Organic Light-emitting Diodes", Organic Light Emitting Materials and Devices XI, Proc. of SPIE vol. 6655, pp. 665508-1 to 665508-8. (2007).

Lin, J.T., "Light-emitting carbazole derivatives for electroluminescent materials", Organic Light Emitting Materials and Devices V, Proceedings of SPIE vol. 4464 pp. 307-316. (2002).

International Search Report issued on Jan. 18, 2011 in PCT/JP10/70403 filed on Nov. 16, 2010.

U.S. Appl. No. 13/435,965, filed Mar. 30, 2012, Kato.

* cited by examiner

US 9,278,926 B2

AROMATIC AMINE DERIVATIVE, AND ORGANIC ELECTROLUMINESCENT ELEMENT COMPRISING SAME

This application is a 371 of PCT/JP2010/070403 filed Nov. 16, 2010. Priority to Japanese patent application 2009-261263, filed Nov. 16, 2009, is claimed.

TECHNICAL FIELD

The present invention relates to an aromatic amine derivative and an organic electroluminescence device using the same.

BACKGROUND ART

An organic electroluminescence device (organic EL device) is a spontaneous light emitting device which utilizes such a principle that a fluorescent substance emits light by virtue of recombination energy of holes injected from an anode and electrons injected from a cathode by an application of an electric field. Since an organic EL device of the laminate type capable of being driven under a low voltage has been reported by C. W. Tang et al. of Eastman Kodak Company (see Non Patent Literature 1), many studies have been conducted for an organic EL device using an organic material as a constituent material.

Tang et al. discloses an organic EL device having a laminate structure in which tris(8-quinolinolato)aluminum is used in a light emitting layer and a triphenyldiamine derivative is used in a hole transporting layer. Advantages of adopting the laminate structure in the organic EL device include: (i) injection efficiency of holes into the light emitting layer can be increased; (ii) efficiency of forming excitons which are formed through recombination in the light emitting layer can be increased by blocking electrons injected from the cathode toward the light emitting layer in the hole transporting (injecting) layer; and (iii) excitons formed in the light emitting layer can be easily enclosed in the light emitting layer. In order to increase the efficiency of recombination of injected holes and electrons in the organic EL device having such laminate structure, there have been made refinements of the device structure and a method of forming the device, and studies on a material itself for each layer.

In general, when an organic EL device is driven or stored in an environment of high temperature, there occur adverse affects such as a change in luminescent color, a decrease in luminous efficiency, an increase in driving voltage, and a decrease in device lifetime.

In order to prevent such adverse effects, there have been proposed, as hole transporting material, an aromatic monoamine derivative (see Patent Literature 1), an aromatic amine derivative having a carbazole skeleton (see Patent Literature 2), an aromatic amine derivative having a tetraarylmethane skeleton (see Patent Literature 3), and the like.

CITATION LIST

Patent Literature

[PTL 1] JP 2006-352088 A
[PTL 2] JP 2009-021335 A
[PTL 3] JP 2002-083685 A

Non Patent Literature

[NPL 1] C. W. Tang, S. A. Vanslyke, "Applied Physics Letters," Vol. 51, p. 913, 1987

SUMMARY OF INVENTION

Technical Problem

However, the aromatic amine derivatives disclosed in Patent Literatures 1 to 3 are still susceptible to improvement because it cannot be said that the driving voltage, luminous efficiency, and device lifetime of an organic EL device are satisfactory.

In view of the foregoing, it is an object of the present invention to provide an organic EL device material capable of reducing the driving voltage of an organic EL device, and improving its luminous efficiency and device lifetime as compared with a conventional organic EL device material, and an organic EL device using the material.

Solution to Problem

The inventors of the present invention have made extensive studies to solve the problems, and as a result, have found that the use of an aromatic amine derivative having an aromatic hydrocarbon group of a specific structure and a branched aromatic hydrocarbon group together as a material for an organic EL device, in particular, a hole transporting material reduces the driving voltage of the organic EL device, and improves its luminous efficiency and device lifetime.

That is, the present invention relates to the following items [1] and [2].

[1] An aromatic amine derivative, which is represented by the following formula (I):

[Chem. 1]

$$Ar^C - N(Ar^A) - Ar^B \quad (I)$$

in the formula (I), $Ar^A$ is represented by the following formula (II-1) or (II-2):

[Chem. 2]

$$-L^a \!-\! (Ar^a)_n \quad (II\text{-}1)$$

$$-L^a \!-\! CH_{3-n} \!-\! (Ar^a)_n \quad (II\text{-}2)$$

in the formulae (II-1) and (II-2):

$L^a$ represents a substituted or unsubstituted aromatic ring having 6 to 25 ring carbon atoms, or a substituted or unsubstituted heteroaromatic ring having 5 to 25 ring atoms;

$Ar^a$ represents a substituted or unsubstituted aryl group having 6 to 25 ring carbon atoms, or a substituted or unsubstituted heteroaryl group having 5 to 25 ring atoms; and n represents 2 or 3, and a plurality of $Ar^a$'s may be identical to or different from each other, in the formula (I), $Ar^B$ is represented by the following formula (III):

[Chem. 3]

(III)

[structure: fluorene-type biphenyl system with $-L^b-$ substituent, X bridge, and substituents $(R^1)_o$ and $(R^2)_p$]

in the formula (III):

$L^b$ represents a single bond, a substituted or unsubstituted arylene group having 6 to 25 ring carbon atoms, or a substituted or unsubstituted heteroarylene group having 5 to 25 ring atoms;

$R^1$ and $R^2$ each independently represent an alkyl group having 1 to 15 carbon atoms, an alkenyl group having 2 to 15 carbon atoms, a cycloalkyl group having 3 to 15 ring carbon atoms, an aryl group having 6 to 25 ring carbon atoms, a heteroaryl group having 5 to 25 ring atoms, a trialkylsilyl group formed of alkyl groups each having 1 to 15 carbon atoms, a triarylsilyl group formed of aryl groups each having 6 to 25 ring carbon atoms, an alkylarylsilyl group formed of an alkyl group having 1 to 15 carbon atoms and an aryl group having 6 to 25 ring carbon atoms, a carbazolyl group, a halogen atom, or a cyano group;

o represents an integer of 0 to 3, p represents an integer of 0 to 4, and a plurality of $R^1$'s or $R^2$'s adjacent to each other, or $R^1$ and $R^2$ may be bonded to each other to form a ring; and X represents $CR^3R^4$, $NR^5$, an oxygen atom, or a sulfur atom, and $R^3$, $R^4$, and $R^5$ each independently represent an alkyl group having 1 to 15 carbon atoms, or a substituted or unsubstituted aryl group having 6 to 25 ring carbon atoms, and in the formula (I), $Ar^C$ represents a substituted or unsubstituted aryl group having 6 to 50 ring carbon atoms, or a substituted or unsubstituted heteroaryl group having 5 to 25 ring atoms, or is represented by the formula (II-1), (II-2), or (III).

[2] An organic electroluminescence device, including at least one organic thin-film layer between an anode and a cathode, wherein at least one layer of the organic thin-film layer contains the aromatic amine derivative according to the item [1].

Advantageous Effects of Invention

In the case where the aromatic amine derivative of the present invention is used as a material for an organic EL device, the driving voltage of the organic EL device reduces, and its luminous efficiency and device lifetime are improved as compared with the case where a conventional organic EL device material is used.

DESCRIPTION OF EMBODIMENTS

Aromatic Amine Derivative

An aromatic amine derivative of the present invention is represented by the following formula (I).

[Chem. 4]

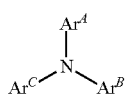
(I)

In the formula (I), $Ar^A$ is represented by the following formula (II-1) or (II-2) (hereinafter, sometimes collectively referred to as "formulae (II).")

[Chem. 5]

(II-1)

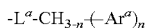
(II-2)

In the formulae (II), $L^a$ represents a substituted or unsubstituted aromatic ring having 6 to 25 ring carbon atoms, or a substituted or unsubstituted heteroaromatic ring having 5 to 25 ring atoms.

Examples of the aromatic ring represented by $L^a$ include a benzene ring, a naphthylbenzene ring, a biphenyl ring, a terphenyl ring, a quaterphenyl ring, a naphthalene ring, a phenylnaphthalene ring, an acenaphthylene ring, an anthracene ring, a benzanthracene ring, an aceanthracene ring, a phenanthrene ring, a benzophenanthrene ring, a phenalenyl ring, a fluorene ring, a 9,9-dimethylfluorene ring, a 7-phenyl-9,9-dimethylfluorene ring, a pentacene ring, a picene ring, a pentaphenyl ring, a pyrene ring, a benzopyrene ring, a chrysene ring, a benzochrysene ring, an s-indacene ring, an as-indacene ring, a perylene ring, a fluoranthene ring, and a naphthacene ring. Of those, an aromatic ring having 6 to 18 ring carbon atoms is preferred from the viewpoints of the driving voltage, luminous efficiency, and device lifetime of an organic EL device, and an aromatic ring having 6 to 12 ring carbon atoms is more preferred. More specifically, a benzene ring, a biphenyl ring, a terphenyl ring, a quaterphenyl ring, a naphthalene ring, a phenanthrene ring, or any one of the following structures is preferred, and a benzene ring or a biphenyl ring is more preferred.

[Chem. 6]

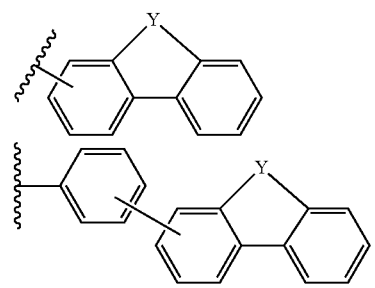

(Here, Y represents $CR^{3'}R^{4'}$, $R^{3'}$ and $R^{4'}$ each independently represent an alkyl group having 1 to 15 carbon atoms, or a substituted or unsubstituted aryl group having 6 to 25 ring carbon atoms, and a wavy line represents a bonding position to a nitrogen atom. It should be noted that the same examples as those of $R^3$ and $R^4$ to be described later can be given as examples of $R^{3'}$ and $R^{4'}$, and preferred examples thereof are also the same.)

Further, when no carbon atom is interposed between $L^a$ and $Ar^a$ like the formula (II-1), $L^a$ is preferably such that two meta positions on one ring are each substituted with $Ar^a$ from the viewpoints of the driving voltage, luminous efficiency, and device lifetime of the organic EL device, and is more preferably such that two meta positions on a benzene ring or the same benzene ring of a biphenyl ring, a terphenyl ring, a quaterphenyl ring, a naphthalene ring, or a phenanthrene ring are each substituted with $Ar^a$.

On the other hand, when a carbon atom is interposed between $L^a$ and $Ar^a$ like the formula (II-2), $L^a$ is preferably para-substituted on one ring from the viewpoints of the driving voltage, luminous efficiency, and device lifetime of the organic EL device, and is more preferably para-substituted on a benzene ring or the same benzene ring of a biphenyl ring, a terphenyl ring, a quaterphenyl ring, a naphthalene ring, or a phenanthrene ring.

(Substituents A)

In addition, the aromatic ring represented by $L^a$ may have a substituent. Examples of the substituent include: alkyl groups each having 1 to 15 (preferably 1 to 10, more preferably 1 to 5) carbon atoms such as a methyl group, an ethyl group, an n-propyl group, an isopropyl group, an n-butyl group, an isobutyl group, an s-butyl group, a t-butyl group, various pentyl groups (the term "various" means that a linear group and all kinds of branched groups are included, and the same holds true for the following), and various hexyl groups; cycloalkyl groups each having 3 to 15 (preferably 3 to 10, more preferably 5 to 6) ring carbon atoms such as a cyclopropyl group, a cyclopentyl group, a cyclohexyl group, a cyclooctyl group, and a cyclodecyl group; trialkylsilyl groups each formed of alkyl groups each having 1 to 15 (preferably 1 to 10, more preferably 1 to 5) carbon atoms such as a trimethylsilyl group and a triethylsilyl group; triarylsilyl groups each formed of aryl groups each having 6 to 25 (preferably 6 to 18, more preferably 6 to 12) ring carbon atoms such as a triphenylsilyl group; alkylarylsilyl groups each formed of an alkyl group having 1 to 15 (preferably 1 to 10, more preferably 1 to 5) carbon atoms and an aryl group having 6 to 25 (preferably 6 to 18, more preferably 6 to 12) ring carbon atoms; halogen atoms such as a fluorine atom, a chlorine atom, a bromine atom, and an iodine atom; and a cyano group (hereinafter, these substituents are referred to as "substituents A").

Examples of the heteroaromatic ring represented by $L^a$ include a pyrrole ring, a pyrazine ring, a pyridine ring, an indole ring, an isoindole ring, a furan ring, a benzofuran ring, an isobenzofuran ring, a quinoline ring, an isoquinoline ring, a quinoxaline ring, a carbazole ring, a 9-phenylcarbazole ring, a phenanthridine ring, an acridine ring, a phenazine ring, a phenothiazine ring, a phenoxazine ring, an oxazole ring, an oxadiazole ring, a furazan ring, a thienyl ring, a thiophene ring, a benzothiophene ring, a 1-phenylbenzothiophene ring, a dibenzothiophene ring, a 1-phenyldibenzothiophene ring, a dibenzofuran ring, a 1-phenyldibenzofuran ring, and a benzothiazole ring. Of those, any one of the following structures is preferred from the viewpoints of the driving voltage, luminous efficiency, and device lifetime of the organic EL device, a heteroaromatic ring having 5 to 15 ring atoms is more preferred, and a carbazole ring, a dibenzofuran ring, or a dibenzothiophene ring is still more preferred.

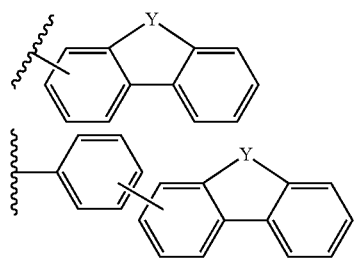

[Chem. 7]

(In this formula, Y represents $NR^{5'}$, an oxygen atom, or a sulfur atom, $R^{5'}$ represents an alkyl group having 1 to 15 carbon atoms, or a substituted or unsubstituted aryl group having 6 to 25 ring carbon atoms, and a wavy line represents a bonding position to a nitrogen atom. It should be noted that the same examples as those of $R^5$ to be described later can be given as examples of $R^{5'}$, and preferred examples thereof are also the same.)

In addition, the heteroaromatic ring represented by $L^a$ may have a substituent. The same substituents as the substituents A can be given as examples of the substituent.

$L^a$ preferably represents a substituted or unsubstituted benzene ring, or a substituted or unsubstituted biphenyl ring from the viewpoints of the driving voltage, luminous efficiency, and device lifetime of the organic EL device. Particularly when no carbon atom is interposed between $L^a$ and $Ar^a$ like the formula (II-1), $L^a$ represents more preferably a substituted or unsubstituted biphenyl ring from the viewpoints of the driving voltage, luminous efficiency, and device lifetime of the organic EL device, still more preferably a biphenyl ring. On the other hand, when a carbon atom is interposed between $L^a$ and $Ar^a$ like the formula (II-2), $L^a$ represents more preferably a substituted or unsubstituted benzene ring from the same viewpoints, still more preferably a benzene ring.

In the formulae (II), $Ar^a$ represents a substituted or unsubstituted aryl group having 6 to 25 ring carbon atoms, or a substituted or unsubstituted heteroaryl group having 5 to 25 ring atoms.

Examples of the aryl group represented by $Ar^a$ include a phenyl group, a naphthylphenyl group, a biphenylyl group, a terphenylyl group, a quaterphenylyl group, a naphthyl group, a phenylnaphthyl group, an acenaphthyl group, an anthryl group, a benzanthryl group, an aceanthryl group, a phenanthryl group, a benzophenanthryl group, a phenalenylyl group, a fluorenyl group, a 9,9-dimethylfluorenyl group, a 7-phenyl-9,9-dimethylfluorenyl group, a pentacenyl group, a picenyl group, a pentaphenylyl group, a pyrenyl group, a benzopyrenyl group, a chrysenyl group, a benzochrysenyl group, an s-indacenyl group, an as-indacenyl group, a perylenyl group, a fluoranthenyl group, and a naphthacenyl group. Of those, an aryl group having 6 to 18 ring carbon atoms is preferred from the viewpoints of the driving voltage, luminous efficiency, and device lifetime of the organic EL device, an aryl group having 6 to 12 ring carbon atoms is more preferred, a phenyl group or a biphenylyl group is still more preferred, and a phenyl group is particularly preferred.

In addition, the aryl group represented by $Ar^a$ may have a substituent. The same substituents as the substituents A can be given as examples of the substituent.

Examples of the heteroaryl group represented by $Ar^a$ include a pyrrolyl group, a pyrazinyl group, a pyridinyl group, an indolyl group, an isoindolyl group, a furyl group, a benzofuranyl group, an isobenzofuranyl group, a quinolyl group, an isoquinolyl group, a quinoxalinyl group, a carbazolyl group, a 9-phenylcarbazolyl group, a phenanthridinyl group, an acridinyl group, a phenazinyl group, a phenothiazinyl group, a phenoxazinyl group, an oxazolyl group, an oxadiazolyl group, a furazanyl group, a thienylyl group, a thiophenyl group, a 1-phenylthiophenyl group, a 1,4-diphenylthiophenyl group, a benzothiophenyl group, a 1-phenylbenzothiophenyl group, a dibenzothiophenyl group, a 1-phenyldibenzothiophenyl group, a dibenzofuranyl group, a 1-phenyldibenzofuranyl group, and a benzothiazolyl group. Of those, a heteroaryl group having 5 to 15 ring atoms is preferred from the viewpoints of the driving voltage, luminous efficiency, and device lifetime of the organic EL device, a carbazolyl group (preferably substituted at its 9-position), a 9-phenylcarbazolyl group (preferably substituted at its 3-position), a dibenzofuranyl group (preferably substituted at its 1- or 3-position), or a dibenzothiophenyl group is more preferred, and a carbazolyl group, a 9-phenylcarbazolyl group, or a dibenzofuranyl group is still more preferred.

In addition, the heteroaryl group represented by $Ar^a$ may have a substituent. The same substituents as the substituents A can be given as examples of the substituent.

$Ar^a$ represents preferably a substituted or unsubstituted aryl group having 6 to 25 (preferably 6 to 18, more preferably 6 to 12) ring carbon atoms from the viewpoints of the driving voltage, luminous efficiency, and device lifetime of the organic EL device, more preferably a substituted or unsubstituted phenyl group, or a substituted or unsubstituted biphenylyl group, still more preferably a phenyl group or a biphenylyl group, particularly preferably a phenyl group.

In the formulae (II), n represents 2 or 3.

When no carbon atom is interposed between $L^a$ and $Ar^a$ like the formula (II-1), n more preferably represents 2 from the viewpoints of the driving voltage, luminous efficiency, and device lifetime of the organic EL device. On the other hand, when a carbon atom is interposed between $L^a$ and $Ar^a$ like the formula (II-2), n more preferably represents 3 from the same viewpoints.

Here, specific examples of $Ar^A$ are shown below. However, $Ar^A$ is not particularly limited to these examples. It should be noted that a wavy line represents a bonding site.

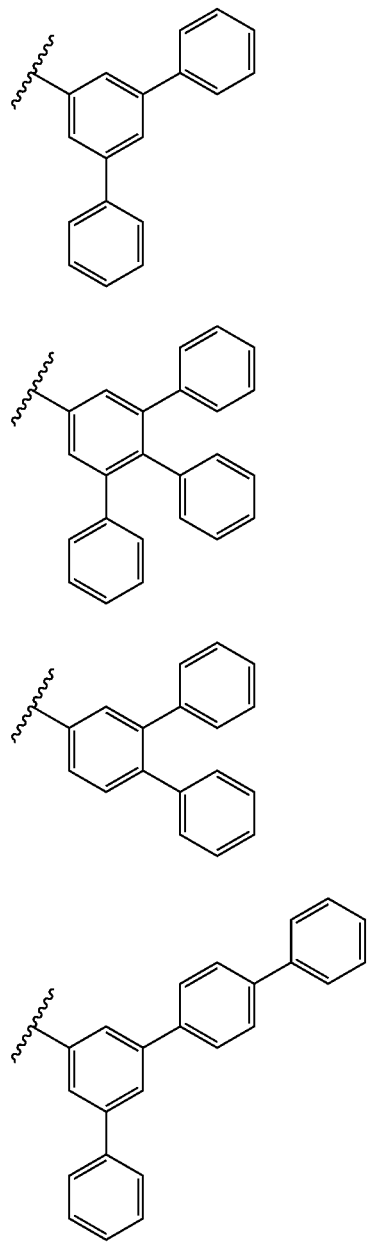

-continued

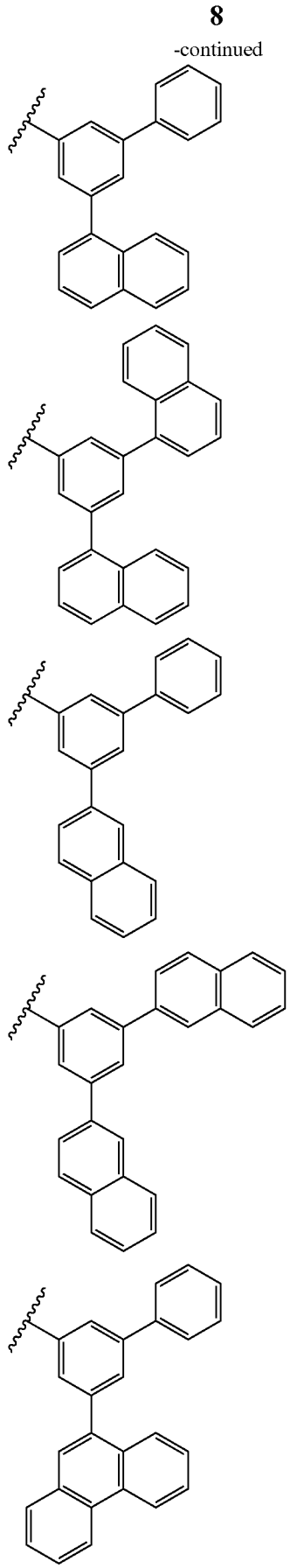

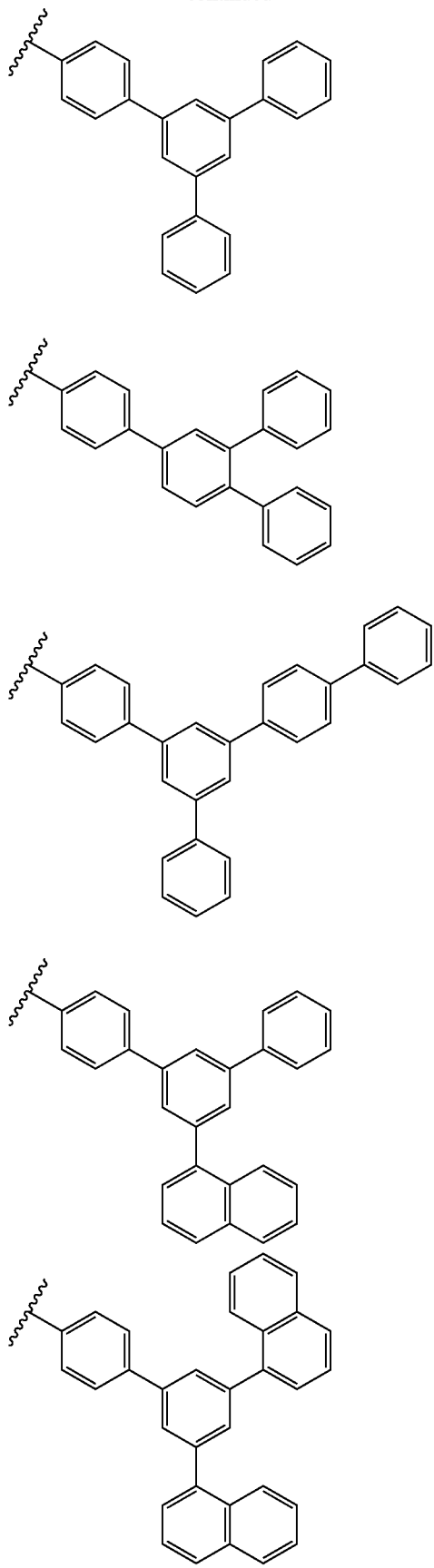

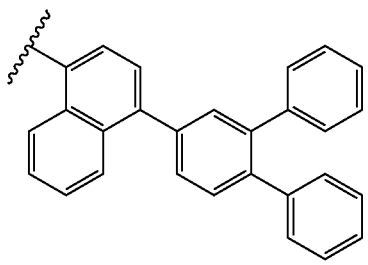
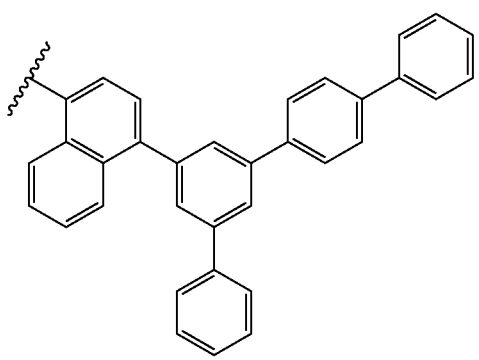
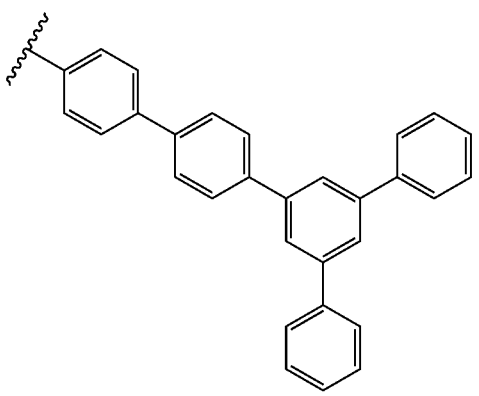
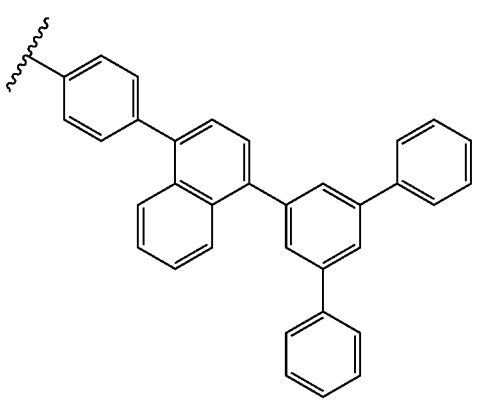
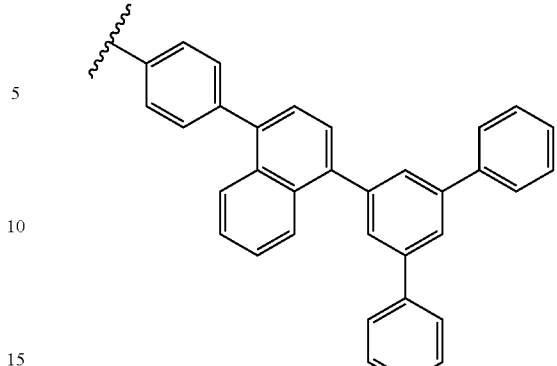
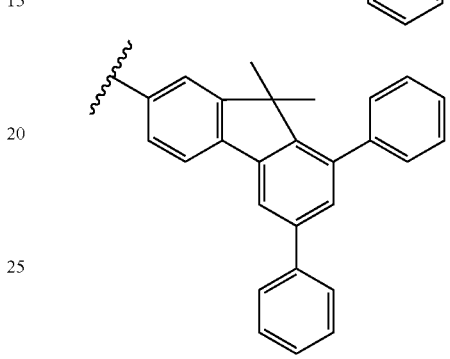
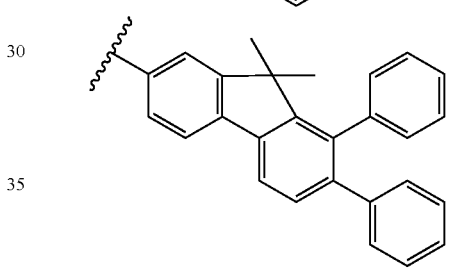
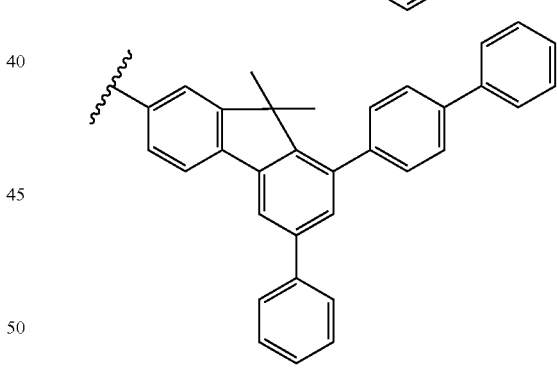
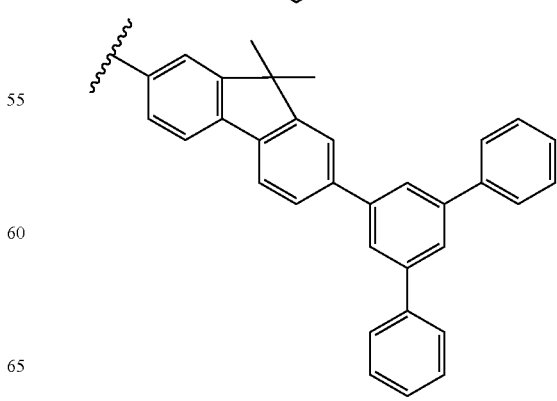

13
-continued
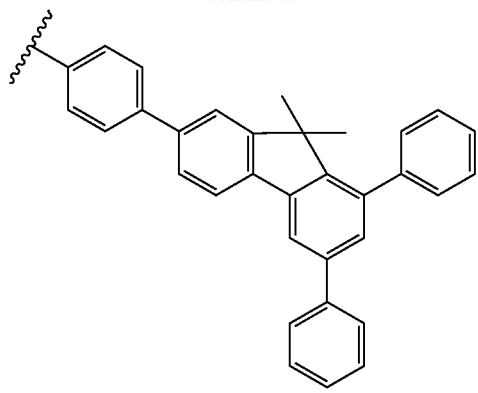
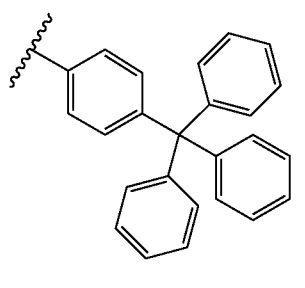
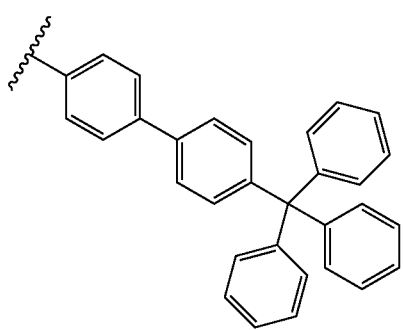
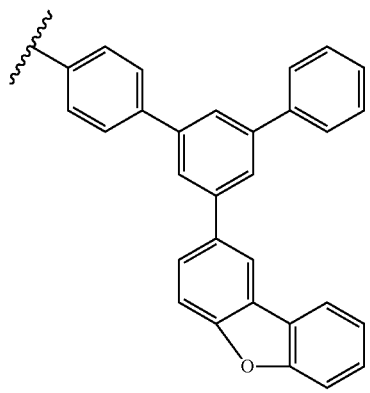
14
-continued
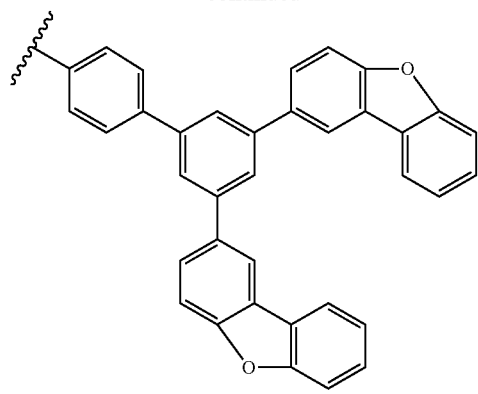
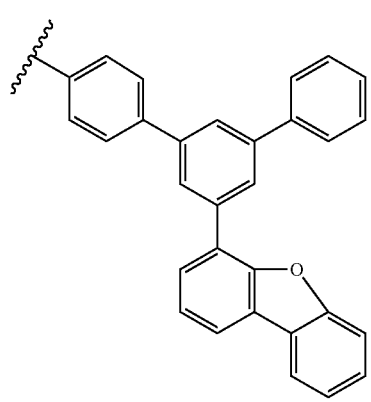
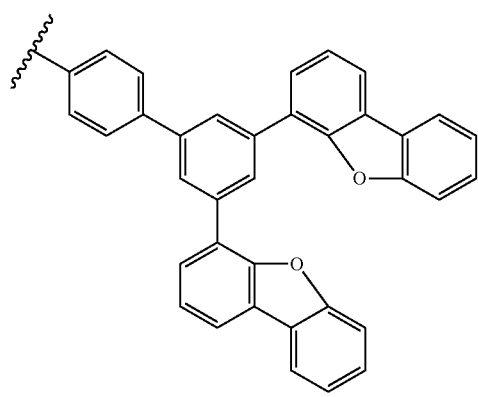
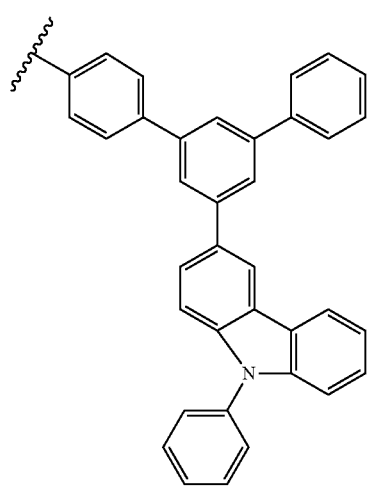

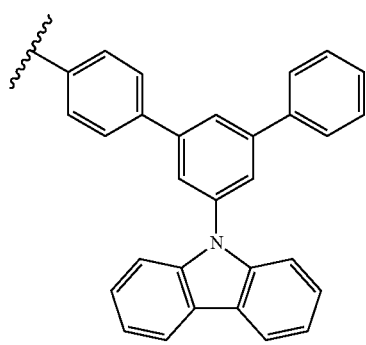
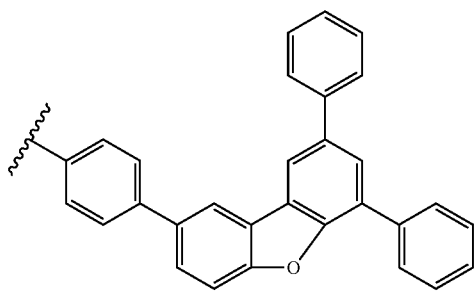
Of those, any one of the groups selected from
[Chem. 9]
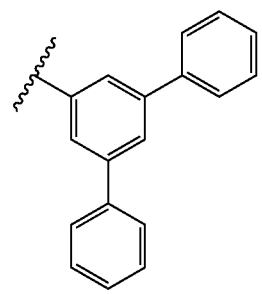
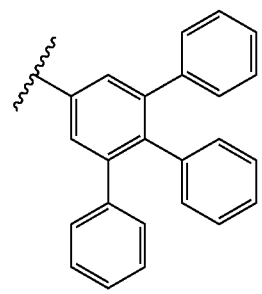
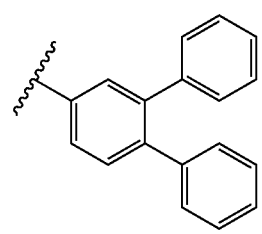
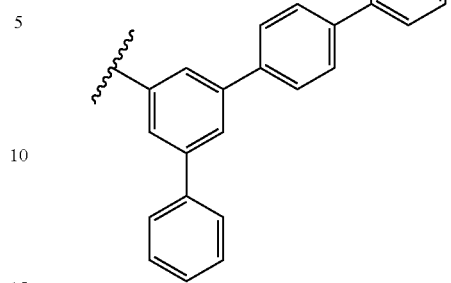
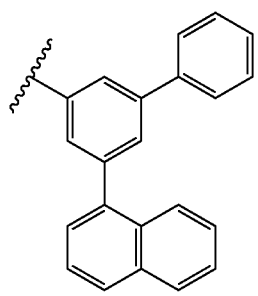
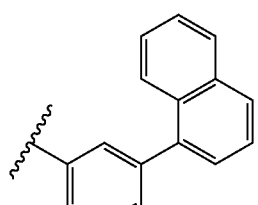
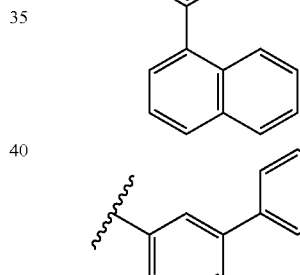
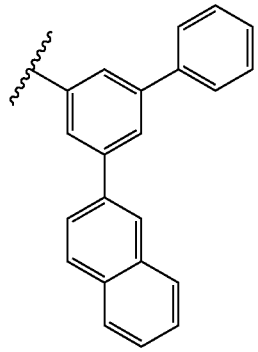
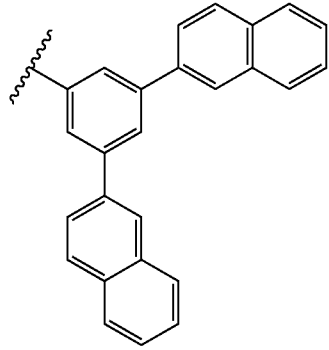

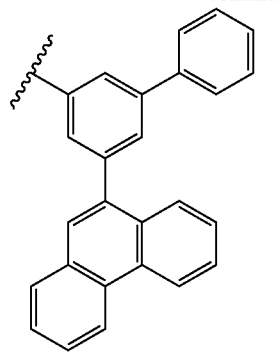
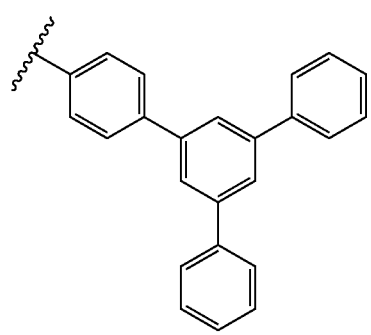
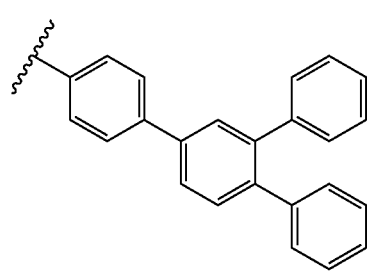
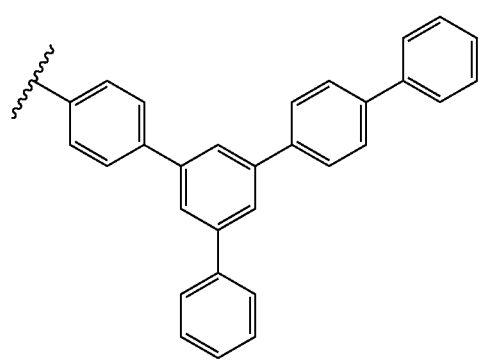
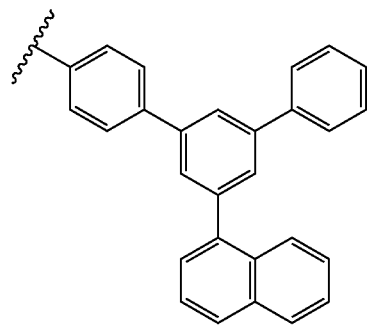
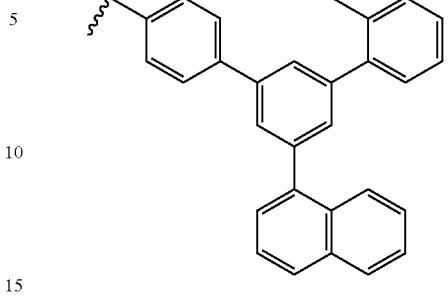
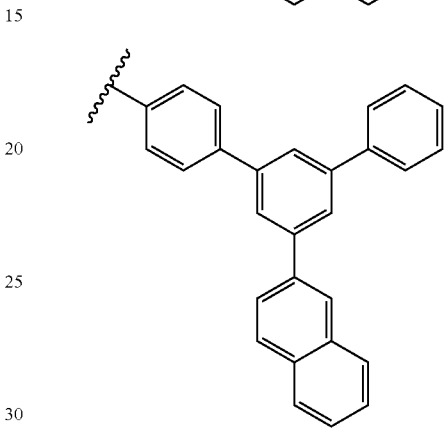
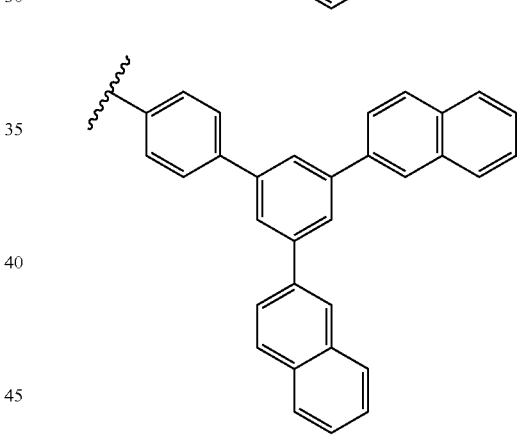
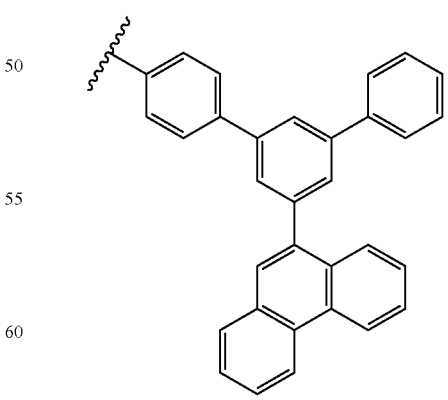
is preferred as $Ar^4$ from the viewpoints of the driving voltage, luminous efficiency, and device lifetime of the organic EL device, any one of the groups selected from

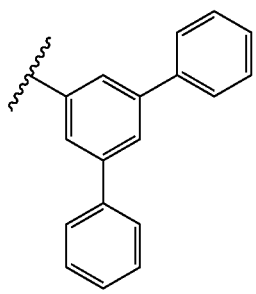

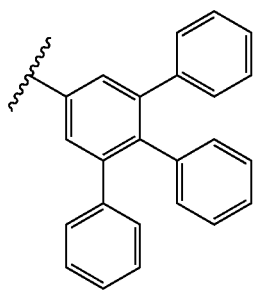

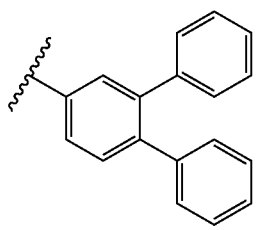

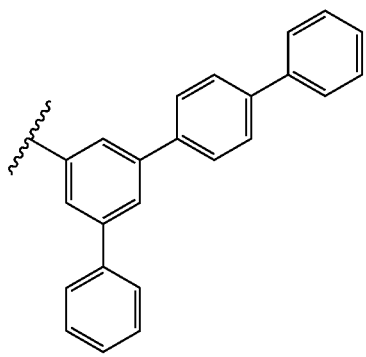

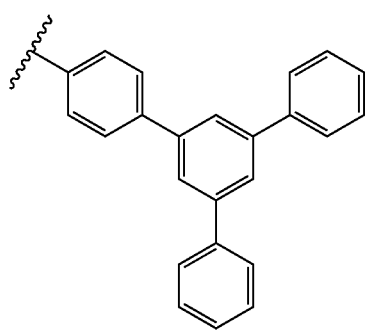

[Chem. 10]

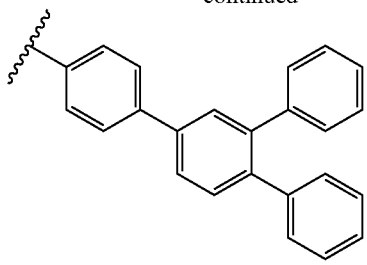

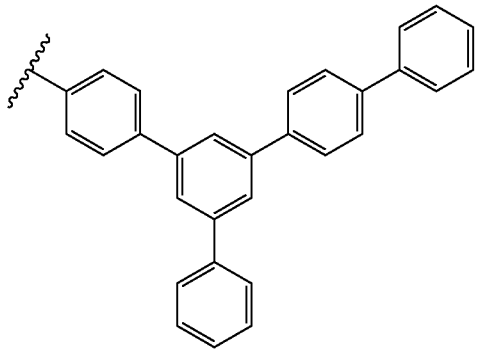

is more preferred, and a group represented by

[Chem. 11]

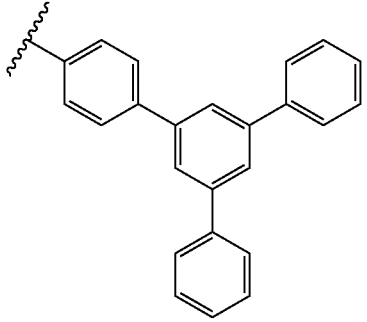

is still more preferred.

In the formula (I), $Ar^B$ is represented by the following formula (III).

[Chem. 12]

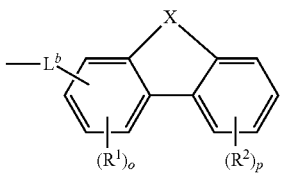

(III)

In the formula (III), $L^b$ represents a single bond, a substituted or unsubstituted arylene group having 6 to 25 ring carbon atoms, or a substituted or unsubstituted heteroarylene group having 5 to 25 ring atoms.

Examples of the arylene group represented by $L^b$ include a phenylene group, a naphthylphenylene group, a biphenyldiyl group, a terphenyldiyl group, a quaterphenyldiyl group, a naphthylylene group, a phenylnaphthylylene group, an acenaphthylylene group, an anthrylene group, a benzoanthrylene group, an aceanthrylene group, a phenanthrylene group, a benzophenanthrylene group, a phenalenylylene group, a fluorenylene group, a 9,9-dimethylfluorenylene group, a 7-phenyl-9,9-dimethylfluorenylene group, a pentacenylene group, a picenylene group, a pentaphenylene group, a pyrenylene group, a benzopyrenylene group, a chrysenylene group, a benzochrysenylene group, an s-indacenylene group, an as-indacenylene group, a perylenylene group, a fluoranthenylene group, and a naphthacenylene group. Of those, an arylene group having 6 to 18 ring carbon atoms is preferred from the viewpoints of the driving voltage, luminous efficiency, and device lifetime of the organic EL device, an arylene group having 6 to 12 ring carbon atoms is more preferred, a phenylene group, a naphthylene group, a biphenyldiyl group, a terphenyldiyl group, or a phenanthrylene group is still more preferred, and a phenylene group, a naphthylene group, or a biphenyldiyl group is particularly preferred.

In addition, the arylene group represented by $L^b$ may have a substituent. The same substituents as the substituents A can be given as examples of the substituent.

Examples of the heteroarylene group represented by $L^b$ include a pyrrolylene group, a pyrazinylene group, a pyridinylene group, an indolylene group, an isoindolylene group, a furylene group, a benzofuranylene group, an isobenzofuranylene group, a quinolylene group, an isoquinolylene group, a quinoxalinylene group, a carbazolylene group, a 9-phenylcarbazolylene group, a phenanthridinylene group, an acridinylene group, a phenazinylene group, a phenothiazinylene group, a phenoxazinylene group, an oxazolylene group, an oxadiazolylene group, a furazanylene group, a thienylylene group, a thiophenylene group, a 1-phenylthiophenylene group, a 1,4-diphenylthiophenylene group, a benzothiophenylene group, a 1-phenylbenzothiophenylene group, a dibenzothiophenylene group, a 1-phenyldibenzothiophenylene group, a dibenzofuranylene group, a 1-phenyldibenzofuranylene group, and a benzothiazolylene group. Of those, a heteroarylene group having 5 to 15 ring atoms is preferred from the viewpoints of the driving voltage, luminous efficiency, and device lifetime of the organic EL device.

In addition, the heteroarylene group represented by $L^b$ may have a substituent. The same substituents as the substituents A can be given as examples of the substituent.

$L^b$ represents preferably a single bond, or a substituted or unsubstituted arylene group having 6 to 25 (preferably 6 to 18, more preferably 6 to 12) ring carbon atoms from the viewpoints of the driving voltage, luminous efficiency, and device lifetime of the organic EL device, more preferably a single bond, a phenylene group, a naphthylene group, a biphenyldiyl group, a terphenyldiyl group, or a phenanthrylene group, still more preferably a single bond, a phenylene group, a naphthylene group, or a biphenyldiyl group.

In the formula (III), $R^1$ and $R^2$ each independently represent an alkyl group having 1 to 15 carbon atoms, an alkenyl group having 2 to 15 carbon atoms, a cycloalkyl group having 3 to 15 ring carbon atoms, an aryl group having 6 to 25 ring carbon atoms, a heteroaryl group having 5 to 25 ring atoms, a trialkylsilyl group formed of alkyl groups each having 1 to 15 carbon atoms, a triarylsilyl group formed of aryl groups each having 6 to 25 ring carbon atoms, an alkylarylsilyl group formed of an alkyl group having 1 to 15 carbon atoms and an aryl group having 6 to 25 ring carbon atoms, a carbazolyl group, a halogen atom, or a cyano group.

Examples of the alkyl group which $R^1$ and $R^2$ each independently represent include a methyl group, an ethyl group, an n-propyl group, an isopropyl group, an n-butyl group, an isobutyl group, an s-butyl group, a t-butyl group, various pentyl groups, various hexyl groups, various heptyl groups, various octyl groups, various nonyl groups, various decyl groups, various undecyl groups, and various dodecyl groups. When the alkyl chain of the alkyl group is extended, the solubility of the aromatic amine derivative of the present invention is improved and hence the derivative can be suitably used for the production of the organic EL device by an application method. The alkyl group suitable for the application method is preferably an alkyl group having 1 to 10 carbon atoms, more preferably an alkyl group having 1 to 8 carbon atoms. In addition, when the alkyl group has 1 to 5 carbon atoms, the molecular weight of the aromatic amine derivative of the present invention can be suppressed and hence the derivative can be suitably used for the production of the organic EL device by a vapor deposition method. The alkyl group suitable for the vapor deposition method is preferably an alkyl group having 1 to 5 carbon atoms, more preferably an alkyl group having 1 to 3 carbon atoms.

Examples of the alkenyl group which $R^1$ and $R^2$ each independently represent include groups each obtained by making at least one carbon-carbon bond in a group having 2 to 15 carbon atoms out of the alkyl groups represented by the $R^1$ and the $R^2$ a double bond.

Examples of the cycloalkyl group which $R^1$ and $R^2$ each independently represent include a cyclopropyl group, a cyclopentyl group, a cyclohexyl group, a cyclooctyl group, a cyclodecyl group, a cyclopentylmethyl group, a cyclohexylmethyl group, a cyclohexylethyl group, a 1-adamantyl group, a 2-adamantyl group, a 1-norbornyl group, and a 2-norbornyl group. Of those, a cycloalkyl group having 3 to 10 ring carbon atoms is preferred, and a cycloalkyl group having 3 to 6 ring carbon atoms is more preferred.

The same examples as those of the aryl group represented by $Ar^a$ can be given as examples of the aryl group which $R^1$ and $R^2$ each independently represent. The aryl group is preferably an aryl group having 6 to 18 ring carbon atoms, more preferably an aryl group having 6 to 12 ring carbon atoms.

The same examples as those of the heteroaryl group represented by $Ar^a$ can be given as examples of the heteroaryl group which $R^1$ and $R^2$ each independently represent. The heteroaryl group is preferably a heteroaryl group having 5 to 15 ring atoms.

Examples of the alkyl groups in the trialkylsilyl group which $R^1$ and $R^2$ each independently represent include the same examples as those of the alkyl group represented by each of the $R^1$ and the $R^2$, and preferred examples thereof are also the same. In addition, the three alkyl groups with which a silyl group is substituted may be identical to or different from one another.

Examples of the aryl groups in the triarylsilyl group which $R^1$ and $R^2$ each independently represent include the same examples as those of the aryl group represented by each of the $R^1$ and the $R^2$, and preferred examples thereof are also the same. In addition, the three aryl groups with which a silyl group is substituted may be identical to or different from one another.

Examples of the alkyl group and the aryl group in the alkylarylsilyl group which $R^1$ and $R^2$ each independently represent include the same examples as those of the alkyl group and the aryl group each represented by each of the $R^1$ and the $R^2$, and preferred examples thereof are also the same. Examples of the alkylarylsilyl group include a monoalkyldiarylsilyl group and a dialkylmonoarylsilyl group.

Examples of the halogen atom which $R^1$ and $R^2$ each independently represent include a fluorine atom, a chlorine atom, a bromine atom, and an iodine atom.

In the formula (III), o represents an integer of 0 to 3, preferably 0 or 1, more preferably 0, and p represents an integer of 0 to 4, preferably 0 or 1. When o represents 2 or 3, or p represents an integer of 2 to 4, a plurality of $R^1$'s or $R^2$'s may be identical to or different from each other.

When o represents 2 or 3, or p represents an integer of 2 to 4, or when o represents an integer of 1 to 3 and p represents an integer of 1 to 4, a plurality of $R^1$'s or $R^2$'s adjacent to each other, or $R^1$ and $R^2$ may be bonded to each other to form a ring. The formed ring may include a saturated hydrocarbon moiety as a part thereof, or may be an aromatic ring.

When a plurality of $R^1$'s or $R^2$'s adjacent to each other, or $R^1$ and $R^2$ are bonded to each other to form a ring, specific examples of the structure of the $Ar^B$ include, but not particularly limited to, the following structures.

[Chem. 13]

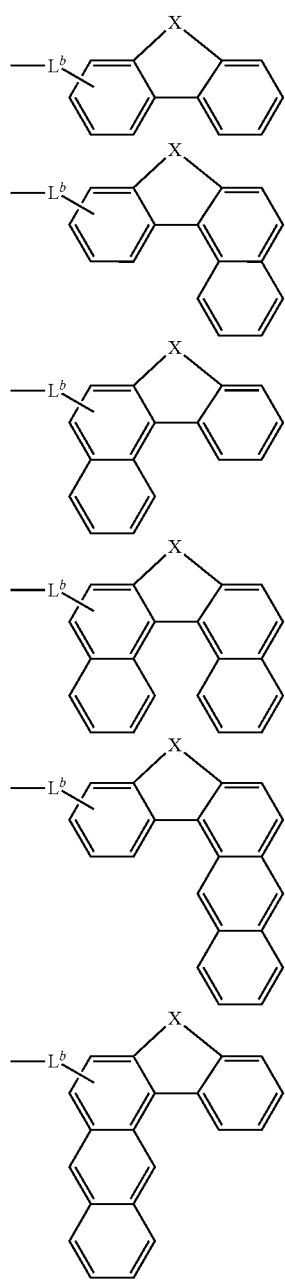

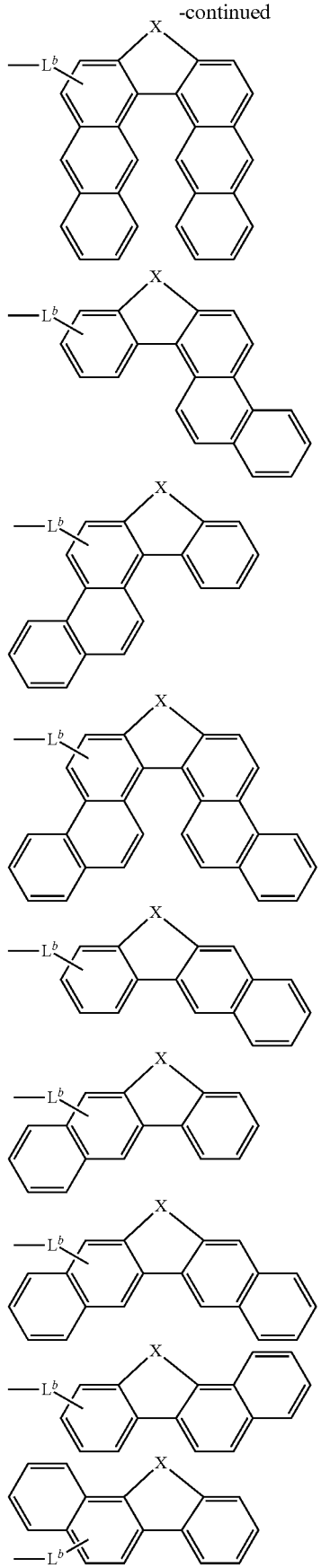

-continued
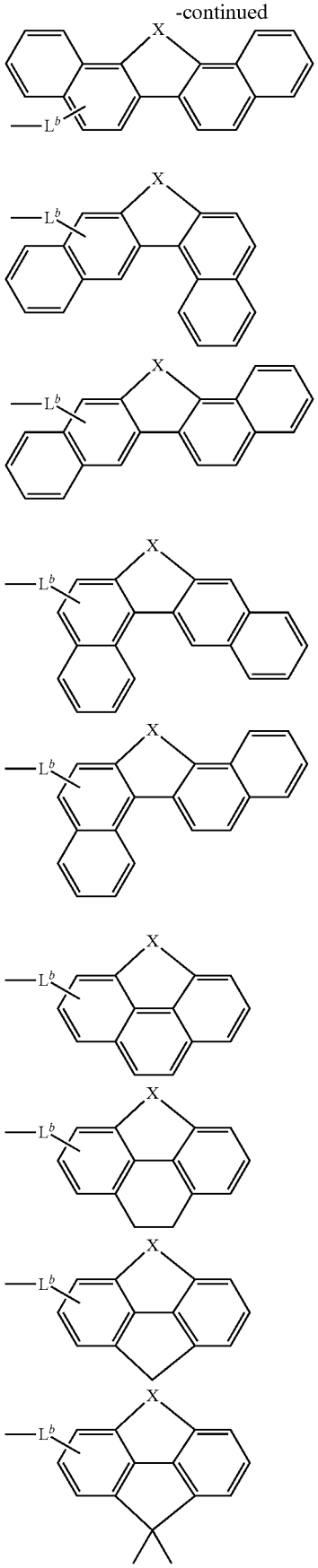
Of those, any one of the groups selected from
[Chem. 14]
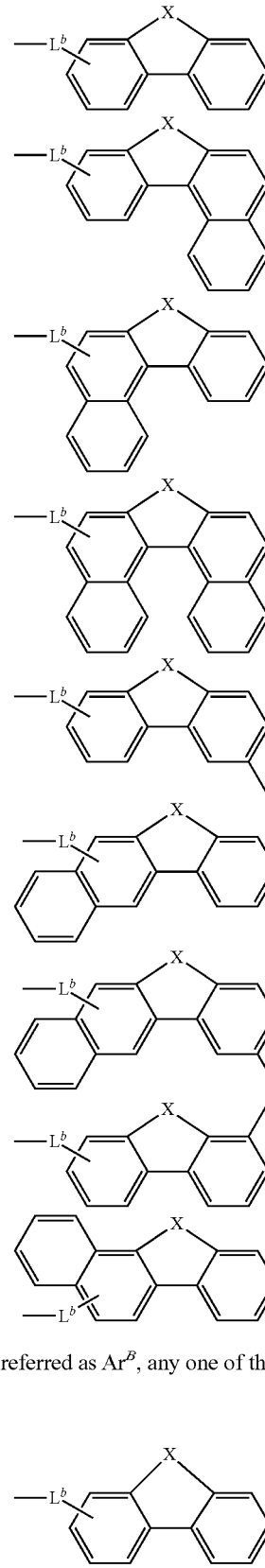
is preferred as $Ar^B$, any one of the groups selected from
[Chem. 15]

-continued

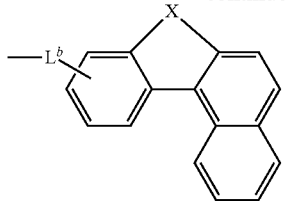

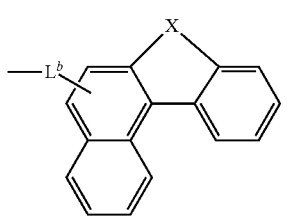

is more preferred, and a group represented by

[Chem. 16]

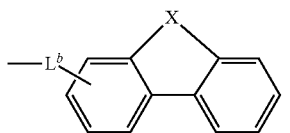

is still more preferred.

In the formula (III), X represents CR³R⁴, NR⁵, an oxygen atom, or a sulfur atom.

R³, R⁴, and R⁵ each independently represent an alkyl group having 1 to 15 carbon atoms, or a substituted or unsubstituted aryl group having 6 to 25 ring carbon atoms. The same examples as those of the alkyl group and the aryl group each represented by each of R¹ and R² can be given as examples of the alkyl group and the aryl group. Of those, an alkyl group having 1 to 10 carbon atoms is preferred as the alkyl group from the viewpoints of the driving voltage, luminous efficiency, and device lifetime of the organic EL device, an alkyl group having 1 to 5 carbon atoms is more preferred, and a methyl group is still more preferred. In addition, of those, an aryl group having 6 to 18 ring carbon atoms is preferred as the aryl group from the same viewpoints, an aryl group having 6 to 12 ring carbon atoms is more preferred, and a phenyl group is still more preferred. It should be noted that the aryl group may have a substituent and the same substituents as the substituents A can be given as examples of the substituent.

Each of R³ and R⁴ represents preferably an alkyl group having 1 to 15 carbon atoms from the viewpoints of the driving voltage, luminous efficiency, and device lifetime of the organic EL device, more preferably an alkyl group having 1 to 10 carbon atoms, still more preferably an alkyl group having 1 to 5 carbon atoms, particularly preferably a methyl group.

R⁵ represents preferably an aryl group having 6 to 25 ring carbon atoms from the viewpoints of the driving voltage, luminous efficiency, and device lifetime of the organic EL device, more preferably an aryl group having 6 to 18 ring carbon atoms, still more preferably an aryl group having 6 to 12 ring carbon atoms, particularly preferably a phenyl group.

$Ar^B$ represents preferably any one of the following structures:

[Chem. 17]

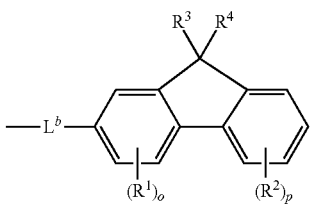

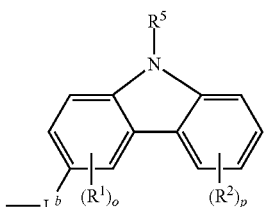

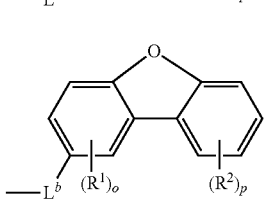

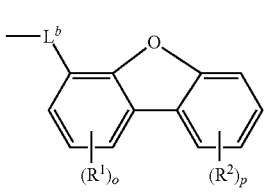

(where $L^b$, $R^1$, $R^2$, $R^3$, $R^4$, $R^5$, o, and p are as defined in the formula (III), and preferred examples thereof are also the same) from the viewpoints of the driving voltage, luminous efficiency, and device lifetime of the organic EL device, more preferably any one of

[Chem. 18]

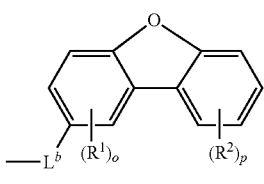

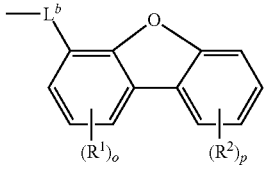

(where $L^b$, $R^1$, $R^2$, $R^3$, $R^4$, $R^5$, o, and p are as defined in the formula (III), and preferred examples thereof are also the same).

Here, specific examples of $Ar^B$ are shown below. However, $Ar^B$ is not particularly limited to these examples. It should be noted that a wavy line represents a bonding site.

[Chem. 19]
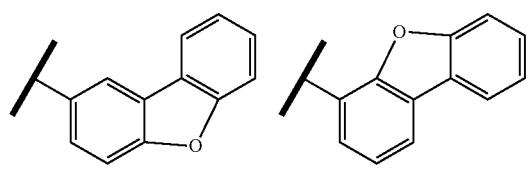
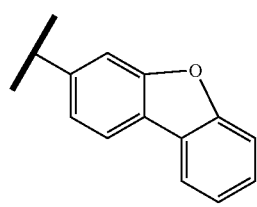
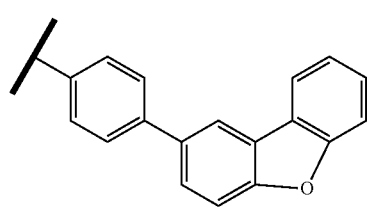
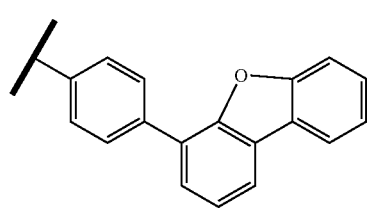
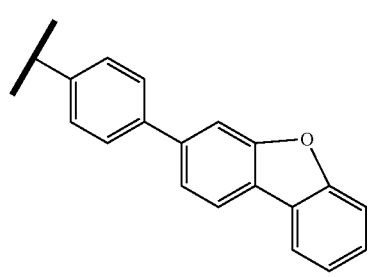
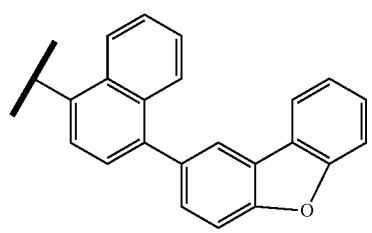
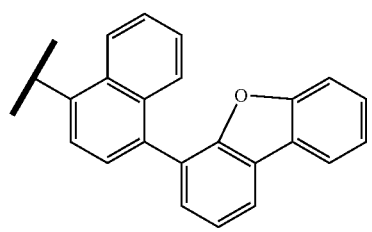

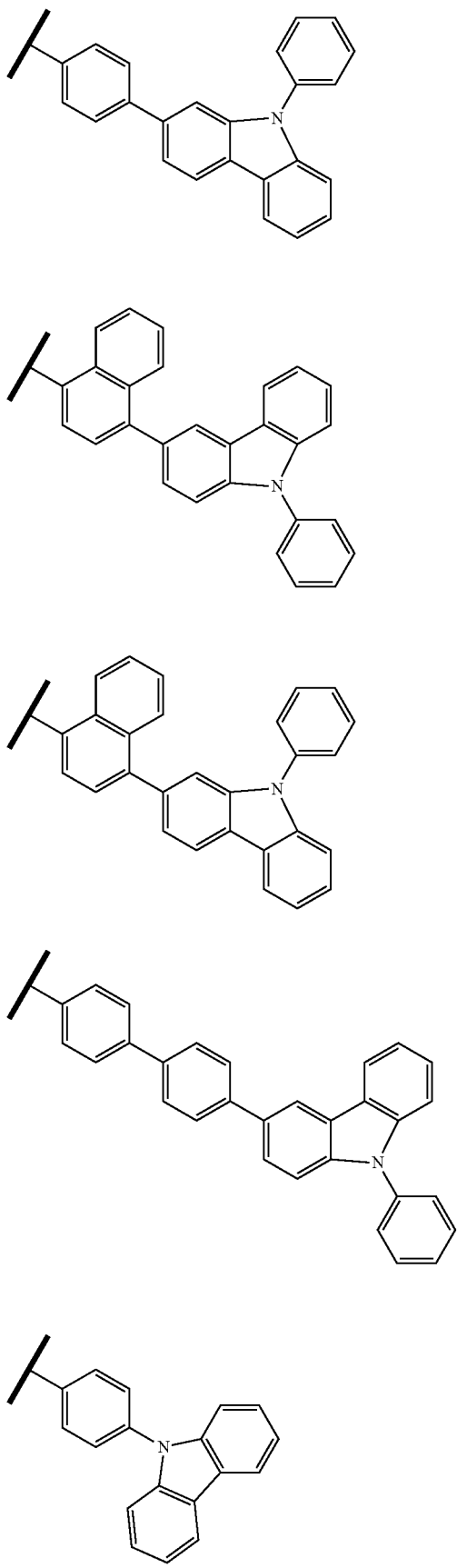
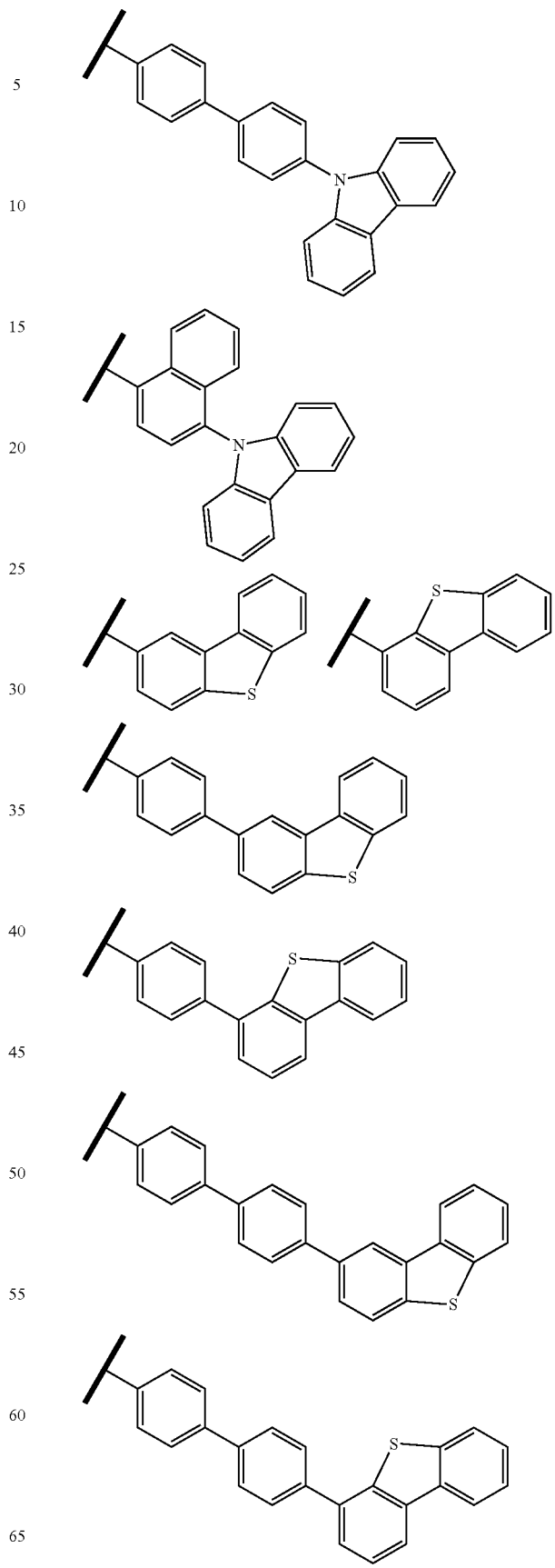

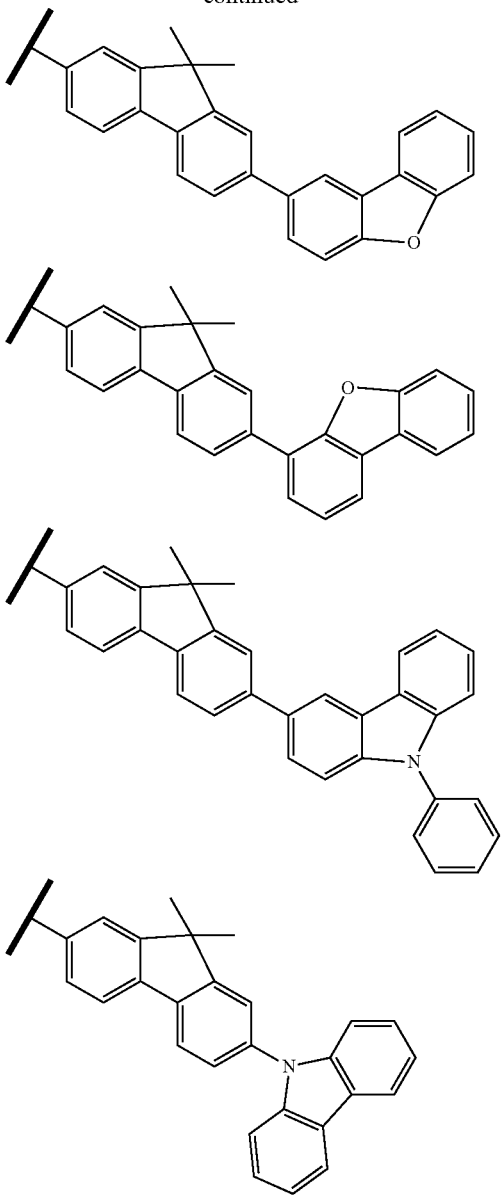

In addition, in the formula (I), Ar$^C$ represents a substituted or unsubstituted aryl group having 6 to 50 ring carbon atoms, or a substituted or unsubstituted heteroaryl group having 5 to 25 ring atoms, or is represented by the formula (II-1), (II-2), or (III).

Examples of the aryl group represented by Ar$^C$ include a phenyl group, a naphthylphenyl group, a biphenylyl group, a naphthylbiphenylyl group, a terphenylyl group, a quaterphenylyl group, a naphthyl group, a phenylnaphthyl group, a biphenylylnaphthyl group, an acenaphthyl group, an anthryl group, an anthrylphenyl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a 7-naphthyl-9,9-dimethyl fluorenyl group, a pentacenyl group, a picenyl group, a pentaphenylyl group, pyrenyl group, a benzopyrenyl group, a chrysenyl group, a benzochrysenyl group, an s-indacenyl group, an as-indacenyl group, a fluoranthenyl group, a benzofluoranthenyl group, a fluoranthenylphenyl group, a perylenyl group, and a naphthacenyl group. Of those, an aryl group having 6 to 25 ring carbon atoms is preferred from the viewpoints of the driving voltage, luminous efficiency, and device lifetime of the organic EL device, and an aryl group having 6 to 18 ring carbon atoms is more preferred.

The aryl group may have a substituent, and the same substituents as the substituents A and a carbazolyl group can be given as examples of the substituent.

Examples of the heteroaryl group represented by Ar$^C$ include a pyrrolyl group, a pyrazinyl group, a pyridinyl group, an indolyl group, an isoindolyl group, a furyl group, a benzofuranyl group, an isobenzofuranyl group, a quinolyl group, an isoquinolyl group, a quinoxalinyl group, a carbazolyl group, a 9-phenylcarbazolyl group, a phenanthridinyl group, an acridinyl group, a phenazinyl group, a phenothiazinyl group, a phenoxazinyl group, an oxazolyl group, an oxadiazolyl group, a furazanyl group, a thienylyl group, an indolyl group, a thiophenyl group, a 1-phenylthiophenyl group, a 1,4-diphenylthiophenyl group, a benzothiophenyl group, a 1-phenylbenzothiophenyl group, a dibenzothiophenyl group, a 1-phenyldibenzothiophenyl group, a dibenzofuranyl group, a 1-phenyldibenzofuranyl group, and a benzothiazolyl group. Of those, a heteroaryl group having 5 to 15 ring atoms is preferred from the viewpoints of the driving voltage, luminous efficiency, and device lifetime of the organic EL device, and a carbazolyl group, a dibenzofuranyl group, or a dibenzothiophenyl group is more preferred. The heteroaryl group may have a substituent and the same substituents as the substituents A can be given as examples of the substituent.

In addition, Ar$^C$ may be represented by the formula (II-1), (II-2), or (III), is preferably represented by the formula (II-1), (II-2), or (III), and is more preferably represented by the formula (III). In this case, the definition of each group in the formula (II-1), (II-2), or (III) is the same as that described in the foregoing, and preferred examples thereof are also the same.

When Ar$^C$ is represented by the formula (II-1) or (II-2), Ar$^C$, which may be identical to or different from Ar$^A$, is preferably identical to Ar$^A$ from the viewpoints of the driving voltage, luminous efficiency, and device lifetime of the organic EL device.

When Ar$^C$ is represented by the formula (III), Ar$^C$, which may be identical to or different from Ar$^B$, is preferably identical to Ar$^B$ from the viewpoints of the driving voltage, luminous efficiency, and device lifetime of the organic EL device.

Here, specific examples of Ar$^C$ are shown below. However, Ar$^C$ is not particularly limited to these examples. It should be noted that a wavy line represents a bonding site.

[Chem. 20]

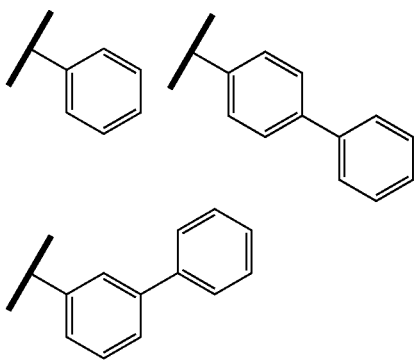

35
-continued
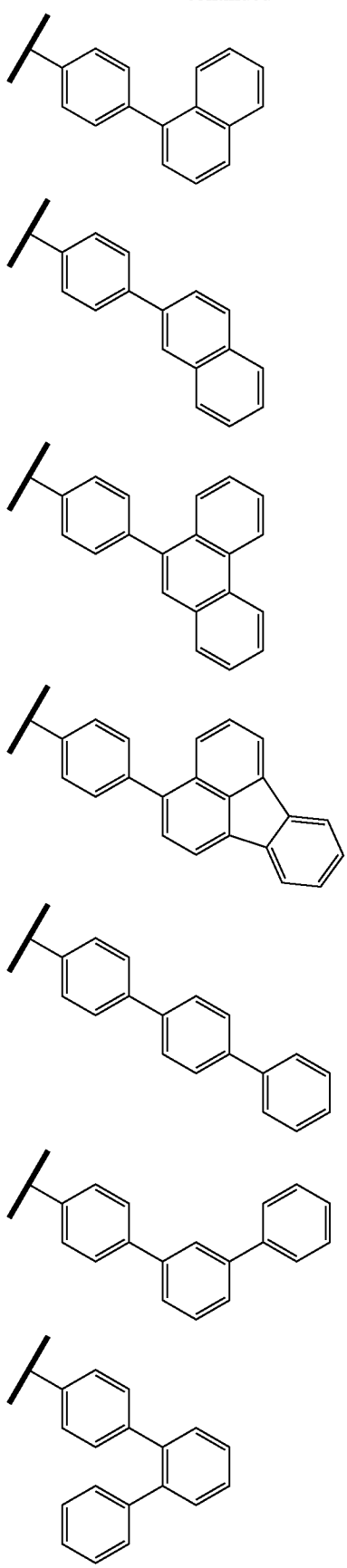
36
-continued
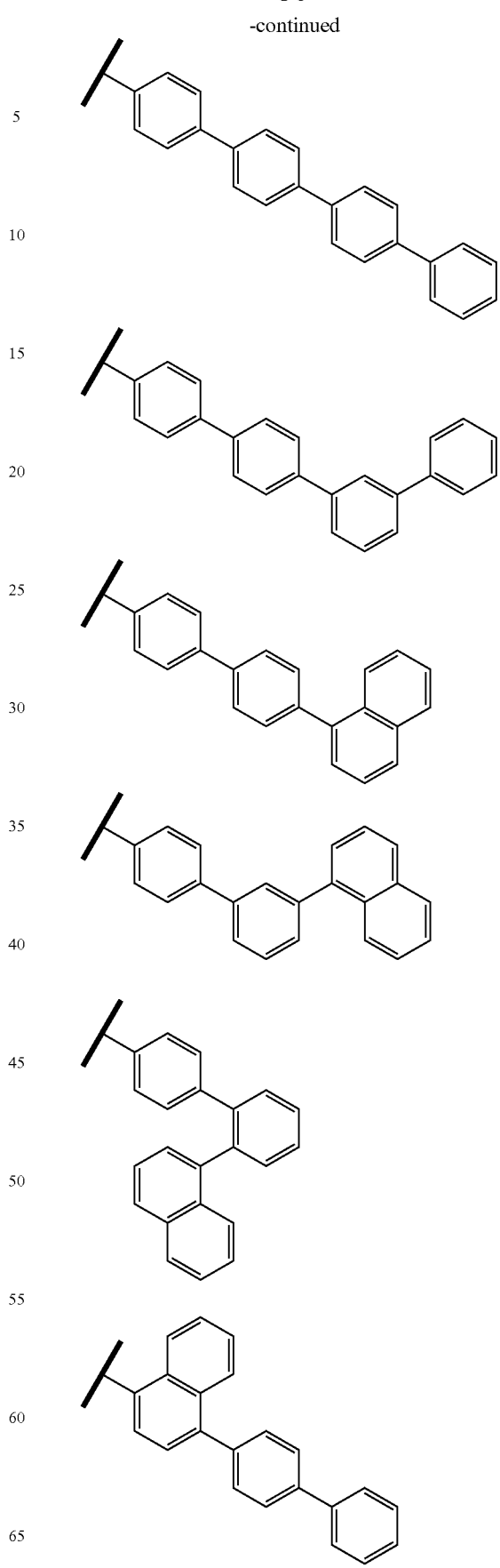

37
-continued
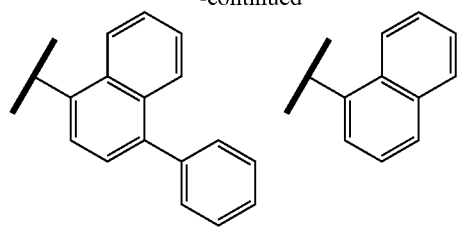
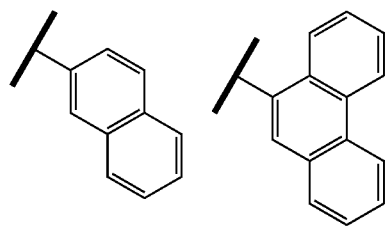
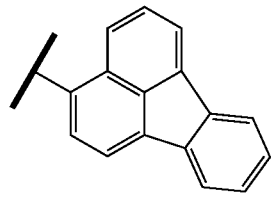
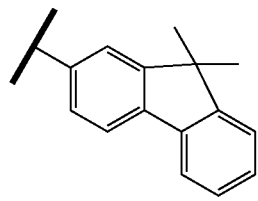
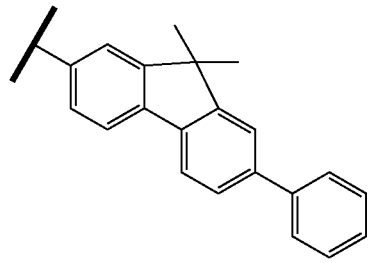
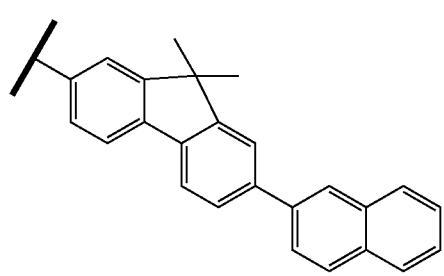
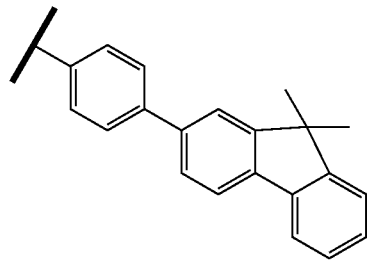
38
-continued
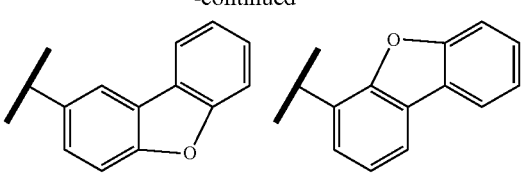
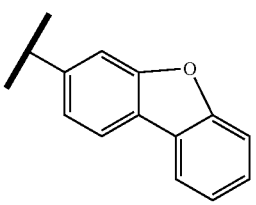
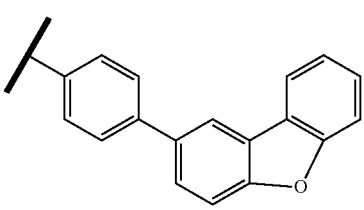
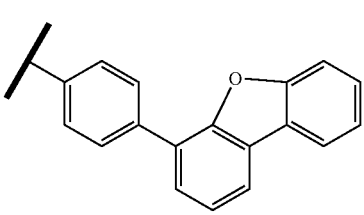
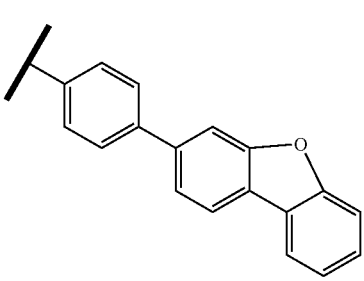
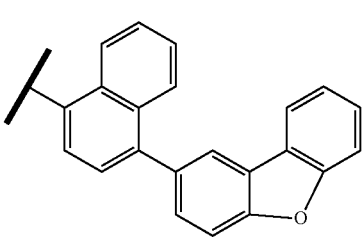
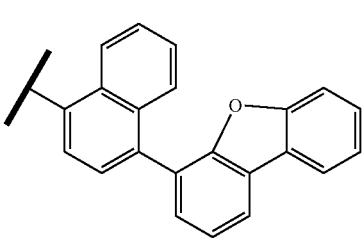

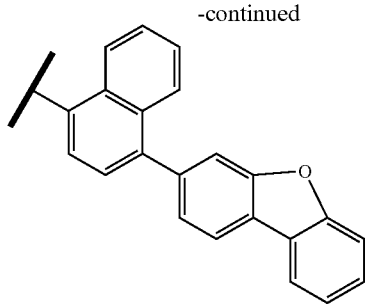
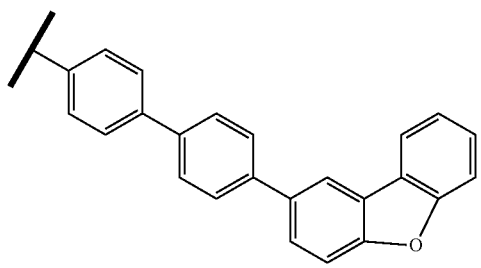
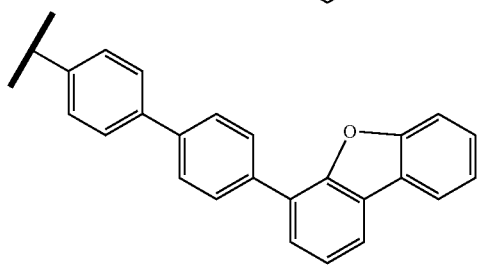
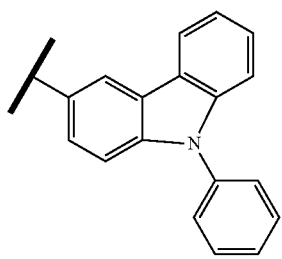
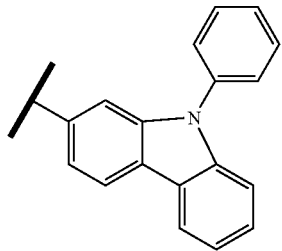
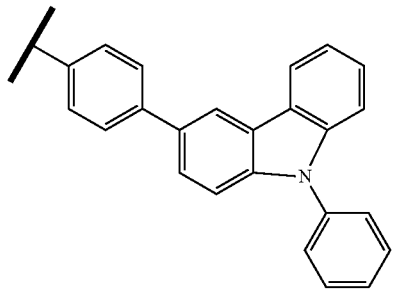
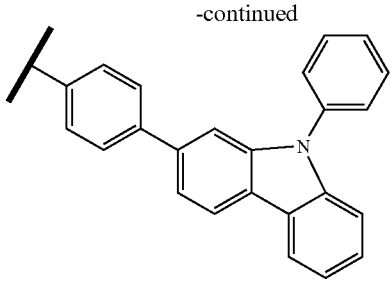
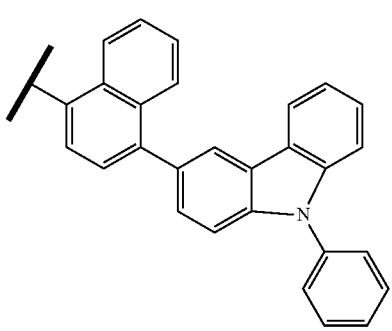
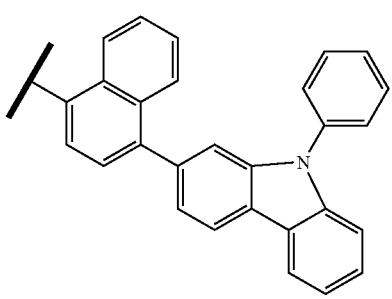
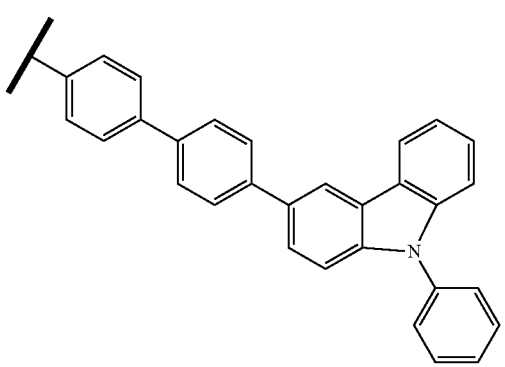
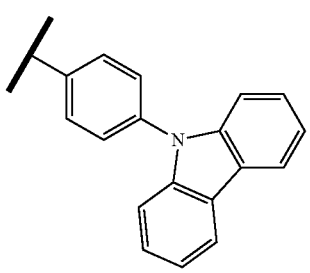

-continued

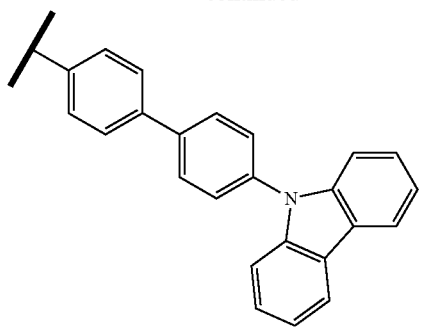
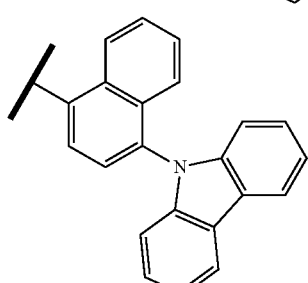
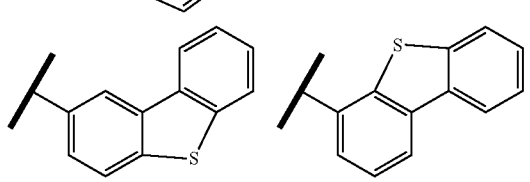
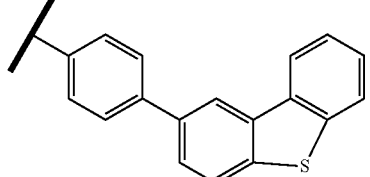
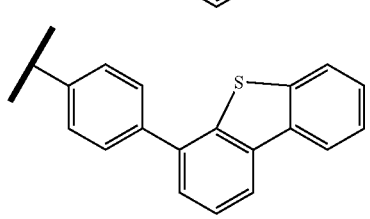
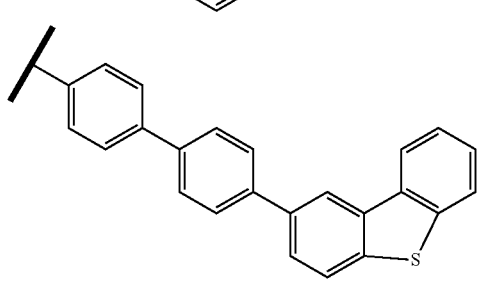

-continued

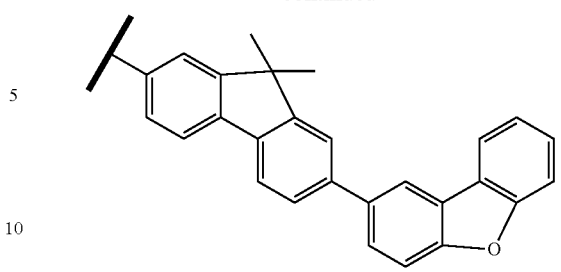
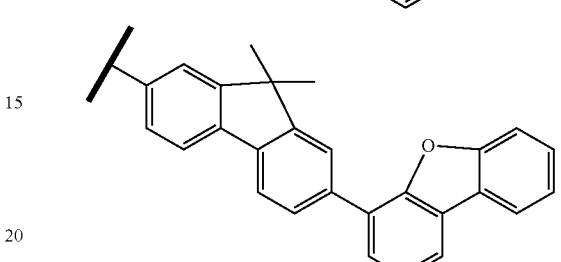
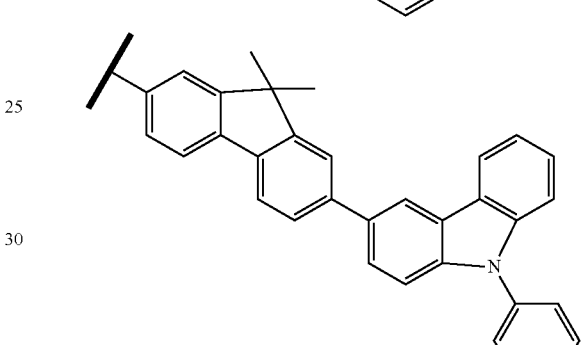
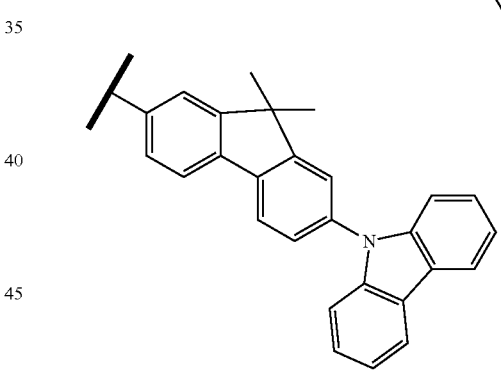

Chemical structural formulae each obtained by additionally making part of $Ar^A$, $Ar^B$, and $Ar^C$ in the aromatic amine derivative of the present invention represented by the formula (I) concrete include the following formulae (where each of $Ar^C$, $Ar^a$, $R^1$, $R^2$, $L^a$, $L^b$, n, o, p, and X is as defined in the foregoing, and preferred examples thereof are also the same).

[Chem. 21]

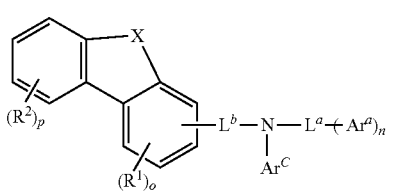

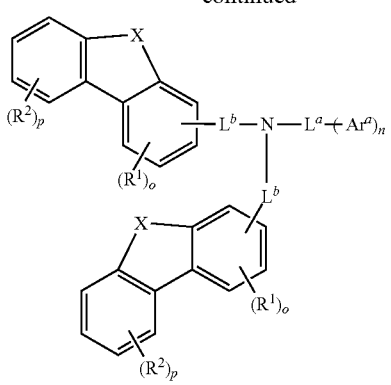
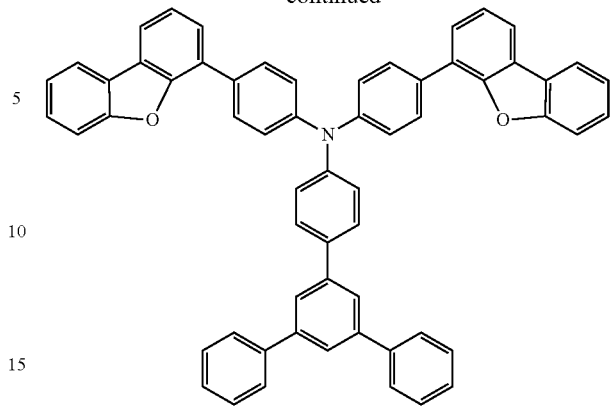
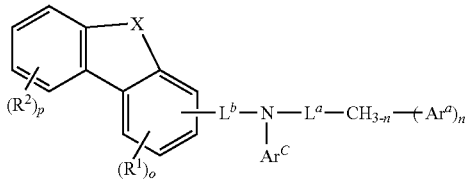
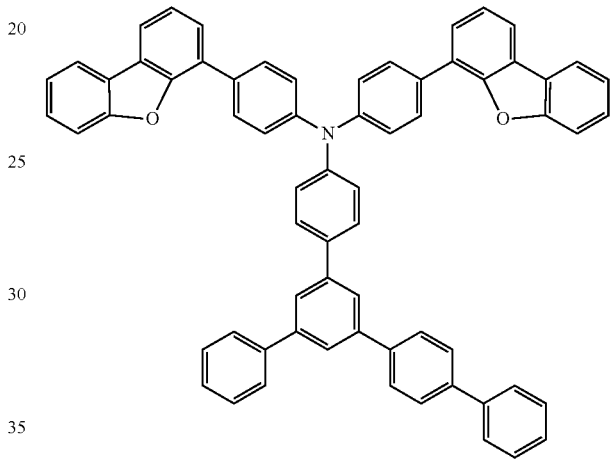
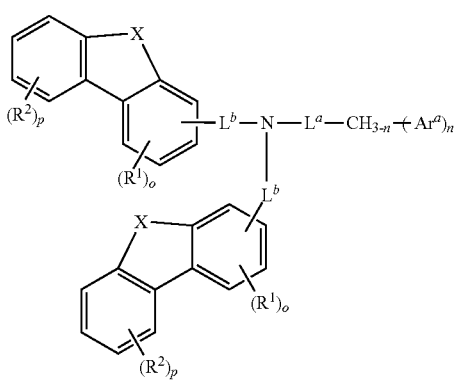
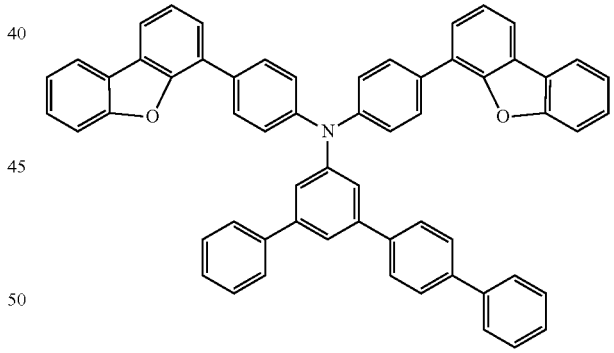
Next, specific examples of the aromatic amine derivative of the present invention represented by the formula (I) are shown below. However, the derivative is not particularly limited to these examples.
[Chem. 22]
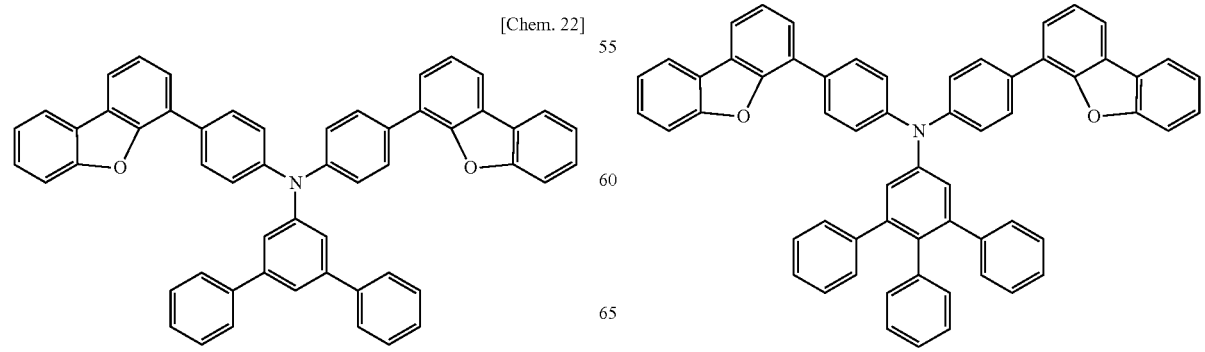

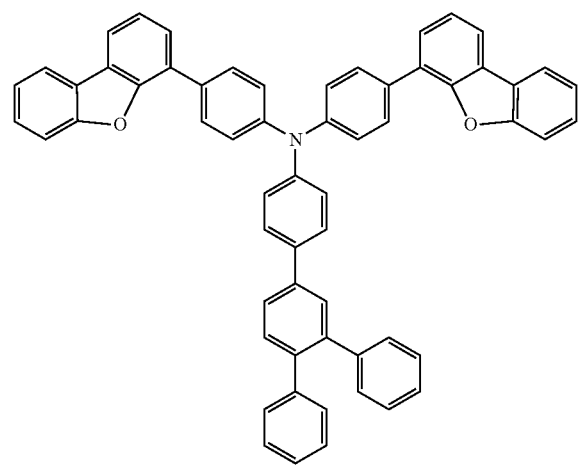
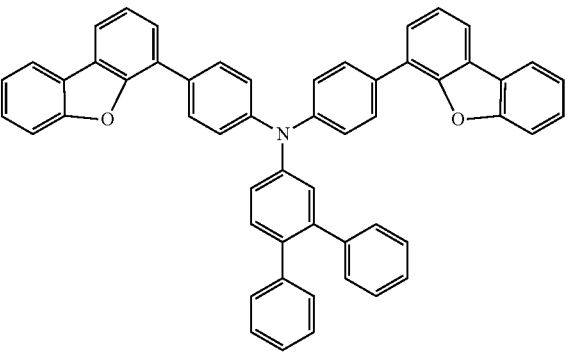
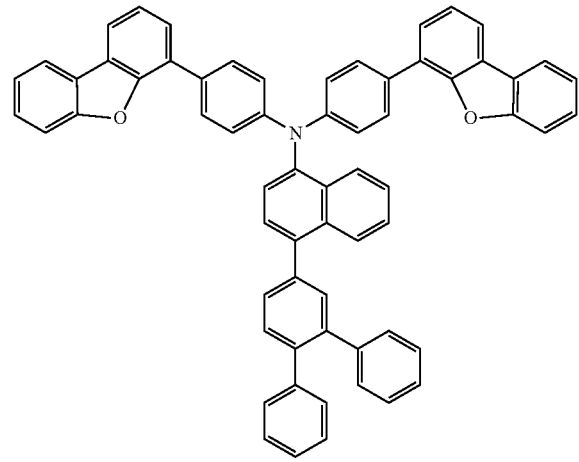
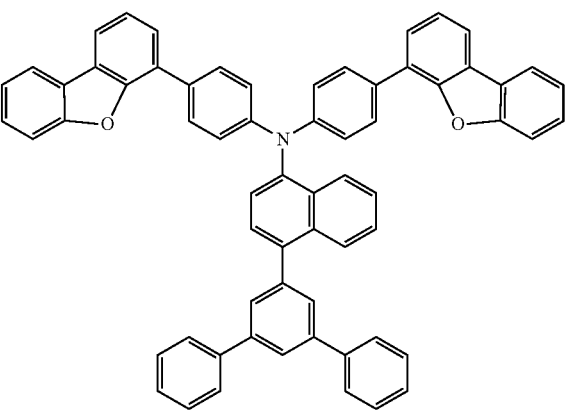
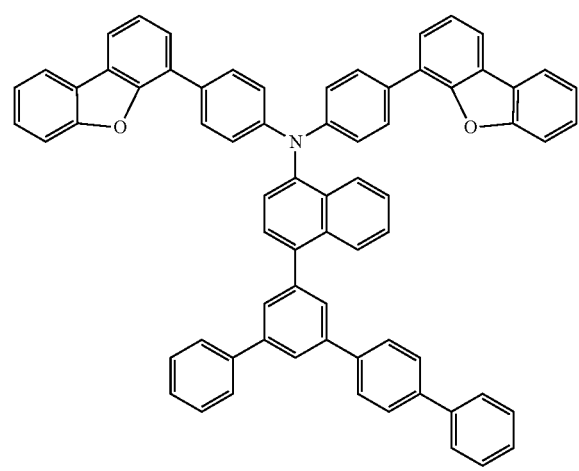
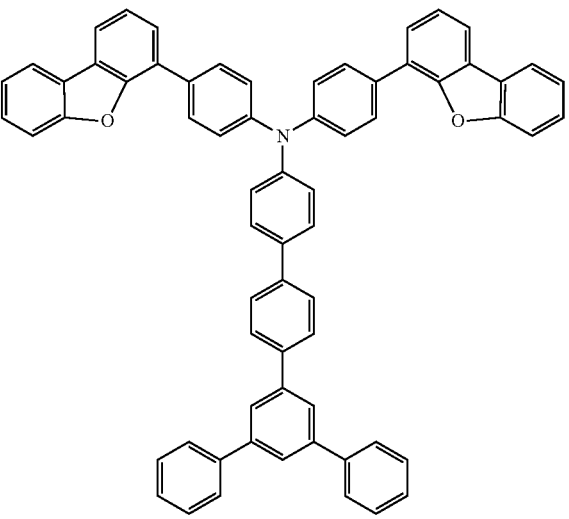

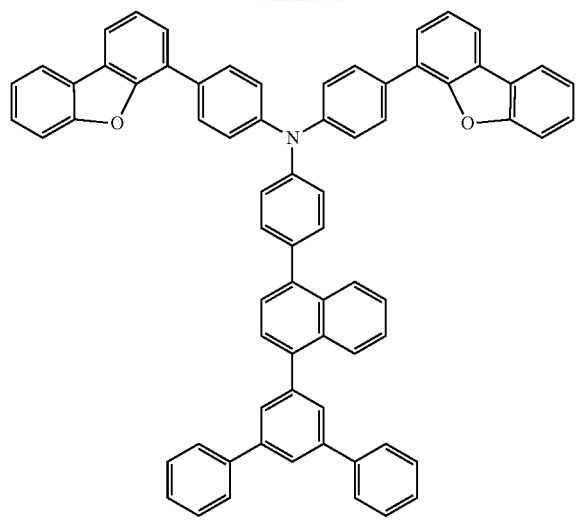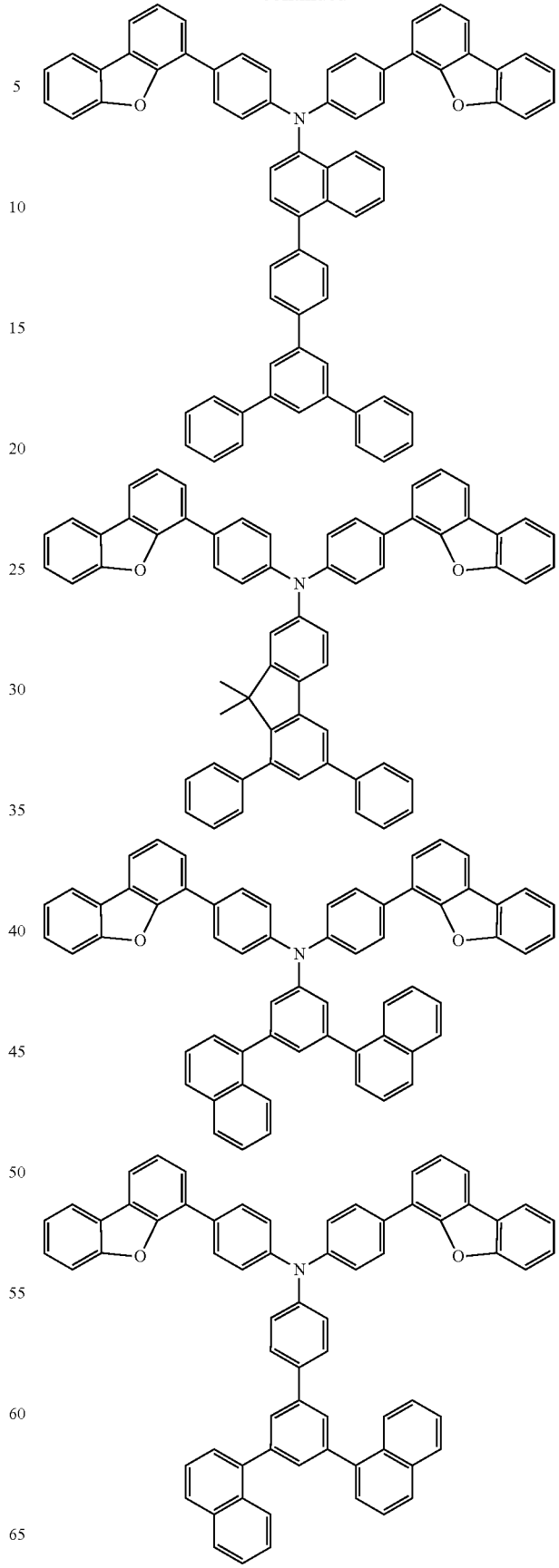

49
-continued
50
-continued
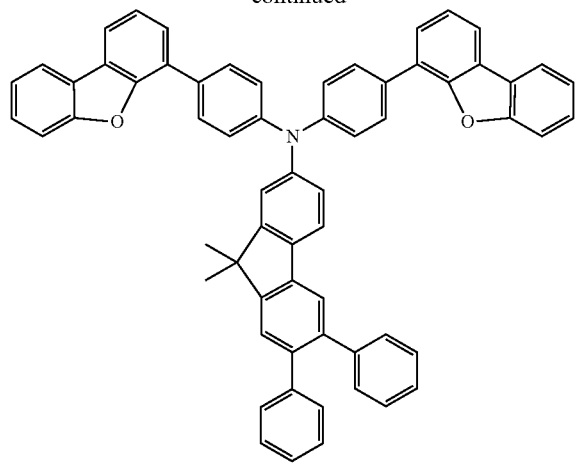
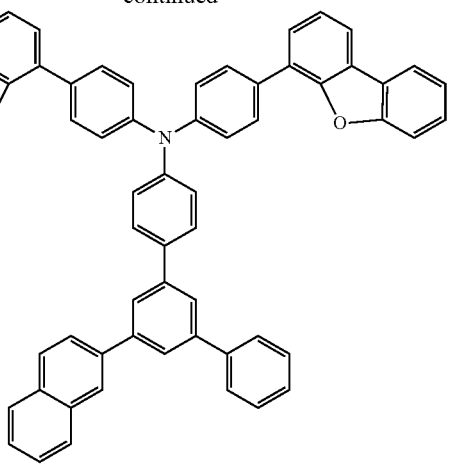
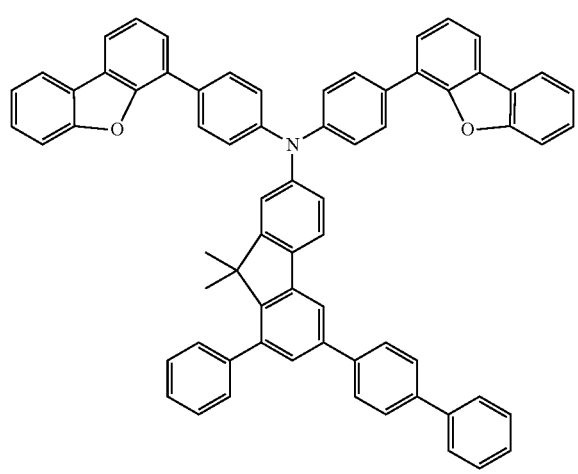
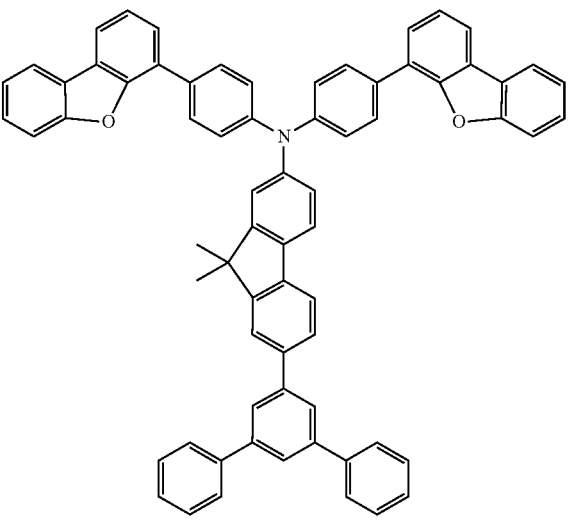

51
-continued
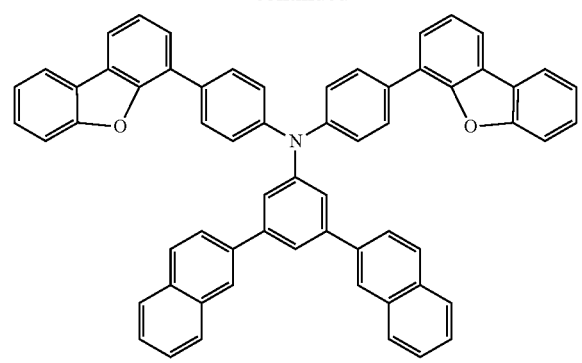
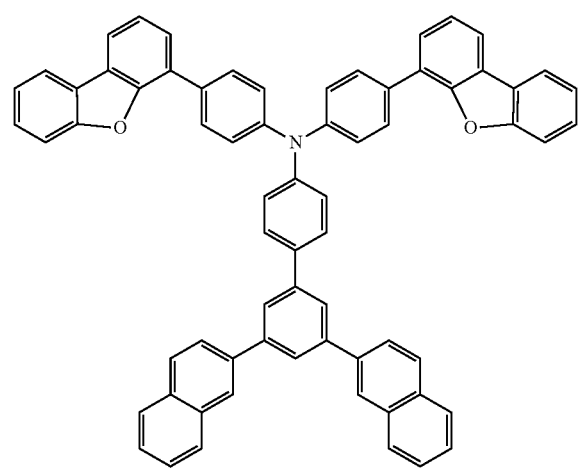
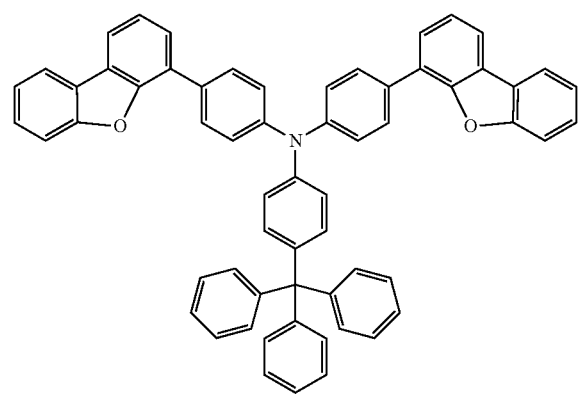
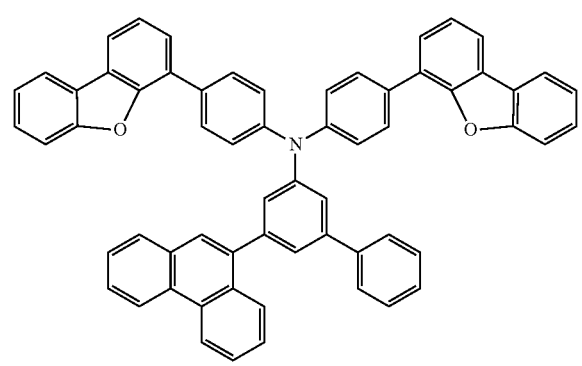
52
-continued
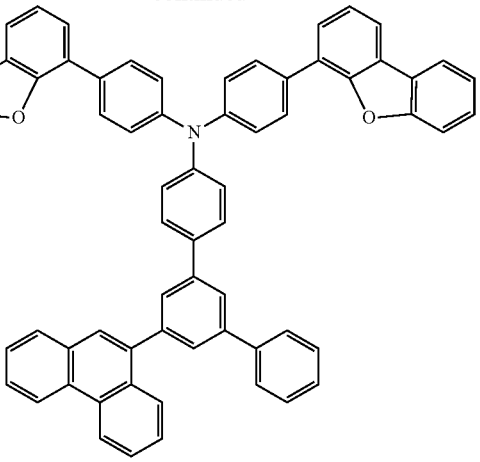
[Chem. 23]
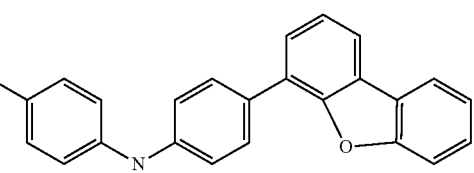
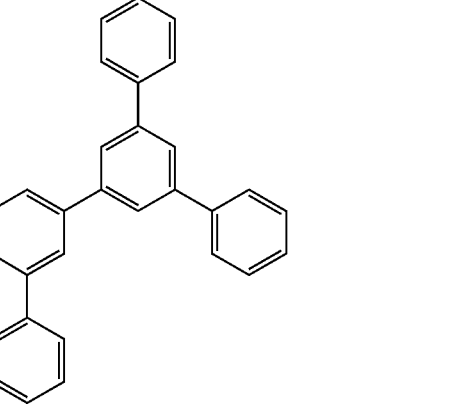
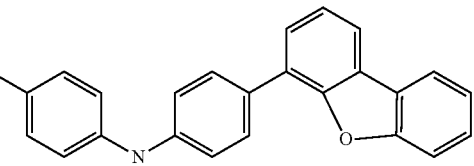
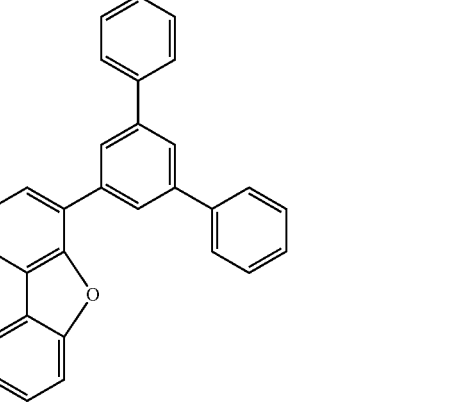

53
-continued
54
-continued
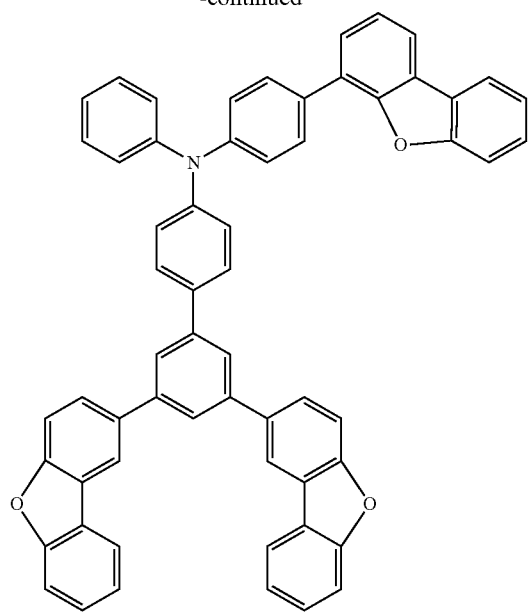
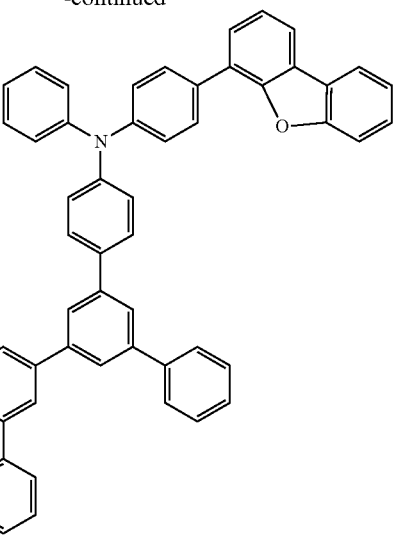

55
-continued
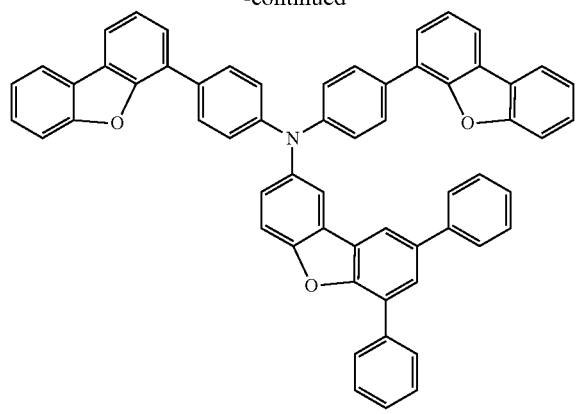
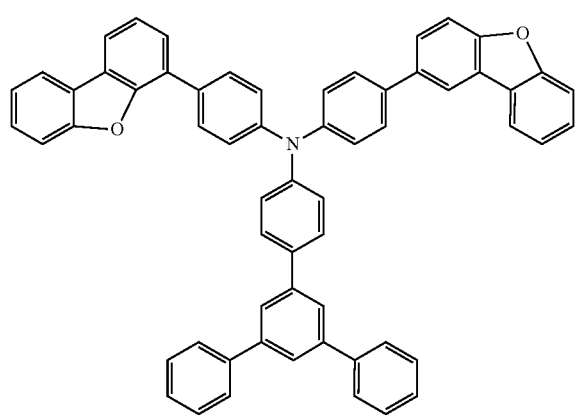
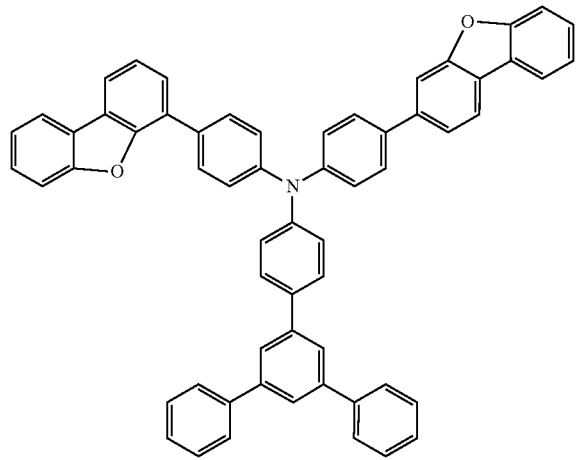
56
-continued
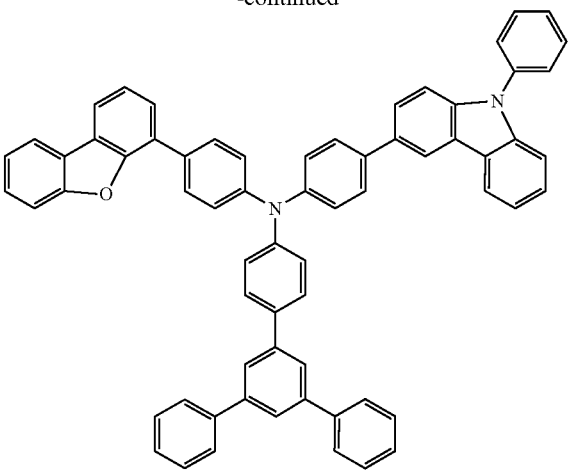
[Chem. 24]
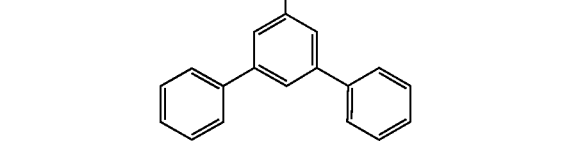
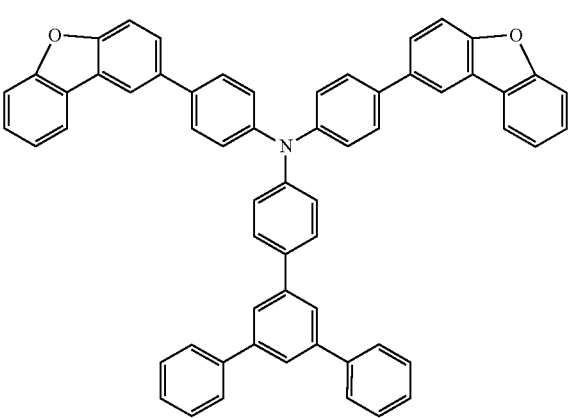

57
-continued
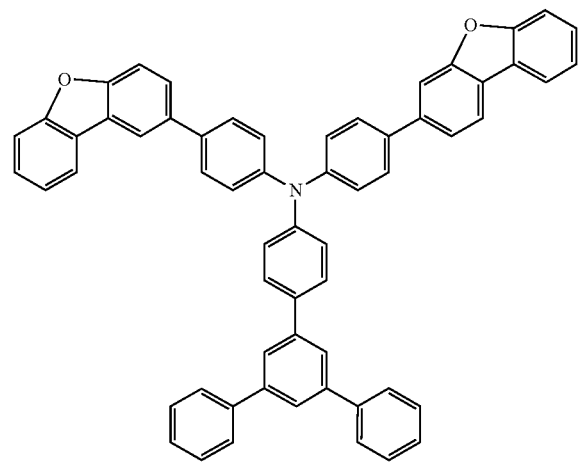
58
-continued
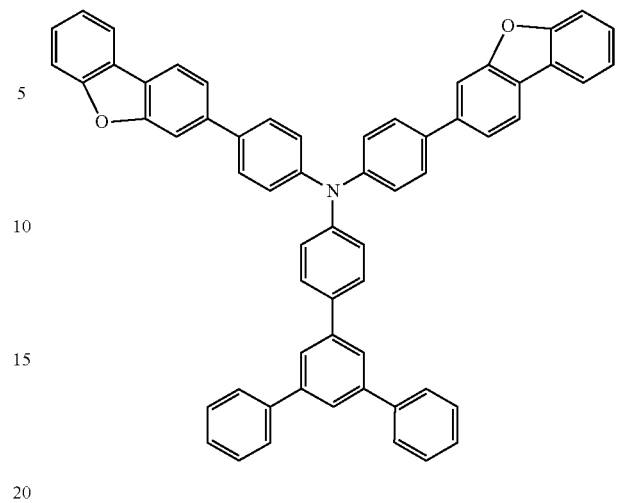
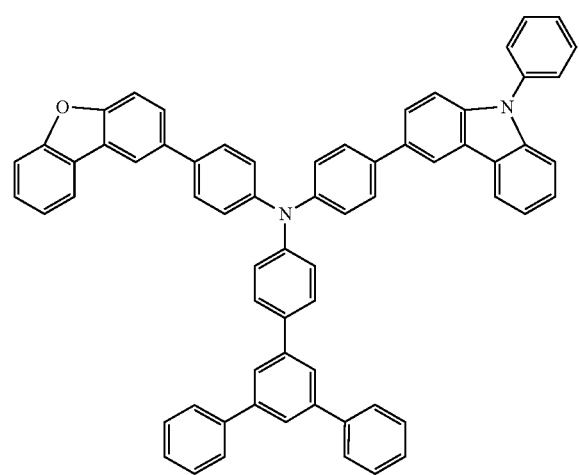
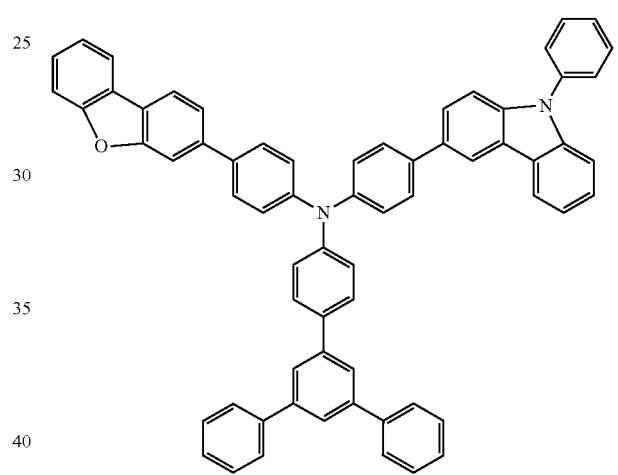
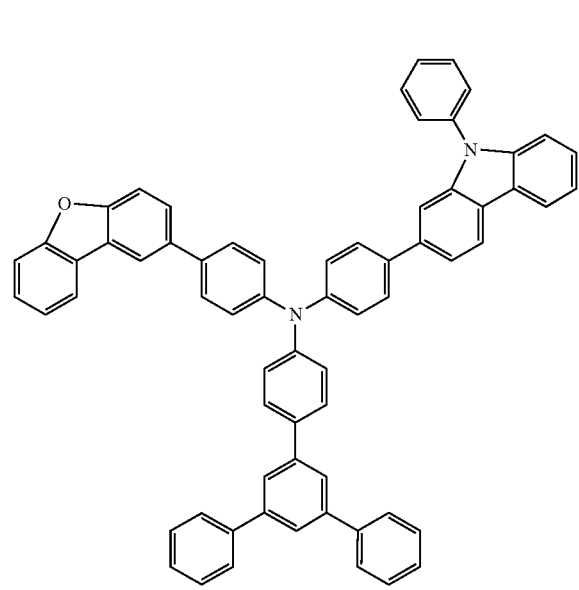
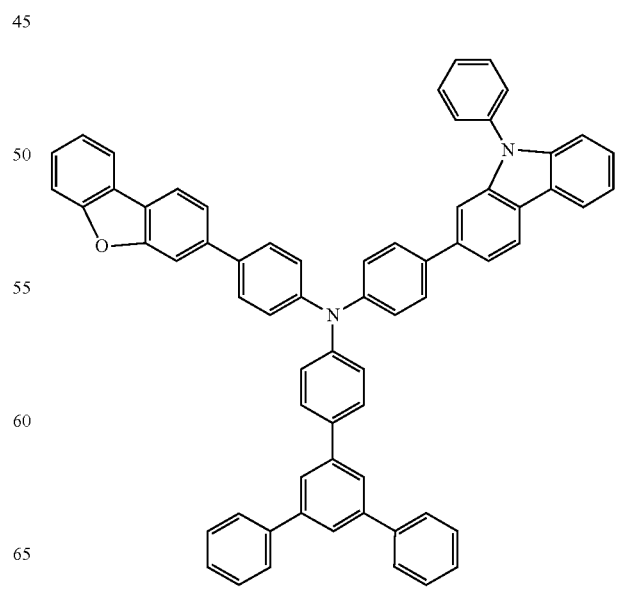

-continued
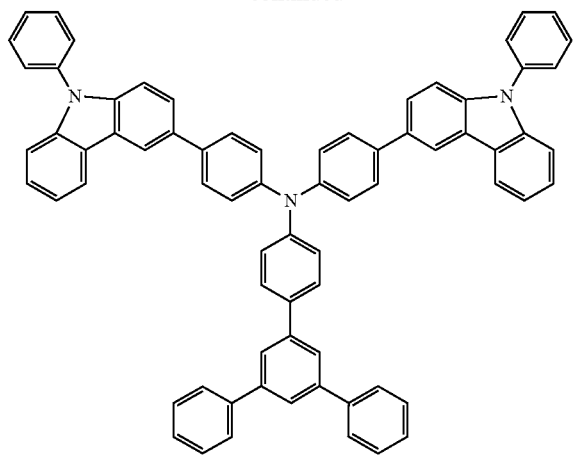
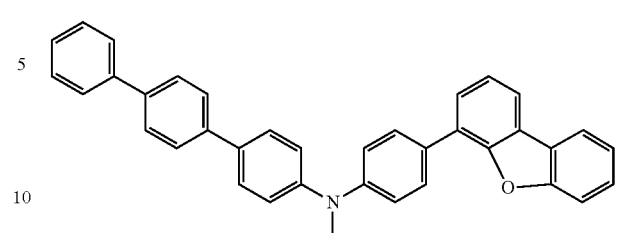
[Chem. 25]
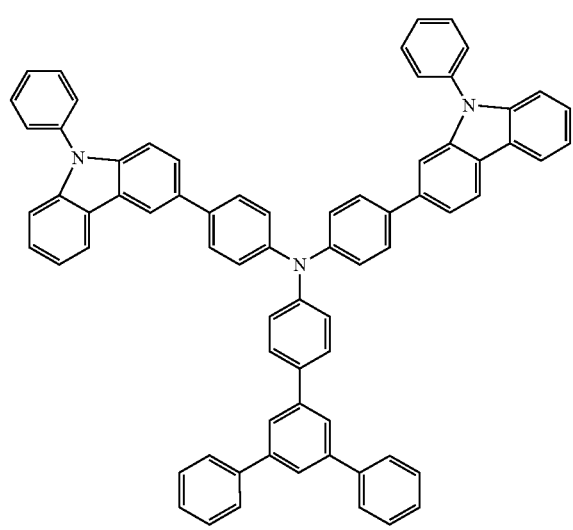
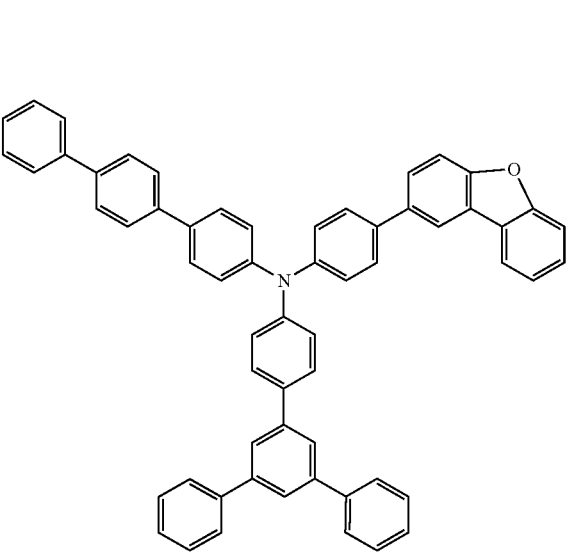
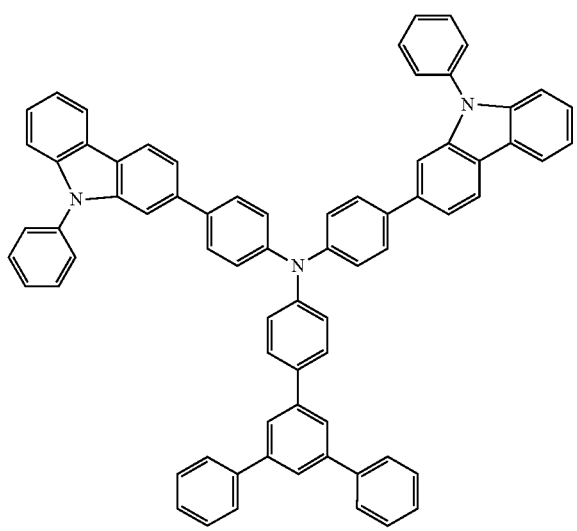
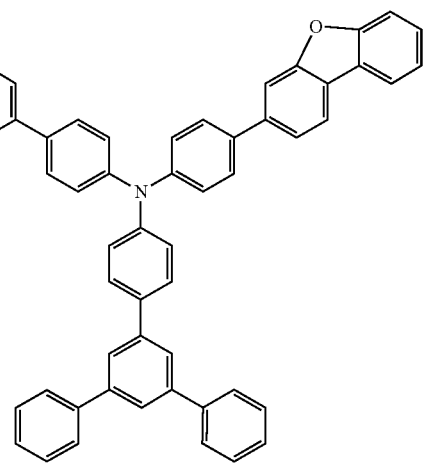

61
-continued
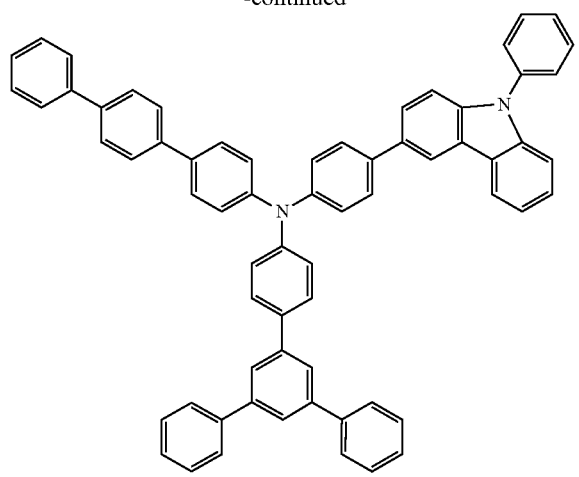
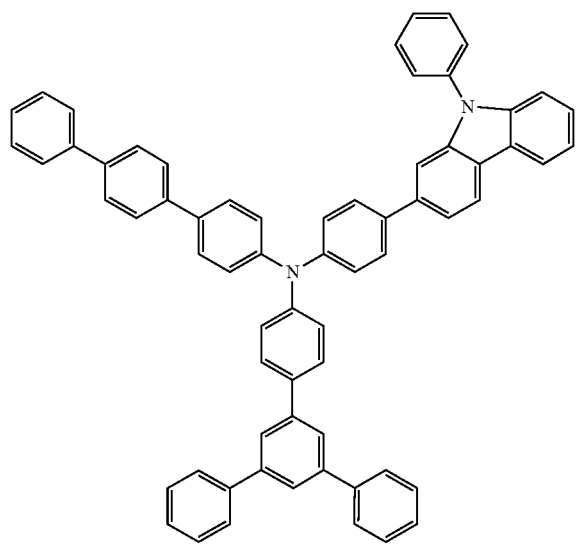
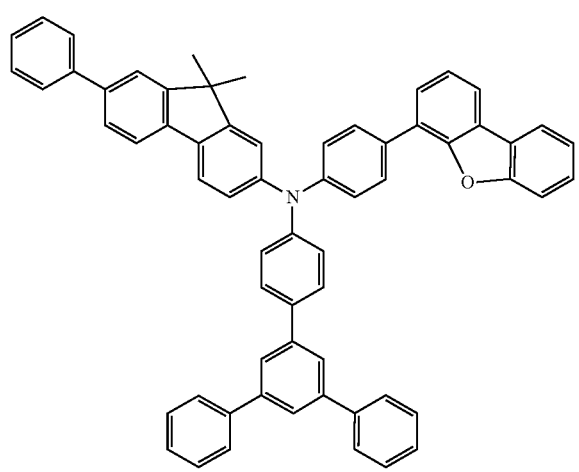
62
-continued
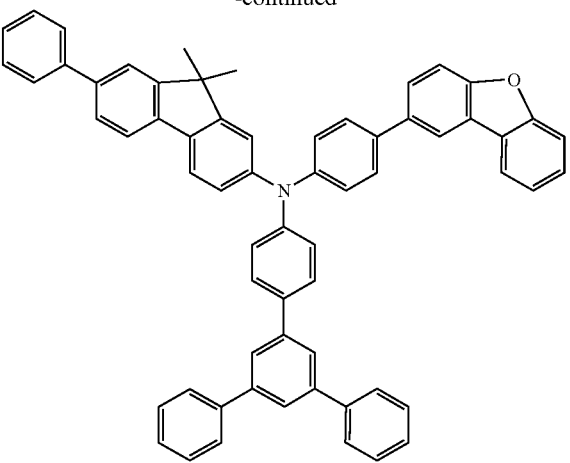
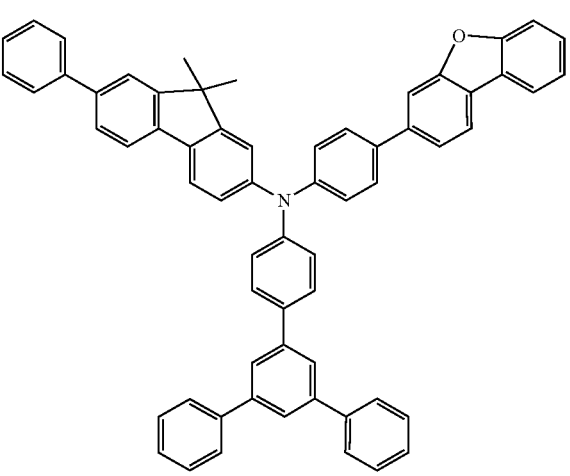
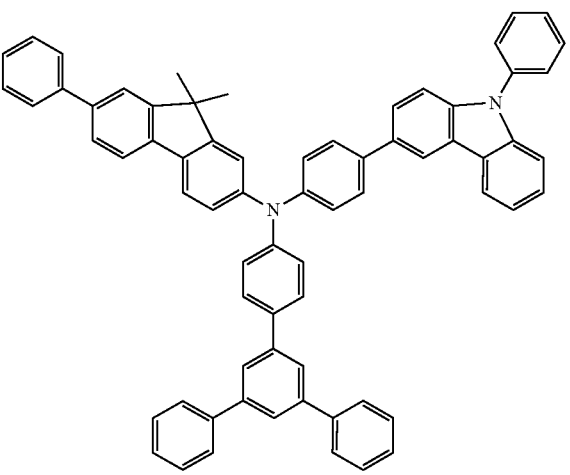

63
-continued
64
-continued
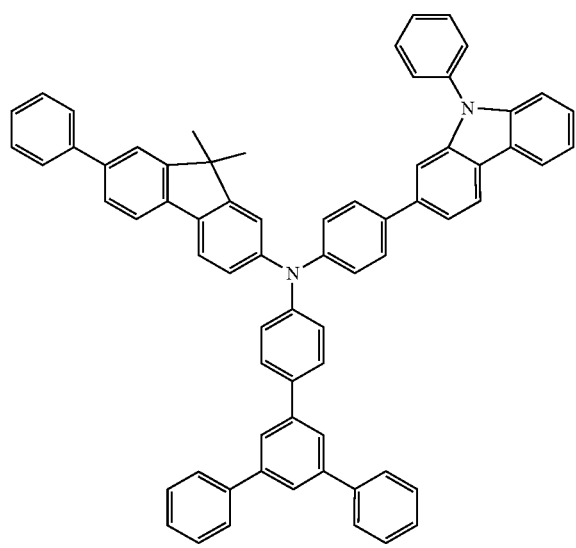
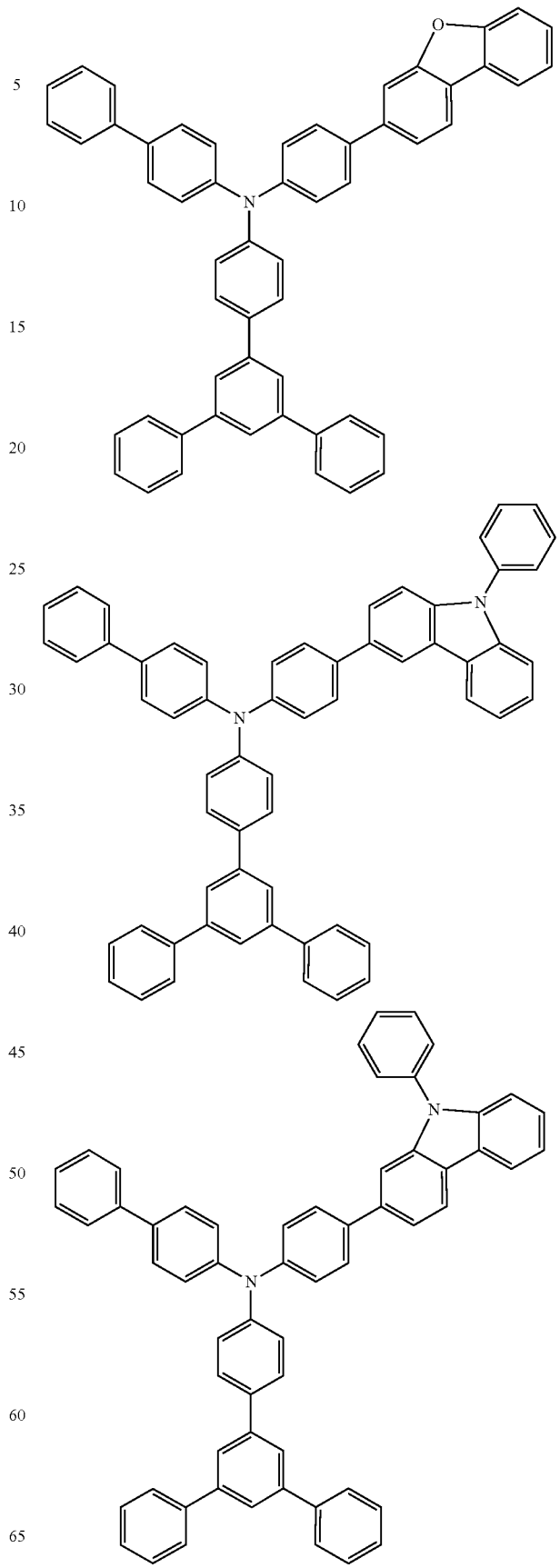

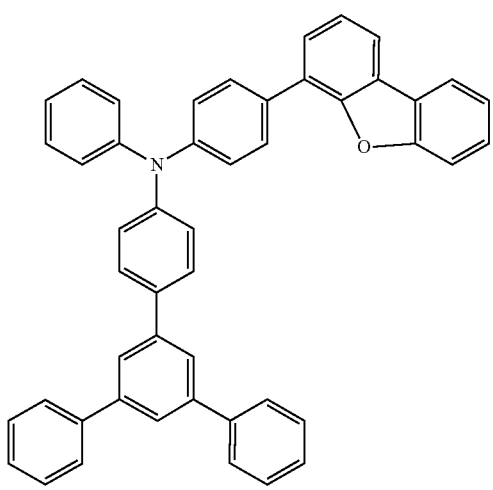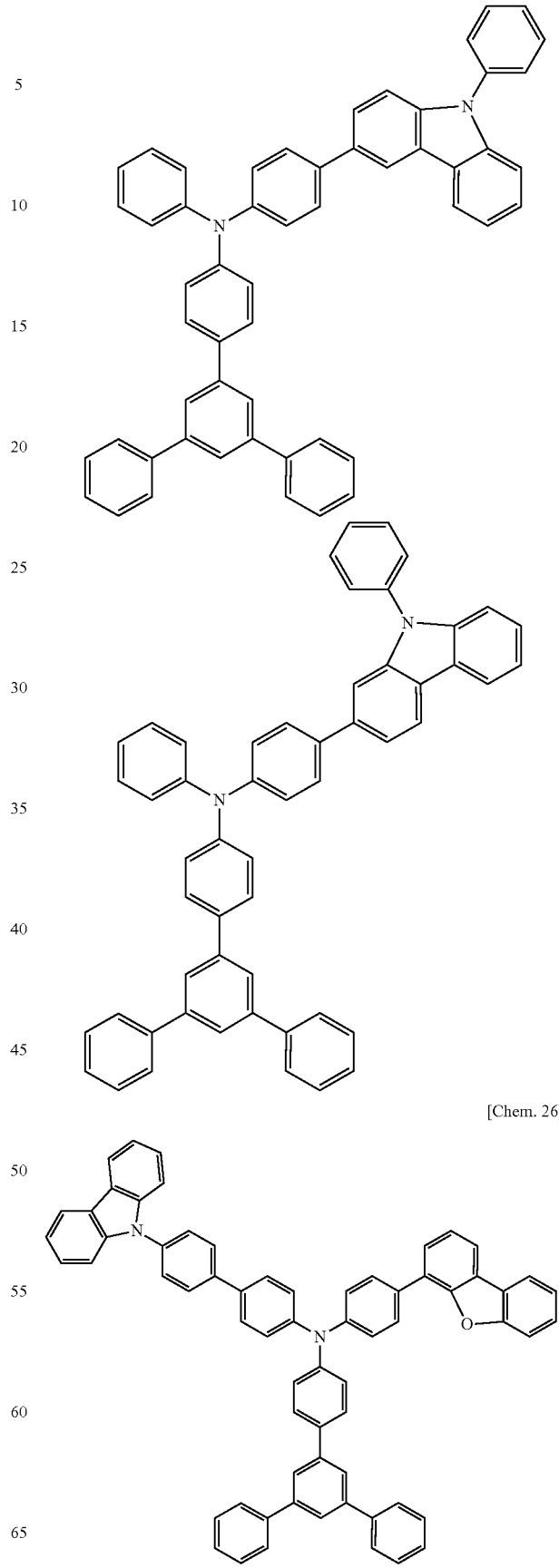
[Chem. 26]

67
-continued
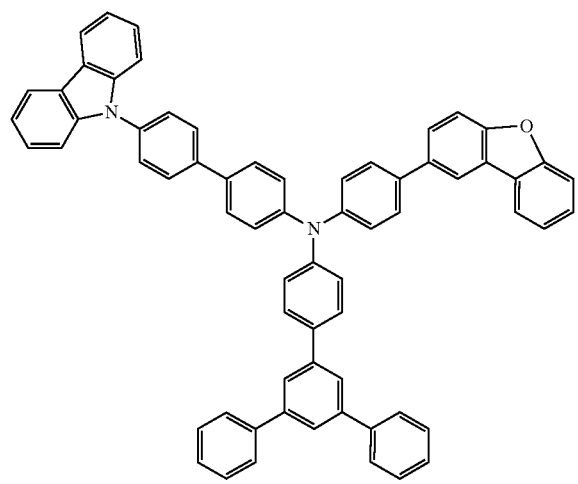
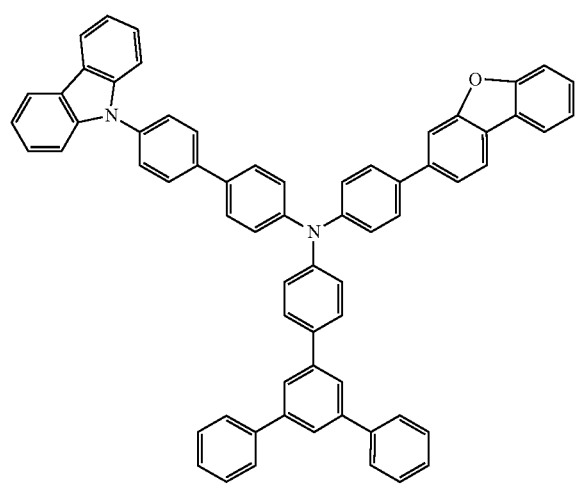
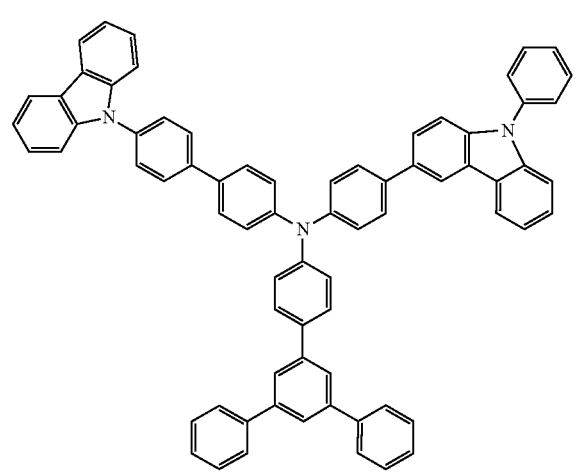
68
-continued
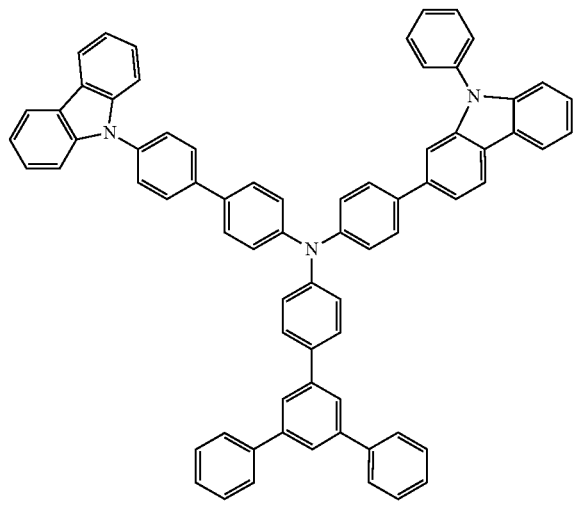
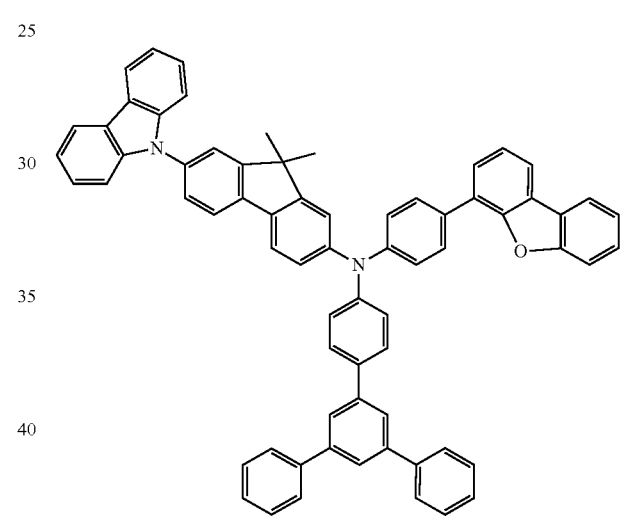
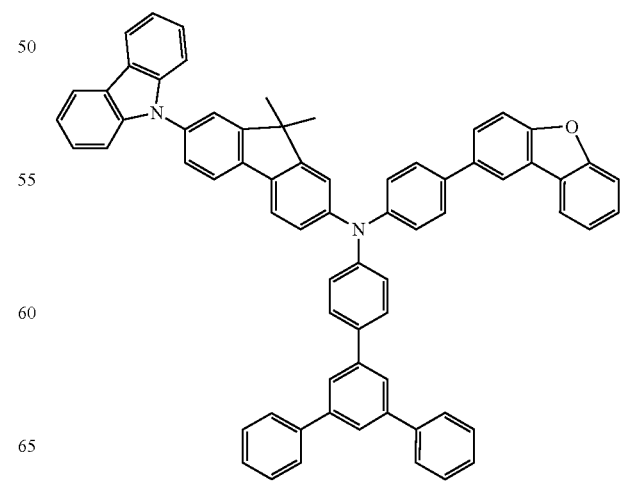

69
-continued
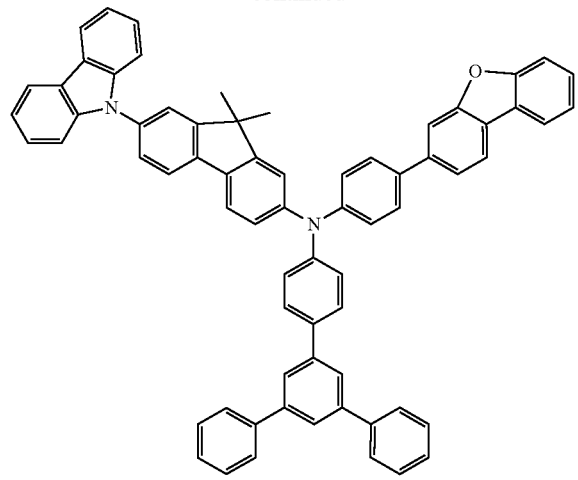
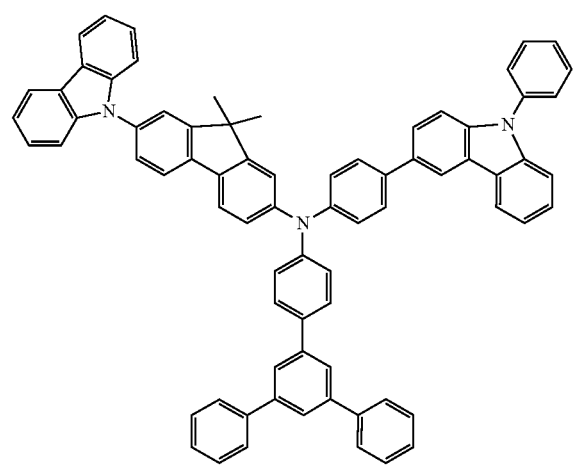
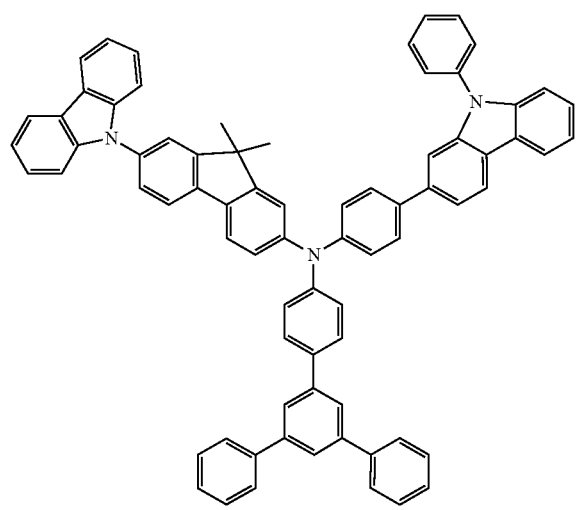
70
-continued
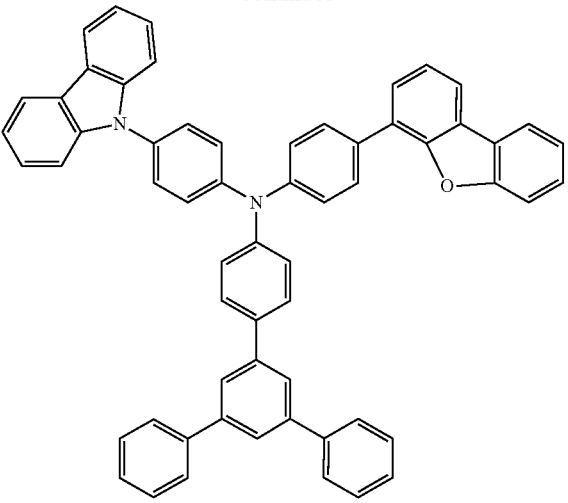
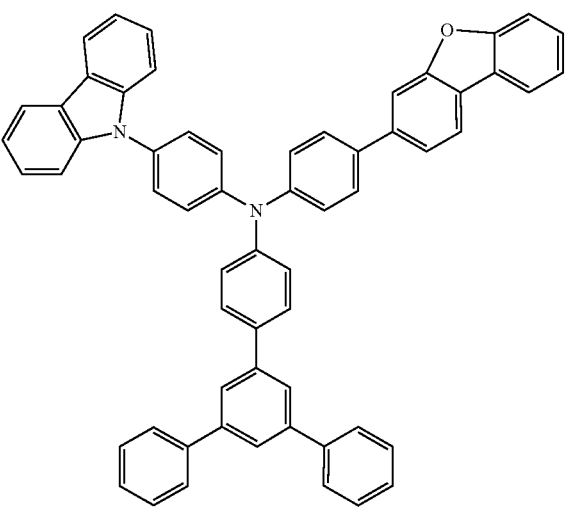

71
-continued
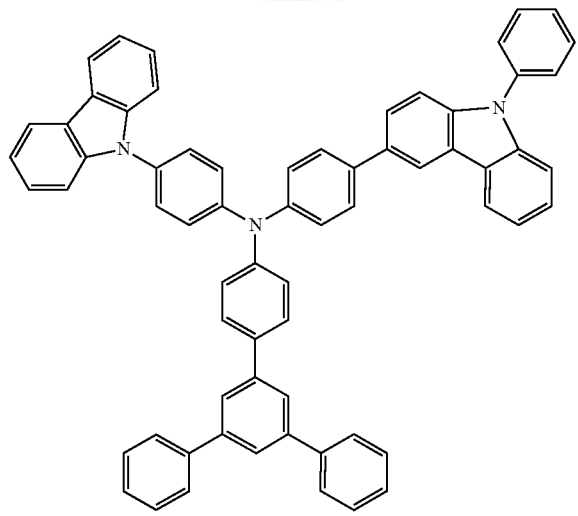
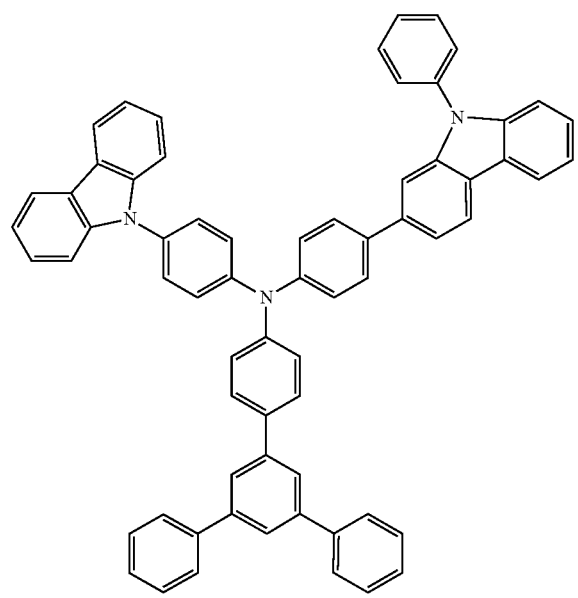
[Chem. 27]
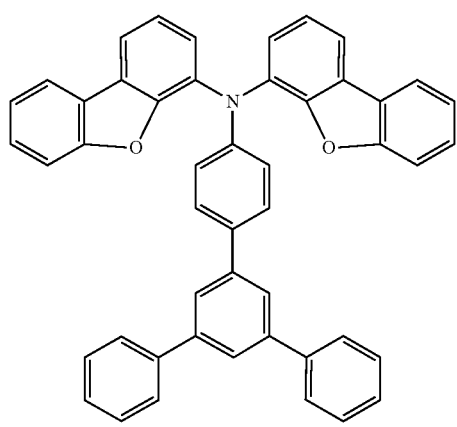
72
-continued
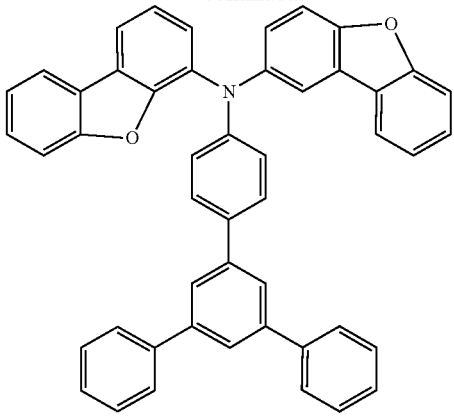
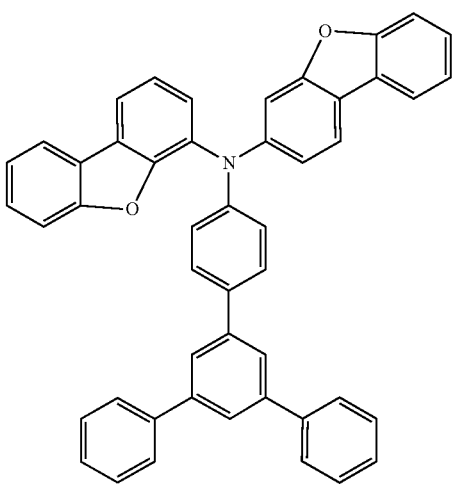
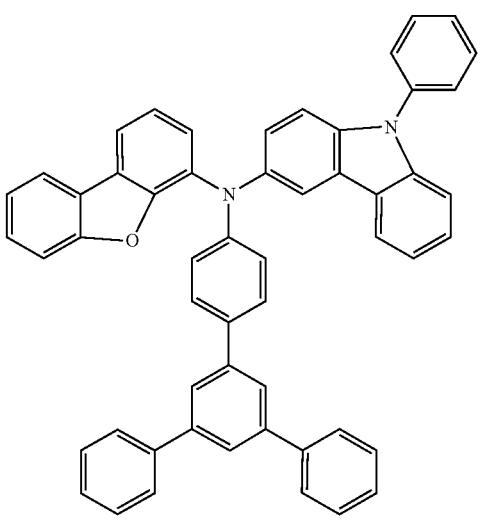

73
-continued
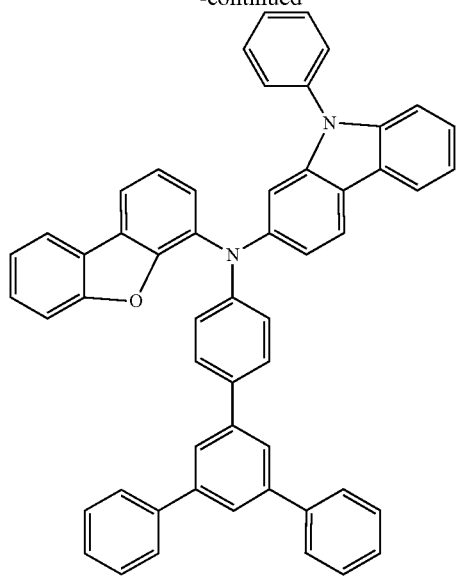
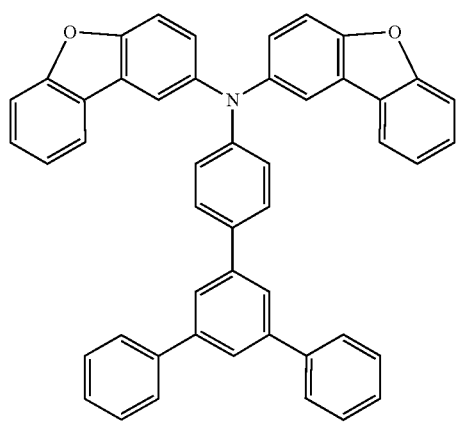
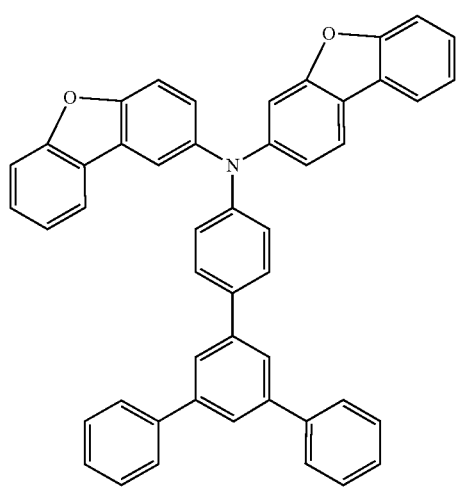
74
-continued
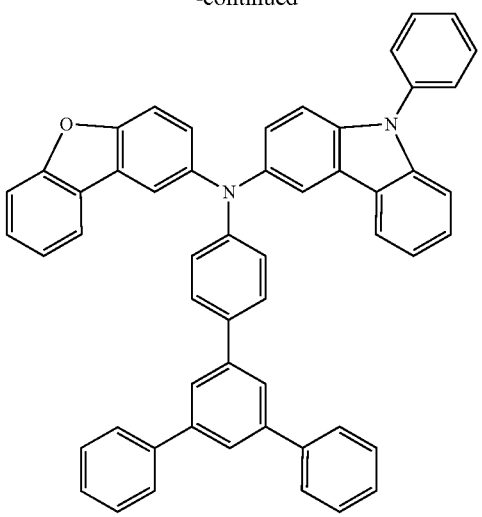
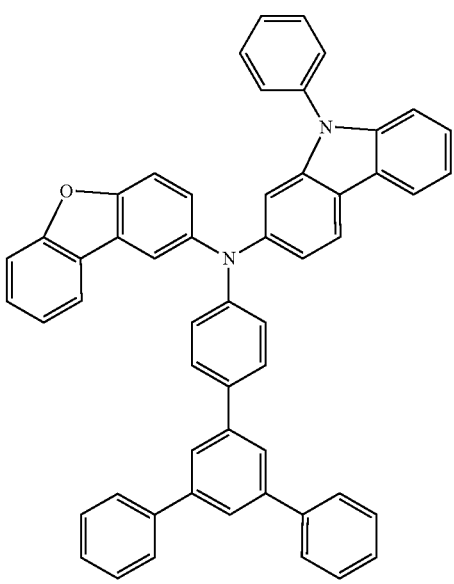
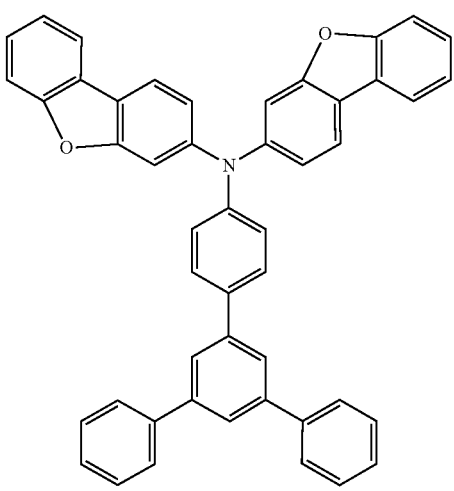

75
-continued
76
-continued
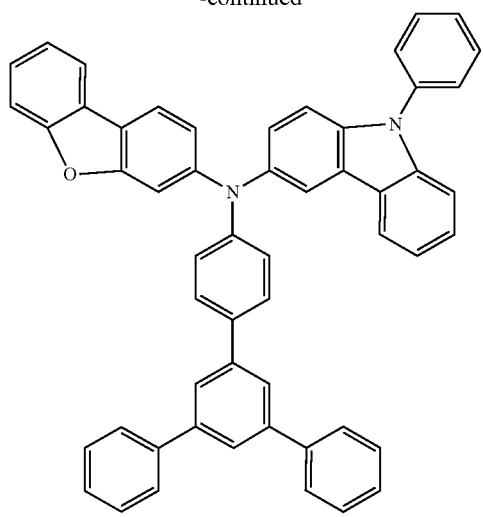
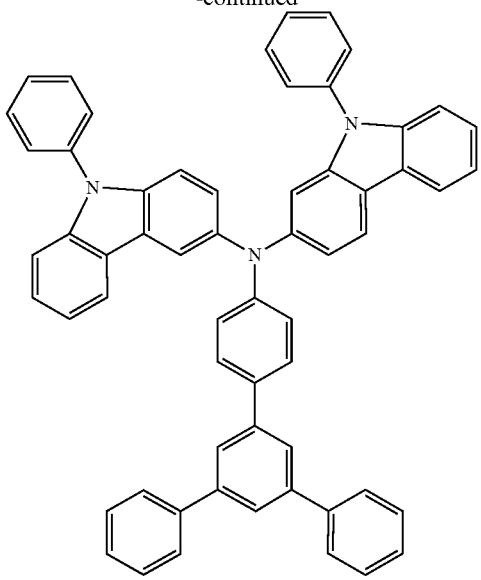
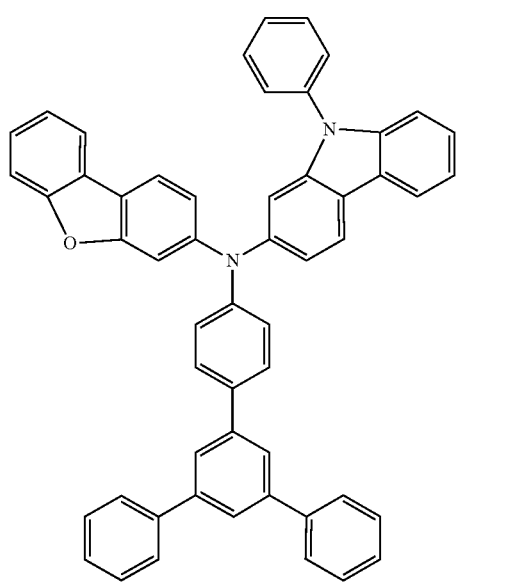
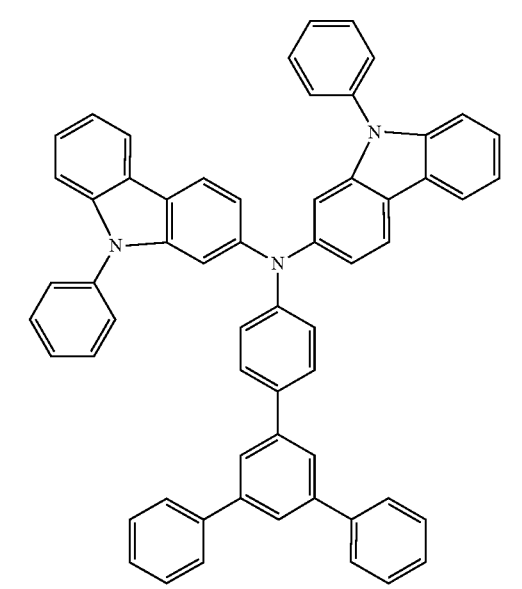
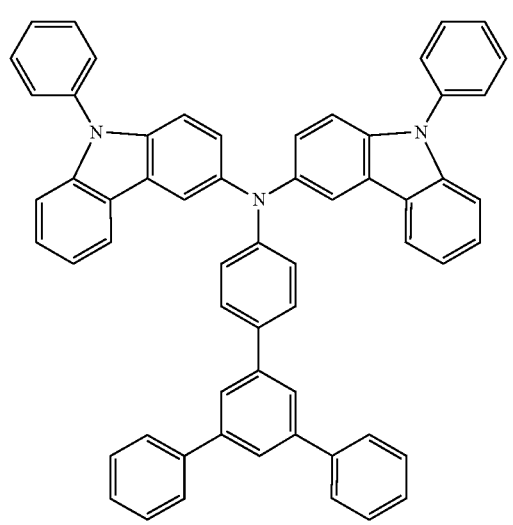
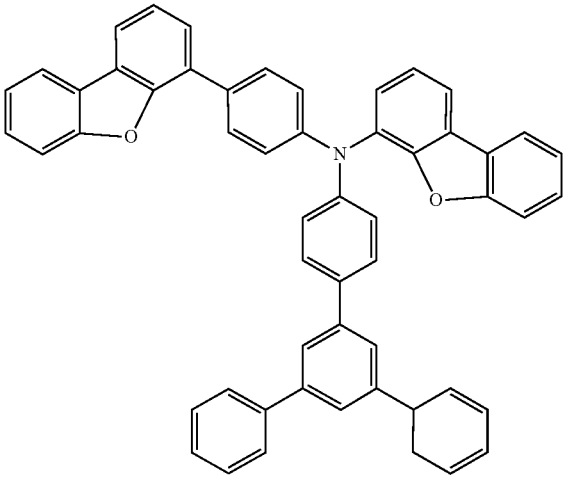

77
-continued
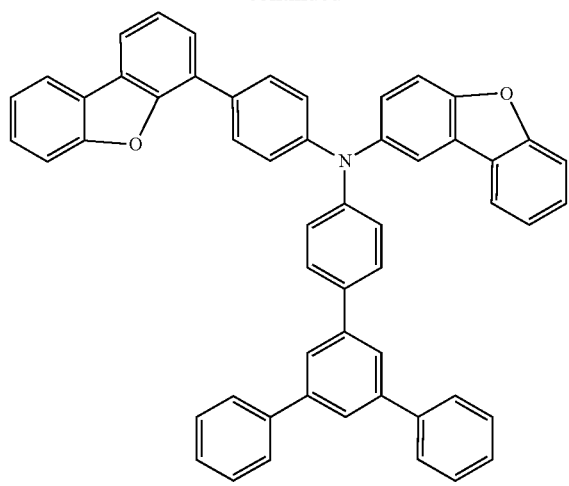
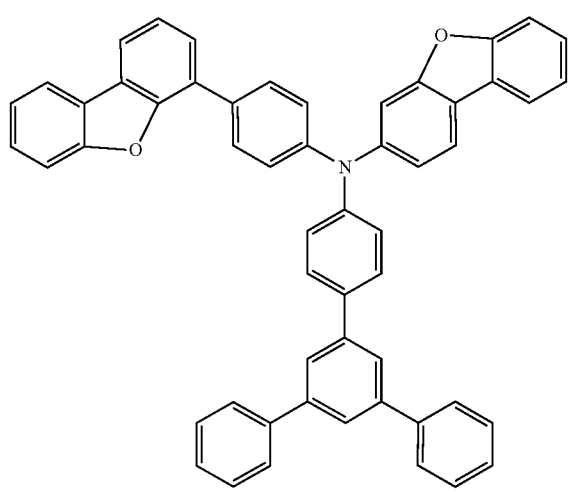
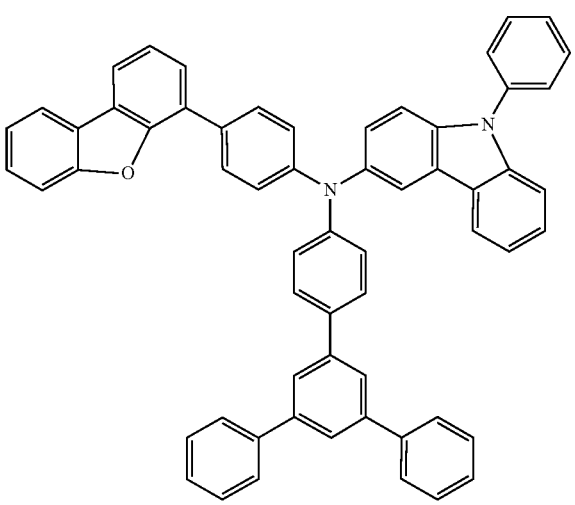
78
-continued
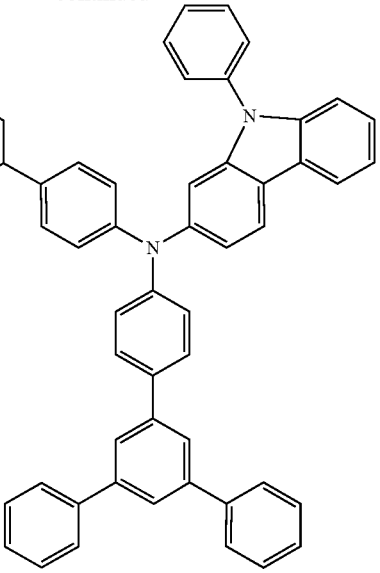
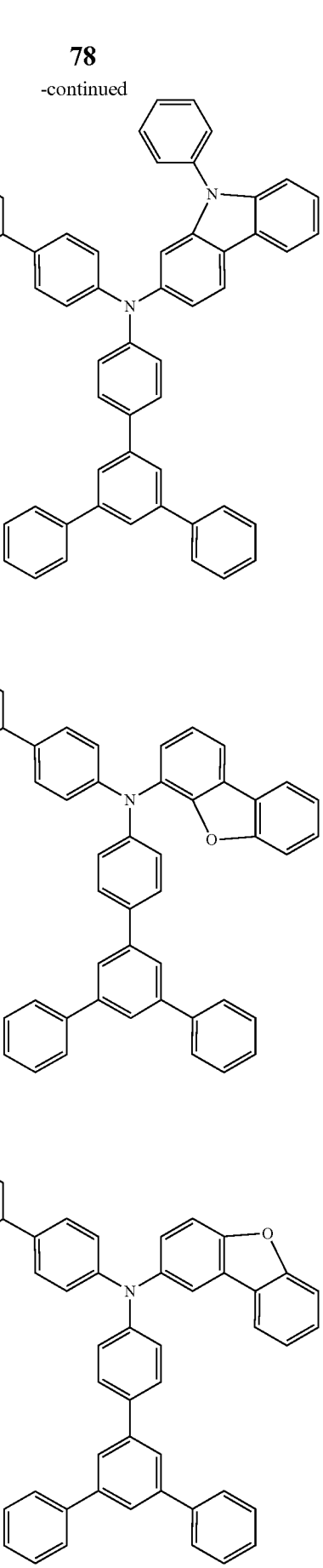

79
-continued
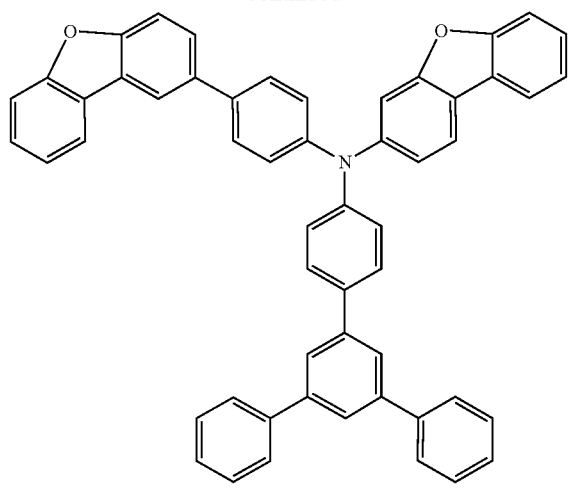
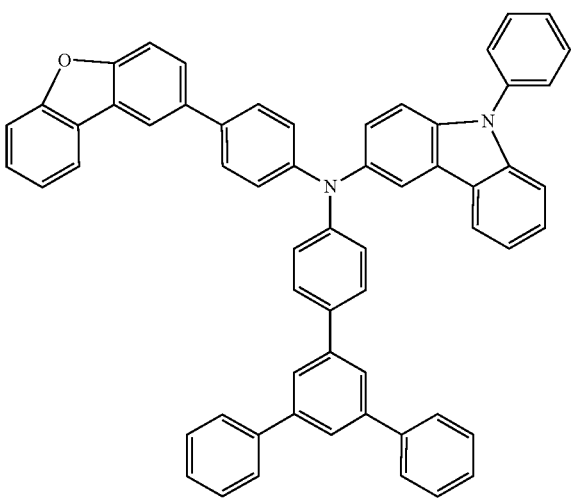
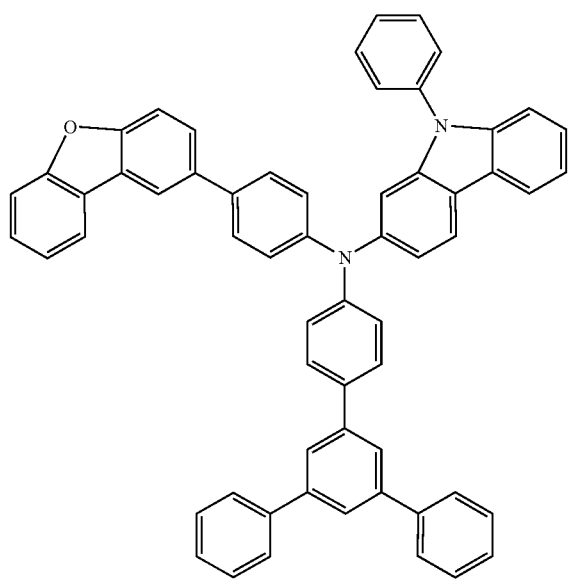
80
-continued
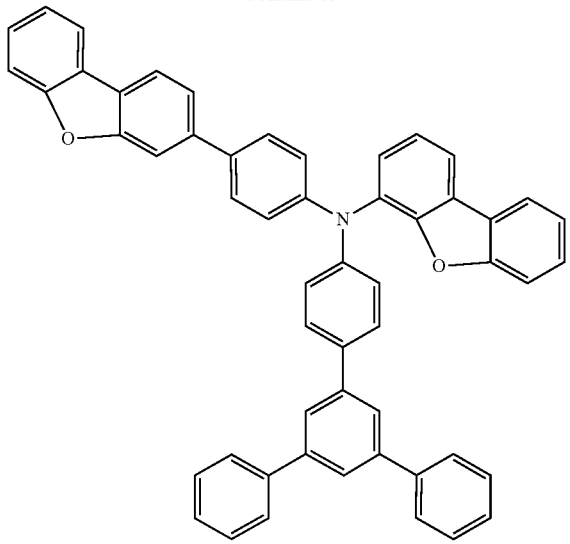

81
-continued
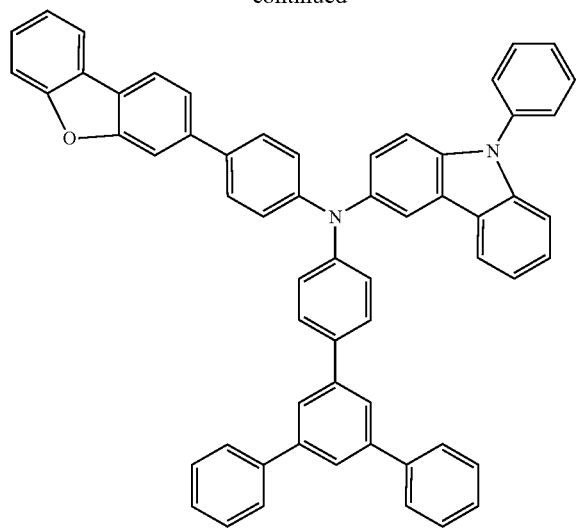
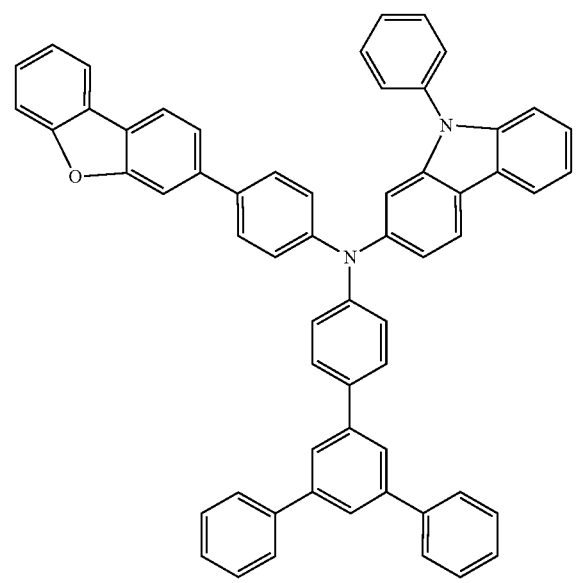
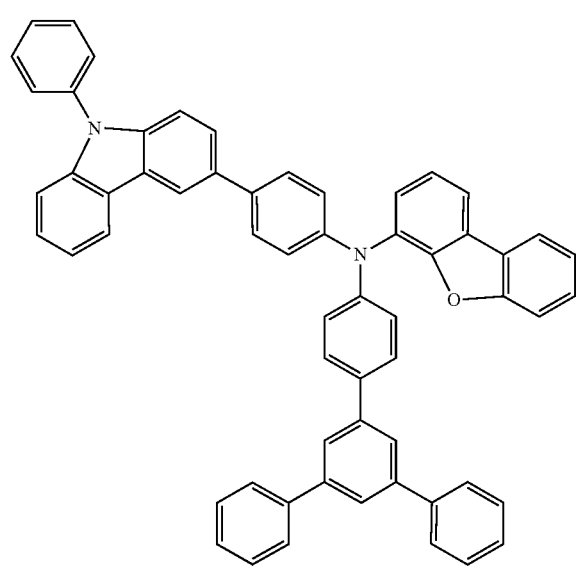
82
-continued
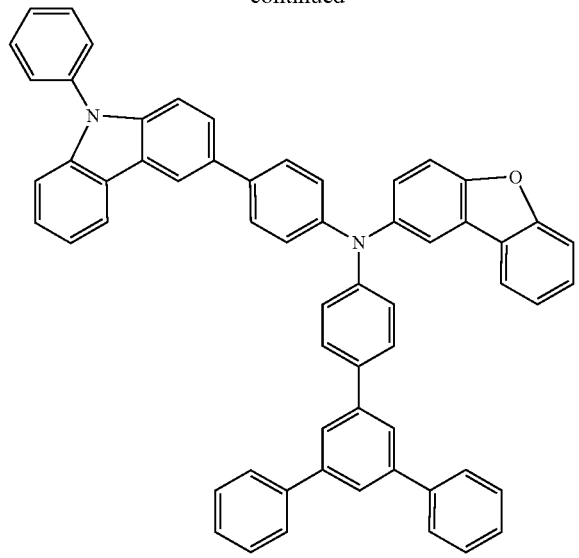
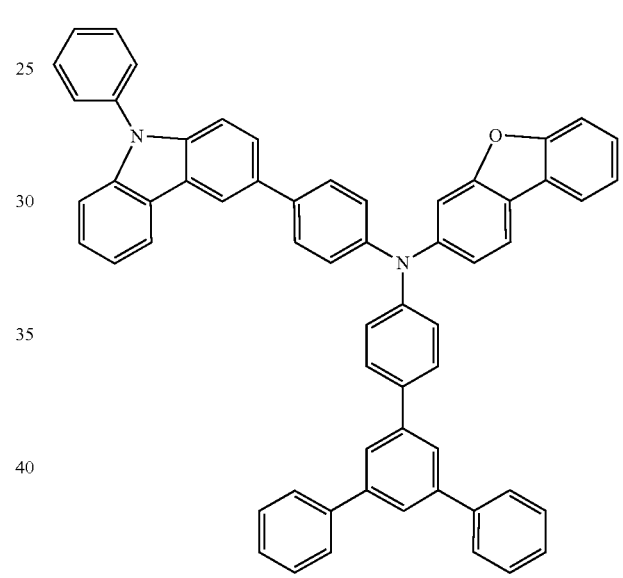
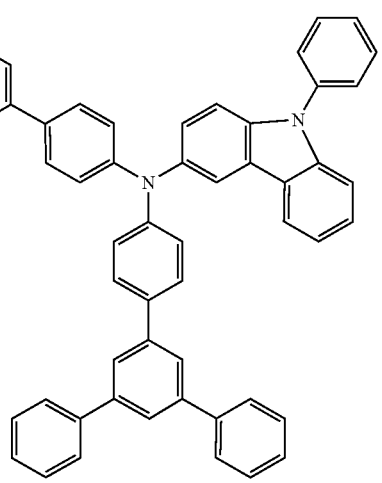

83
-continued
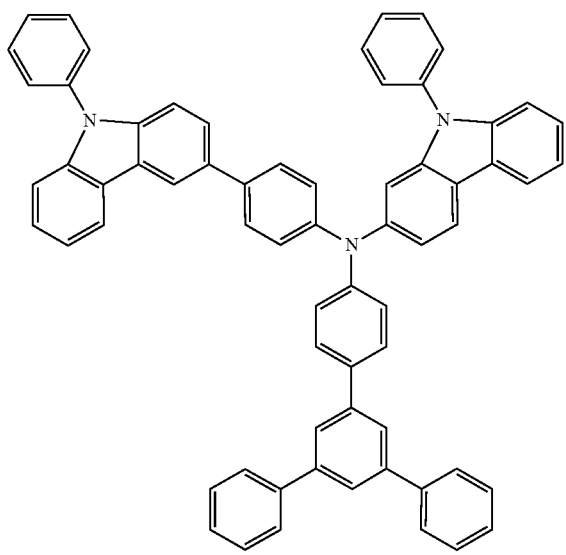
84
-continued
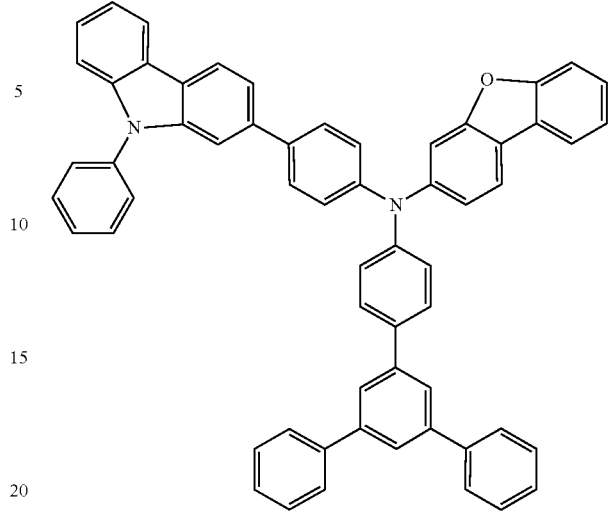
[Chem. 28]
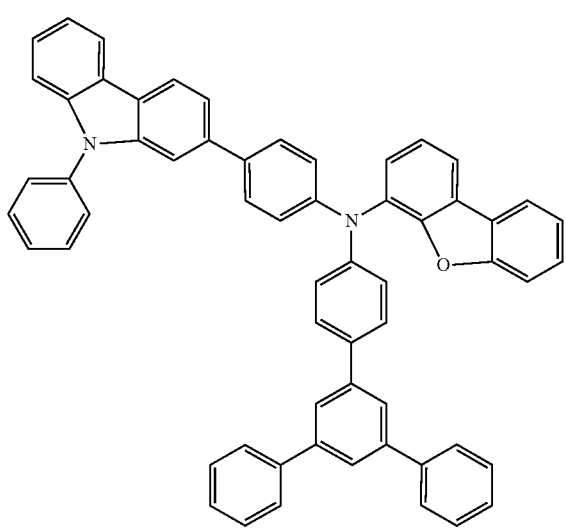
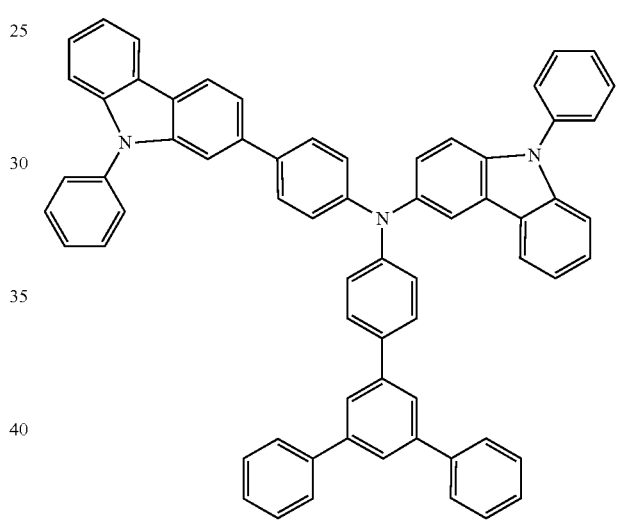
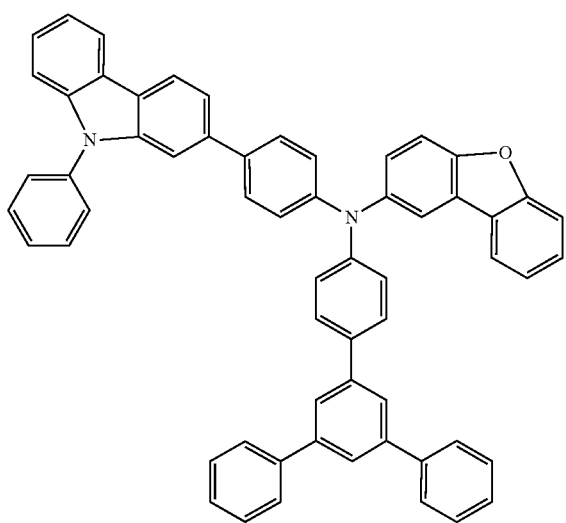
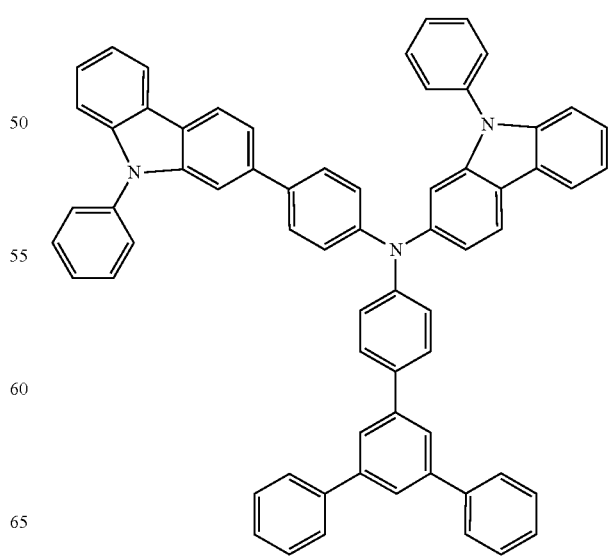

85
-continued
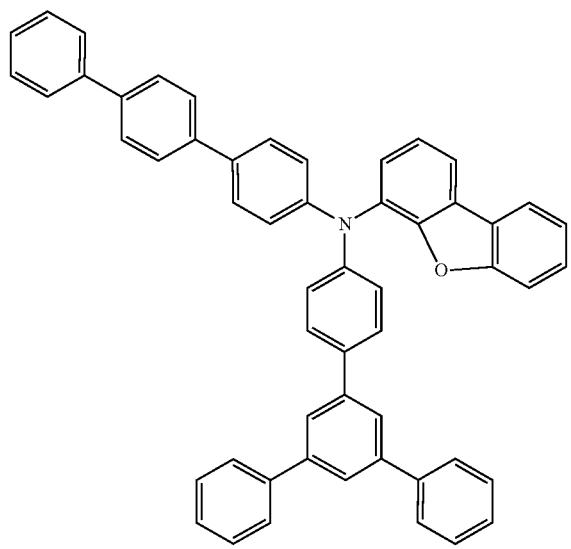
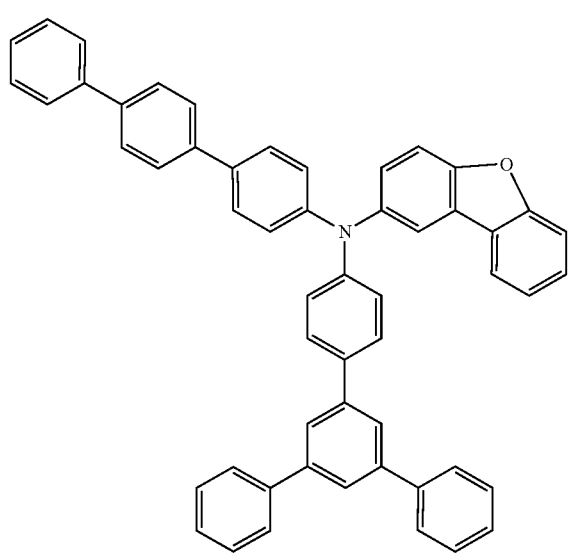
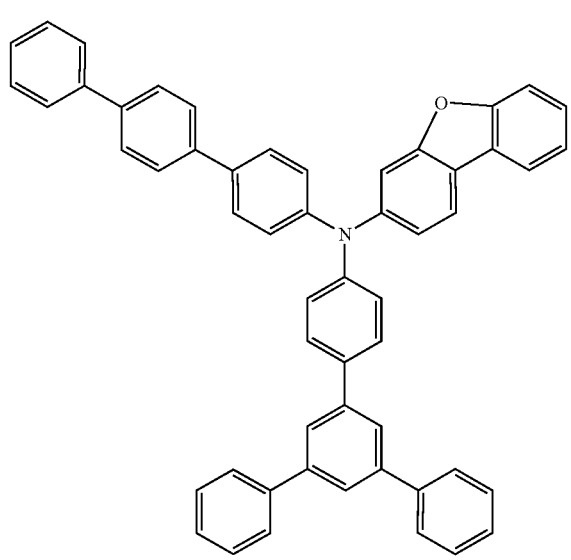
86
-continued
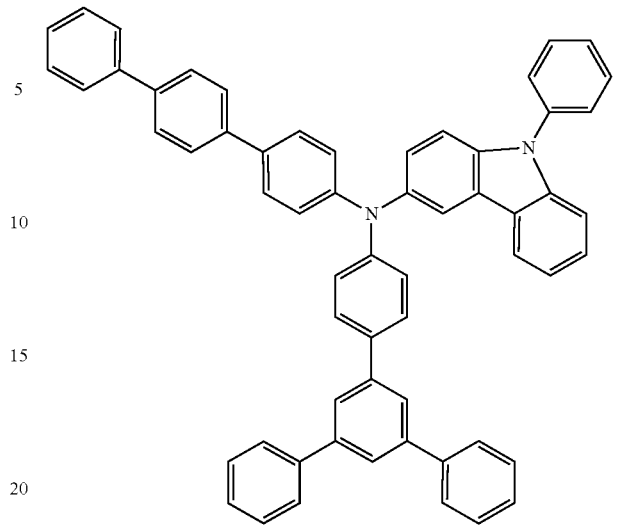
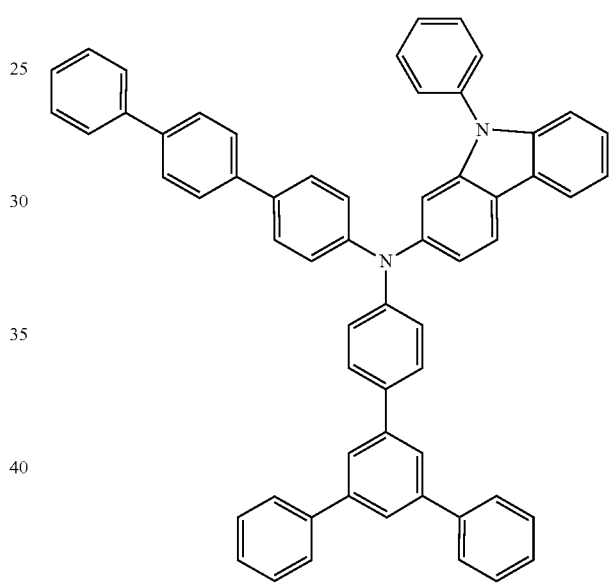
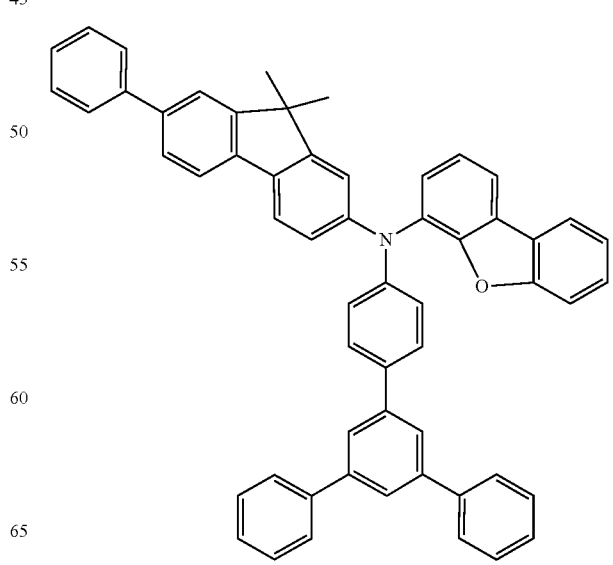

87
-continued
88
-continued
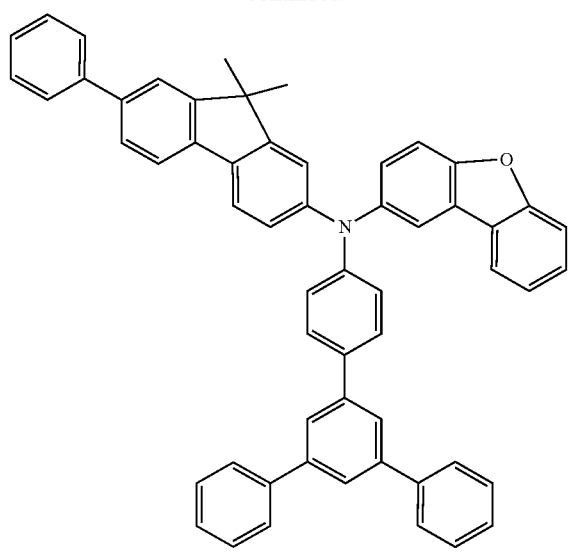
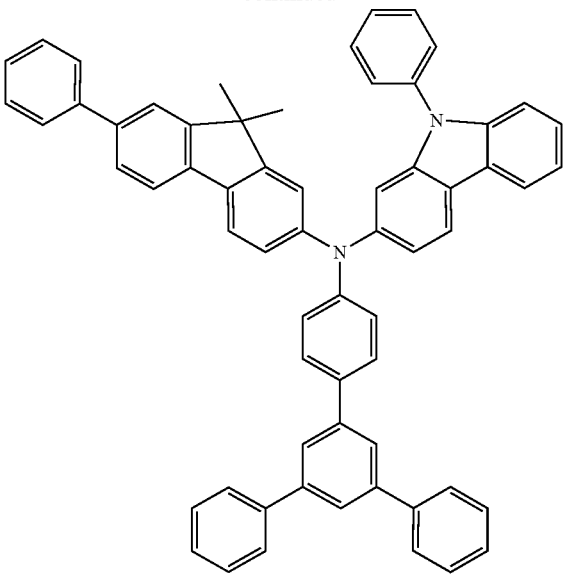
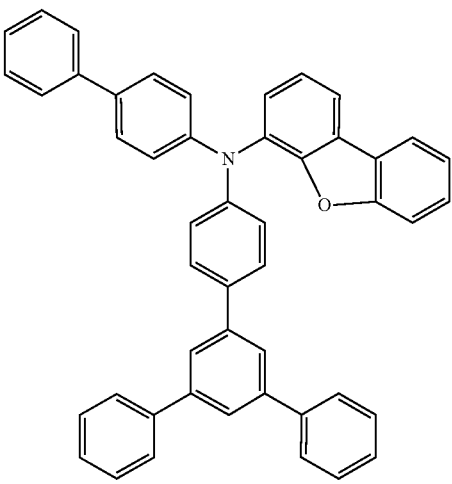
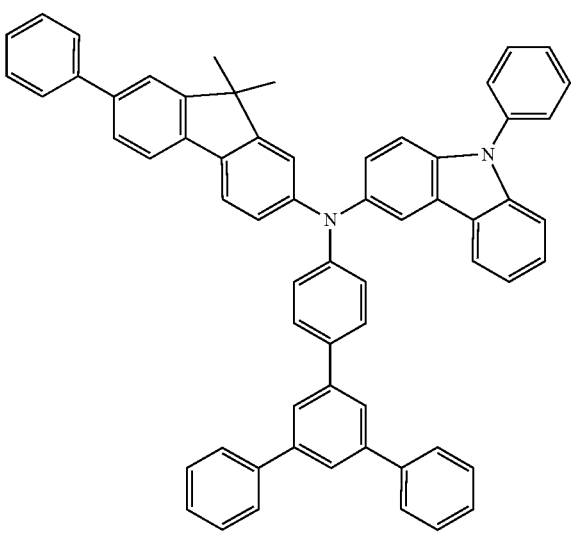
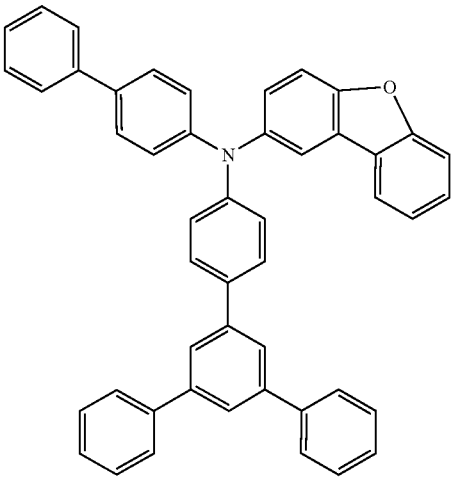

89
-continued
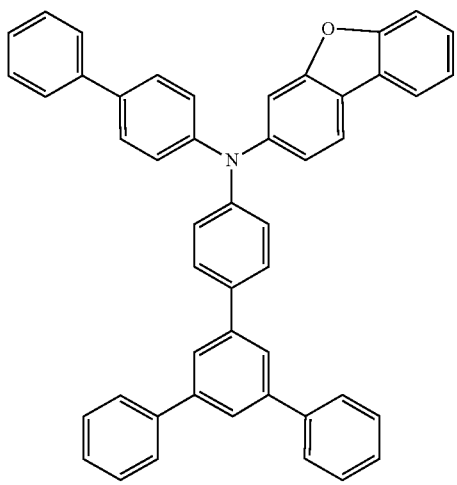
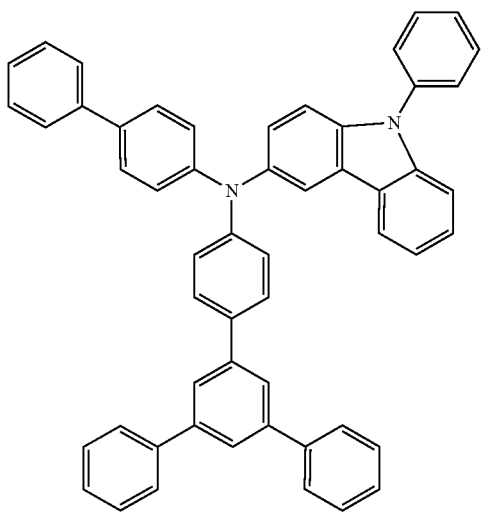
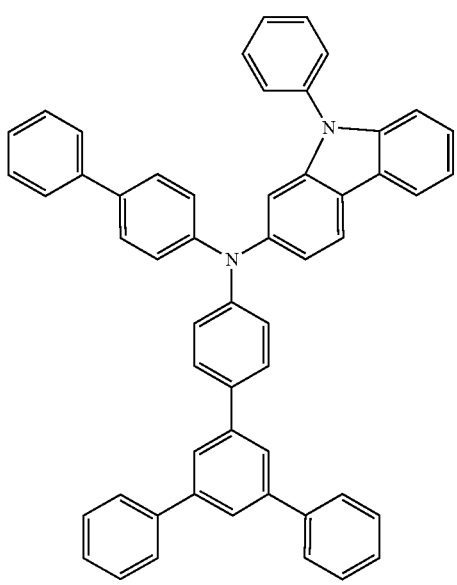
90
-continued
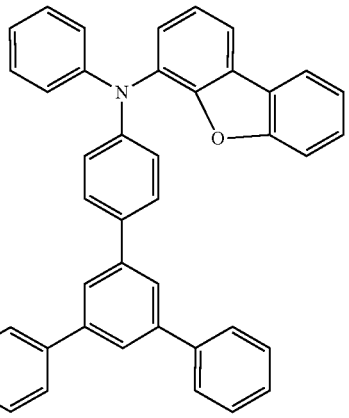
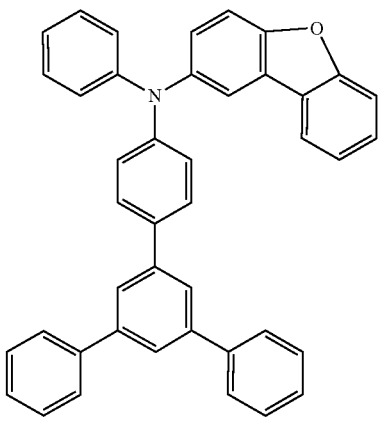
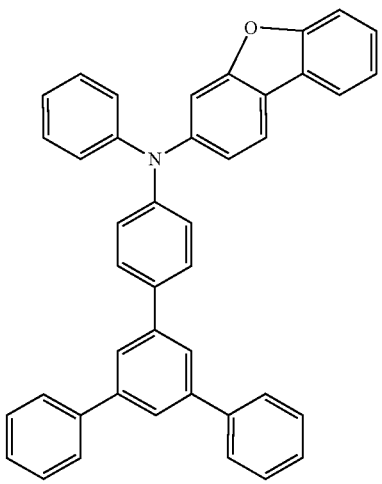

91
-continued
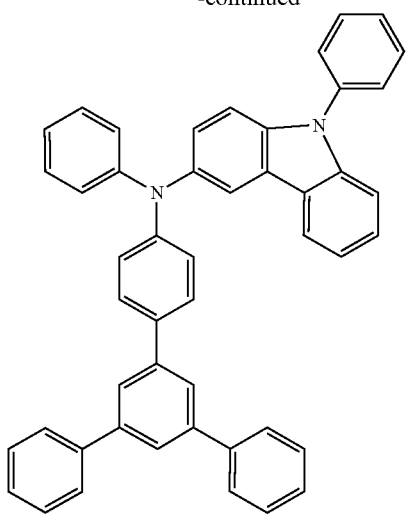
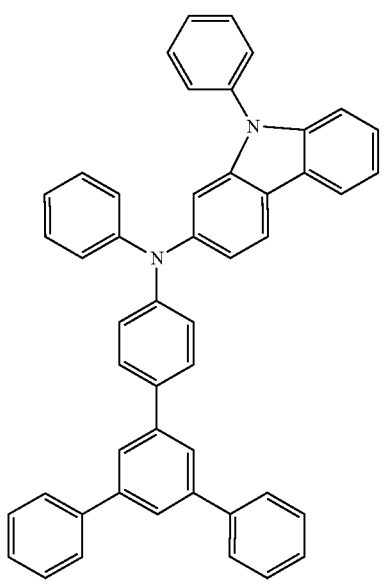
[Chem. 29]
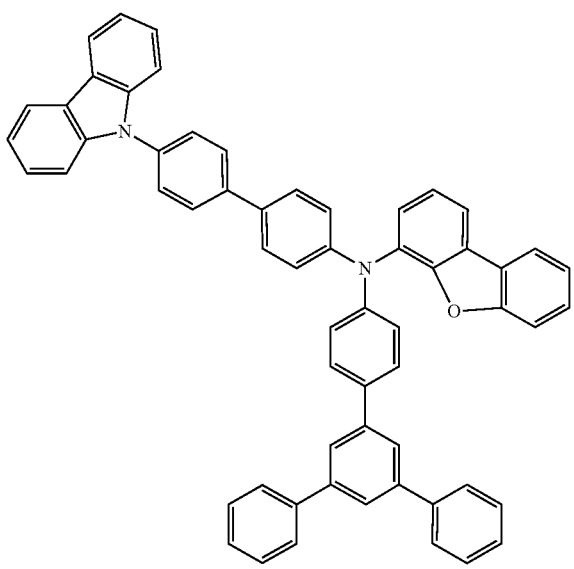
92
-continued
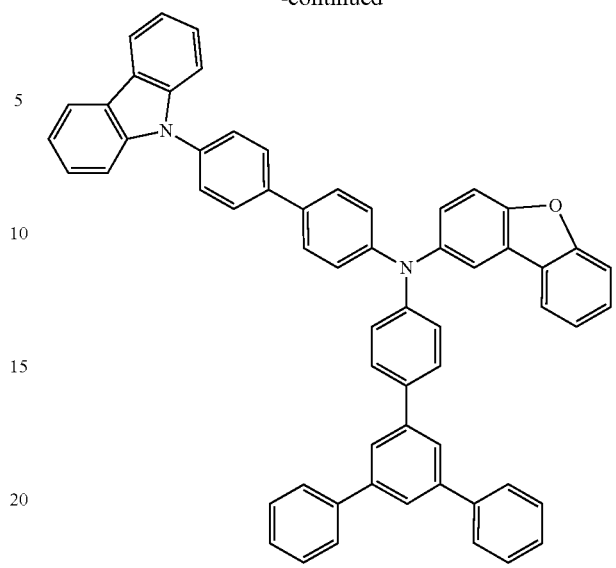
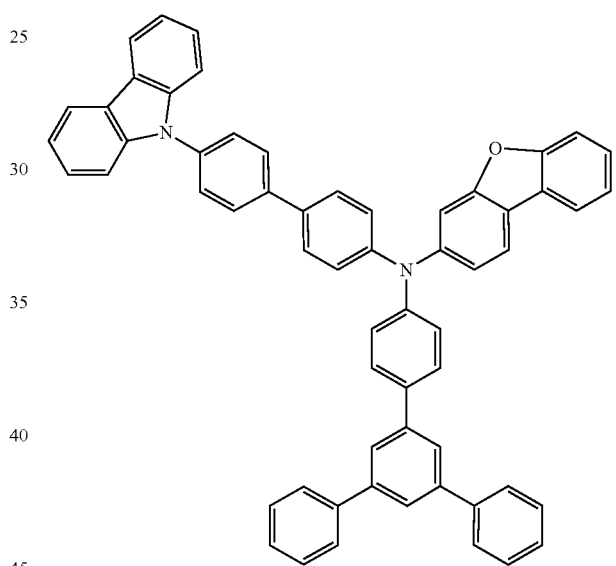
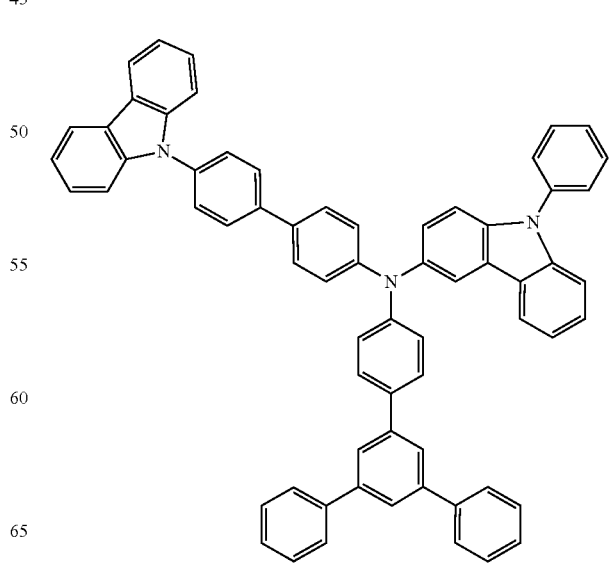

93
-continued
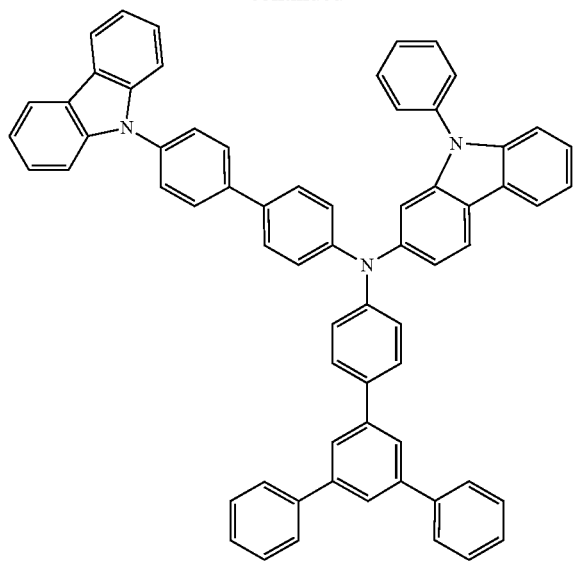
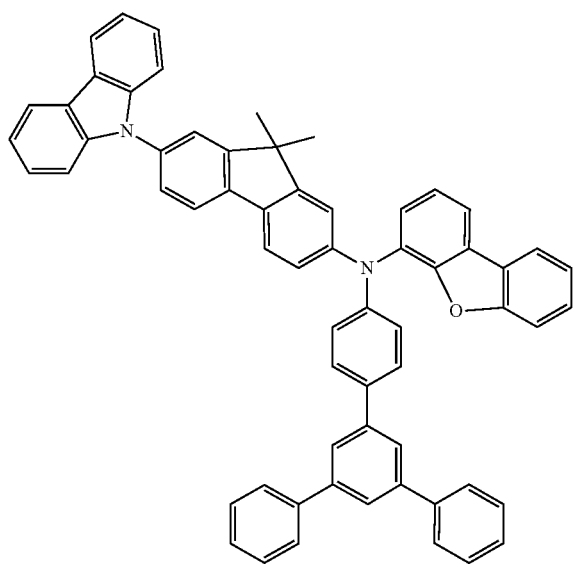
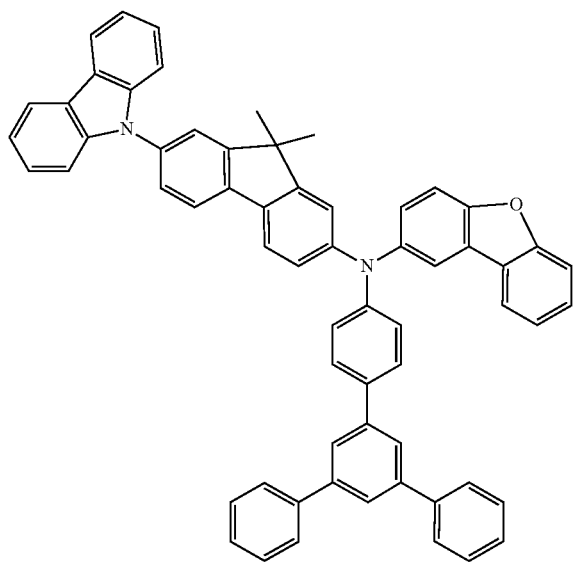
94
-continued
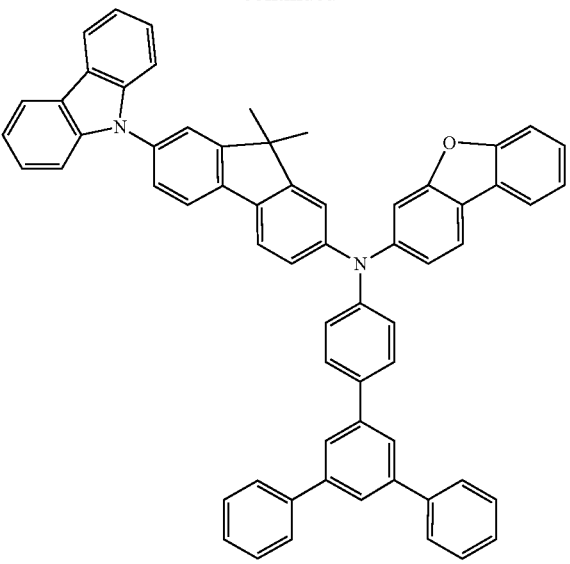
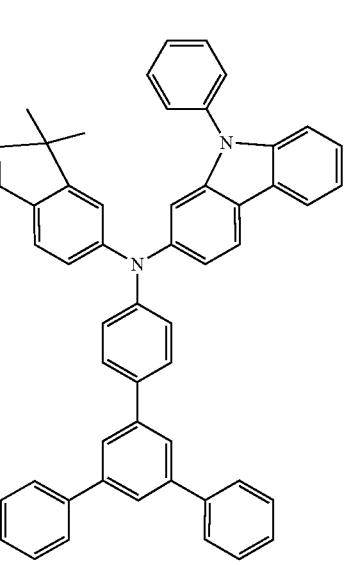

95
-continued
96
-continued
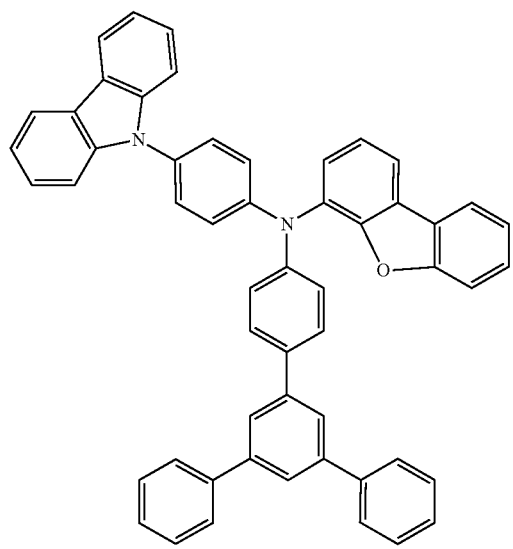
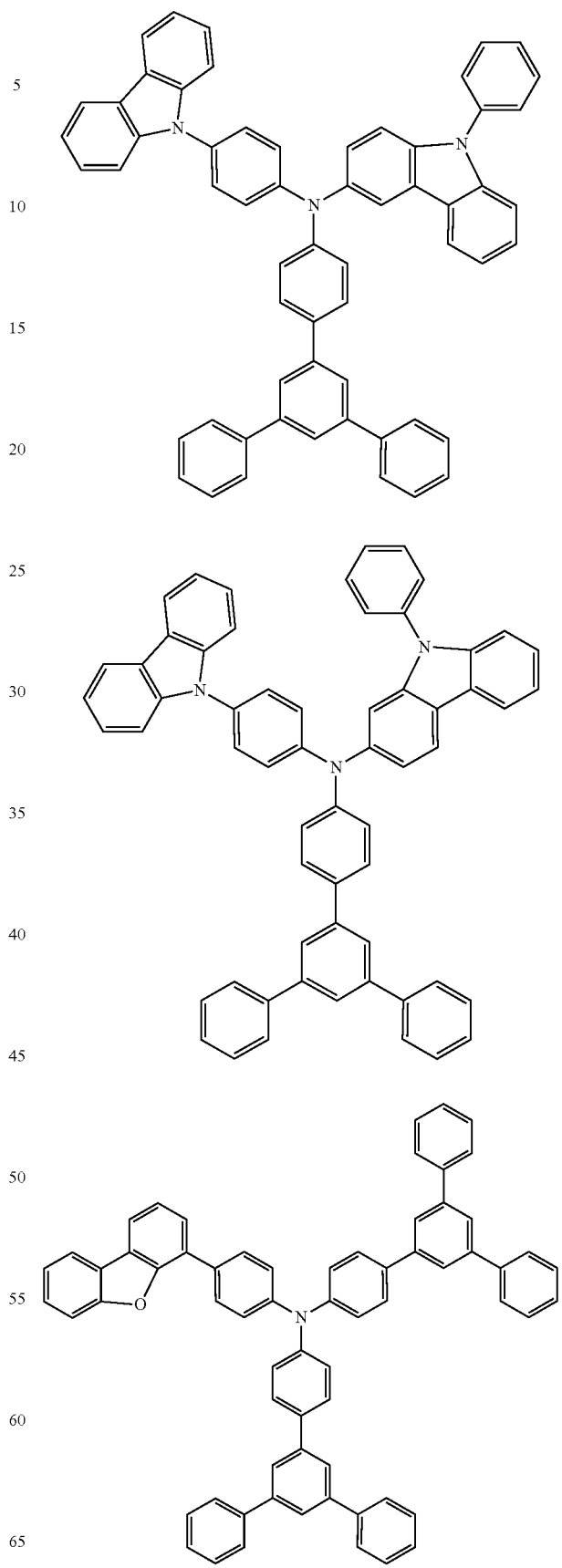

97
-continued
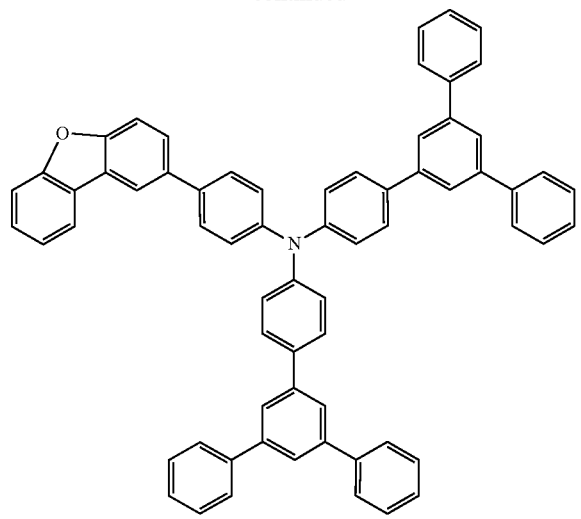
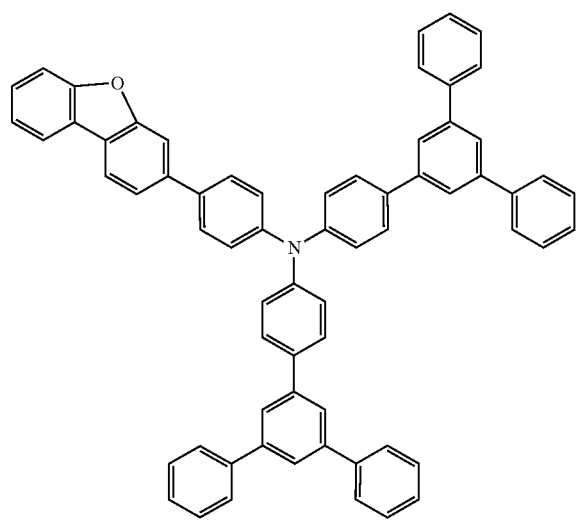
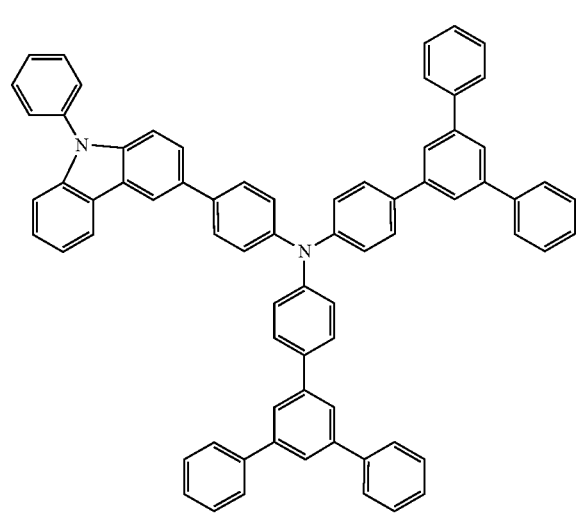
98
-continued
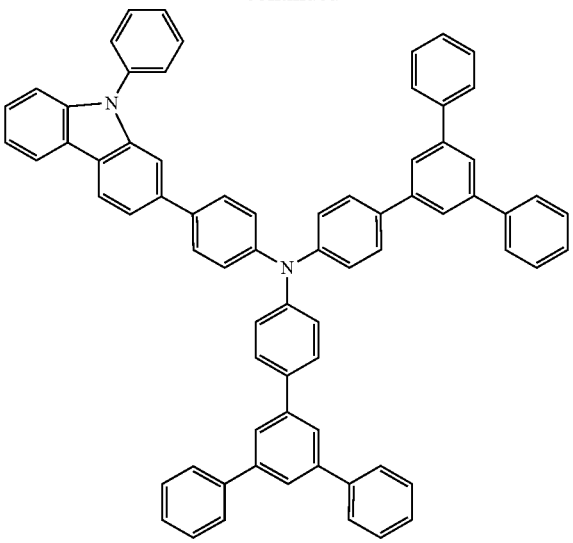
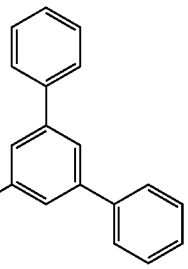
[Chem. 30]
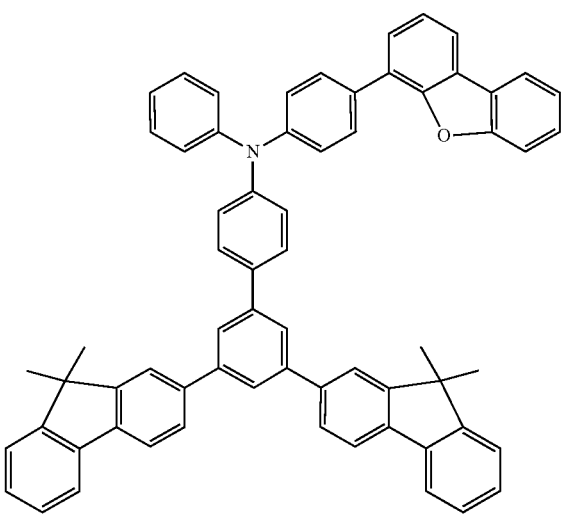

99
-continued
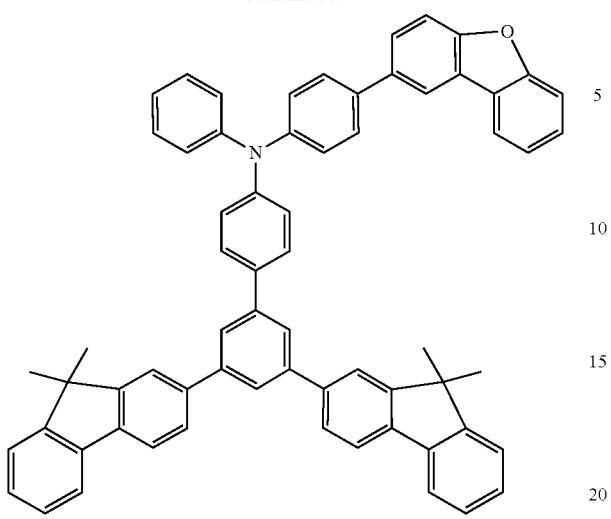
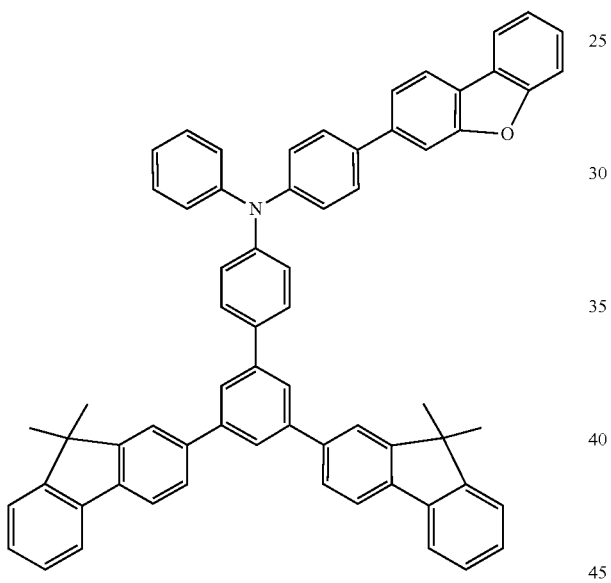
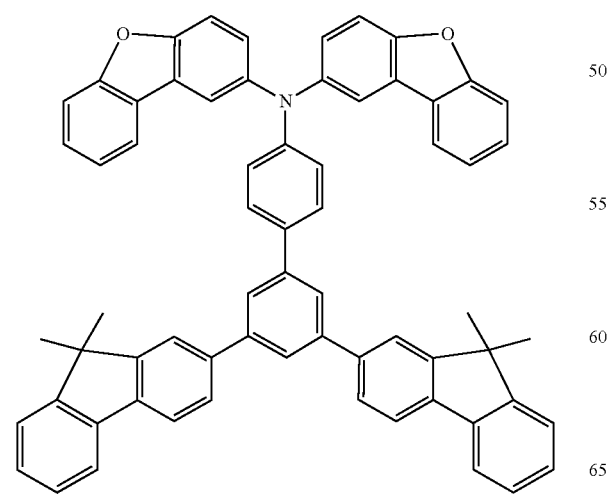
100
-continued
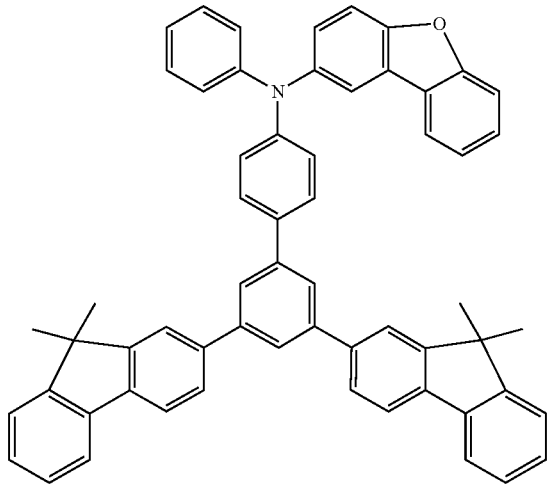
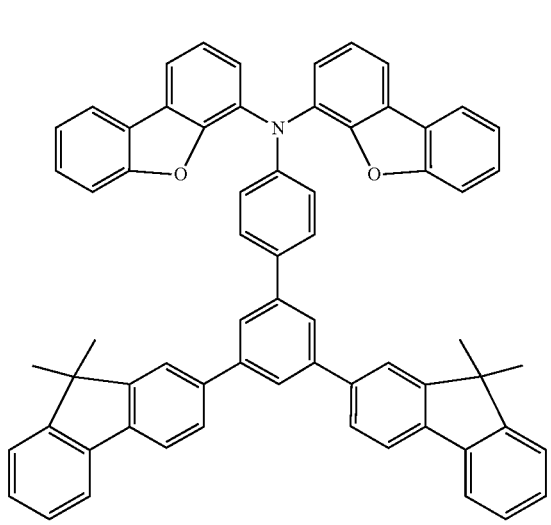
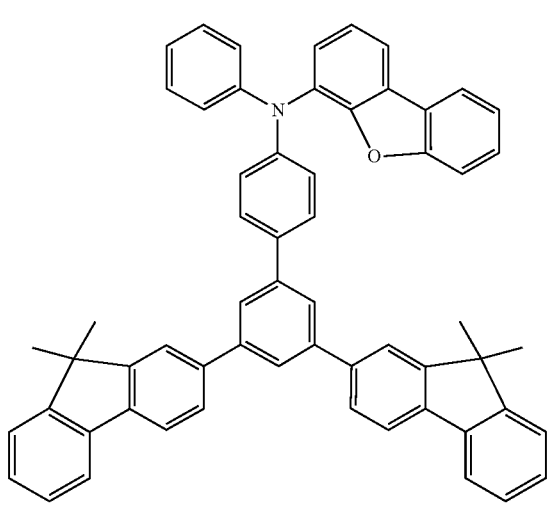

101
-continued
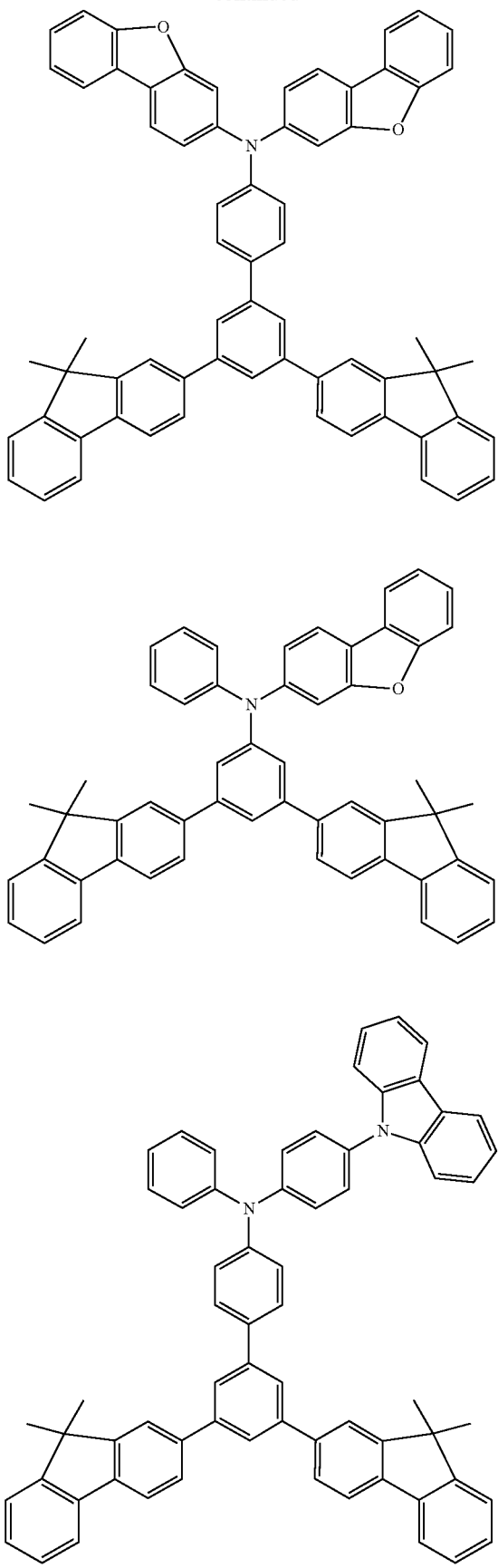
102
-continued
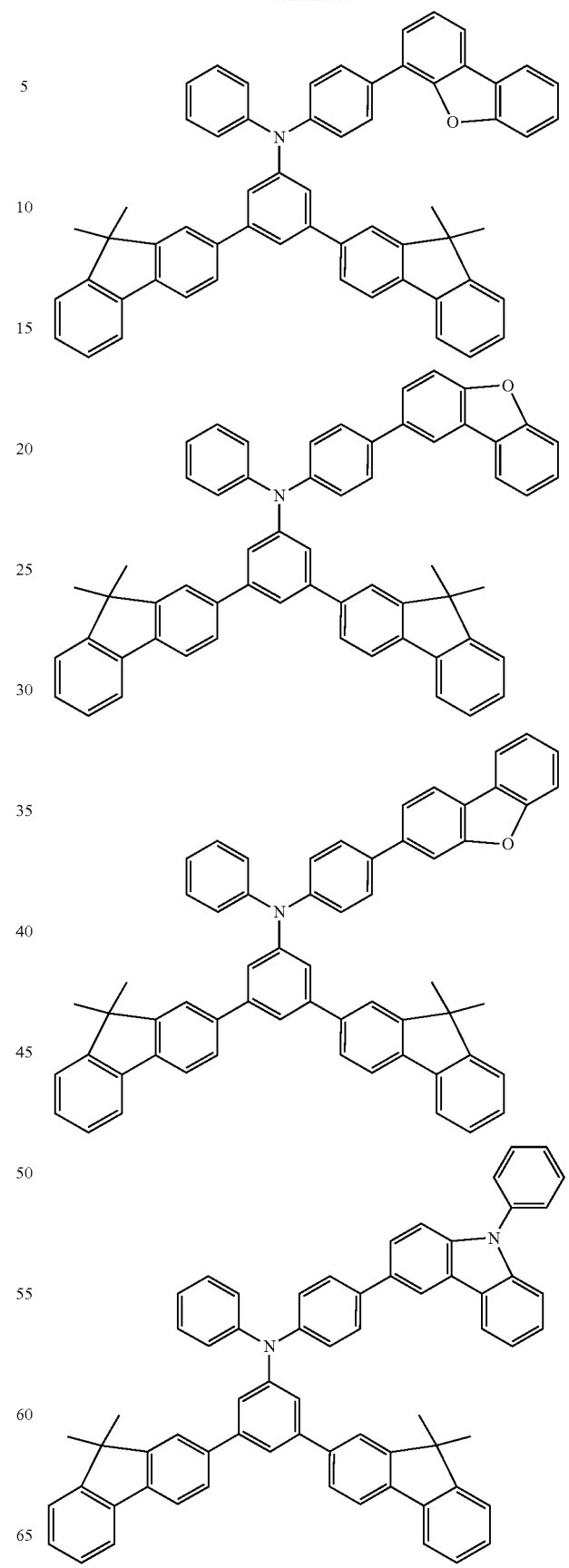

103
-continued
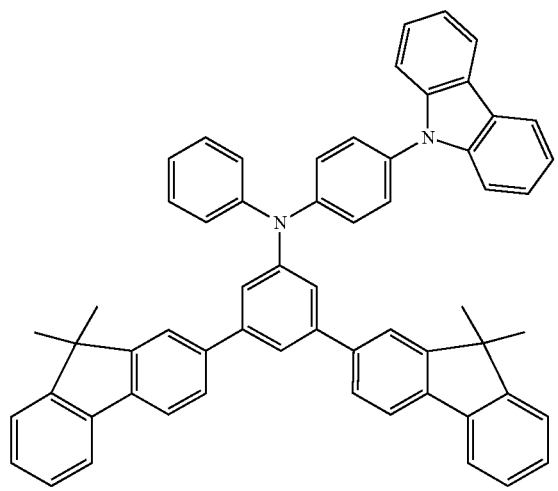
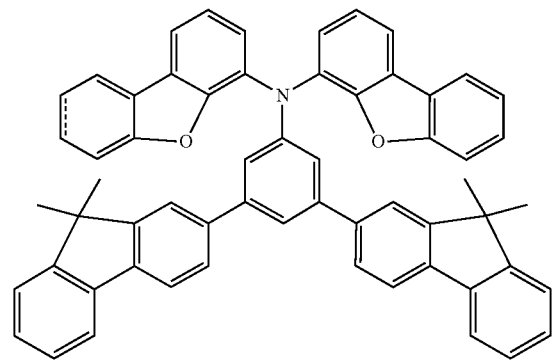
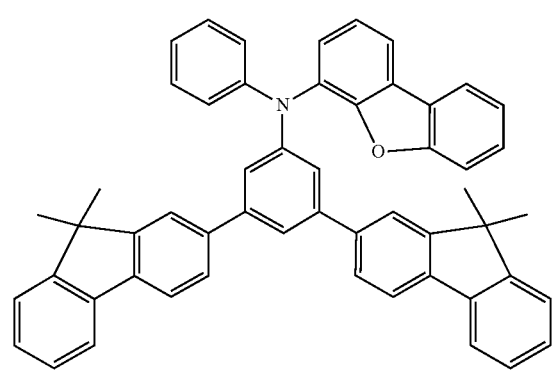
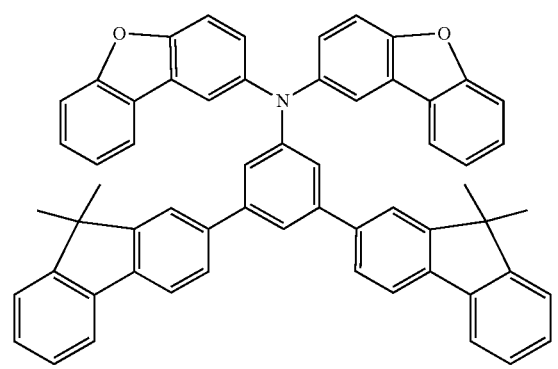
104
-continued
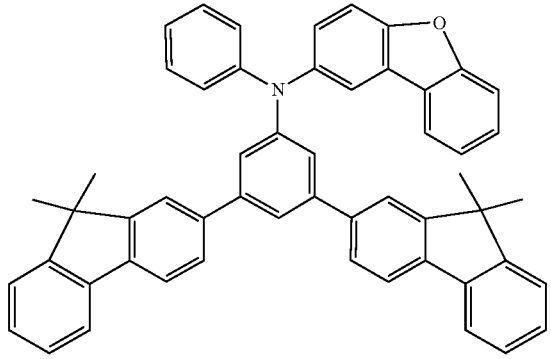
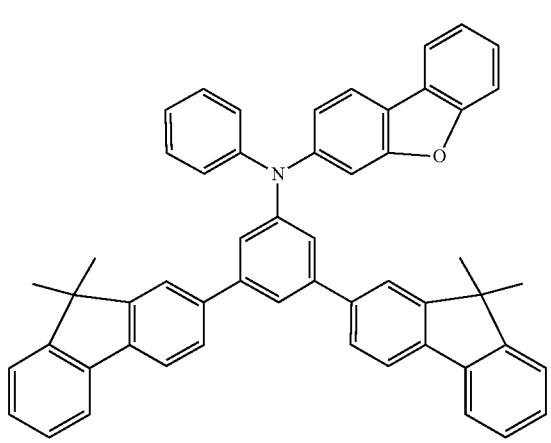
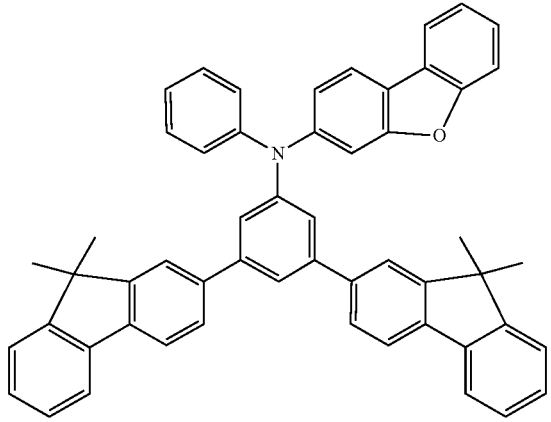
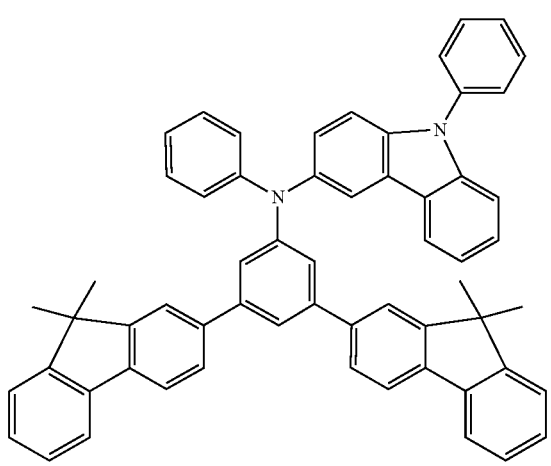

105
-continued
[Chem. 31]
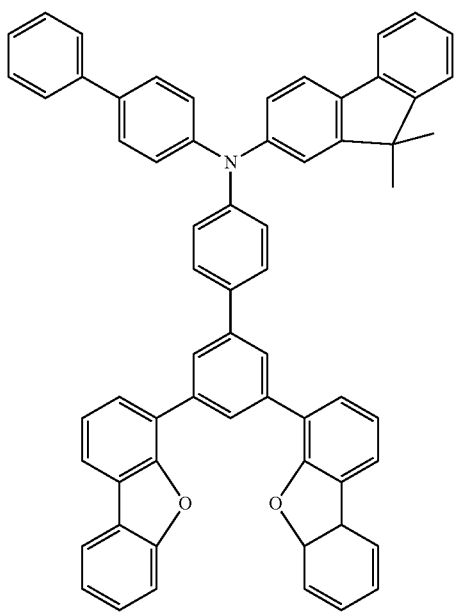
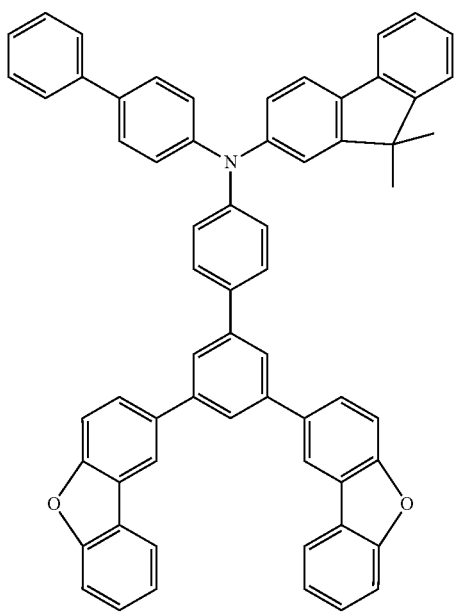
106
-continued
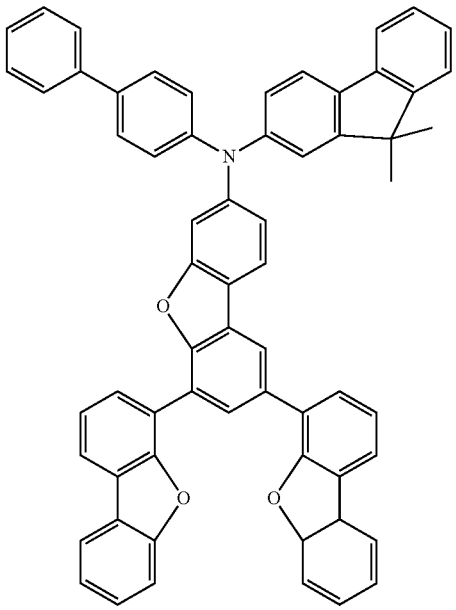
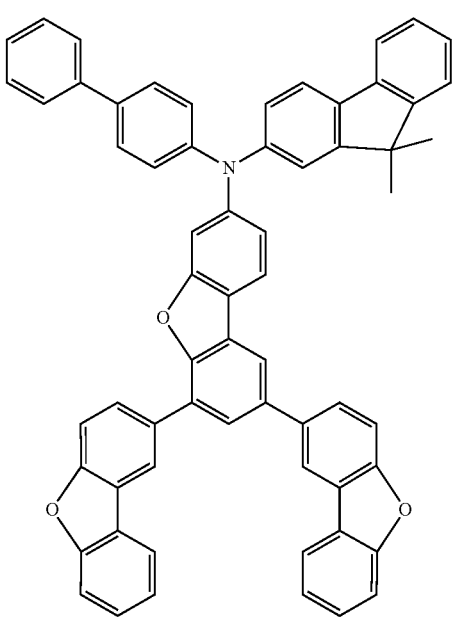

107
-continued
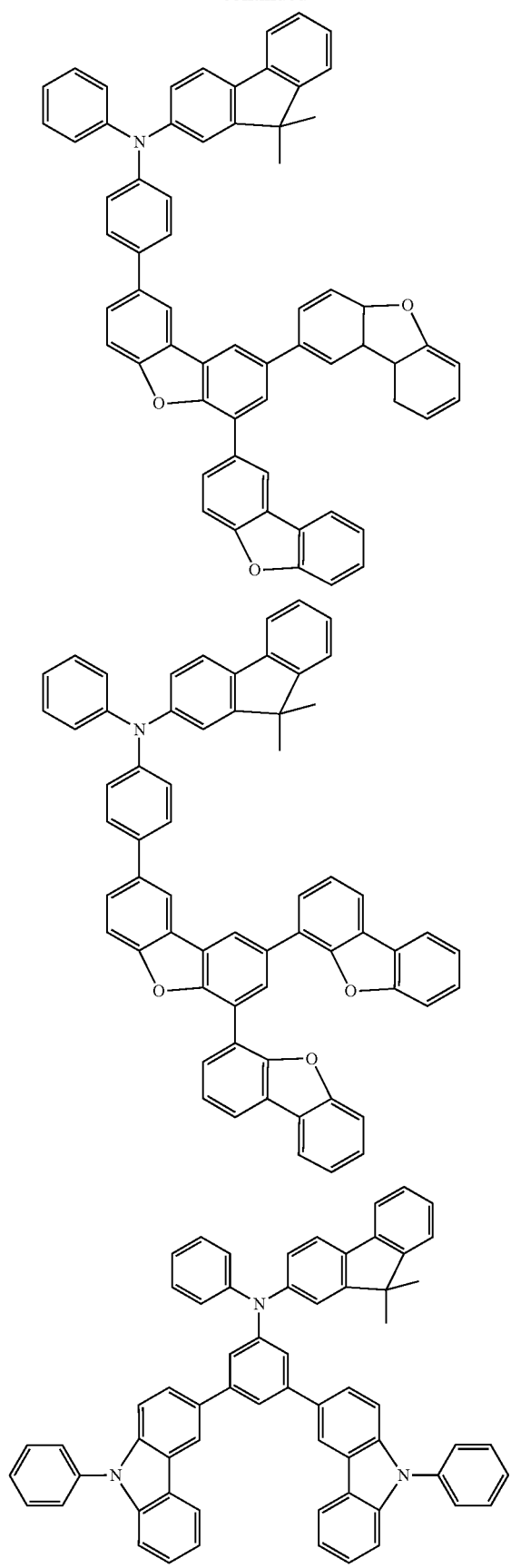
108
-continued
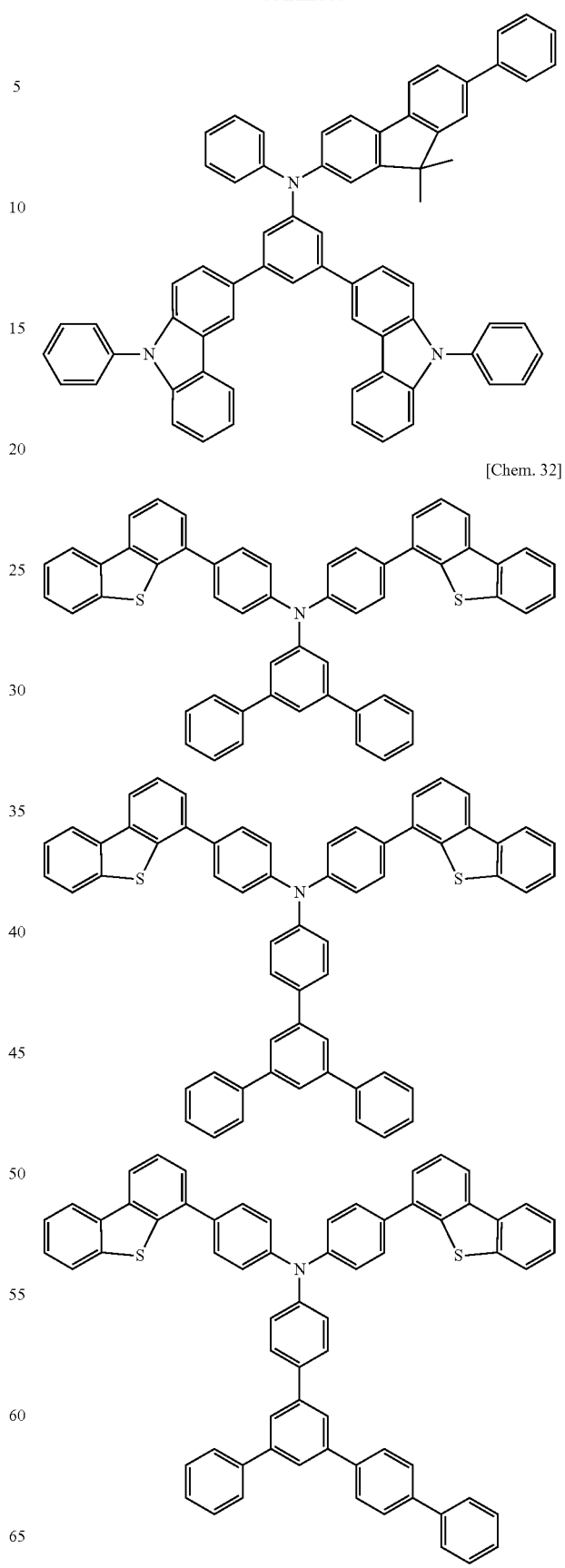
[Chem. 32]

109
-continued
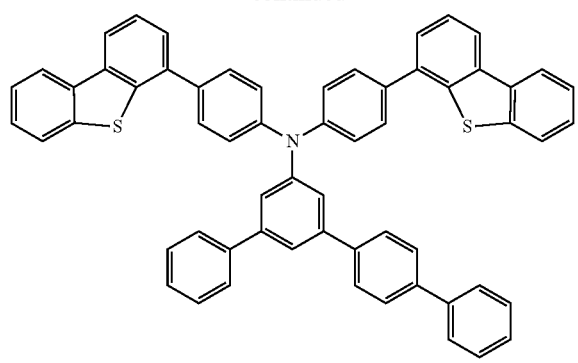
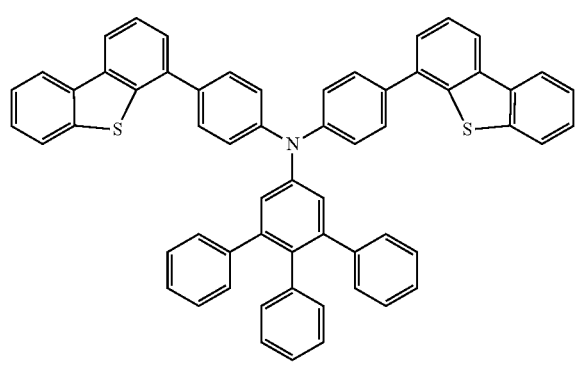
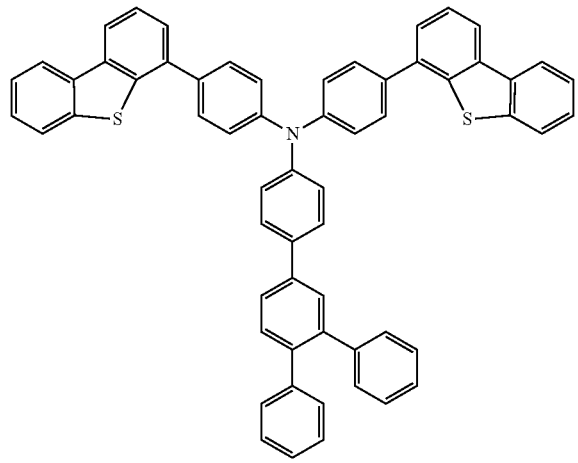
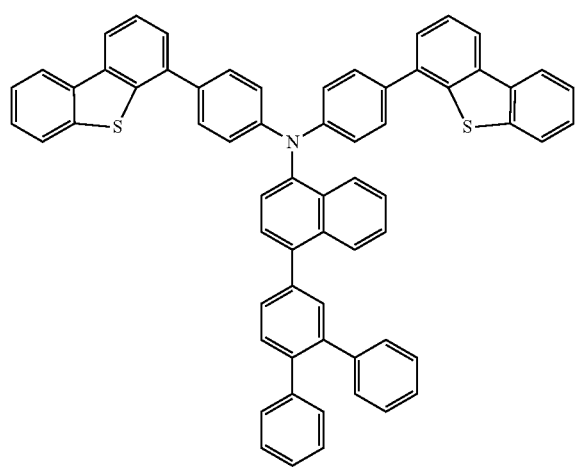
110
-continued
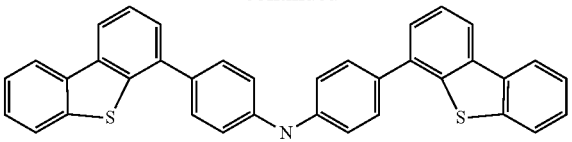
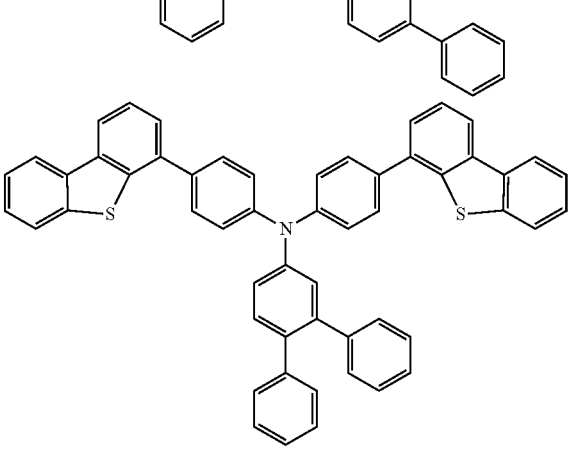
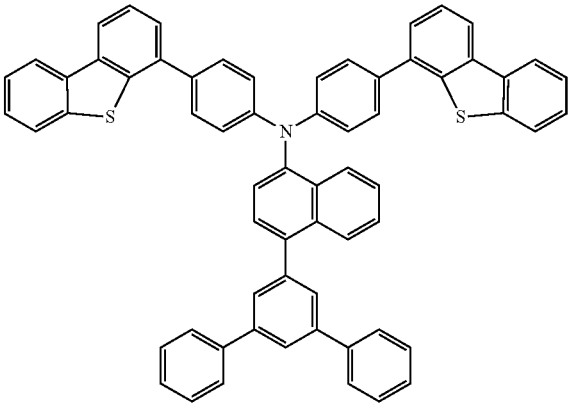
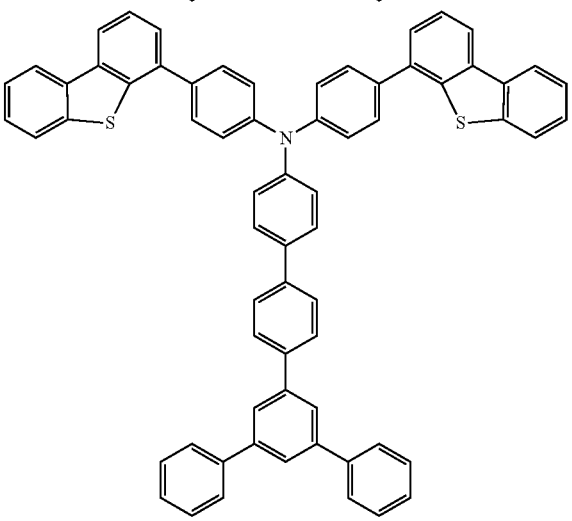

111
-continued
112
-continued
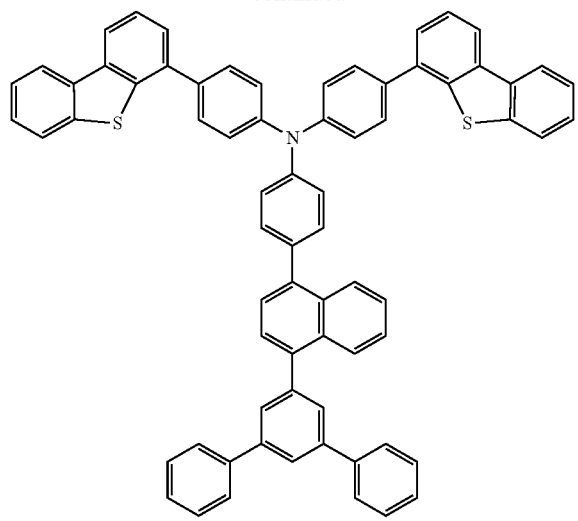
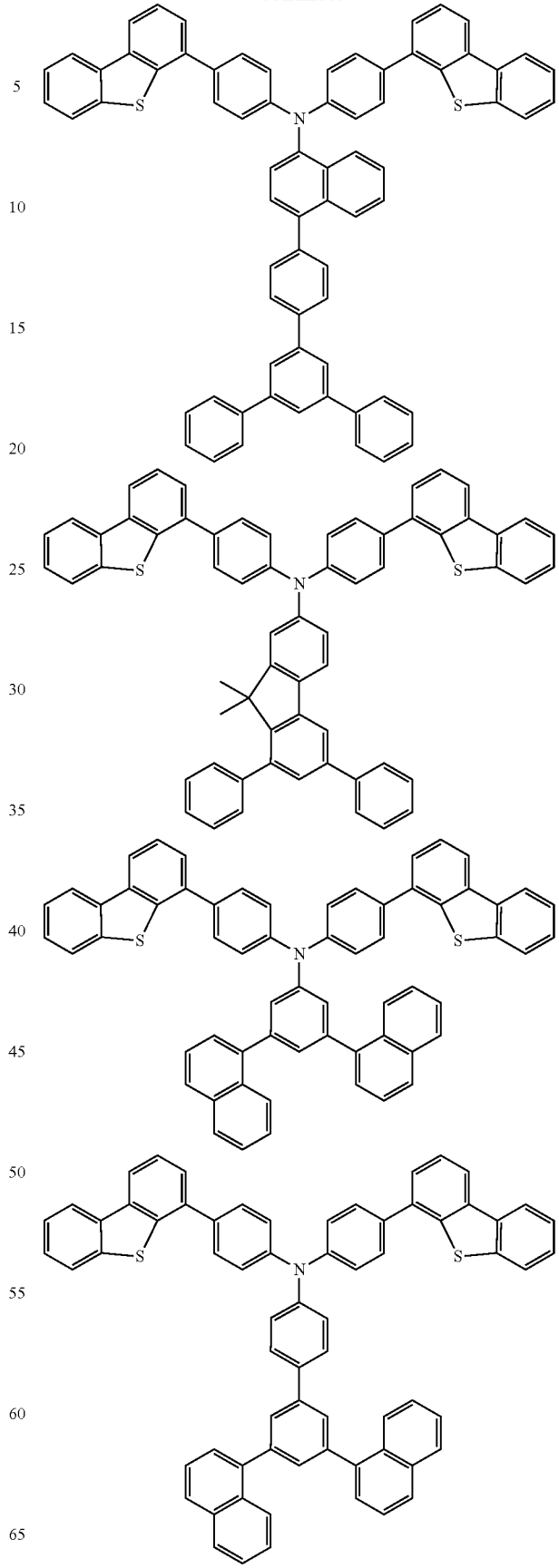

113
-continued
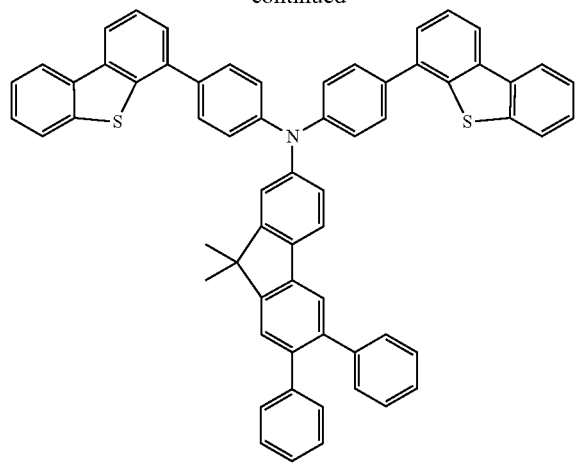
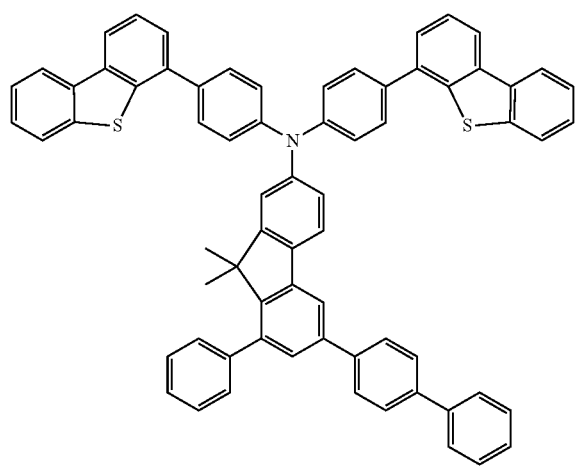
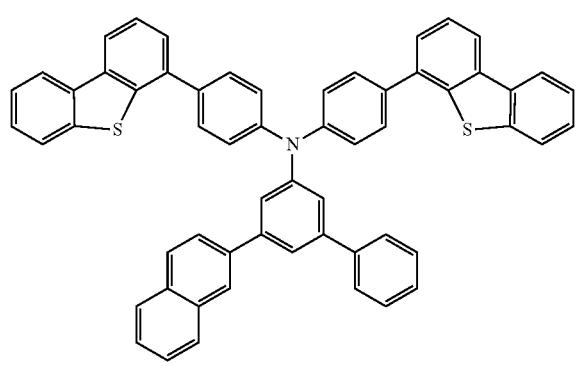
114
-continued
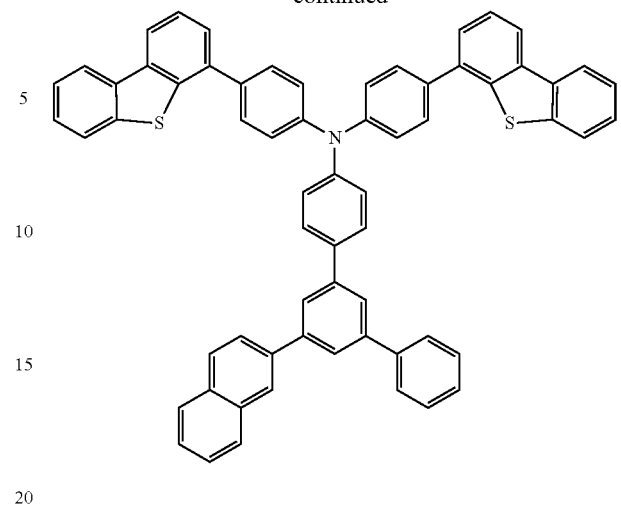
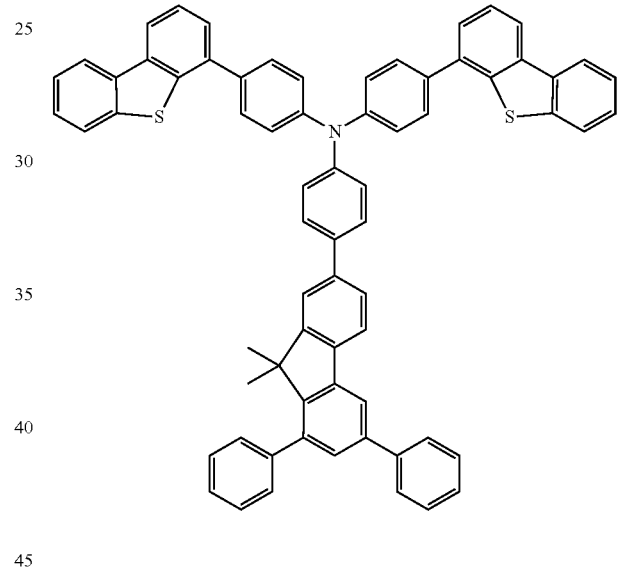
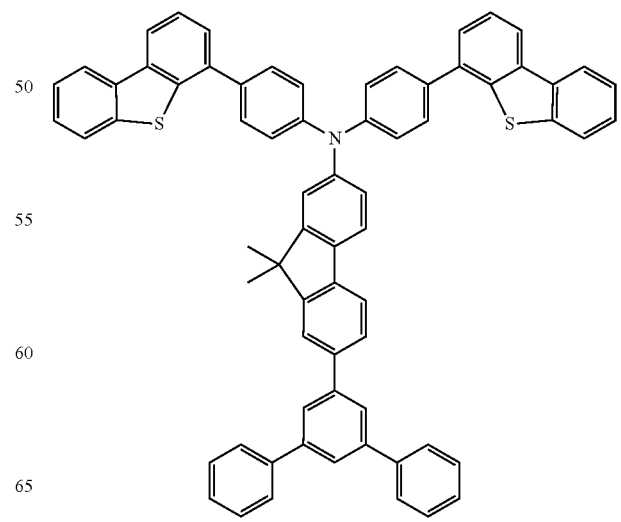

115
-continued
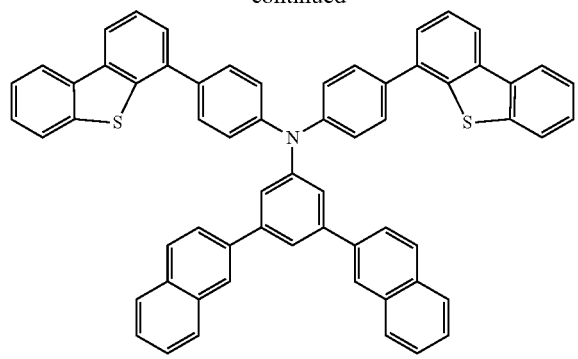
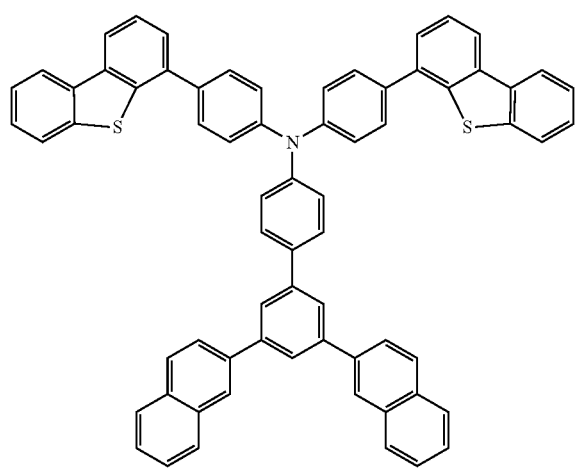
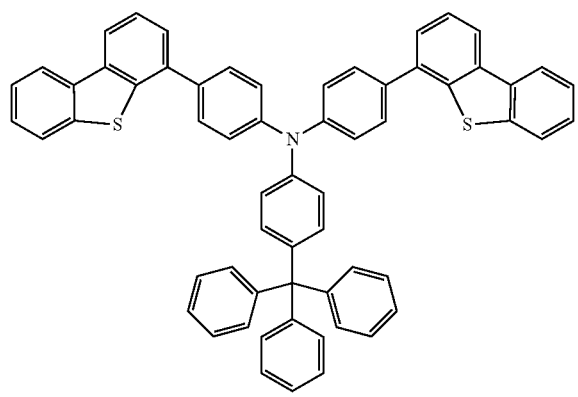
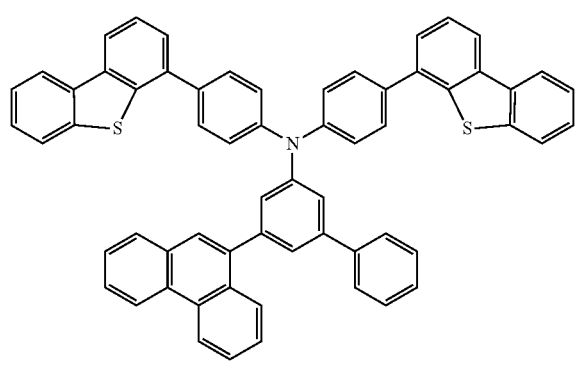
116
-continued
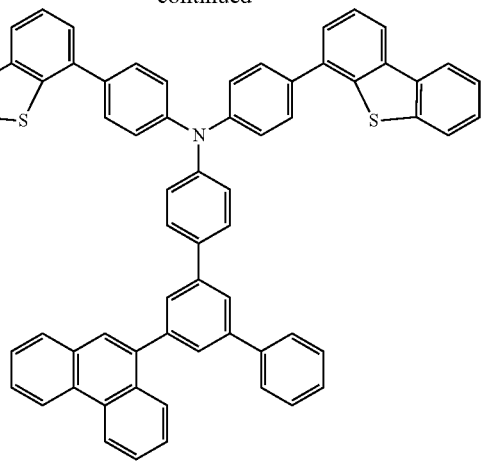
[Chem. 33]
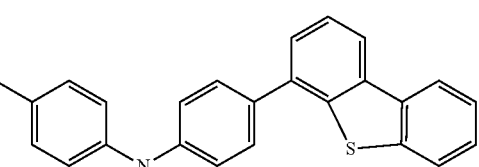
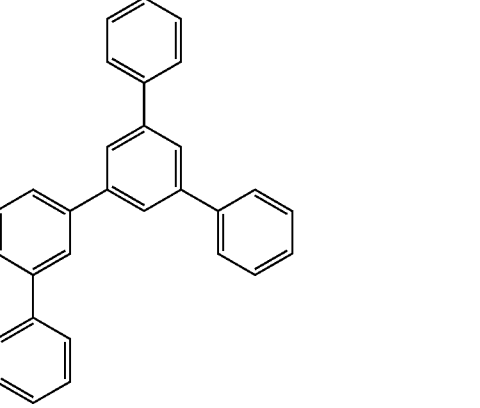
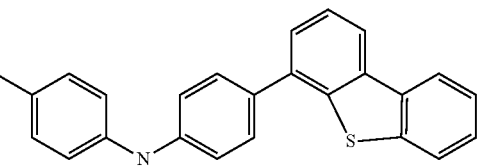
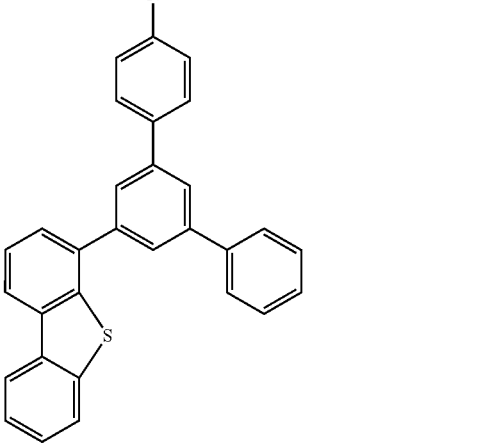

117
-continued
118
-continued
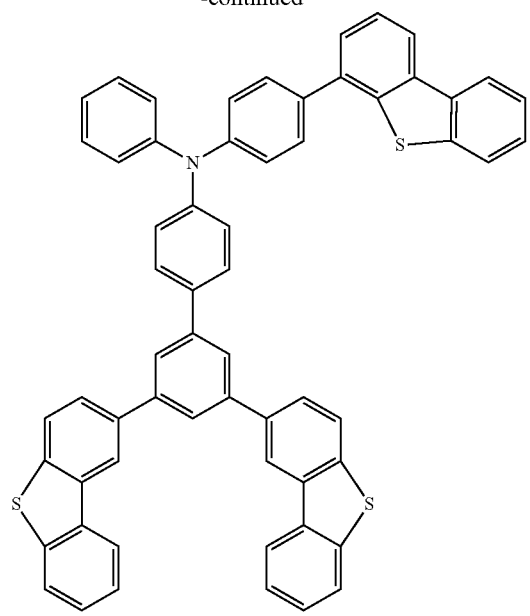
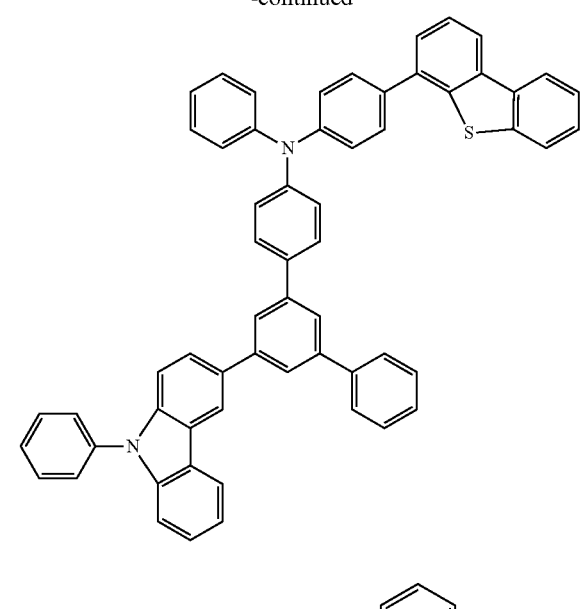

119
-continued
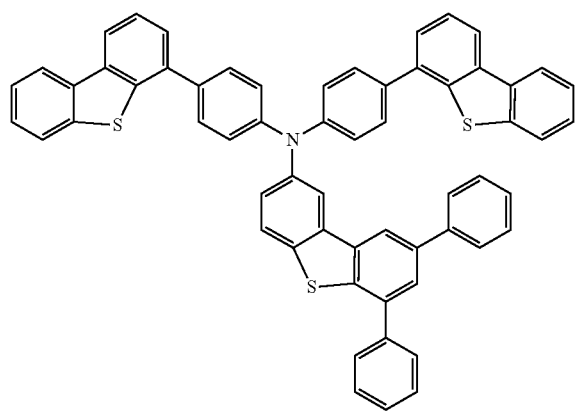
[Chem. 34]
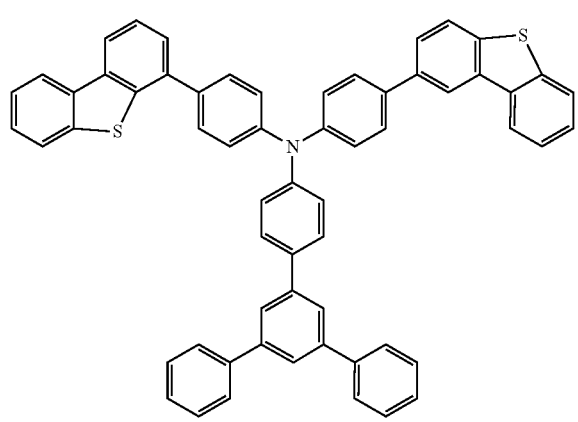
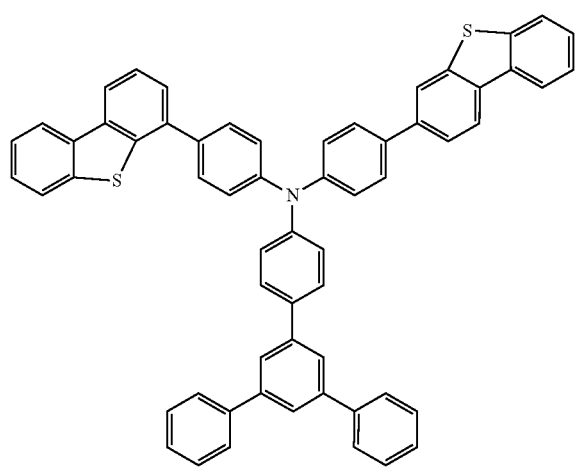
120
-continued
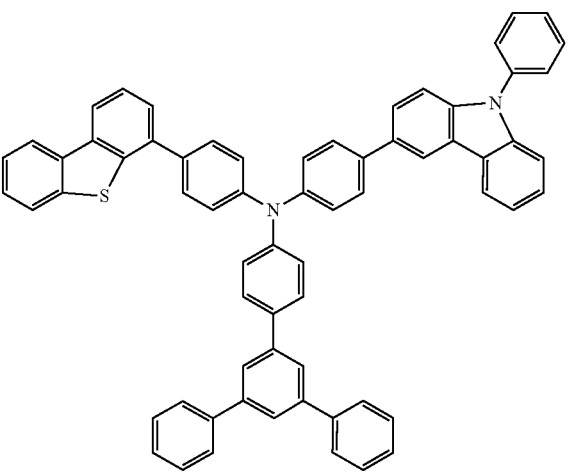
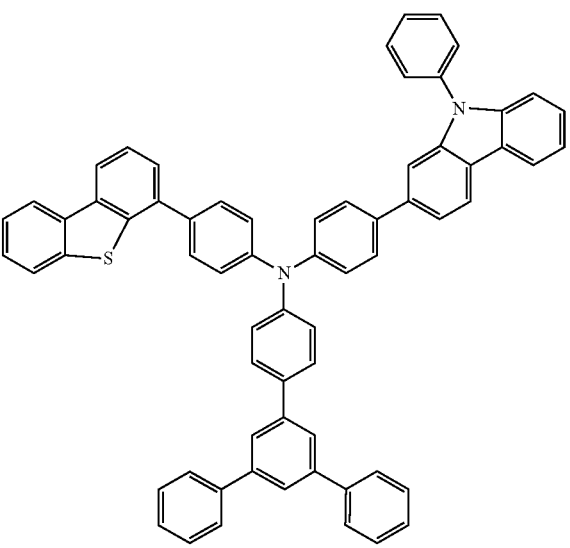
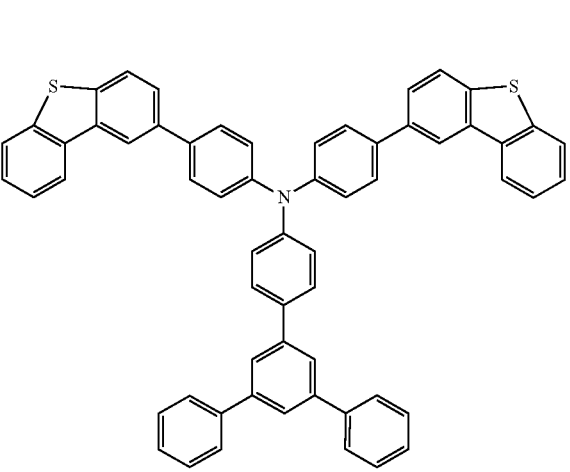

| 121 -continued | 122 -continued |
|---|---|
| 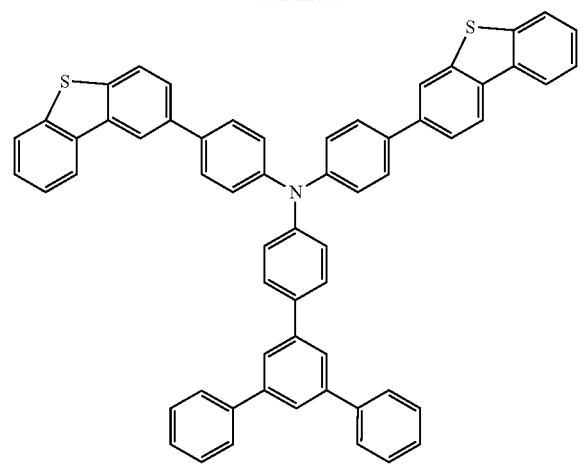 | 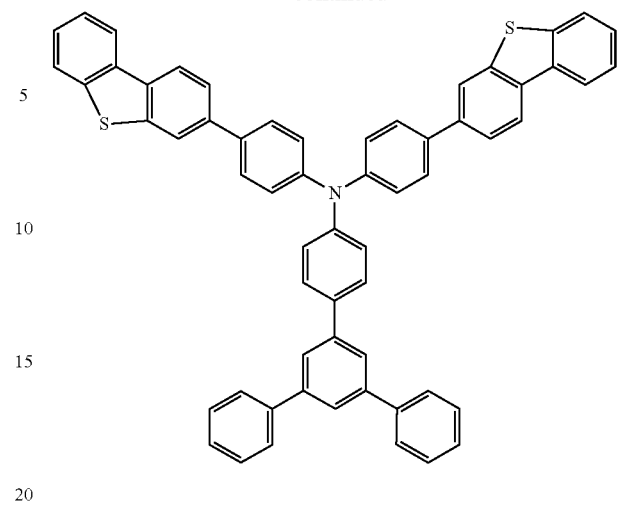 |
| 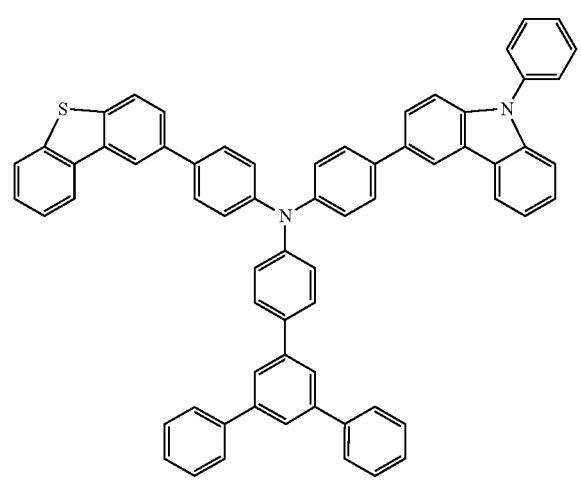 | 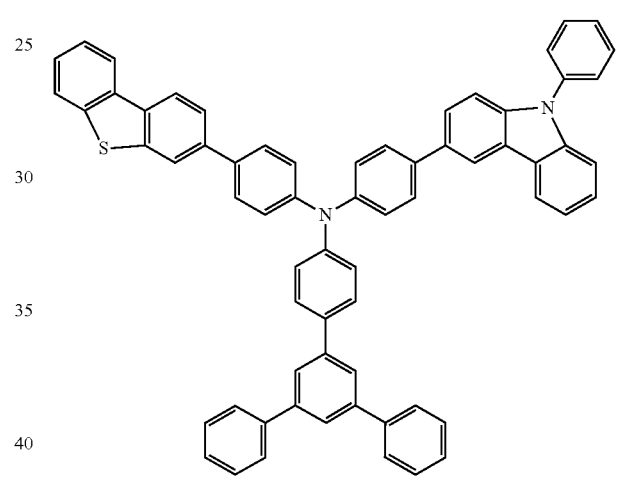 |
| 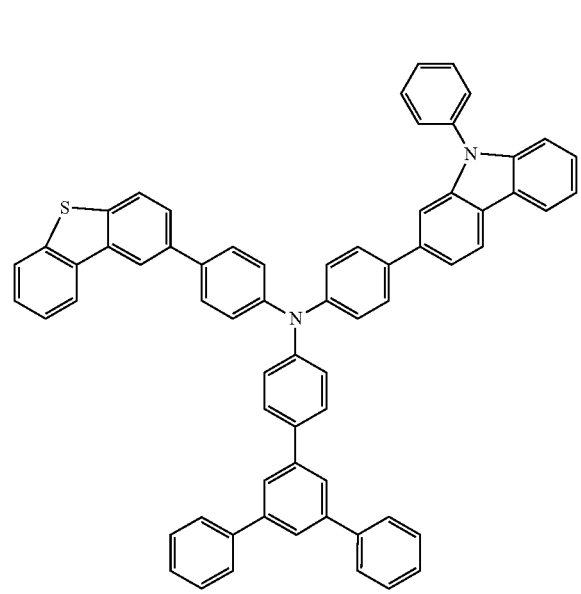 | 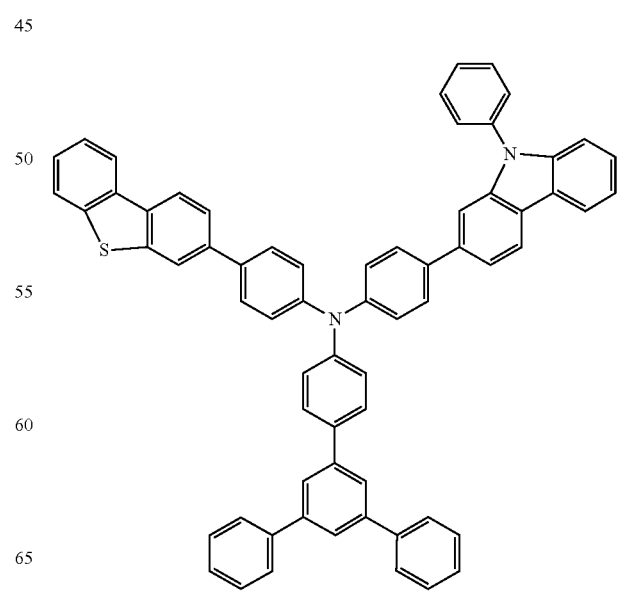 |

[Chem. 35]
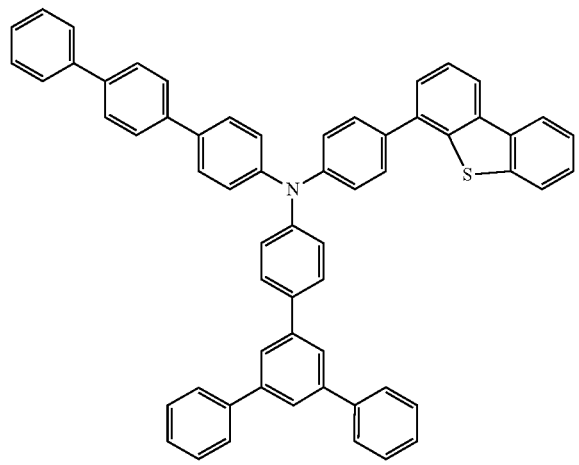
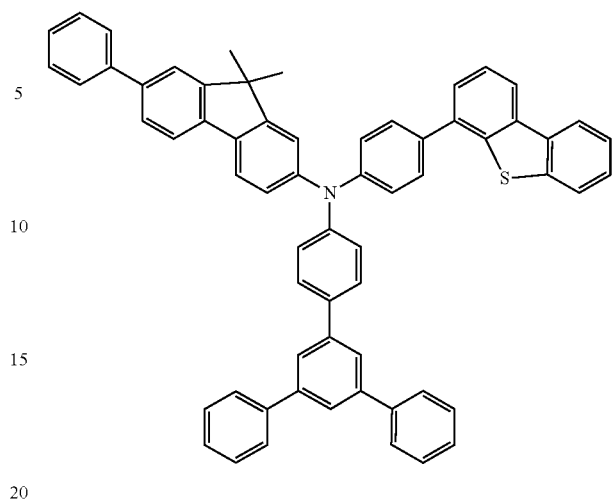
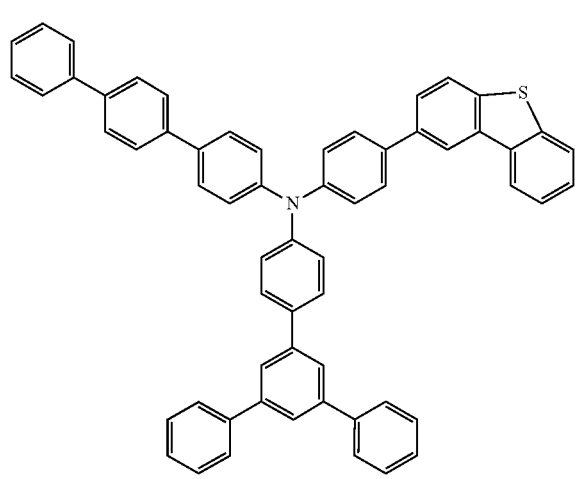
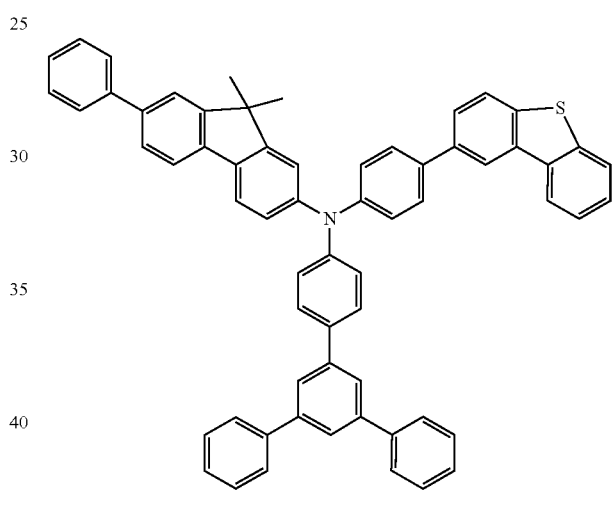
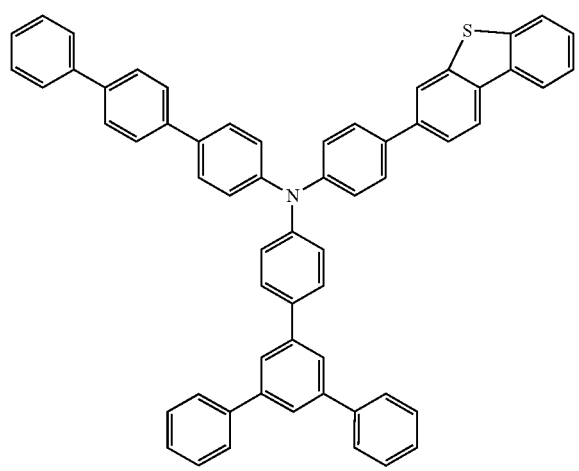
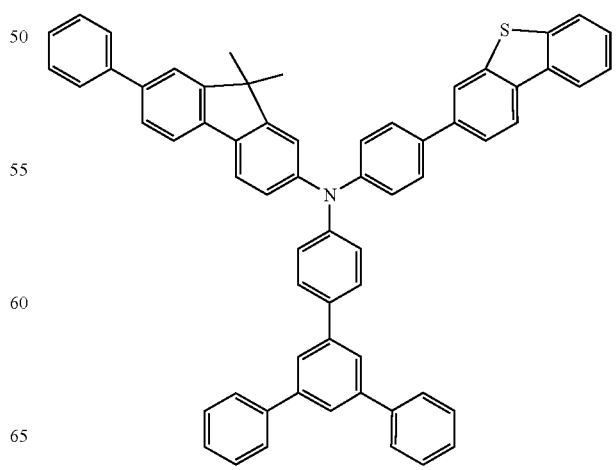

125
-continued
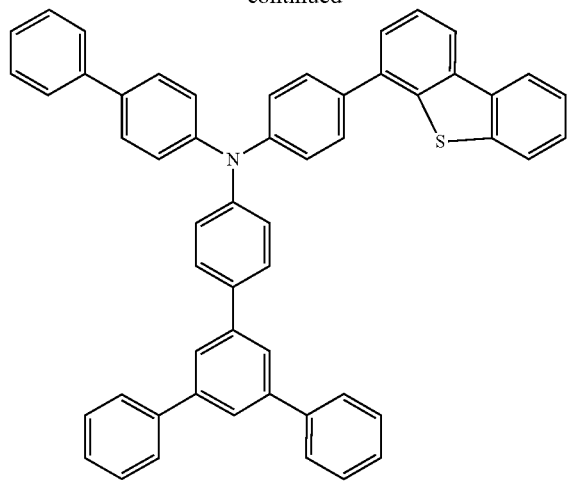
126
-continued
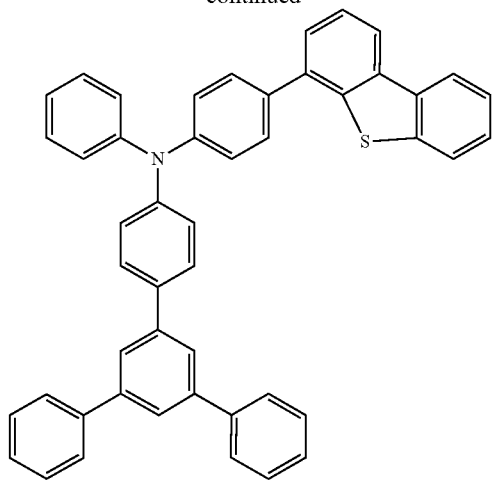
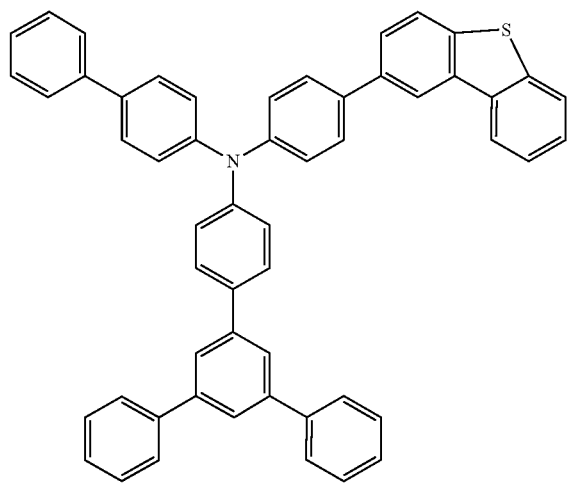
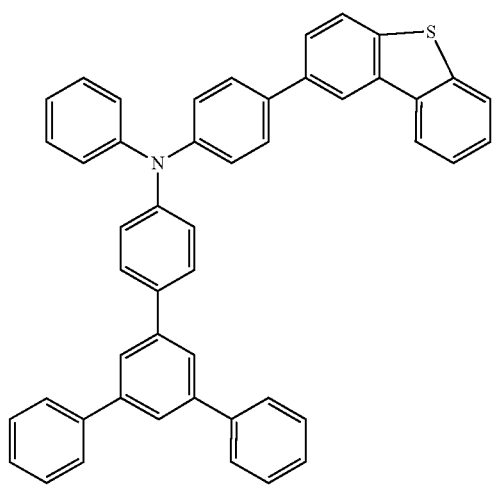
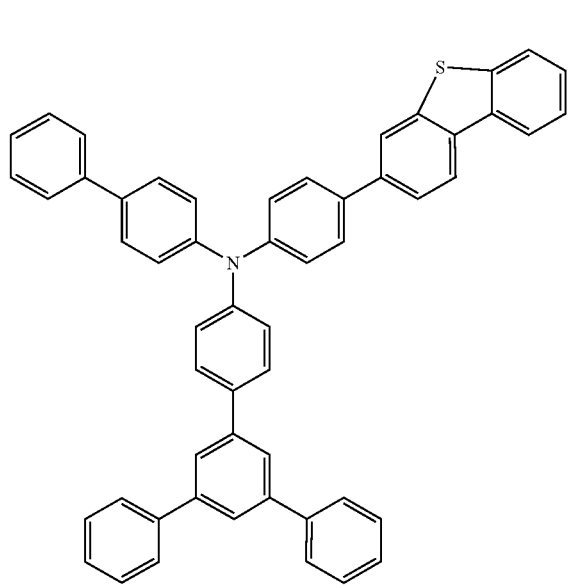
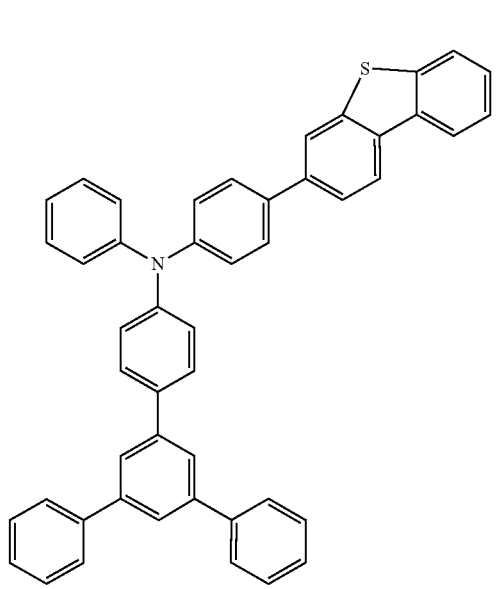

127
-continued
[Chem. 36]
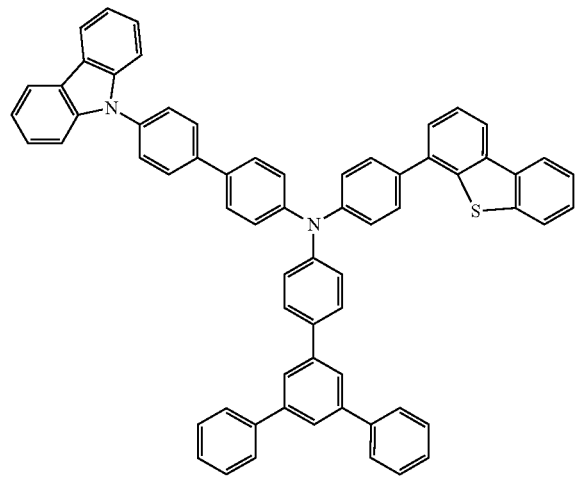
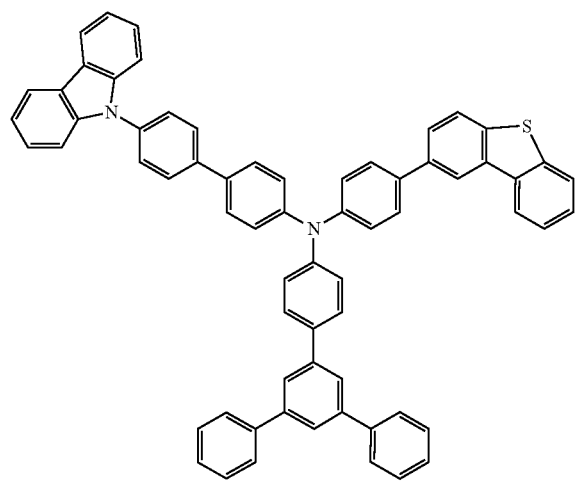
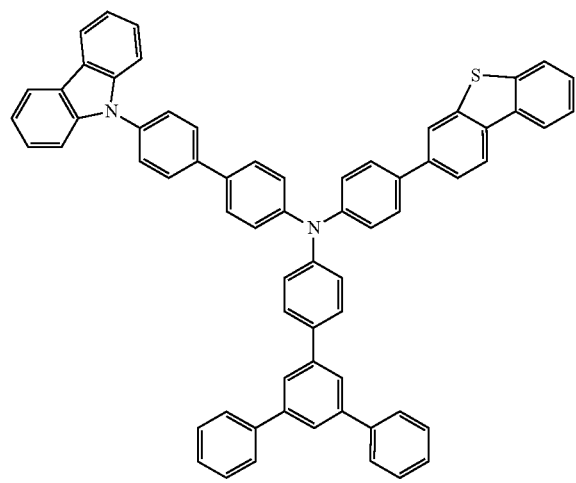
128
-continued
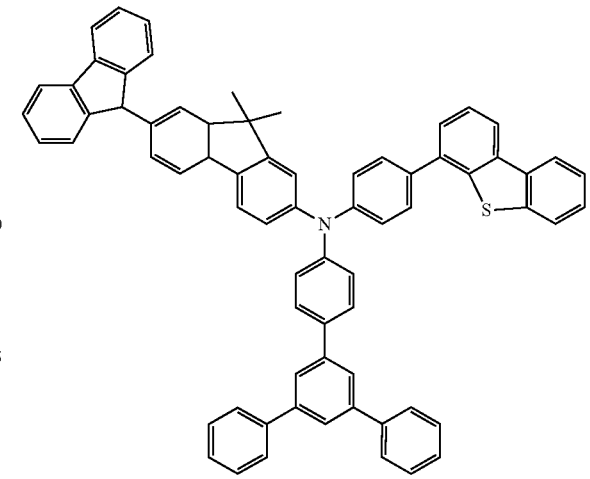
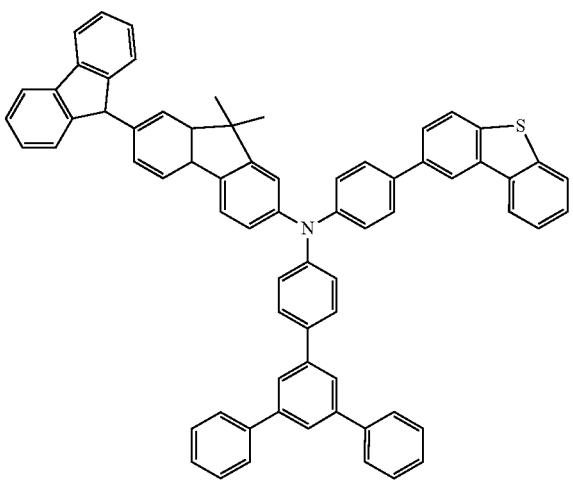
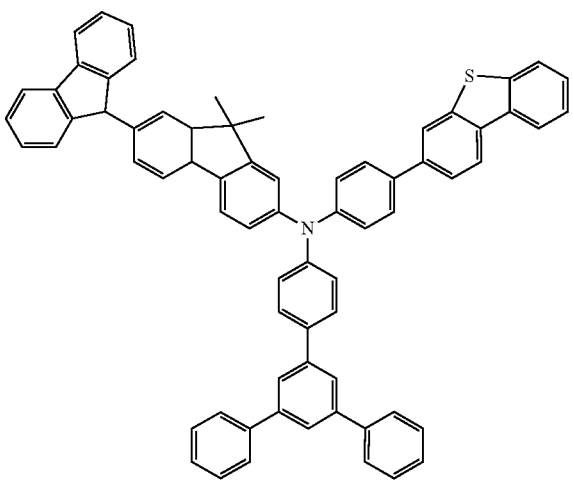

129
-continued
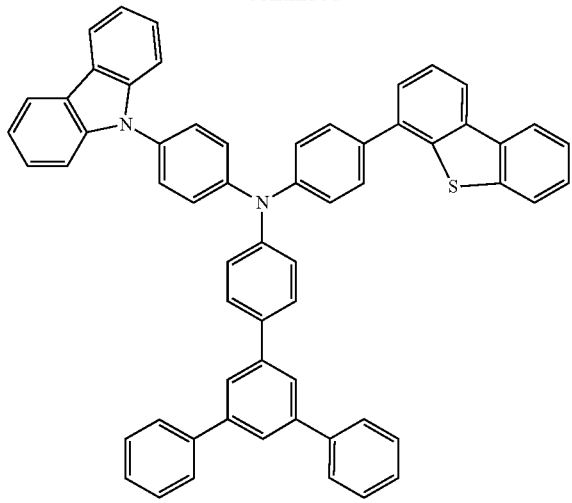
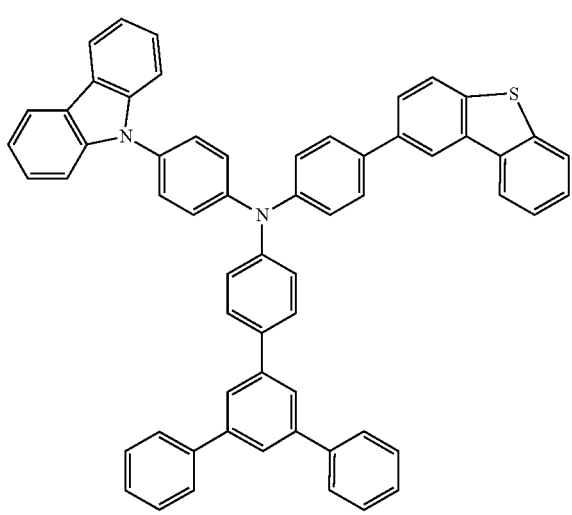
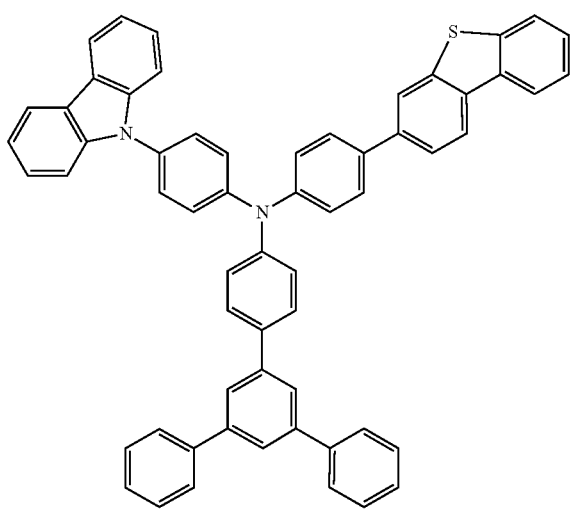
130
-continued
[Chem. 37]
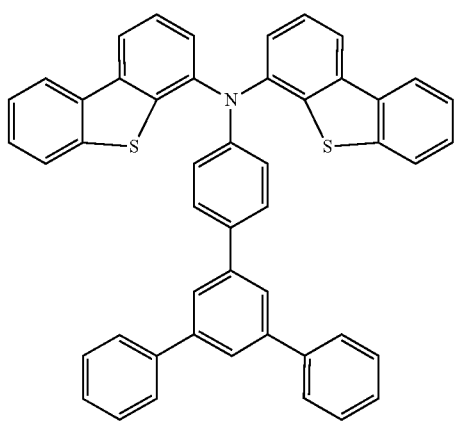
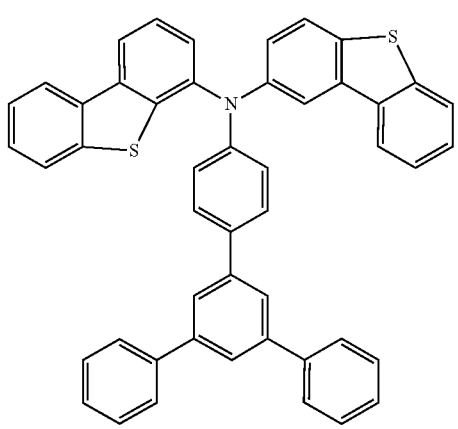
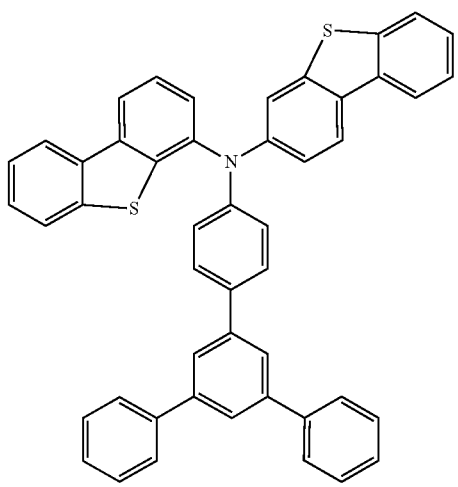

131
-continued

132
-continued

133
-continued
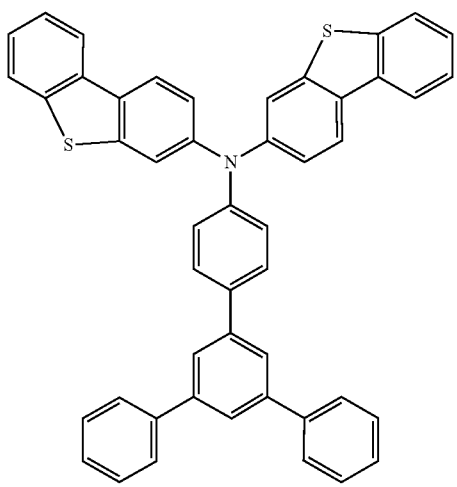
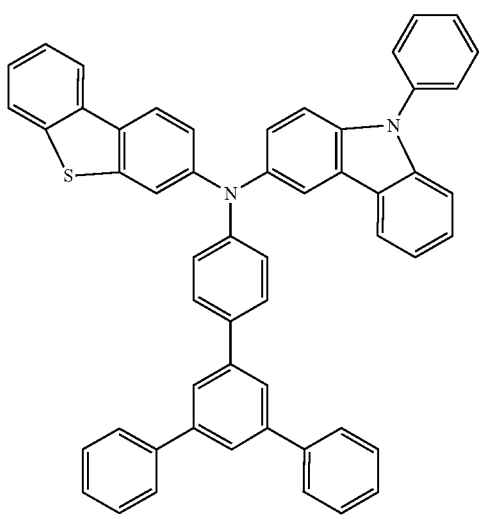
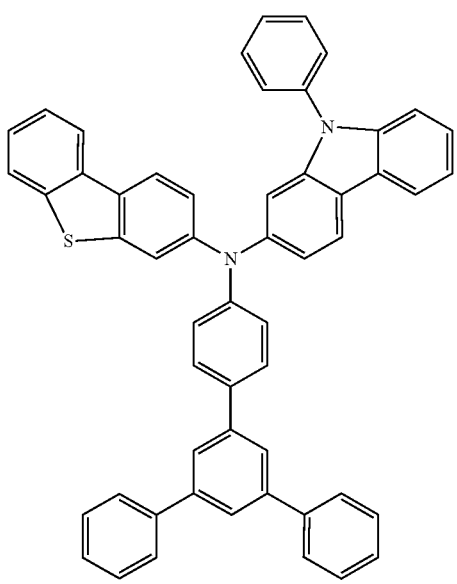
134
-continued
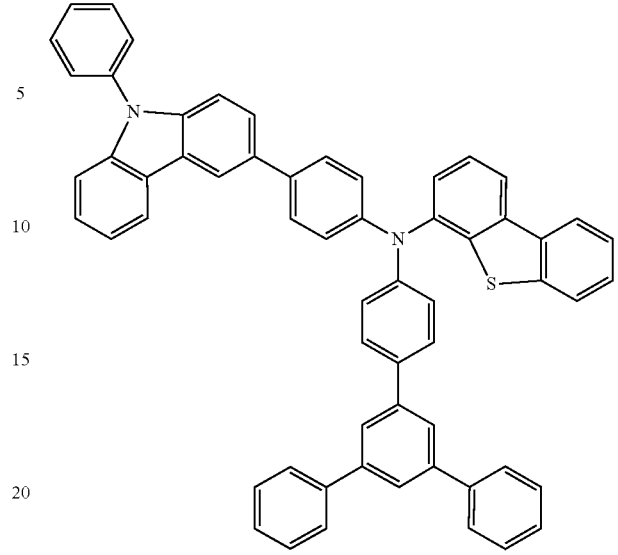
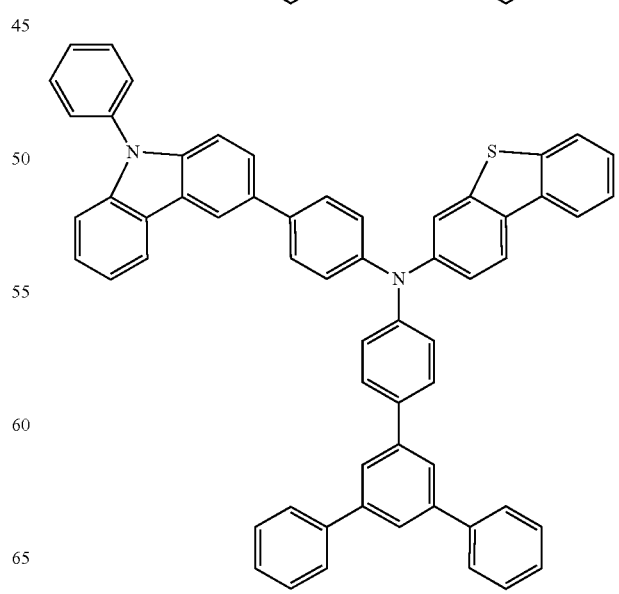

135
-continued
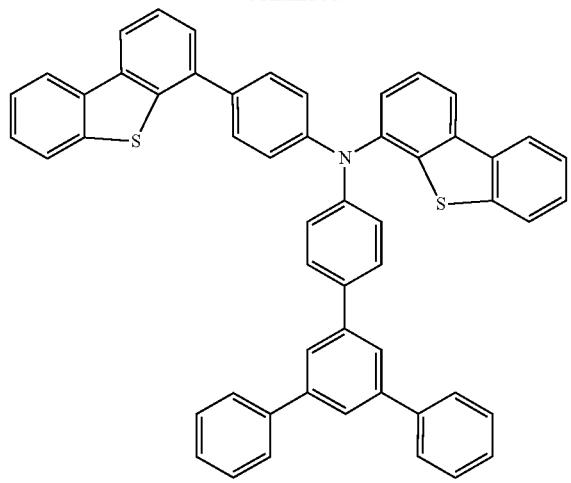
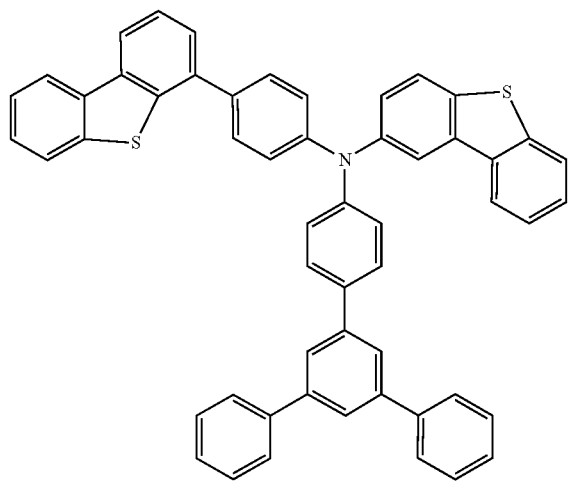
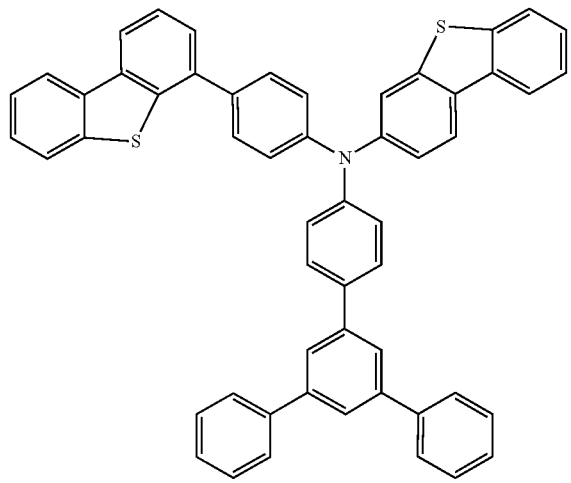
136
-continued
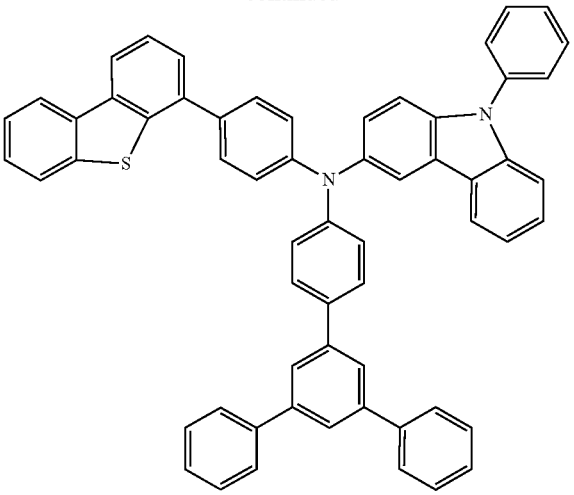
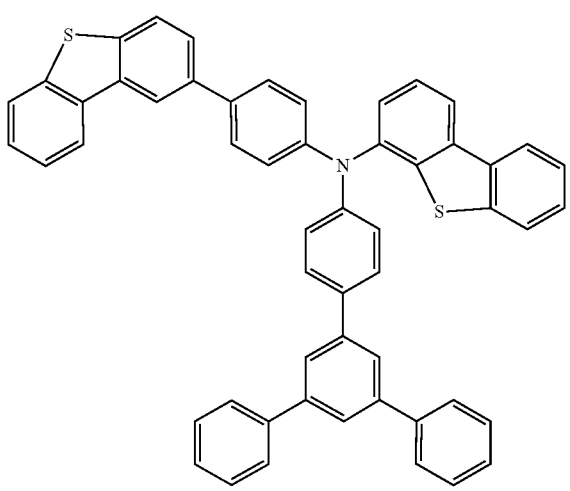

137
-continued
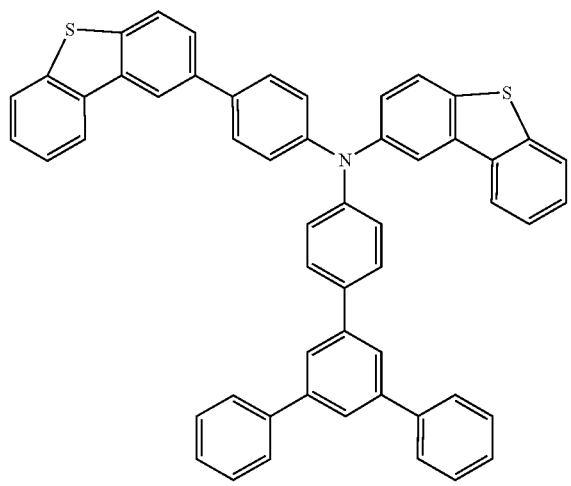
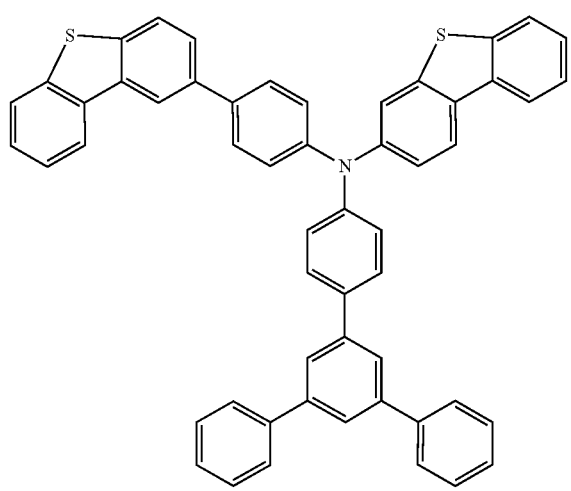
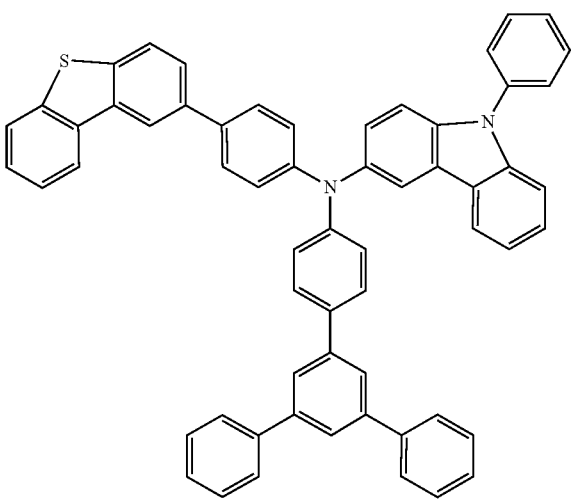
138
-continued
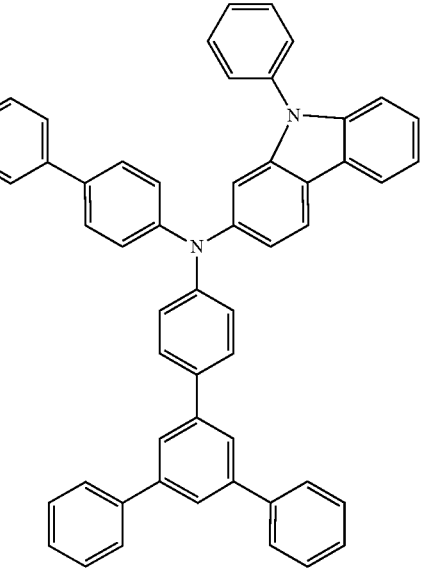
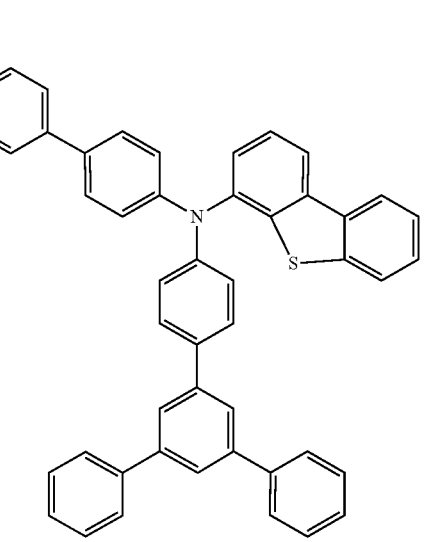
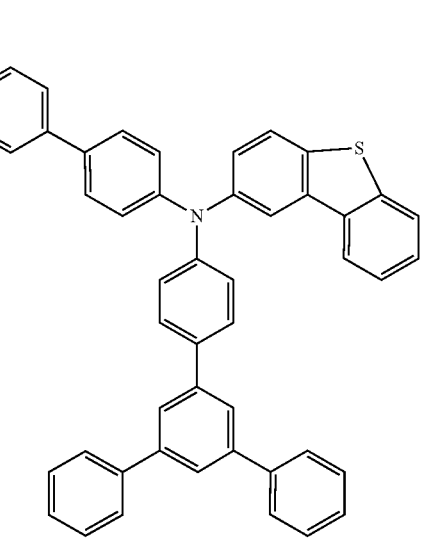

139
-continued
140
-continued
[Chem. 38]
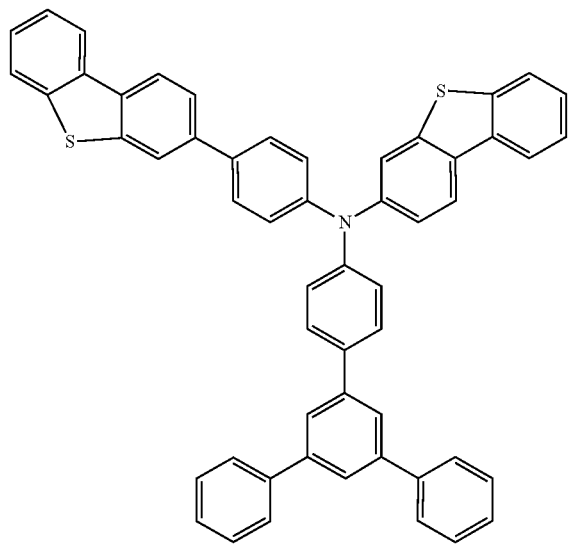
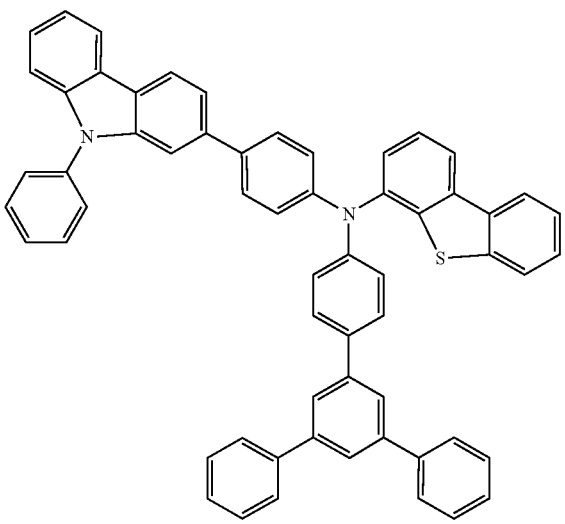
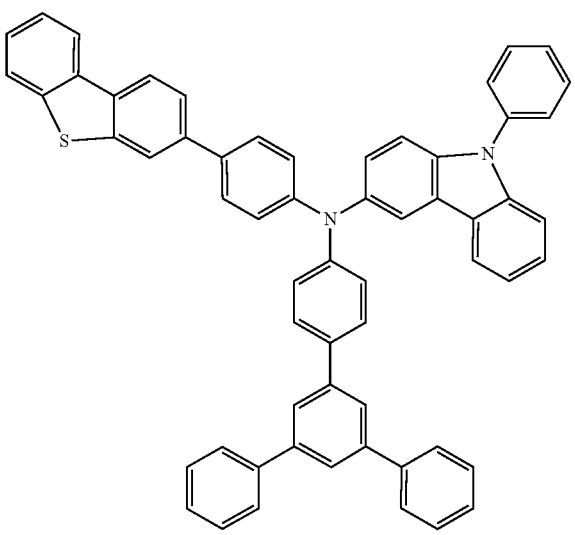
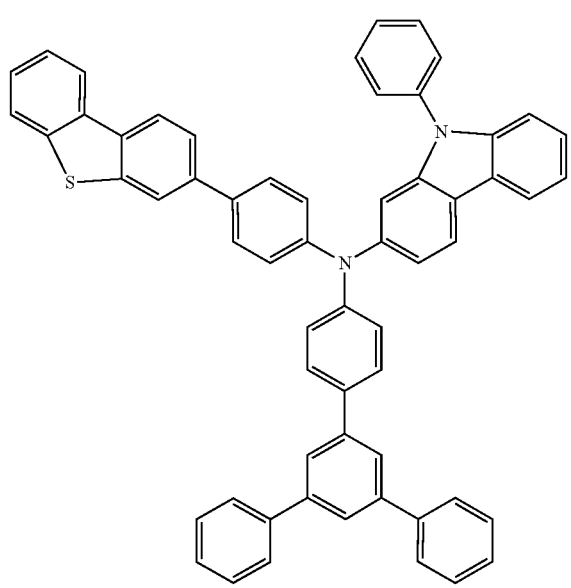

141
-continued
142
-continued
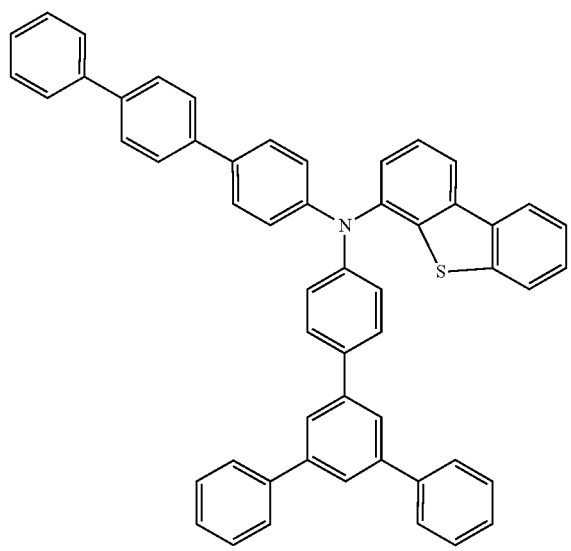
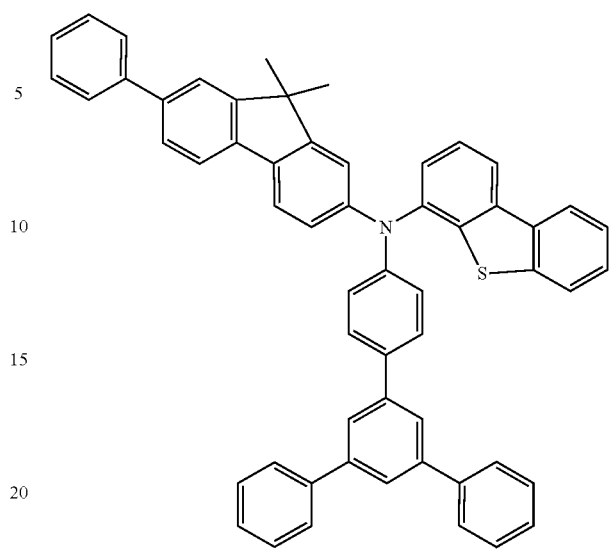
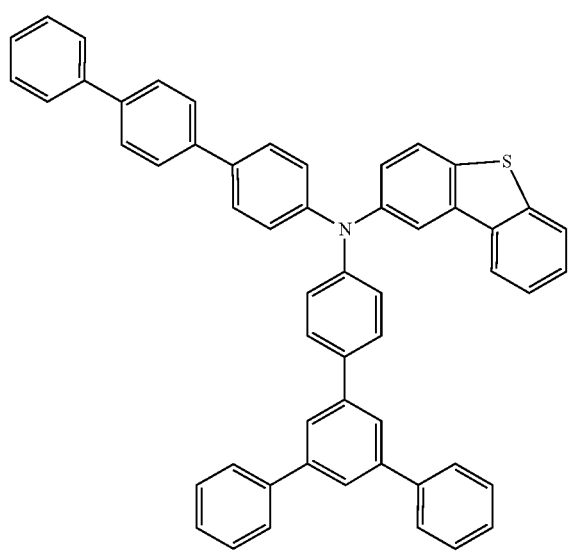
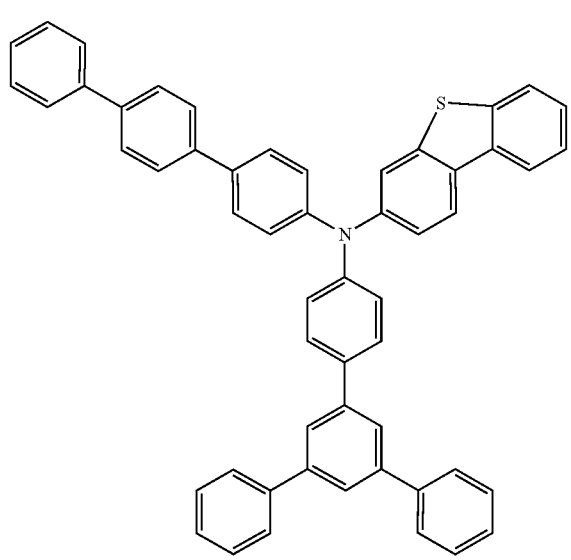
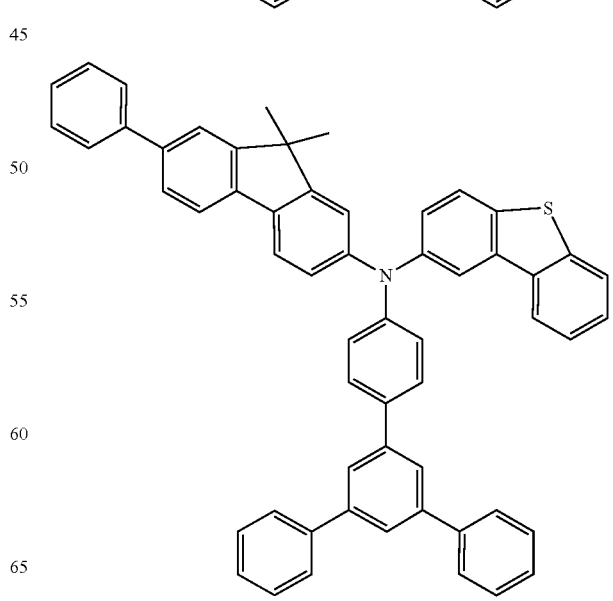

143
-continued
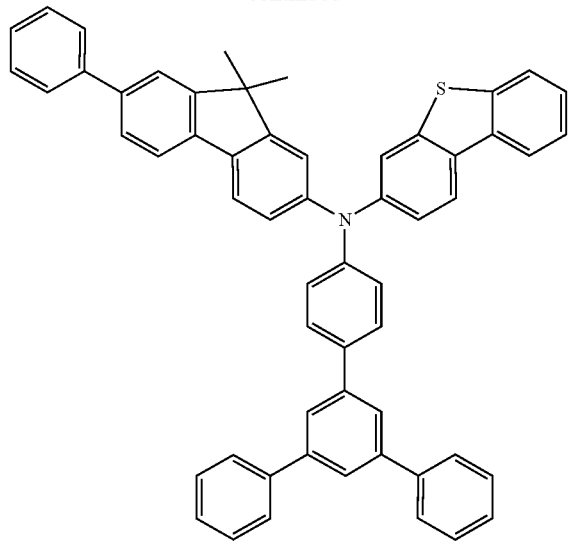
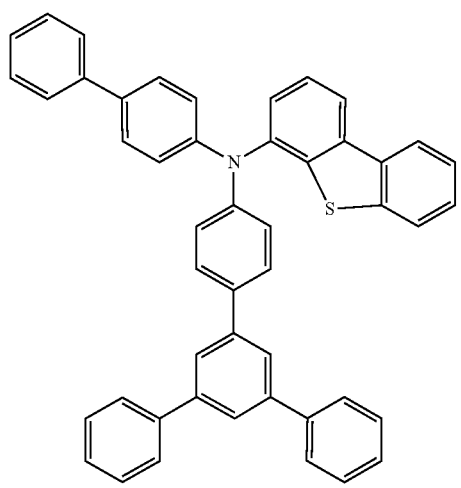
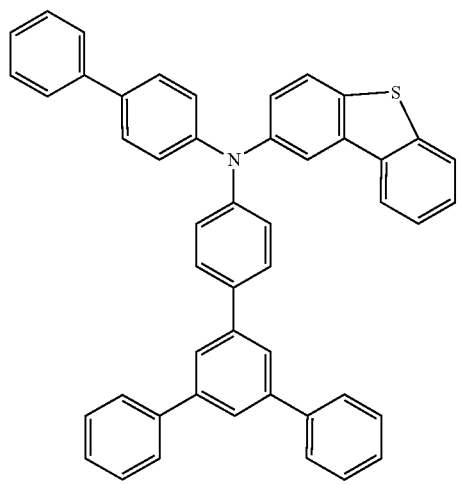
144
-continued
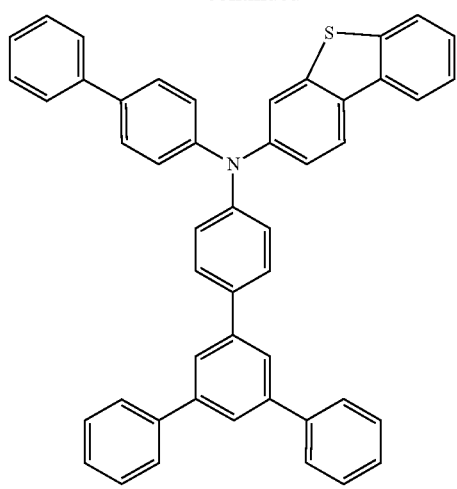
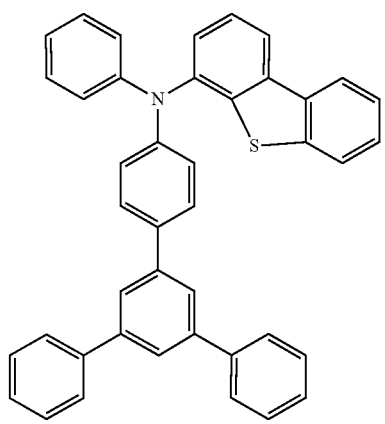
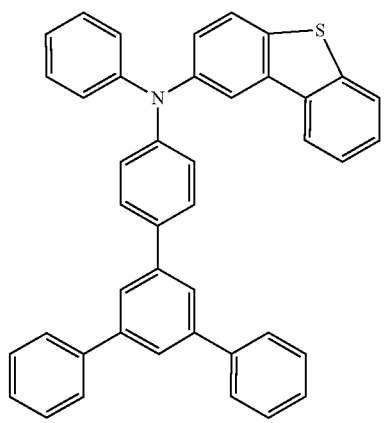

145
-continued
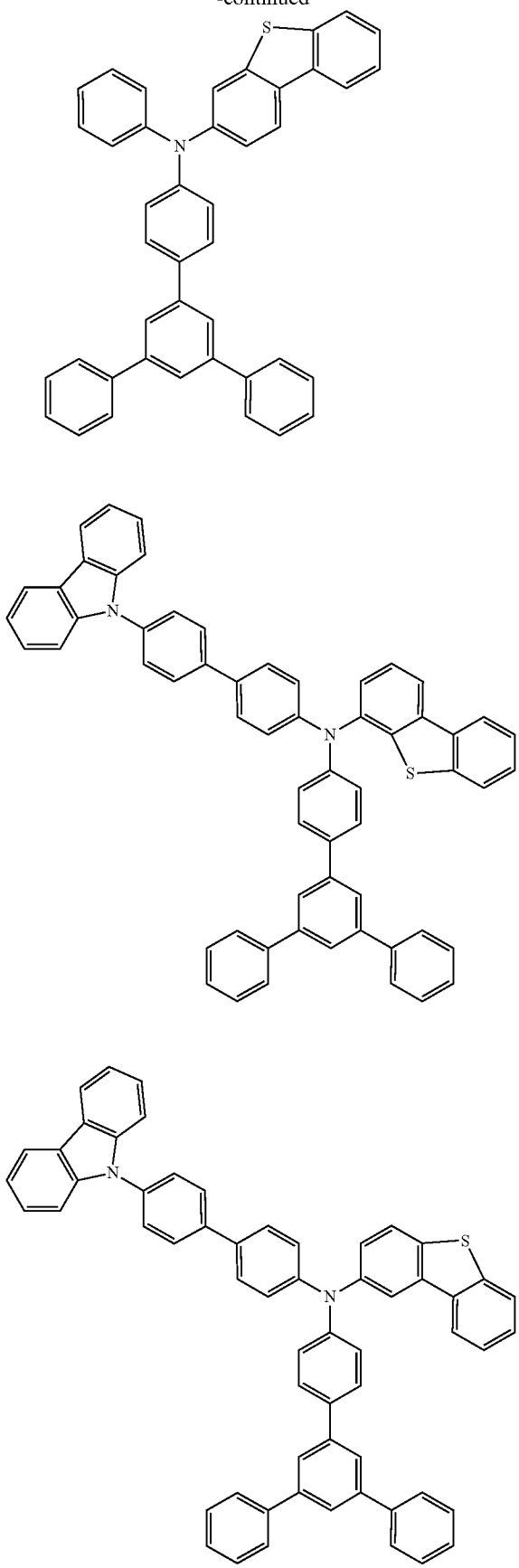
146
-continued
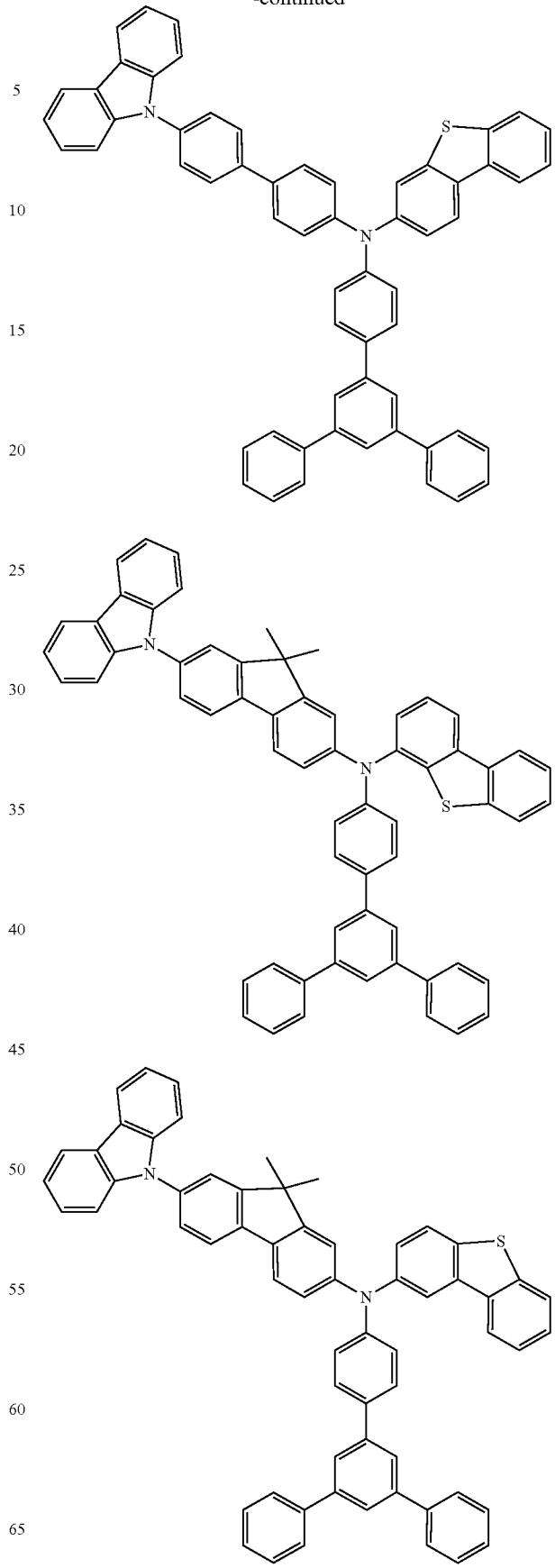

147
-continued
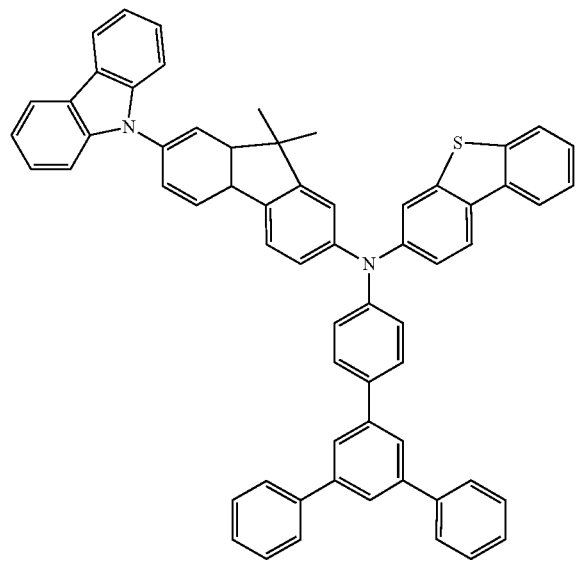
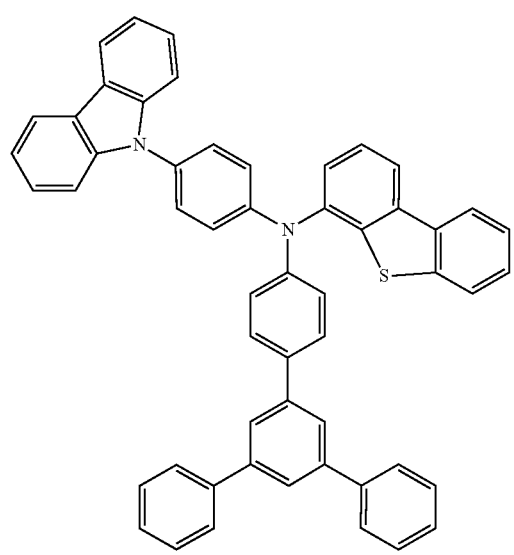
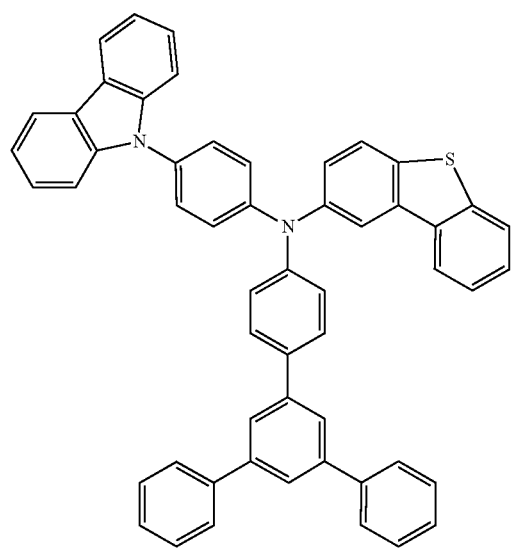
148
-continued
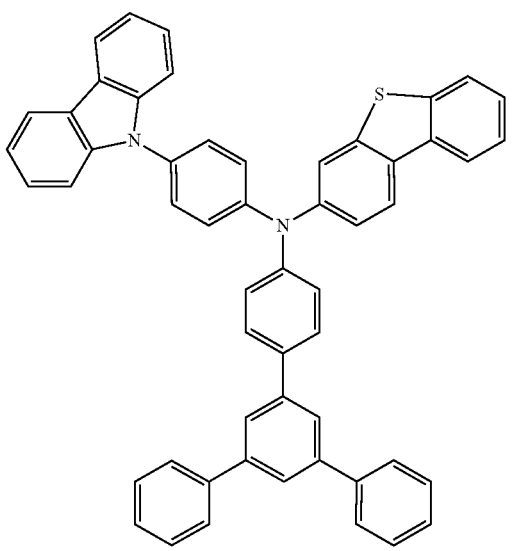
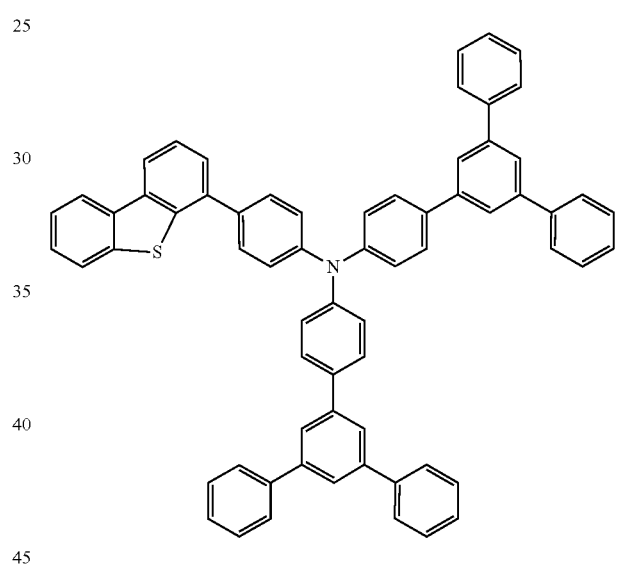
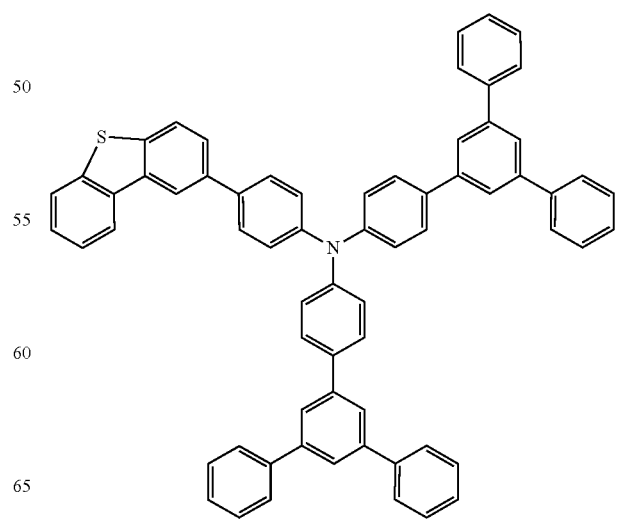

149
-continued
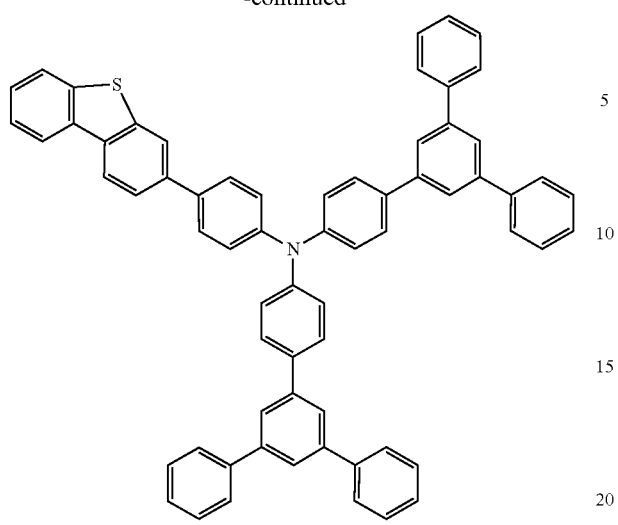
150
-continued
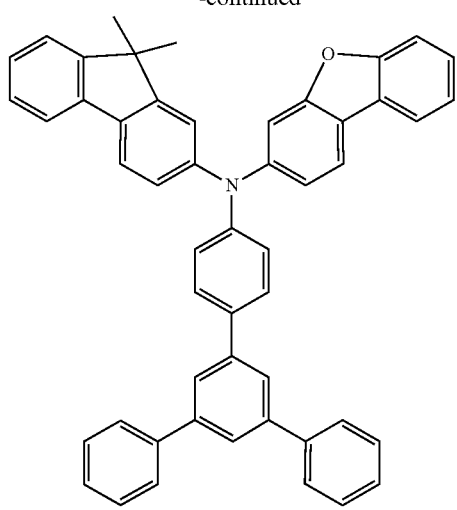
[Chem. 39]
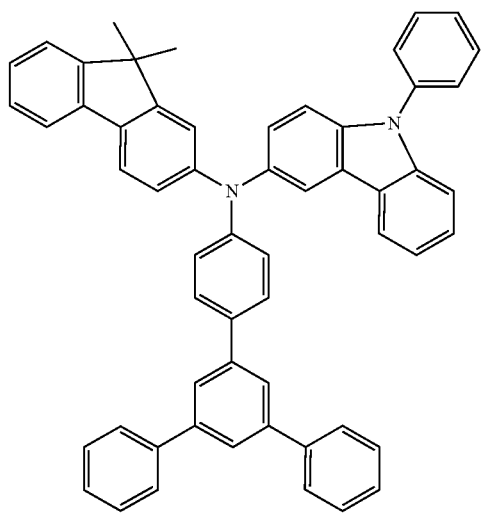
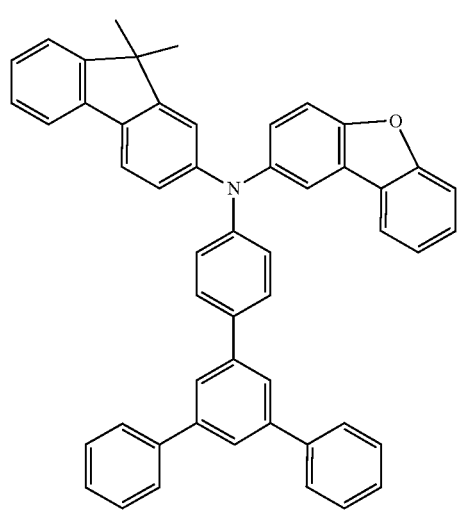
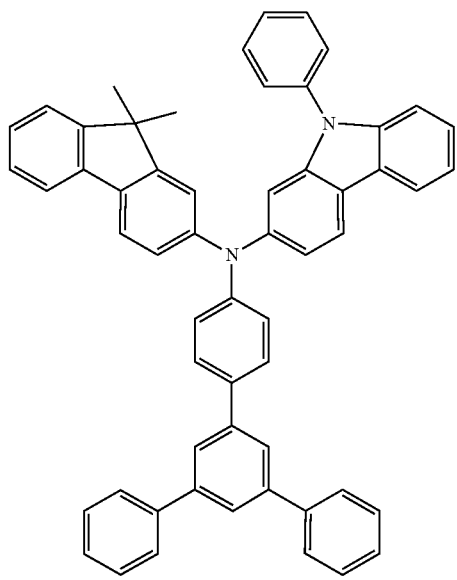

151
-continued
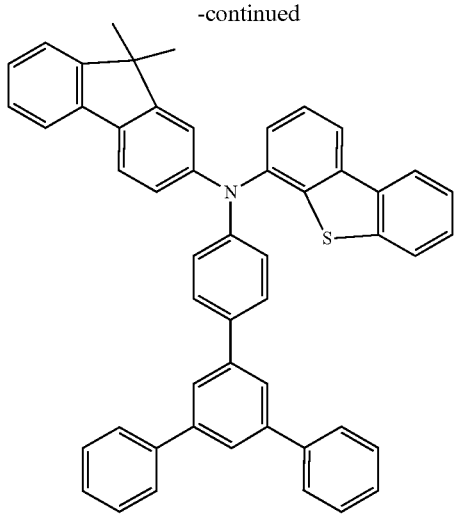
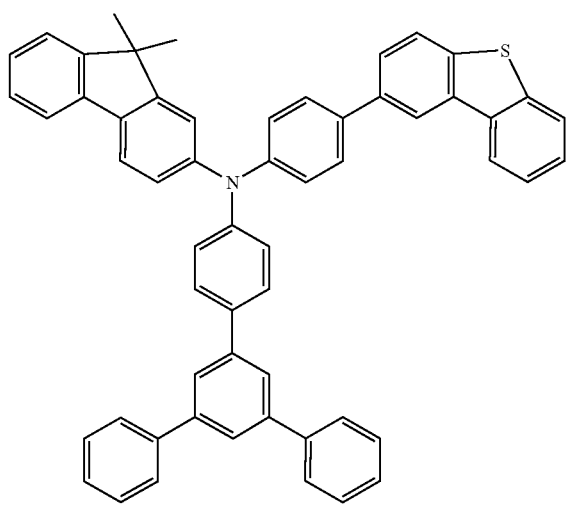
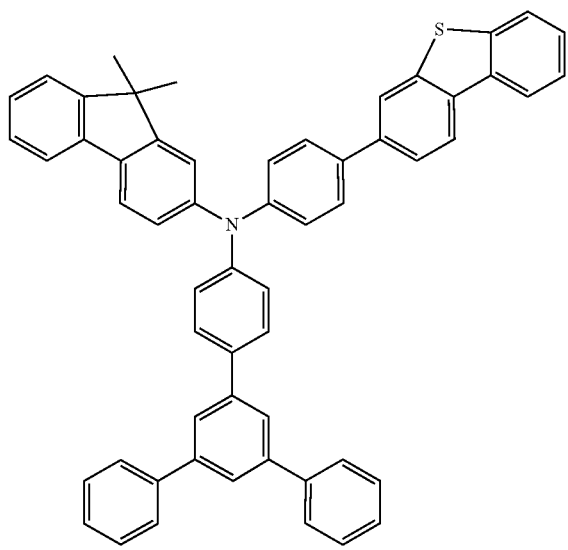
152
-continued
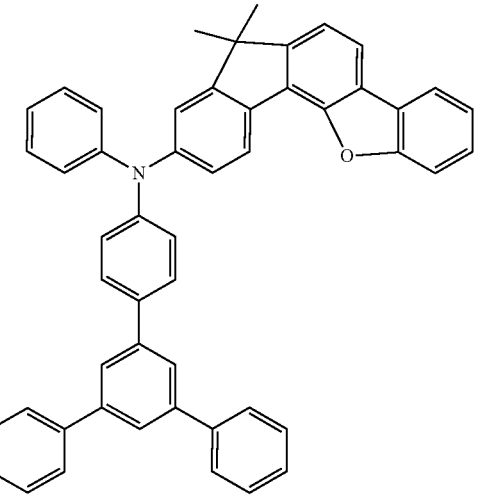
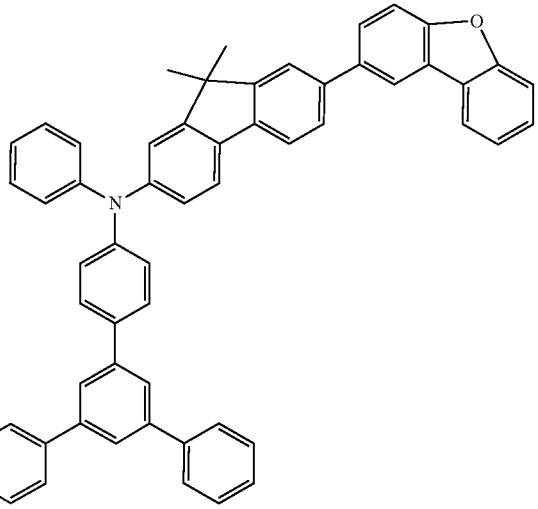
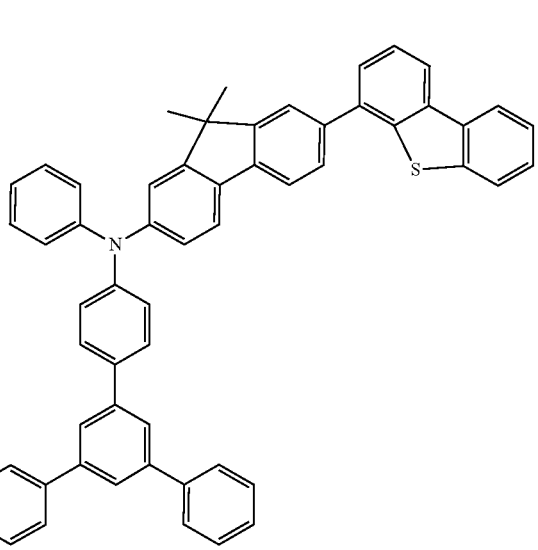

153
-continued
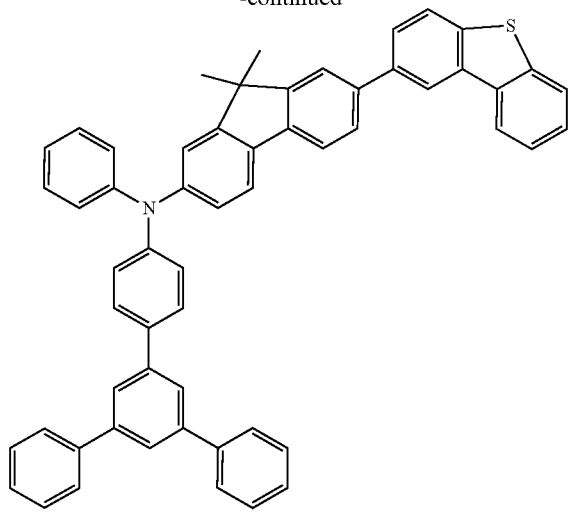
154
-continued
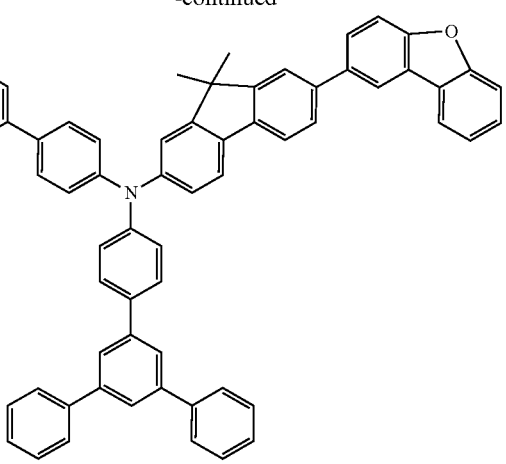
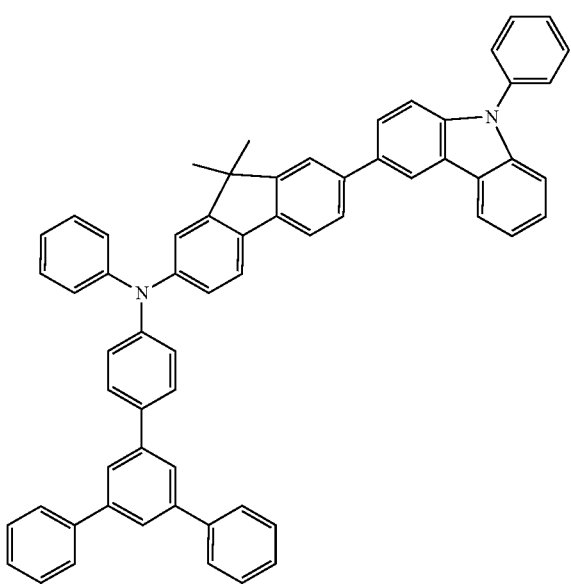
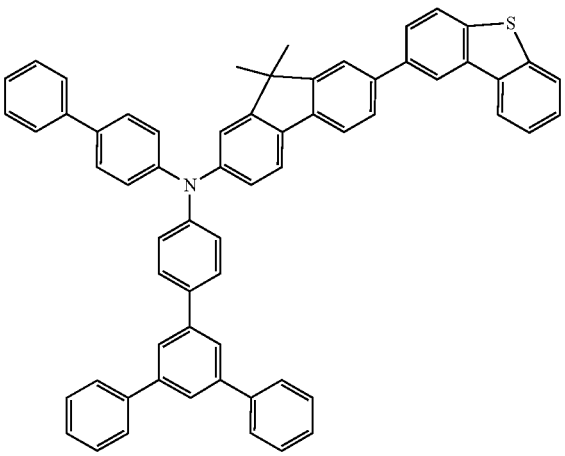

-continued

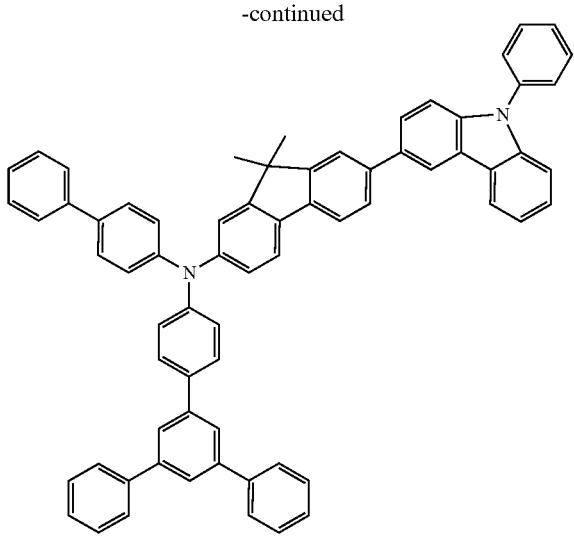

The aromatic amine derivative represented by the formula (I) of the present invention is useful as a material for an organic electroluminescence device.

It should be noted that a method of producing the aromatic amine derivative of the present invention is not particularly limited, and the derivative can be produced with reference to examples of the description by utilizing and applying a known method.

(Organic Electroluminescence Device)

Hereinafter, the structure of the organic EL device of the present invention is described.

Typical examples of the device structure of the organic EL device of the present invention may include, but not particularly limited to, the following structures (1) to (13). It should be noted that the device structure (8) is preferably used.

(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semiconductor layer/light emitting layer/adhesion improving layer/cathode
(8) Anode/hole injecting layer/hole transporting layer/light emitting layer/(electron transporting layer/)electron injecting layer/cathode
(9) Anode/insulating layer/light emitting layer/insulating layer/cathode
(10) Anode/inorganic semiconductor layer/insulating layer/light emitting layer/insulating layer/cathode
(11) Anode/organic semiconductor layer/insulating layer/light emitting layer/insulating layer/cathode
(12) Anode/insulating layer/hole injecting layer/hole transporting layer/light emitting layer/insulating layer/cathode
(13) Anode/insulating layer/hole injecting layer/hole transporting layer/light emitting layer/(electron transporting layer/)electron injecting layer/cathode An additional known light emitting material, doping material, hole injecting material, or electron injecting material as well as the aromatic amine derivative of the present invention can be used in the plurality of organic thin-film layers as required. Alternatively, the aromatic amine derivative of the present invention can be used as a doping material.

Reductions in the luminance and lifetime of the organic EL device due to quenching can be prevented by providing the organic thin-film layers with a multilayer structure. A light emitting material, a doping material, a hole injecting material, and an electron injecting material can be used in combination as required. In addition, the doping material enables the achievement of improvements in emission luminance and luminous efficiency, and of the emission of red or blue light.

In addition, each of the hole injecting layer, the light emitting layer, and the electron injecting layer may be formed of a layer construction having two or more layers. At that time, in the case of the hole injecting layer, a layer into which a hole is injected from an electrode is referred to as "hole injecting layer," and a layer that receives the hole from the hole injecting layer and transports the hole to the light emitting layer is referred to as "hole transporting layer." Similarly, in the case of the electron injecting layer, a layer into which an electron is injected from an electrode is referred to as "electron injecting layer," and a layer that receives the electron from the electron injecting layer and transports the electron to the light emitting layer is referred to as "electron transporting layer."

Each of those layers is selected and used in consideration of various factors such as the energy level of a material therefor, its heat resistance, and its adhesiveness with an organic layer or a metal electrode.

In addition, in the organic EL device of the present invention, the aromatic amine derivative of the present invention, which may be used in any one of the organic thin-film layers because the derivative hardly crystallizes, is preferably incorporated into the hole injecting layer or the hole transporting layer, more preferably incorporated into the hole transporting layer from the viewpoint of a reduction in the driving voltage of the organic EL device. The organic EL device using the aromatic amine derivative of the present invention is driven at a reduced voltage with high luminous efficiency and has a long device lifetime.

The content at which the aromatic amine derivative of the present invention is incorporated into one organic thin-film layer, preferably the hole injecting layer or the hole transporting layer is preferably 30 to 100 mol %, more preferably 50 to 100 mol %, still more preferably 80 to 100 mol %, particularly preferably substantially 100 mol % with respect to all components of the organic thin-film layer from the viewpoints of the driving voltage, luminous efficiency, and device lifetime of the organic EL device.

Hereinafter, each layer of the organic EL device of such a construction that the aromatic amine derivative of the present invention is incorporated into the hole transporting layer as a preferred embodiment is described.

(Substrate)

The organic EL device is generally prepared on a substrate having light-transmissive property. The substrate having light-transmissive property is the substrate which supports the organic EL device. It is preferred that the light-transmissive substrate have transmissive property which is a transmittance of light of 50% or more in the visible light region where the wavelength is 400 to 700 nm and still preferably be flat and smooth.

Examples of the light-transmissive substrate include a glass plate and a synthetic resin plate. In particular, examples of the glass plate include plates formed of soda-lime glass, glass containing barium and strontium, lead glass, aluminosilicate glass, borosilicate glass, barium borosilicate glass, and quartz. Further, examples of the synthetic resin plate include plates formed of a polycarbonate resin, an acrylic resin, a polyethylene terephthalate resin, a polyether sulfide resin, and a polysulfone resin.

(Anode)

The anode has a role in injecting holes to the hole transporting layer or the light emitting layer. It is effective that the anode has a work function of 4 eV or more (preferably 4.5 eV or more). A material for the anode used in the present invention is specifically exemplified by carbon, aluminum, vanadium, iron, cobalt, nickel, tungsten, silver, gold, platinum, palladium, and alloys thereof, metal oxides such as tin oxide and indium oxide used for an ITO substrate and an NESA substrate, and organic conductive resins such as polythiophene and polypyrrole.

The anode is obtained by forming a thin film with one of the materials for electrodes by, for example, a vapor deposition method or a sputtering method.

As described above, when light emitted from the light emitting layer is obtained through the anode, it is preferred that the anode have a transmittance of more than 10% with respect to the emitted light. It is also preferred that the sheet resistance of the anode be several hundred $\Omega/\square$ or less. The thickness of the anode is generally 10 nm to 1 µm, preferably 10 to 200 nm although the value varies depending on materials.

(Cathode)

As the cathode, a material such as a metal, an alloy, an electroconductive compound, or a mixture of those materials, which have a small work function (less than 4 eV) and are used as electrode materials, is used. Specific examples of the electrode material to be used include, but not particularly limited to, magnesium, calcium, tin, lead, titanium, yttrium, lithium, ruthenium, manganese, aluminum, lithium fluoride, and alloys thereof. Representative examples of the alloys include, but not particularly limited to, magnesium/silver, magnesium/indium, and lithium/aluminum. A ratio of the alloy components is controlled by, for example, the temperature of a vapor deposition source, an atmosphere, and a degree of vacuum, and an appropriate ratio is selected for the ratio. The anode and the cathode may each be formed of a layer construction having two or more layers, as required.

The cathode can be obtained by forming a thin film of the electrode material described above in accordance with a method such as vapor deposition or sputtering.

Here, when light emitted from the light emitting layer is obtained through the cathode, it is preferred that the cathode have a transmittance of more than 10% with respect to the emitted light. It is also preferred that the sheet resistivity of the cathode be several hundred $\Omega/\square$ or less. In addition, the thickness of the cathode is generally 10 nm to 1 µm, preferably 50 nm to 200 nm.

(Insulating Layer)

In addition, in general, defects in pixels are liable to be formed in organic EL devices due to leak and short circuit because an electric field is applied to ultra-thin films. In order to prevent the formation of the defects, an insulating layer formed of a thin-film layer having insulating property may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. It should be noted that a mixture or a laminate of those materials may be used.

(Light Emitting Layer)

The light emitting layer of the organic EL device has a combination of the following functions (1) to (3).

(1) The injecting function: the function that allows holes to be injected from the anode or the hole injecting layer and electrons to be injected from the cathode or the electron injecting layer when an electric field is applied.

(2) The transporting function: the function of transporting injected charges (i.e., electrons and holes) by the force of the electric field.

(3) The light emitting function: the function of providing the field for recombination of electrons and holes and leading the recombination to the emission of light.

Although the ease with which a hole is injected and the ease with which an electron is injected may differ from each other, and transporting abilities represented by the mobilities of a hole and an electron may vary in extent, one of the charges is preferably transferred.

A host material or a doping material which can be used in the light emitting layer is not particularly limited, and examples thereof include fused ring aromatic compounds and derivatives thereof, such as naphthalene, phananthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene, and 1,4-bis(9'-ethynylanthracenyl)benzene, organic metal complexes such as tris(8-quinolinolato)aluminum and bis-(2-methyl-8-quinolinolato)-4-(phenylphenolinato)aluminum, an arylamine derivative, a styrylamine derivative, a stilbene derivative, a coumarin derivative, a pyrane derivative, an oxazone derivative, a benzothiazole derivative, a benzoxazole derivative, a benzimidazole derivative, a pyrazine derivative, a cinnamate derivative, a diketopyrrolopyrrole derivative, an acridone derivative, and quinacridone derivative. Of those, an arylamine derivative and a styrylamine derivative are preferred from the viewpoints of the driving voltage, luminous efficiency, and device lifetime of the organic EL device, and a styrylamine derivative is more preferred.

(Hole Injecting Layer and Hole Transporting Layer)

The hole injecting layer and the hole transporting layer are layers which help injection of holes into the light emitting layer and transports the holes to the light emitting region. The layers each exhibit a great mobility of holes and, in general, have an ionization energy as small as 5.7 eV or less. As such hole injecting layer and hole transporting layer, a material which transports holes to the light emitting layer under an electric field of a smaller strength is preferred. A material which exhibits, for example, a mobility of holes of $10^{-4}$ $cm^2/V \cdot sec$ or more under application of an electric field of $10^4$ to $10^6$ V/cm is preferred.

As described above, the aromatic amine derivative of the present invention is particularly preferably used in the hole transporting layer.

When the aromatic amine derivative of the present invention is used in the hole transporting layer, the aromatic amine derivative of the present invention may be used alone or as a mixture with any other material for forming the hole transporting layer.

The other material which can be used as a mixture with the aromatic amine derivative of the present invention for forming the hole transporting layer is not particularly limited as long as the material has the preferred property. The material can be arbitrarily selected from materials which are conventionally used as hole transporting materials in photoconductive materials and known materials which are used for hole transporting layers in organic EL devices. In the description, a material that has a hole transporting ability and can be used in a hole transporting zone is referred to as "hole transporting material."

Specific examples of the other material for a hole transporting layer than the aromatic amine derivative of the present invention include, but not particularly limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, effective hole injecting materials, which are not particularly limited, are exemplified by an aromatic tertiary amine derivative and a phthalocyanine derivative, and an aromatic tertiary amine derivative is preferred.

Examples of the aromatic tertiary amine derivative include, but not particularly limited to: aromatic tertiary monoamine derivatives such as triphenylamine, tritolylamine, and tolyldiphenylamine; aromatic tertiary diamine derivatives such as N,N'-diphenyl-N,N'-(3-methylphenyl)-1,1'-biphenylyl-4,4'-diamine, N,N,N',N'-(4-methylphenyl)-1,1'-phenyl-4,4'-diamine, N,N,N',N'-(4-methylphenyl)-1,1'-biphenylyl-4,4'-diamine, N,N'-diphenyl-N,N'-dinaphthyl-1,1'-biphenylyl-4,4'-diamine, and N,N'-(methylphenyl)-N,N'-(4-n-butylphenyl)-phenanthrene-9,10-diamine; aromatic tertiary triamine derivatives such as N,N-bis(4-di-4-tolylaminophenyl)-4-phenyl-cyclohexane; aromatic tertiary tetraamine derivatives such as N,N'-diphenyl-N,N'-bis(4-diphenylamino)phenyl-1,1'-biphenylyl-4,4'-diamine; and an oligomer or a polymer having one of the aromatic tertiary amine skeletons. Of those, an aromatic tertiary tetraamine derivative is preferred from the viewpoints of the driving voltage, luminous efficiency, and device lifetime of the organic EL device.

Examples of the phthalocyanine (Pc) derivative as a hole injecting material include, but not limited to, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O—GaPc, and naphthalocyanine derivatives.

In addition, the organic EL device of the present invention preferably has formed therein a layer containing the aromatic tertiary amine derivative and/or the phthalocyanine derivative (the hole transporting layer or the hole injecting layer) between a light emitting layer and an anode.

A material for the hole injecting layer other than the aromatic tertiary amine derivative and the phthalocyanine derivative is not particularly limited as long as the material has the preferred properties. An arbitrary material selected from a material conventionally used as a hole injecting material in a photoconductive material and a known material used in the hole transporting layer of an organic EL device can be used. In the description, a material that has a hole injecting ability and can be used in a hole injection zone is referred to as "hole injecting material."

In the organic EL device of the present invention, a hexaazatriphenylene compound represented by the following formula (A) is also preferably used as a hole injecting material.

[Chem. 40]

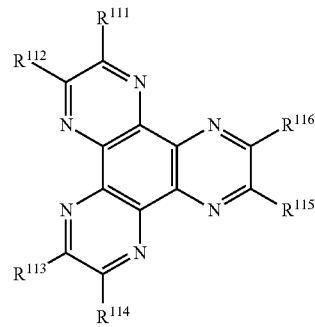

(A)

In the formula (A), $R^{111}$ to $R^{116}$ each independently represent a cyano group, —$CONH_2$, a carboxyl group, or —$COOR^{117}$ (where $R^{117}$ represents an alkyl group having 1 to 20 carbon atoms), or $R^{111}$ and $R^{112}$, $R^{113}$ and $R^{114}$, or $R^{115}$ and $R^{116}$ combine with each other to represent a group represented by —CO—O—CO—.

It should be noted that when $R^{111}$ to $R^{116}$ each represent a cyano group, —$CONH_2$, a carboxyl group, or —$COOR^{117}$, $R^{111}$ to $R^{116}$ preferably represent the same group. When $R^{111}$ and $R^{112}$, $R^{113}$ and $R^{114}$, or $R^{115}$ and $R^{116}$ combine with each other to represent a group represented by —CO—O—CO—, each of the pairs preferably represents a group represented by —CO—O—CO—.

In addition, $R^{111}$ to $R^{116}$ each preferably represent a cyano group from the viewpoints of the driving voltage, luminous efficiency, and device lifetime of the organic EL device.

(Electron Injecting Layer and Electron Transporting Layer)

Each of the electron injecting layer and the electron transporting layer is a layer which helps injection of electrons into the light emitting layer, transports the electrons to the light emitting region, and exhibits a great mobility of electrons. Further, the organic EL device may have a layer formed of a material exhibiting particularly improved adhesion with the cathode (adhesion improving layer) out of such electron injecting layers.

It is known that, in an organic EL device, emitted light is reflected by an electrode (cathode in this case), and hence emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. In particular, when the thickness of the electron transporting layer is large, an electron mobility is preferably at least $10^{-5}$ $cm^2/V \cdot s$ or more upon application of an electric field of $10^4$ to $10^6$ V/cm in order to avoid an increase in voltage.

Specific examples of the material to be used for the electron injecting layer include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the material is not particularly limited thereto. In addition, an electron-accepting substance can be added to the hole injecting material or an electron-donating substance can be added to the electron injecting material to thereby sensitize the hole injecting material or the electron injecting material, respectively.

In the organic EL device of the present invention, more effective electron injecting materials are a metal complex compound and a nitrogen-containing five-membered ring derivative.

Examples of the metal complex compound include, but not particularly limited to, 8-hydroxyquinolinatolithium, tris(8-hydroxyquinolinato)aluminum, and bis(2-methyl-8-quinolinato)(1-naphtholato)aluminum.

Examples of the nitrogen-containing five-membered ring derivative preferably include an oxazole derivative, a thiazole derivative, an oxadiazole derivative, a thiadiazole derivative, and a triazole derivative.

In the organic EL device of the present invention, the nitrogen-containing five-membered ring derivative is particularly preferably a benzimidazole derivative represented by any one of the following formulae (1) to (3).

[Chem. 41]

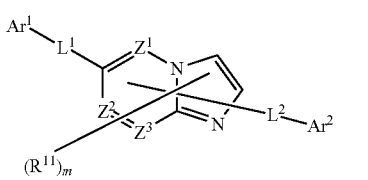
(1)

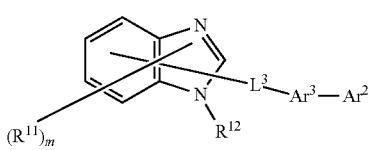
(2)

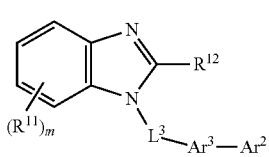
(3)

In the formulae (1) to (3), $Z^1$, $Z^2$, and $Z^3$ each independently represent a nitrogen atom or a carbon atom.

$R^{11}$ and $R^{12}$ each independently represent a substituted or unsubstituted aryl group having 6 to 60 ring carbon atoms, a substituted or unsubstituted heteroaryl group having 5 to 60 ring atoms, an alkyl group having 1 to 20 carbon atoms, an alkyl group having 1 to 20 carbon atoms and substituted with a halogen atom, or an alkoxy group having 1 to 20 carbon atoms.

m represents an integer of 0 to 5, and when m represents an integer of 2 or more, a plurality of $R^{11}$'s may be identical to or different from each other. In addition, a plurality of $R^{11}$'s adjacent to each other may be bonded to each other to form a substituted or unsubstituted aromatic hydrocarbon ring. Examples of the substituted or unsubstituted aromatic hydrocarbon ring which the plurality of $R^{11}$'s adjacent to each other are bonded to each other to represent when m represents an integer of 2 or more include a benzene ring, a naphthalene ring, and an anthracene ring.

$Ar^1$ represents a substituted or unsubstituted aryl group having 6 to 60 ring carbon atoms, or a substituted or unsubstituted heteroaryl group having 5 to 60 ring atoms.

$Ar^2$ represents a hydrogen atom, an alkyl group having 1 to 20 carbon atoms, an alkyl group having 1 to 20 carbon atoms and substituted with a halogen atom, an alkoxy group having 1 to 20 carbon atoms, a substituted or unsubstituted aryl group having 6 to 60 ring carbon atoms, or a substituted or unsubstituted heteroaryl group having 5 to 60 ring atoms.

At least one (preferably one) of $Ar^1$ and $Ar^2$ preferably represents a substituted or unsubstituted aryl group having 10 to 50 ring carbon atoms, or a substituted or unsubstituted heteroaryl group having 9 to 50 ring atoms.

$Ar^3$ represents a substituted or unsubstituted arylene group having 6 to 60 ring carbon atoms, or a substituted or unsubstituted heteroarylene group having 5 to 60 ring atoms.

$L^1$, $L^2$, and $L^3$ each independently represent a single bond, a substituted or unsubstituted arylene group having 6 to 60 ring carbon atoms, a substituted or unsubstituted heterofused ring group having 9 to 60 ring atoms, or a substituted or unsubstituted fluorenylene group.

In the organic EL device of the present invention, a light emitting material, a doping material, a hole injecting material, or an electron injecting material may be incorporated into the layer containing the aromatic amine derivative of the present invention.

In addition, the surface of the organic EL device obtained by the present invention can be provided with a protective layer, or the entirety of the device can be protected with silicone oil, a resin, or the like from the viewpoint of an improvement in the stability of the device against a temperature, a humidity, an atmosphere, or the like.

Any one of dry film forming methods such as vacuum deposition, sputtering, plasma, and ion plating, and wet film forming methods such as spin coating, dipping, and flow coating is applicable to the formation of each layer of the organic EL device of the present invention.

The thickness of each layer is not particularly limited, but may be set to an appropriate thickness as an organic EL device. An excessively large thickness requires an increased applied voltage for obtaining certain optical output, resulting in poor efficiency. An excessively small thickness causes a pin hole or the like, with the result that sufficient emission luminance cannot be obtained even when an electric field is applied. In general, the thickness is in the range of preferably 5 nm to 10 μm, more preferably 10 nm to 0.2 μm.

In the case of a wet film forming method, a material for forming each layer is dissolved or dispersed into an appropriate solvent such as ethanol, chloroform, tetrahydrofuran, or dioxane, to thereby form a thin film. At that time, any one of the solvents may be used.

An organic EL material-containing solution containing the aromatic amine derivative of the present invention as an organic EL material and a solvent can be used as a solution suitable for such wet film forming method. In addition, an appropriate resin or additive may be used in each of the organic thin-film layers for, for example, improving film formability or preventing a pin hole in the layer. Examples of the resin include: insulating resins such as polystyrene, polycarbonate, polyallylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. In addition, examples of the additive include an antioxidant, a UV absorber, and a plasticizer.

EXAMPLES

Hereinafter, the present invention is specifically described by way of examples. However, the present invention is by no means limited by these examples.

It should be noted that the structures of intermediates synthesized in Synthesis Examples 1 to 23 below are as shown below.
[Chem. 42]
Intermediate-1
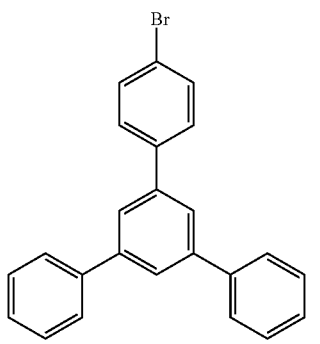
Intermediate-2
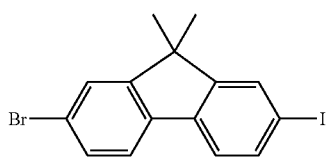
Intermediate-3
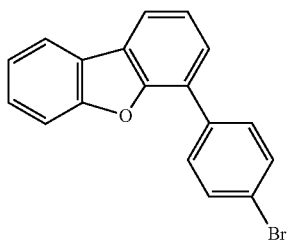
Intermediate-4
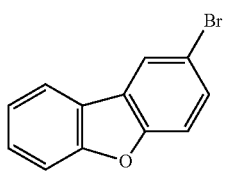
Intermediate-5
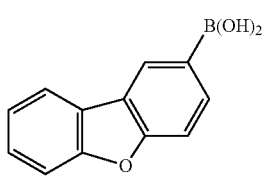
Intermediate-6
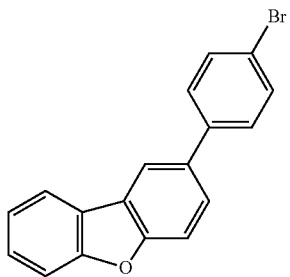
Intermediate-7
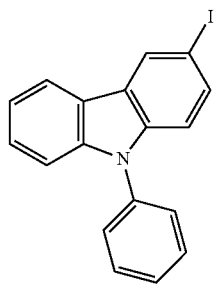
Intermediate-8
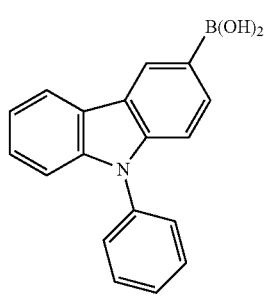
Intermediate-9
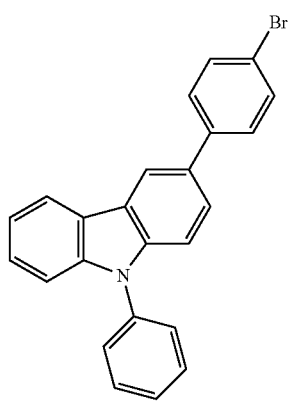
Intermediate-10
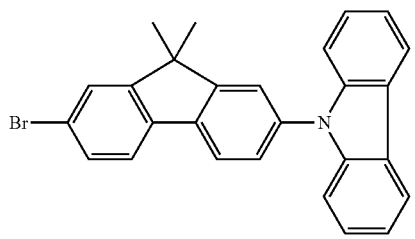
Intermediate-11
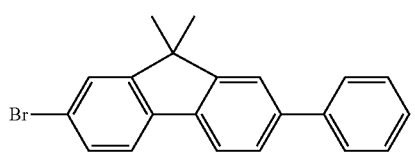

Intermedaite-12
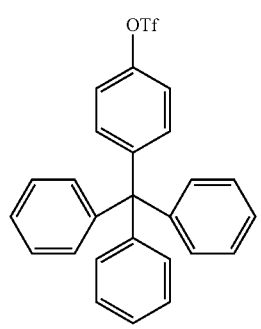
Intermediate-15
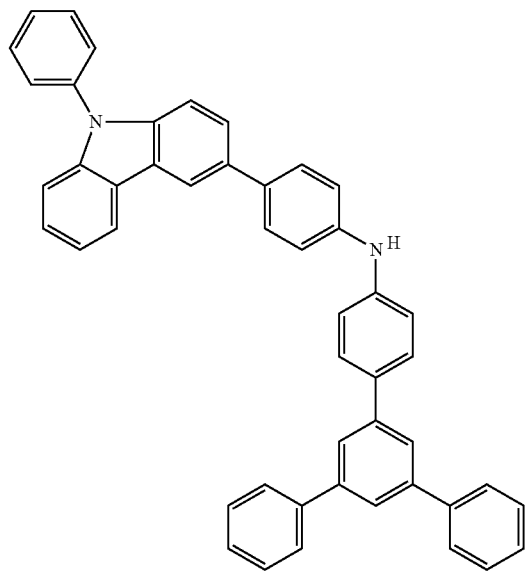
Intermediate-13
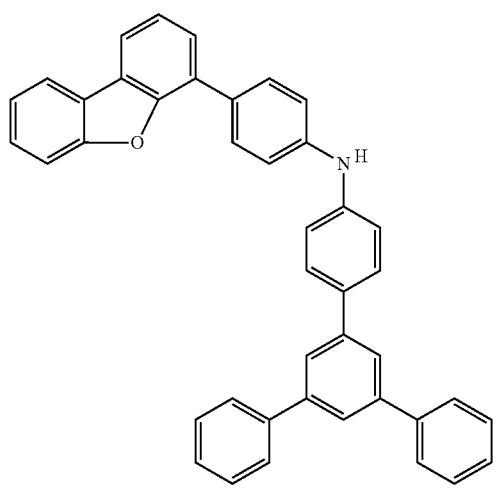
Intermediate-16
Intermediate-14
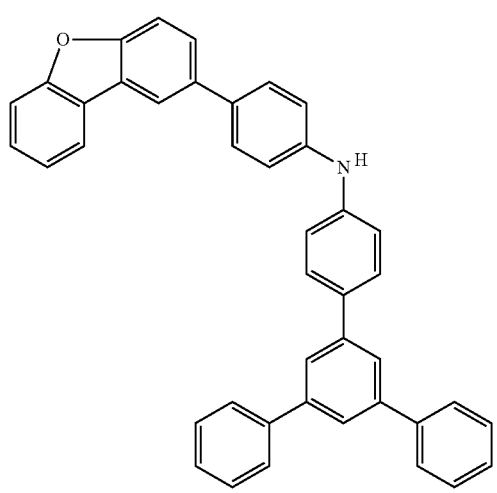
Intermediate-17
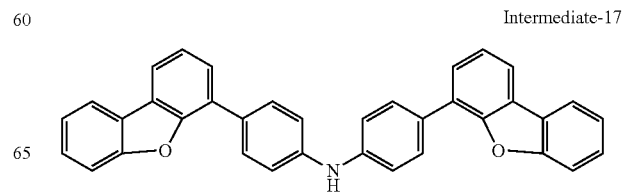

[Chem. 43]

Intermediate-13

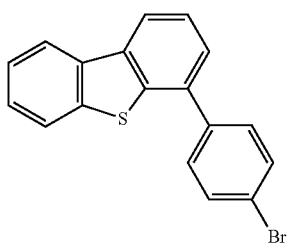

Intermediate-14

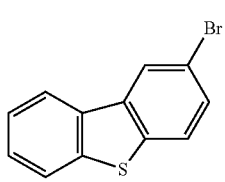

Intermediate-15

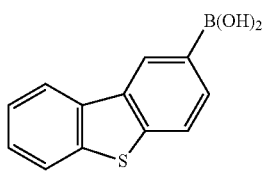

Intermediate-16

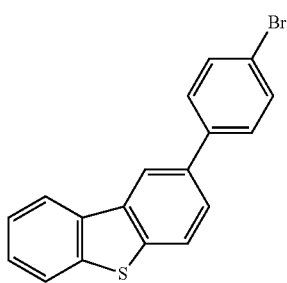

Intermediate-17

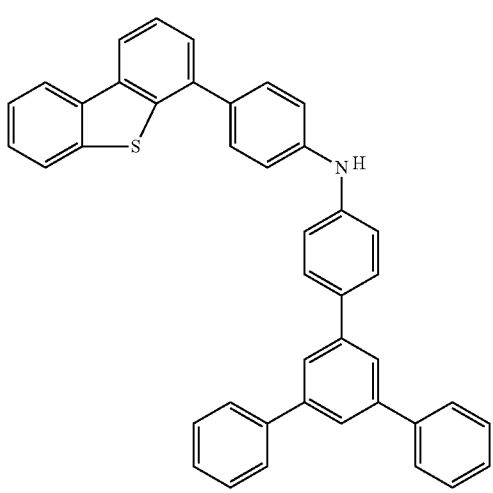

Intermediate-18

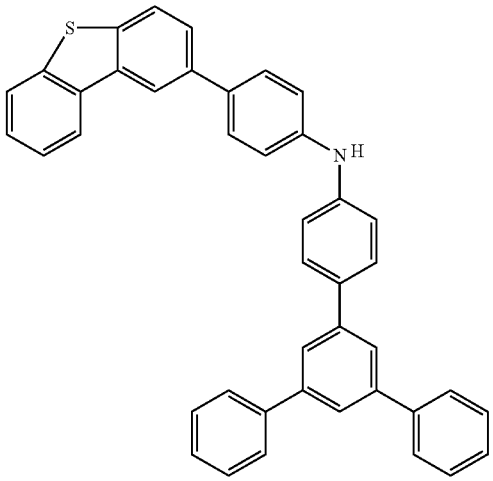

Synthesis Example 1

Synthesis of Intermediate 1

Under an argon atmosphere, 1,200 mL of toluene and 650 mL of a 2 mol/L aqueous solution of sodium carbonate were added to 70 g of 1,3,5-tribromobenzene, 54 g of phenylboronic acid, and 10.2 g of tetrakis(triphenylphosphine)palladium, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 23.9 g of a white crystal were obtained. The white crystal was identified as 3,5-diphenyl-1-bromobenzene by field desorption mass spectral (hereinafter referred to as "FD-MS") analysis.

Under an argon atmosphere, 250 mL of anhydrous tetrahydrofuran were added to 23.9 g of 3,5-diphenyl-1-bromobenzene, and then the mixture was stirred at −40° C. During the stirring, 60 mL of a 1.6 mol/L solution of n-butyllithium in hexane were added to the mixture. The reaction solution was stirred for 1 hour while being heated to 0° C. The reaction solution was cooled to −78° C. again, and then a solution of 43.6 g of triisopropyl borate in 50 mL of anhydrous tetrahydrofuran was dropped to the solution. The reaction solution was stirred at room temperature for 5 hours. 200 mL of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 14.8 g of a solid were obtained. The solid was identified as 3,5-diphenylphenylboronic acid by FD-MS analysis.

Under an argon atmosphere, 300 mL of toluene and 80 mL of an aqueous solution of sodium carbonate having a concentration of 2 M were added to 16.1 g of 4-bromoiodobenzene, 14.8 g of 3,5-diphenylphenylboronic acid, and 1.3 g of tetrakis(triphenylphosphine)palladium(0), and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 12.5 g of a white crystal were obtained. The white crystal was identified as the intermediate 1 by FD-MS analysis.

Synthesis Example 2

Synthesis of Intermediate 2

In a stream of argon, 23 g of iodine, 9.4 g of periodic acid dihydrate, 42 mL of water, 360 mL of acetic acid, and 11 mL of sulfuric acid were added to 55 g of 2-bromo-9,9-dimethylfluorene, and the mixture was stirred at 65° C. for 30 minutes and was then subjected to a reaction at 90° C. for 6 hours. The reactant was poured into ice water, followed by filtering. The resultant was washed with water, and then washed with methanol, whereby 61 g of a white powder were obtained. The white powder was identified as the intermediate 2 by FD-MS analysis.

Synthesis Example 3

Synthesis of Intermediate 3

Under an argon atmosphere, 300 mL of toluene and 150 mL of a 2 mol/L aqueous solution of sodium carbonate were added to 28.3 g of 4-iodobromobenzene, 22.3 g of dibenzofuran-4-boronic acid, and 2.31 g of tetrakis(triphenylphosphine)palladium, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 26.2 g of a white crystal were obtained. The white crystal was identified as the intermediate 3 by FD-MS analysis.

Synthesis Example 4

Synthesis of Intermediate 4

Under a nitrogen atmosphere, 1 L of acetic acid was added to 150 g of dibenzofuran, and then the contents were dissolved under heat. 188 g of bromine were dropped to the solution while the solution was occasionally water cooled. After that, the mixture was stirred for 20 hours under air cooling. The precipitated crystal was separated by filtration, and was then sequentially washed with acetic acid and water. The washed crystal was dried under reduced pressure. The resultant crystal was purified by distillation under reduced pressure, and was then repeatedly recrystallized with methanol several times. Thus, 66.8 g of a solid was obtained. The solid was identified as an intermediate-4 by FD-MS analysis.

Synthesis Example 5

Synthesis of Intermediate-5

Under an argon atmosphere, 400 mL of anhydrous THF were 24.7 g of the intermediate 4, and then 63 mL of a 1.6 mol/L solution of n-butyllithium in hexane were added to the mixture during the stirring of the mixture at –40° C. The reaction solution was stirred for 1 hour while being heated to 0° C. The reaction solution was cooled to –78° C. again, and then a solution of 26.0 g of trimethyl borate in 50 mL of anhydrous tetrahydrofuran was dropped to the solution. The reaction solution was stirred at room temperature for 5 hours. 200 mL of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 15.2 g of a solid was obtained. The solid was identified as the intermediate 5 by FD-MS analysis.

Synthesis Example 6

Synthesis of Intermediate 6

A reaction was performed in the same manner as in Synthesis Example 3 except that 22.3 g of the intermediate 5 was used instead of dibenzofuran-4-boronic acid. As a result, 23.1 g of a white powder were obtained. The white powder was identified as the intermediate 6 by FD-MS analysis.

Synthesis Example 7

Synthesis of Intermediate 7

5.90 mL of sulfuric acid, and ethanol were added to 17.7 g of 9-phenylcarbazole, 6.03 g of potassium iodide, and 7.78 g of potassium iodate, and then the mixture was subjected to a reaction at 75° C. for 2 hours.

After the resultant had been cooled, water and ethyl acetate were added to perform separation and extraction. After that, the organic layer was washed with baking soda water and water, and was then concentrated. The resultant coarse product was purified by silica gel chromatography (developing solvent: toluene), and then the resultant solid was dried under reduced pressure. Thus, 21.8 g of a white solid were obtained. The white solid was identified as the intermediate 7 by FD-MS analysis.

Synthesis Example 8

Synthesis of Intermediate 8

In a stream of argon, dry toluene and dry ether were added to 13.1 g of the intermediate 7, and then the mixture was cooled to –45° C. 25 mL of a solution (1.58 mol/L) of n-butyllithium in hexane were dropped to the mixture, and then the temperature was increased to –5° C. over 1 hour while the mixture was stirred. The mixture was cooled to –45° C. again, and then 25 mL of boronic acid triisopropyl ester were slowly dropped to the mixture. After that, the mixture was subjected to a reaction for 2 hours.

After the temperature of the resultant had been returned to room temperature, a 10% diluted hydrochloric acid solution was added to the resultant, and then the mixture was stirred so that an organic layer was extracted. After having been washed with a saturated salt solution, the organic layer was dried with anhydrous magnesium sulfate and separated by filtration. After that, the separated product was concentrated. The resultant solid was purified by silica gel chromatography (developing solvent: toluene), and then the resultant solid was washed with n-hexane and dried under reduced pressure. Thus, 7.10 g of a solid were obtained. The solid was identified as the intermediate 8 by FD-MS analysis.

Synthesis Example 9

Synthesis of Intermediate 9

Under an argon atmosphere, 300 mL of toluene and 150 mL of a 2 mol/L aqueous solution of sodium carbonate were added to 28.3 g of 4-iodobromobenzene, 30.1 g of the intermediate 8, and 2.31 g of tetrakis(triphenylphosphine)palladium, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 20.2 g of a white crystal were obtained. The white crystal was identified as the intermediate 9 by FD-MS analysis.

Synthesis Example 10

Synthesis of Intermediate 10

Under an argon atmosphere, 2 mL of trans-1,2-cyclohexanediamine and 300 mL of 1,4-dioxane were added to 40.0 g of the intermediate 2, 16.7 g of carbazole, 0.2 g of copper iodide (CuI), and 42.4 g of tripotassium phosphate, and then the mixture was stirred at 100° C. for 20 hours.

Immediately after the completion of the reaction, 300 mL of water was added to the resultant, the mixture was filtrated, and then the aqueous layer was removed. The organic layer was dried with sodium sulfate, and was then concentrated. The residue was purified by silica gel column chromatography. Thus, 24.1 g of a white crystal were obtained. The white crystal was identified as the intermediate 10 by FD-MS analysis.

Synthesis Example 11

Synthesis of Intermediate 11

Under an argon atmosphere, 300 mL of toluene and 150 mL of a 2 mol/L aqueous solution of sodium carbonate were added to 40.0 g of the intermediate 2, 12.8 g of phenylboronic acid, and 2.31 g of tetrakis(triphenylphosphine)palladium, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 19.7 g of a white crystal were obtained. The white crystal was identified as the intermediate 11 by FD-MS analysis.

Synthesis Example 12

Synthesis of Intermediate 12

Under an argon atmosphere, 33.6 g of 4-triphenylmethylphenol were dissolved in 300 mL of dichloromethane, 30.0 g of trifluoromethanesulfonic anhydride and 30.4 g of triethylamine were added to the solution, and then the mixture was stirred for 3 hours.

After the completion of the reaction, 300 mL of water were added to the resultant. After that, the mixture was separated, and then the aqueous layer was removed. The organic layer was dried with sodium sulfate, and was then concentrated. The residue was purified by silica gel column chromatography. Thus, 37.5 g of a white crystal were obtained. The white crystal was identified as the intermediate 12 by FD-MS analysis.

Synthesis Example 13

Synthesis of intermediate 13

In a stream of argon, 5.9 g of acetamide, 32.3 g of the intermediate 3, 2.70 g of copper iodide, 40.8 g of potassium carbonate, 6.3 g of N'N-dimethylethylenediamine, and 300 mL of xylene were loaded, and then the mixture was subjected to a reaction at 175° C. for 19 hours. Further, 38.5 g of the intermediate 1 were loaded into the resultant, and then the mixture was subjected to a reaction at 175° C. for 19 hours.

After the resultant had been cooled, water was added so that the resultant was filtrated. The residue was washed with acetone, methanol, and water three times each. Thus, 28.4 g of an acetamide body of the intermediate 13 were obtained.

28.4 g of the acetamide body of the intermediate 13, 26.3 g of potassium hydroxide, 25 mL of water, and 40 mL of xylene were loaded, and then the mixture was subjected to a reaction at 175° C. for 5 hours.

After the resultant had been cooled, water was added so that the resultant was filtrated. The residue was washed with acetone, methanol, and water three times each, and was then purified with a short column (developing solvent:toluene). The resultant solid was washed with n-hexane and dried under reduced pressure. Thus, 16.6 g of a white solid were obtained. The white solid was identified as the intermediate 13 by FD-MS analysis.

Synthesis Example 14

Synthesis of Intermediate 14

Reactions were performed in the same manner as in Synthesis Example 13 except that 32.3 g of the intermediate 6 were used instead of the intermediate 3. Thus, 15.2 g of a white powder were obtained. The white powder was identified as the intermediate 14 by FD-MS analysis.

Synthesis Example 15

Synthesis of Intermediate 15

Reactions were performed in the same manner as in Synthesis Example 13 except that 39.8 g of the intermediate 9 were used instead of the intermediate 3. Thus, 18.2 g of a white powder were obtained. The white powder was identified as the intermediate 15 by FD-MS analysis.

Synthesis Example 16

Synthesis of Intermediate 16

Reactions were performed in the same manner as in Synthesis Example 13 except that 39.8 g of the intermediate 10 were used instead of the intermediate 3. Thus, 21.8 g of a white powder were obtained. The white powder was identified as the intermediate 16 by FD-MS analysis.

Synthesis Example 17

Synthesis of Intermediate 17

Reactions were performed in the same manner as in Synthesis Example 13 except that: 64.6 g of the intermediate 3 were used; and the intermediate 1 was not used. Thus, 22.4 g of a white powder were obtained. The white powder was identified as the intermediate 17 by FD-MS analysis.

Synthesis Example 18

Synthesis of Intermediate 18

A reaction was performed in the same manner as in Synthesis Example 3 except that 24.0 g of dibenzothiophene-4-boronic acid were used instead of dibenzofuran-4-boronic acid. Thus, 27.5 g of a white powder were obtained. The white powder was identified as the intermediate 18 by FD-MS analysis.

Synthesis Example 19

Synthesis of Intermediate 19

Reactions were performed in the same manner as in Synthesis Example 4 except that 16.4 g of dibenzothiophene were used instead of dibenzofuran. Thus, 70 g of a white powder were obtained. The powder was identified as the intermediate 19 by FD-MS analysis.

Synthesis Example 20

Synthesis of Intermediate 20

Reactions were performed in the same manner as in Synthesis Example 5 except that 26.3 g of the intermediate 19 were used instead of the intermediate 4. Thus, 16.5 g of a white powder were obtained. The white powder was identified as the intermediate 20 by FD-MS analysis.

Synthesis Example 21

Synthesis of Intermediate 21

A reaction was performed in the same manner as in Synthesis Example 3 except that 24.0 g of the intermediate 20 were used instead of dibenzofuran-4-boronic acid. Thus, 24.2 g of a white powder were obtained. The white powder was identified as the intermediate 21 by FD-MS analysis.

Synthesis Example 22

Synthesis of Intermediate 22

Reactions were performed in the same manner as in Synthesis Example 13 except that 33.9 g of the intermediate 18 were used instead of the intermediate 3. Thus, 16.4 g of a white powder were obtained. The white powder was identified as the intermediate 22 by FD-MS analysis.

Synthesis Example 23

Synthesis of Intermediate 23

Reactions were performed in the same manner as in Synthesis Example 13 except that 33.9 g of the intermediate 21 were used instead of the intermediate 3. Thus, 16.2 g of a white powder were obtained. The white powder was identified as the intermediate 23 by FD-MS analysis.

Shown below are the structures of the aromatic amine derivatives of the present invention produced in Synthesis Embodiments 1 to 32 below.

[Chem. 44]

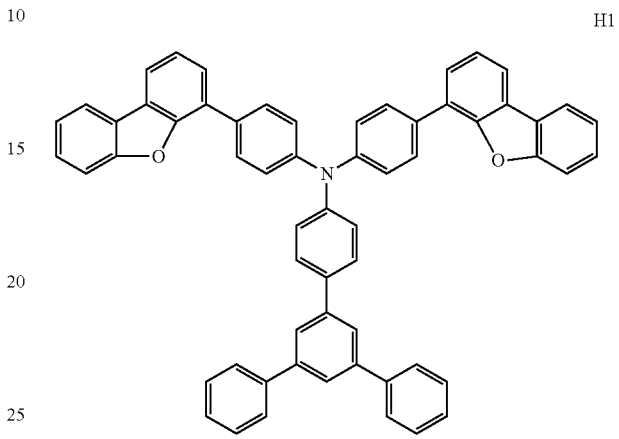

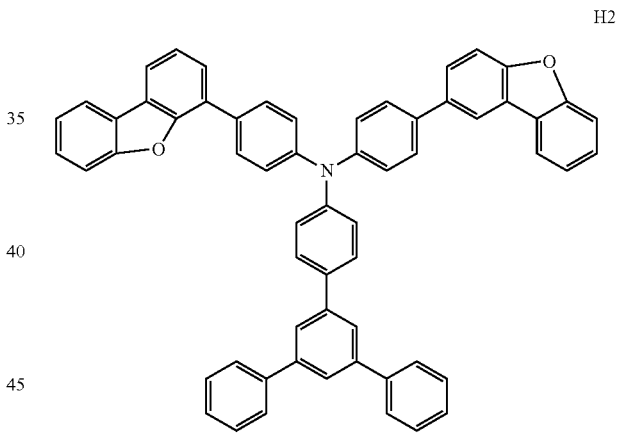

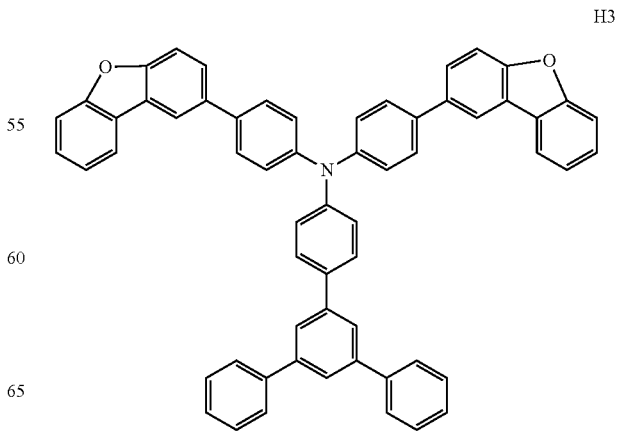

175
-continued
H4
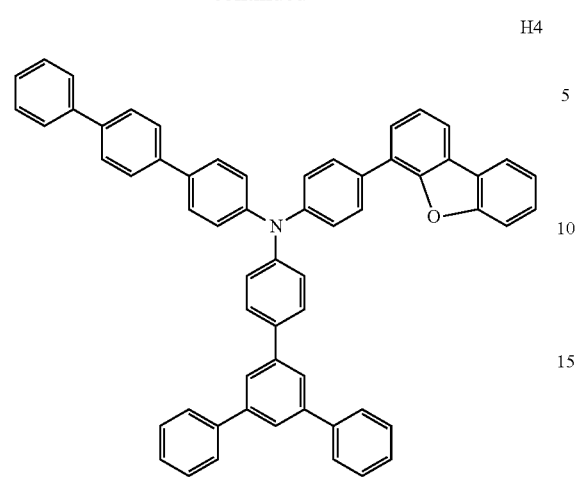
H5
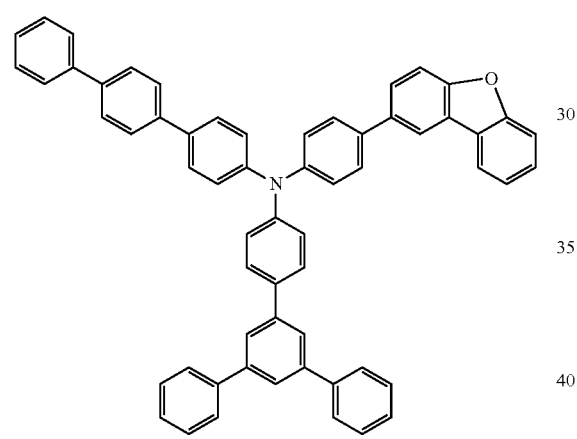
H6
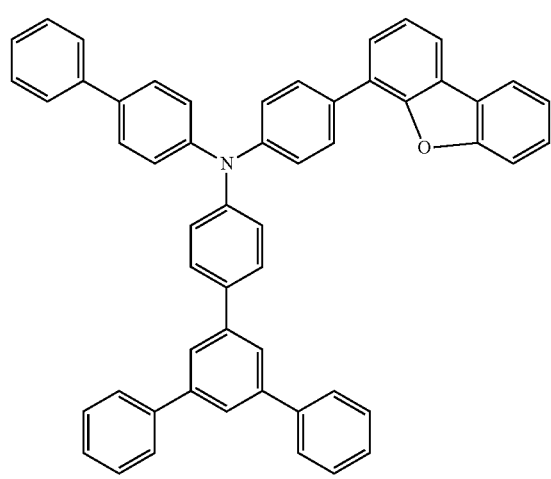
176
-continued
H7
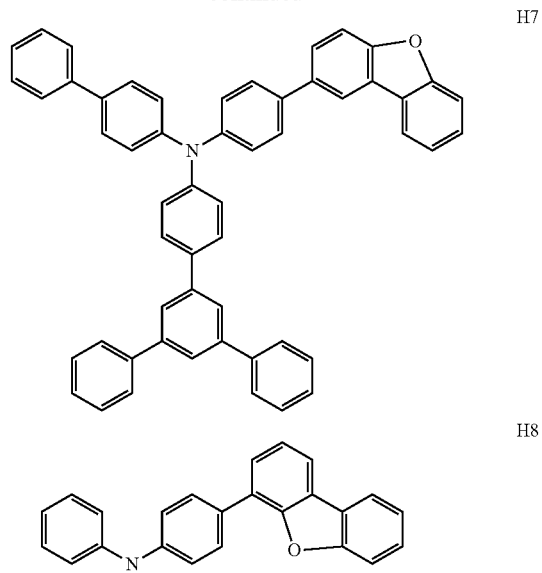
H8
H9
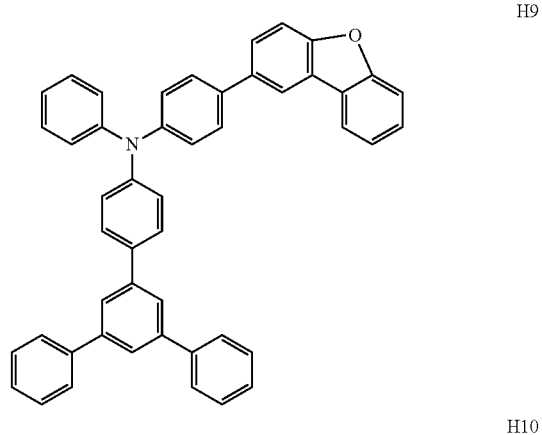
H10
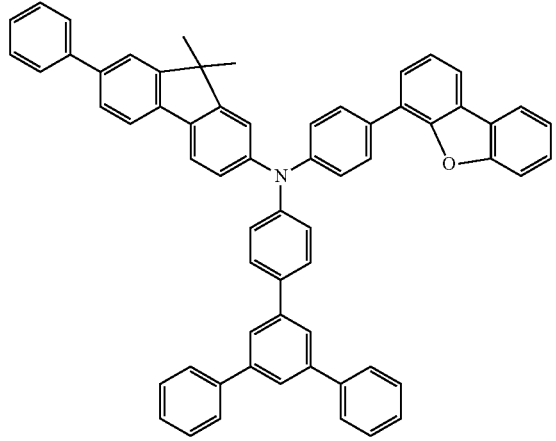

H11
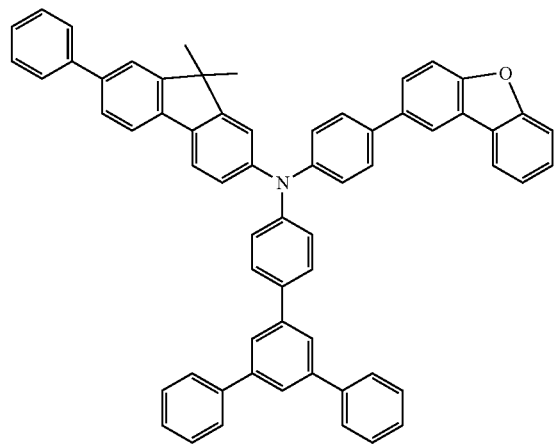
H12
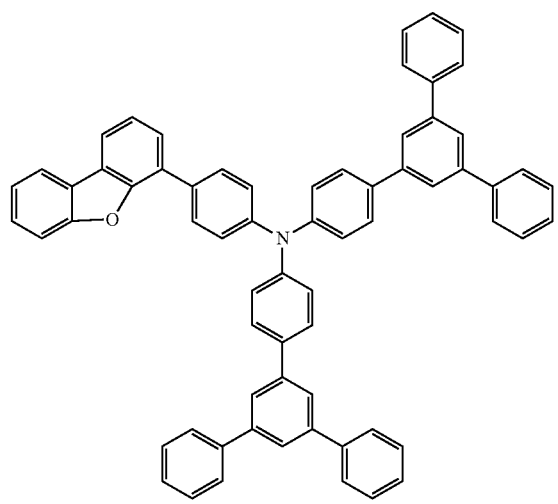
H13
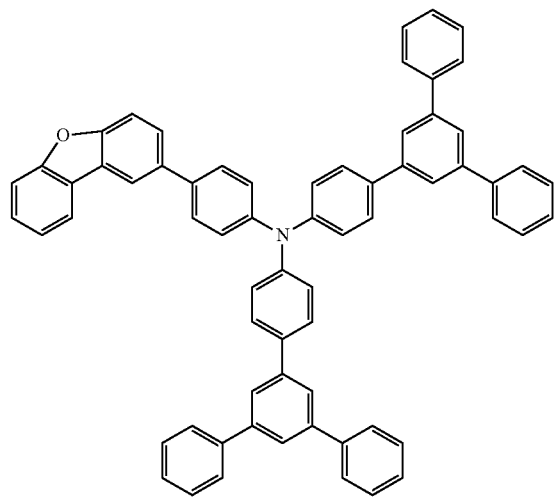
H14
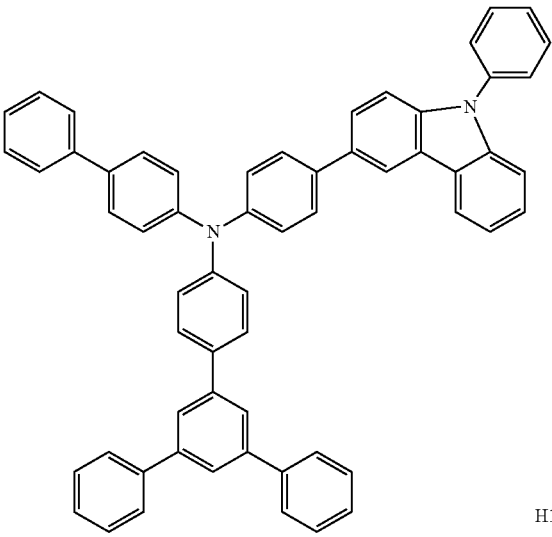
H15
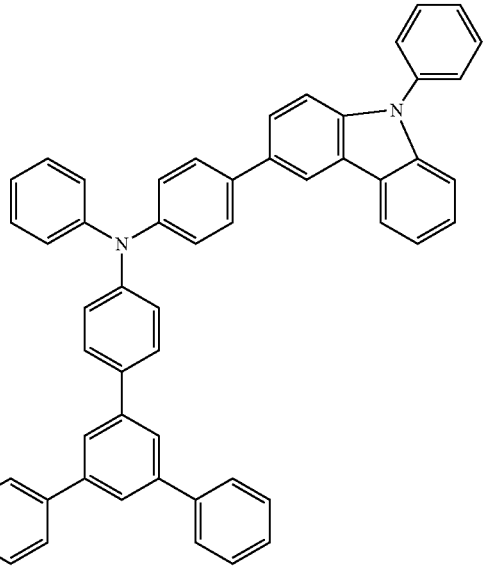
[Chem. 45]
H16
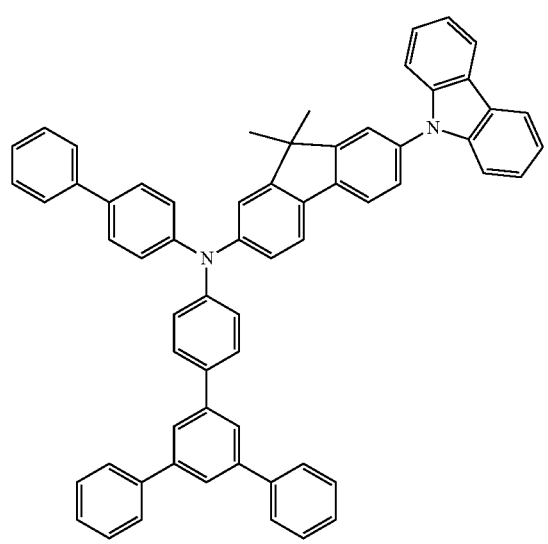

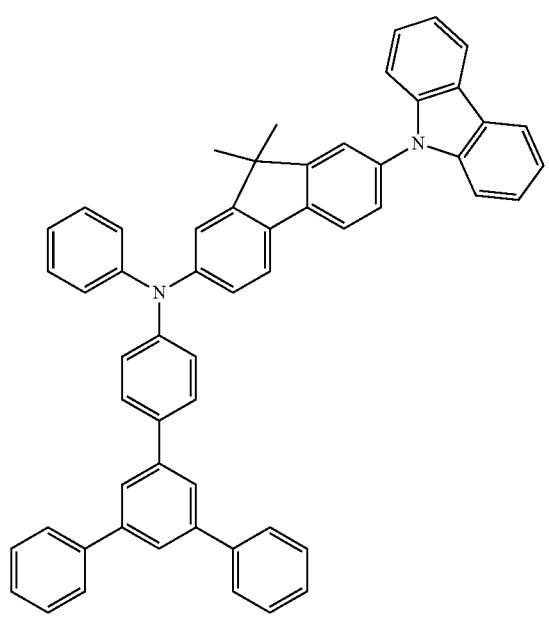
H17
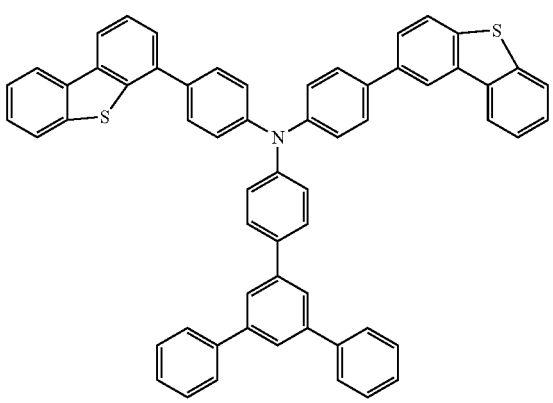
H20
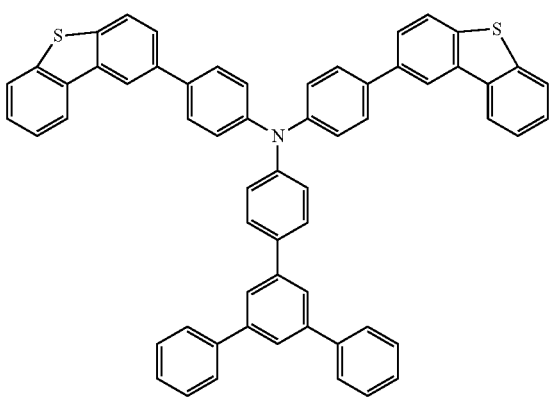
H21
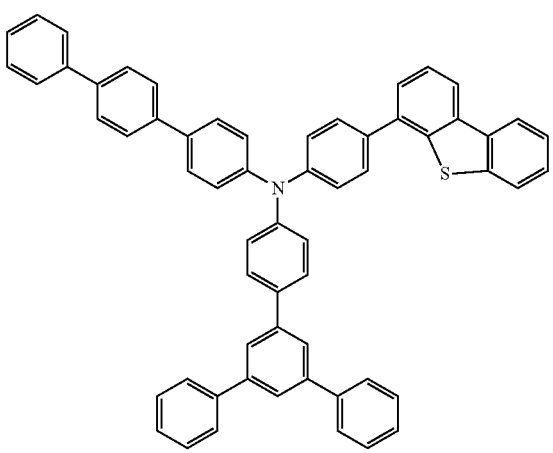
H22

H23
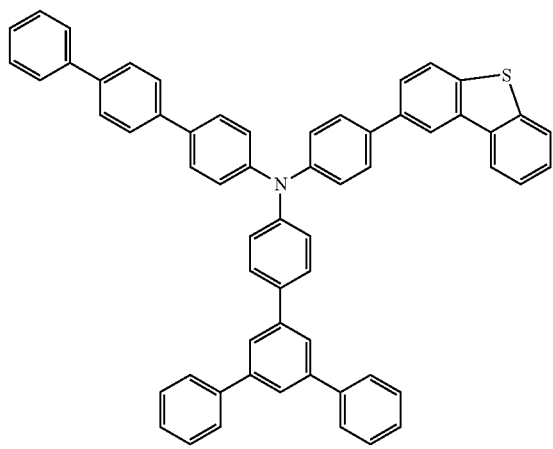
H24
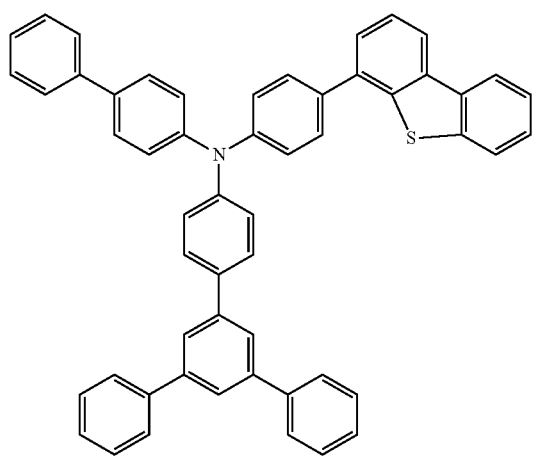
H25
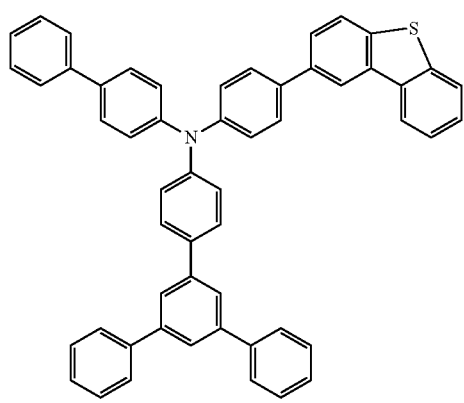
H26
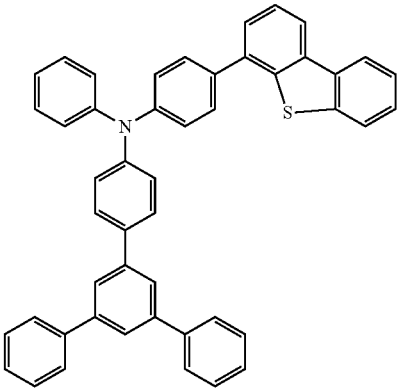
H27
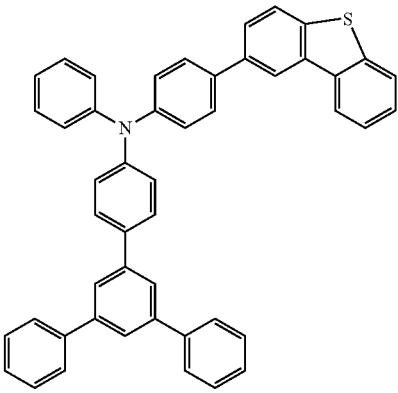
H28
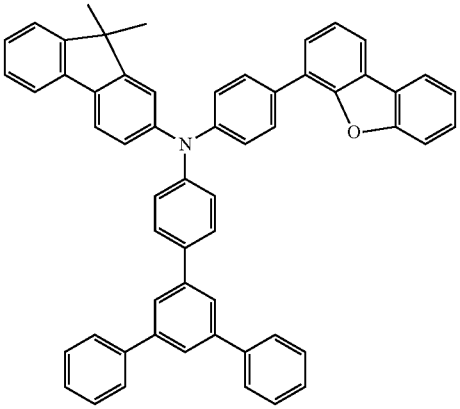
H29
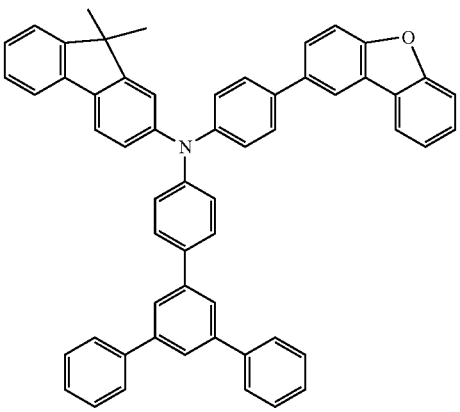

-continued

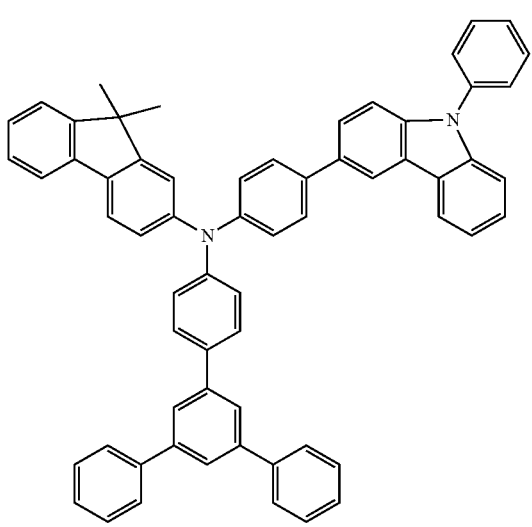

[Chem. 46]

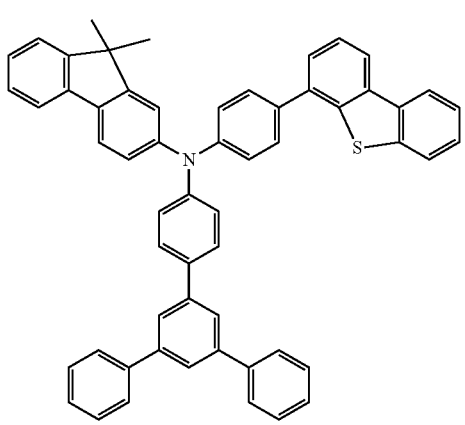

Synthesis Embodiment 1

Production of Aromatic Amine Derivative (H1)

In a stream of argon, 5.6 g of the intermediate 13, 3.2 g of the intermediate 3, 1.3 g of t-butoxy sodium (manufactured by Hiroshima Wako Ltd.), 46 mg of tris(dibenzylideneacetone)dipalladium (manufactured by Sigma-Aldrich, Inc), 21 mg of tri-t-butylphosphine, and 50 mL of dry toluene were loaded, and then the mixture was subjected to a reaction at 80° C. for 8 hours.

After having been cooled, 500 mL of water were added, and then the mixture was subjected to celite filtration. The filtrate was extracted with toluene and dried with anhydrous magnesium sulfate. The dried product was concentrated under reduced pressure, and then the resultant coarse product was subjected to column purification. The purified product was recrystallized with toluene, and then the recrystallized product was taken by filtration. After that, the resultant was dried. Thus, 5.6 g of a pale yellow powder were obtained. The pale yellow powder was identified as the aromatic amine derivative (H1) by FD-MS analysis.

Synthesis Embodiment 2

Production of Aromatic Amine Derivative (H2)

A reaction was performed in the same manner as in Synthesis Embodiment 1 except that 3.2 g of the intermediate 6 were used instead of the intermediate 3. Thus, 5.3 g of a pale yellow powder were obtained. The pale yellow powder was identified as the aromatic amine derivative (H2) by FD-MS analysis.

Synthesis Embodiment 3

Production of Aromatic Amine Derivative (H3)

A reaction was performed in the same manner as in Synthesis Embodiment 1 except that: 5.6 g of the intermediate 14 were used instead of the intermediate 13; and 3.2 g of the intermediate 6 were used instead of the intermediate 3. Thus, 5.5 g of a pale yellow powder were obtained. The pale yellow powder was identified as the aromatic amine derivative (H3) by FD-MS analysis.

Synthesis Embodiment 4

Production of Aromatic Amine Derivative (H4)

A reaction was performed in the same manner as in Synthesis Embodiment 1 except that 3.1 g of 4-bromo-p-terphenyl were used instead of the intermediate 3. Thus, 5.8 g of a pale yellow powder were obtained. The pale yellow powder was identified as the aromatic amine derivative (H4) by FD-MS analysis.

Synthesis Embodiment 5

Production of Aromatic Amine Derivative (H5)

A reaction was performed in the same manner as in Synthesis Embodiment 1 except that: 5.6 g of the intermediate 14 were used instead of the intermediate 13; and 3.1 g of 4-bromo-p-terphenyl were used instead of the intermediate 3. Thus, 5.1 g of a pale yellow powder were obtained. The pale yellow powder was identified as the aromatic amine derivative (H5) by FD-MS analysis.

Synthesis Embodiment 6

Production of Aromatic Amine Derivative (H6)

A reaction was performed in the same manner as in Synthesis Embodiment 1 except that 2.3 g of 4-bromobiphenyl were used instead of the intermediate 3. Thus, 5.1 g of a pale yellow powder were obtained. The pale yellow powder was identified as the aromatic amine derivative (H6) by FD-MS analysis.

Synthesis Embodiment 7

Production of Aromatic Amine Derivative (H7)

A reaction was performed in the same manner as in Synthesis Embodiment 1 except that: 5.6 g of the intermediate 14 were used instead of the intermediate 13; and 2.3 g of 4-bromobiphenyl were used instead of the intermediate 3. Thus, 4.7 g of a pale yellow powder were obtained. The pale yellow powder was identified as the aromatic amine derivative (H7) by FD-MS analysis.

Synthesis Embodiment 8

Production of Aromatic Amine Derivative (H8)

A reaction was performed in the same manner as in Synthesis Embodiment 1 except that 1.6 g of bromobenzene were used instead of the intermediate 3. Thus, 4.5 g of a pale yellow powder were obtained. The pale yellow powder was identified as the aromatic amine derivative (H8) by FD-MS analysis.

Synthesis Embodiment 9

Production of Aromatic Amine Derivative (H9)

A reaction was performed in the same manner as in Synthesis Embodiment 1 except that: 5.6 g of the intermediate 14 were used instead of the intermediate 13; and 1.6 g of bromobenzene were used instead of the intermediate 3. Thus, 4.0 g of a pale yellow powder were obtained. The pale yellow powder was identified as the aromatic amine derivative (H9) by FD-MS analysis.

Synthesis Embodiment 10

Production of Aromatic Amine Derivative (H10)

A reaction was performed in the same manner as in Synthesis Embodiment 1 except that 3.5 g of the intermediate 11 were used instead of the intermediate 3. Thus, 6.0 g of a pale yellow powder were obtained. The pale yellow powder was identified as the aromatic amine derivative (H10) by FD-MS analysis.

Synthesis Embodiment 11

Production of Aromatic Amine Derivative (H11)

A reaction was performed in the same manner as in Synthesis Embodiment 1 except that: 5.6 g of the intermediate 14 were used instead of the intermediate 13; and 3.5 g of the intermediate 11 were used instead of the intermediate 3. Thus, 5.7 g of a pale yellow powder were obtained. The pale yellow powder was identified as the aromatic amine derivative (H11) by FD-MS analysis.

Synthesis Embodiment 12

Production of Aromatic Amine Derivative (H12)

A reaction was performed in the same manner as in Synthesis Embodiment 1 except that 3.9 g of the intermediate 1 were used instead of the intermediate 3. Thus, 6.1 g of a pale yellow powder were obtained. The pale yellow powder was identified as the aromatic amine derivative (H12) by FD-MS analysis.

Synthesis Embodiment 13

Production of Aromatic Amine Derivative (H13)

A reaction was performed in the same manner as in Synthesis Embodiment 1 except that: 5.6 g of the intermediate 14 were used instead of the intermediate 13; and 3.9 g of the intermediate 1 were used instead of the intermediate 3. Thus, 5.8 g of a pale yellow powder were obtained. The pale yellow powder was identified as the aromatic amine derivative (H13) by FD-MS analysis.

Synthesis Embodiment 14

Production of Aromatic Amine Derivative (H14)

A reaction was performed in the same manner as in Synthesis Embodiment 1 except that: 6.4 g of the intermediate 15 were used instead of the intermediate 13; and 2.3 g of 4-bromobiphenyl were used instead of the intermediate 3. Thus, 5.0 g of a pale yellow powder were obtained. The pale yellow powder was identified as the aromatic amine derivative (H14) by FD-MS analysis.

Synthesis Embodiment 15

Production of Aromatic Amine Derivative (H15)

A reaction was performed in the same manner as in Synthesis Embodiment 1 except that: 6.4 g of the intermediate 15 were used instead of the intermediate 13; and 1.6 g of bromobenzene were used instead of the intermediate 3. Thus, 5.0 g of a pale yellow powder were obtained. The pale yellow powder was identified as the aromatic amine derivative (H15) by FD-MS analysis.

Synthesis Embodiment 16

Production of Aromatic Amine Derivative (H16)

A reaction was performed in the same manner as in Synthesis Embodiment 1 except that: 6.8 g of the intermediate 16 were used instead of the intermediate 13; and 2.3 g of 4-bromobiphenyl were used instead of the intermediate 3. Thus, 5.6 g of a pale yellow powder were obtained. The pale yellow powder was identified as the aromatic amine derivative (H16) by FD-MS analysis.

Synthesis Embodiment 17

Production of Aromatic Amine Derivative (H17)

A reaction was performed in the same manner as in Synthesis Embodiment 1 except that: 6.8 g of the intermediate 16 were used instead of the intermediate 13; and 1.6 g of bromobenzene were used instead of the intermediate 3. Thus, 5.2 g of a pale yellow powder were obtained. The pale yellow powder was identified as the aromatic amine derivative (H17) by FD-MS analysis.

Synthesis Embodiment 18

Production of Aromatic Amine Derivative (H18)

A reaction was performed in the same manner as in Synthesis Embodiment 1 except that: 5.0 g of the intermediate 17 were used instead of the intermediate 13; and 4.7 g of the intermediate 12 were used instead of the intermediate 3. Thus, 5.7 g of a pale yellow powder were obtained. The pale yellow powder was identified as the aromatic amine derivative (H18) by FD-MS analysis.

Synthesis Embodiment 19

Production of Aromatic Amine Derivative (H19)

A reaction was performed in the same manner as in Synthesis Embodiment 1 except that: 5.8 g of the intermediate 22 were used instead of the intermediate 13; and 3.4 g of the intermediate 18 were used instead of the intermediate 3. Thus, 5.7 g of a pale yellow powder were obtained. The pale yellow powder was identified as the aromatic amine derivative (H19) by FD-MS analysis.

Synthesis Embodiment 20

Production of Aromatic Amine Derivative (H20)

A reaction was performed in the same manner as in Synthesis Embodiment 1 except that: 5.8 g of the intermediate 22 were used instead of the intermediate 13; and 3.4 g of the intermediate 21 were used instead of the intermediate 3. Thus, 5.7 g of a pale yellow powder were obtained. The pale yellow powder was identified as the aromatic amine derivative (H20) by FD-MS analysis.

Synthesis Embodiment 21

Production of Aromatic Amine Derivative (H21)

A reaction was performed in the same manner as in Synthesis Embodiment 1 except that: 5.8 g of the intermediate 23 were used instead of the intermediate 13; and 3.4 g of the intermediate 21 were used instead of the intermediate 3. Thus, 5.5 g of a pale yellow powder were obtained. The pale yellow powder was identified as the aromatic amine derivative (H21) by FD-MS analysis.

Synthesis Embodiment 22

Production of Aromatic Amine Derivative (H22)

A reaction was performed in the same manner as in Synthesis Embodiment 1 except that: 5.8 g of the intermediate 22 were used instead of the intermediate 13; and 3.1 g of 4-bromo-p-terphenyl were used instead of the intermediate 3. Thus, 5.3 g of a pale yellow powder were obtained. The pale yellow powder was identified as the aromatic amine derivative (H22) by FD-MS analysis.

Synthesis Embodiment 23

Production of Aromatic Amine Derivative (H23)

A reaction was performed in the same manner as in Synthesis Embodiment 1 except that: 5.8 g of the intermediate 23 were used instead of the intermediate 13; and 3.1 g of 4-bromo-p-terphenyl were used instead of the intermediate 3. Thus, 5.3 g of a pale yellow powder were obtained. The pale yellow powder was identified as the aromatic amine derivative (H23) by FD-MS analysis.

Synthesis Embodiment 24

Production of Aromatic Amine Derivative (H24)

A reaction was performed in the same manner as in Synthesis Embodiment 1 except that: 5.8 g of the intermediate 22 were used instead of the intermediate 13; and 2.3 g of 4-bromobiphenyl were used instead of the intermediate 3. Thus, 5.0 g of a pale yellow powder were obtained. The pale yellow powder was identified as the aromatic amine derivative (H24) by FD-MS analysis.

Synthesis Embodiment 25

Production of Aromatic Amine Derivative (H25)

A reaction was performed in the same manner as in Synthesis Embodiment 1 except that: 5.8 g of the intermediate 23 were used instead of the intermediate 13; and 2.3 g of 4-bromobiphenyl were used instead of the intermediate 3. Thus, 4.9 g of a pale yellow powder were obtained. The pale yellow powder was identified as the aromatic amine derivative (H25) by FD-MS analysis.

Synthesis Embodiment 26

Production of Aromatic Amine Derivative (H26)

A reaction was performed in the same manner as in Synthesis Embodiment 1 except that: 5.8 g of the intermediate 22 were used instead of the intermediate 13; and 1.6 g of bromobenzene were used instead of the intermediate 3. Thus, 4.4 g of a pale yellow powder were obtained. The pale yellow powder was identified as the aromatic amine derivative (H26) by FD-MS analysis.

Synthesis Embodiment 27

Production of Aromatic Amine Derivative (H27)

A reaction was performed in the same manner as in Synthesis Embodiment 1 except that: 5.8 g of the intermediate 23 were used instead of the intermediate 13; and 1.6 g of bromobenzene were used instead of the intermediate 3. Thus, 4.6 g of a pale yellow powder were obtained. The pale yellow powder was identified as the aromatic amine derivative (H27) by FD-MS analysis.

Synthesis Embodiment 28

Production of Aromatic Amine Derivative (H28)

A reaction was performed in the same manner as in Synthesis Embodiment 1 except that 2.7 g of 2-bromo-9,9-dimethylfluorene were used instead of the intermediate 3. Thus, 5.4 g of a pale yellow powder were obtained. The pale yellow powder was identified as the aromatic amine derivative (H28) by FD-MS analysis.

Synthesis Embodiment 29

Production of Aromatic Amine Derivative (H29)

A reaction was performed in the same manner as in Synthesis Embodiment 1 except that: 5.6 g of the intermediate 14 were used instead of the intermediate 13; and 2.7 g of 2-bromo-9,9-dimethylfluorene were used instead of the intermediate 3. Thus, 5.0 g of a pale yellow powder were obtained. The pale yellow powder was identified as the aromatic amine derivative (H29) by FD-MS analysis.

Synthesis Embodiment 30

Production of Aromatic Amine Derivative (H30)

A reaction was performed in the same manner as in Synthesis Embodiment 1 except that: 6.4 g of the intermediate 15 were used instead of the intermediate 13; and 2.7 g of 2-bromo-9,9-dimethylfluorene were used instead of the intermediate 3. Thus, 5.2 g of a pale yellow powder were obtained. The pale yellow powder was identified as the aromatic amine derivative (H30) by FD-MS analysis.

Synthesis Embodiment 31

Production of Aromatic Amine Derivative (H31)

A reaction was performed in the same manner as in Synthesis Embodiment 1 except that: 5.8 g of the intermediate 22 were used instead of the intermediate 13; and 2.7 g of 2-bromo-9,9-dimethylfluorene were used instead of the intermediate 3. Thus, 5.5 g of a pale yellow powder were obtained. The pale yellow powder was identified as the aromatic amine derivative (H31) by FD-MS analysis.

Synthesis Embodiment 32

Production of Aromatic Amine Derivative (H32)

A reaction was performed in the same manner as in Synthesis Embodiment 1 except that: 5.8 g of the intermediate 23 were used instead of the intermediate 13; and 2.7 g of 2-bromo-9,9-dimethylfluorene were used instead of the intermediate 3. Thus, 5.1 g of a pale yellow powder were obtained. The pale yellow powder was identified as the aromatic amine derivative (H-32) by FD-MS analysis.

Example 1

Production of Organic EL Device

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the cleaning was mounted on a substrate holder of a vacuum vapor deposition device. First, the following aromatic tertiary amine derivative (H232) was deposited from vapor on the surface on the side where the transparent electrode line was formed so as to cover the transparent electrode. Then, the H232 film having a thickness of 60 nm was formed as the hole injecting layer. The aromatic amine derivative (H1) obtained in Synthesis Embodiment 1 above as a hole transporting material was deposited from vapor and formed into a hole transporting layer having a thickness of 20 nm on the H232 film. Further, the following compound EM1 was deposited from vapor and formed into a light emitting layer having a thickness of 40 nm. Simultaneously with this formation, the following styrylamine derivative (D1), as a light emitting molecule, was deposited from vapor in such a manner that a weight ratio between EMI and D1 (EM1:D1) was 40:2.

The following organic metal complex (Alq) was formed into a film having a thickness of 10 nm on the resultant film. The film functions as an electron injecting layer. After that, Li serving as a reducing dopant (Li source: manufactured by SAES Getters) and Alq were subjected to co-vapor deposition. Thus, an Alq:Li film (having a thickness of 10 nm) was formed as an electron injecting layer (cathode). Metal Al was deposited from vapor onto the Alq:Li film to form a metal cathode. Thus, an organic EL device was formed.

The luminescent color of the resultant organic EL device was observed. Further, the current efficiency, driving voltage, and half lifetime of light emission when the device was driven with a DC constant current at an initial luminance of 5,000 cd/m$^2$ and room temperature were measured. Table 1 shows the results.

[Chem. 47]

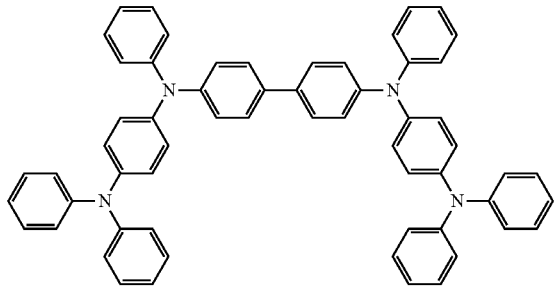

Aromatic tertiary amine derivative
(H232)

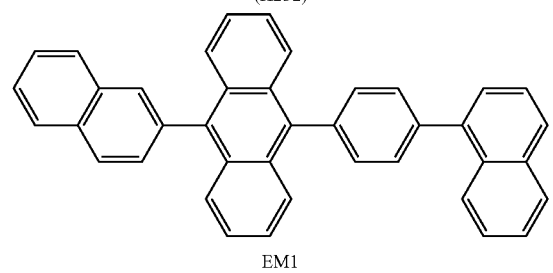

EM1

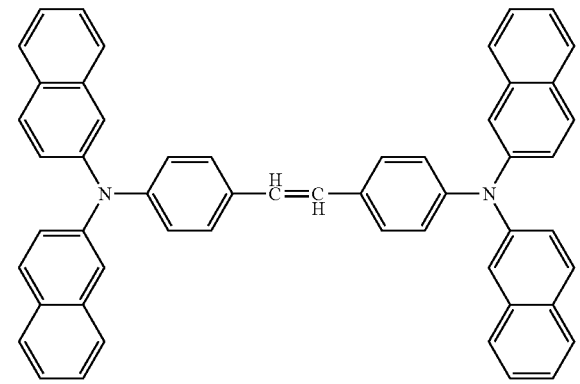

Styrylamine derivative
(D1)

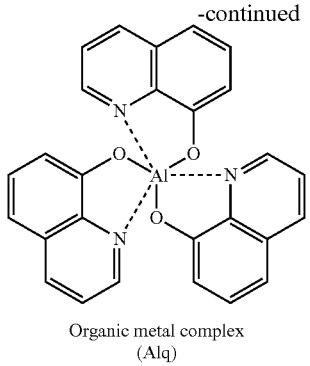

Organic metal complex
(Alq)

Examples 2 to 21

Production of Organic EL Device

Each organic EL device was produced in the same manner as in Example 1 except that the respective aromatic amine derivatives shown in Table 1 were used as hole transporting materials instead of the aromatic amine derivative (H1).

The luminescent color of the resultant organic EL device was observed. Further, the current efficiency, driving voltage, and half lifetime of light emission when the device was driven with a DC constant current at an initial luminance of 5,000 cd/m² and room temperature were measured. Table 1 shows the results.

Example 22

Production of Organic EL Device

An organic EL device was produced in the same manner as in Example 1 except that the following arylamine derivative (D2) was used instead of the styrylamine derivative (D1).

The luminescent color of the resultant organic EL device was observed. Further, the current efficiency, driving voltage, and half lifetime of light emission when the device was driven with a DC constant current at an initial luminance of 5,000 cd/m² and room temperature were measured. Table 1 shows the results.

[Chem. 48]

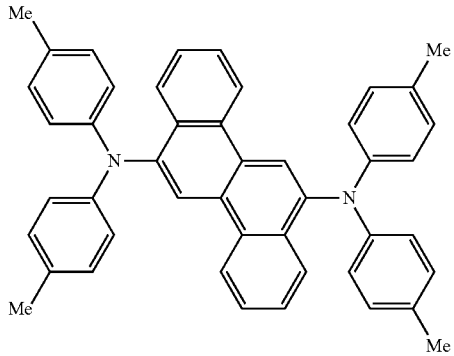

Arylamine derivative (D2)

Example 23

Production of Organic EL Device

An organic EL device was produced in the same manner as in Example 1 except that the following benzimidazole compound (ET1) was used as an electron transporting material instead of the organic metal complex Alq.

The luminescent color of the resultant organic EL device was observed. Further, the current efficiency, driving voltage, and half lifetime of light emission when the device was driven with a DC constant current at an initial luminance of 5,000 cd/m² and room temperature were measured. Table 1 shows the results.

[Chem. 49]

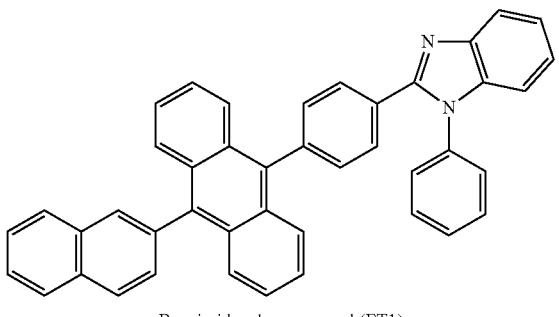

Benzimidazole compound (ET1)

Example 24

Production of Organic EL Device

An organic EL device was produced in the same manner as in Example 1 except that the following acceptor compound (C-1) was formed into a film having a thickness of 10 nm instead of the aromatic tertiary amine derivative (H232), and then the aromatic amine derivative (H1) was formed into a film having a thickness of 70 nm.

The luminescent color of the resultant organic EL device was observed. Further, the current efficiency, driving voltage, and half lifetime of light emission when the device was driven with a DC constant current at an initial luminance of 5,000 cd/m² and room temperature were measured. Table 1 shows the results.

[Chem. 50]

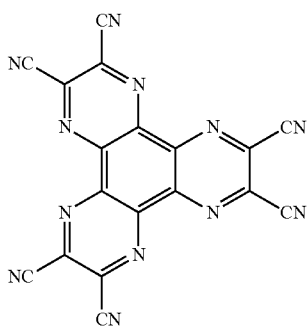

Acceptor compound (C-1)

Comparative Examples 1 and 3

Organic EL devices were each produced in the same manner as in Example 1 except that anyone of the following comparative compounds 1 to 3 shown in Table 1 was used as a hole transporting material instead of the aromatic amine derivative (H1).

The luminescent color of each of the resultant organic EL devices was observed. Further, the current efficiency, driving voltage, and half lifetime of light emission when each of the devices was driven with a DC constant current at an initial luminance of 5,000 cd/m² and room temperature were measured. Table 1 shows the results.

[Chem. 51]

Comparative compound-1

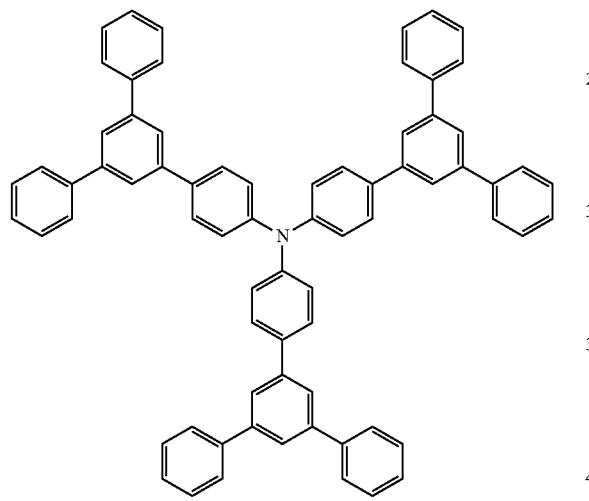

Comparative compound-2

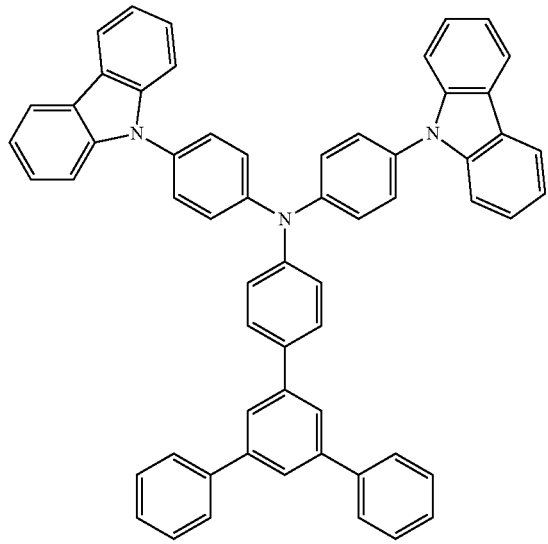

-continued

Comparative compound-3

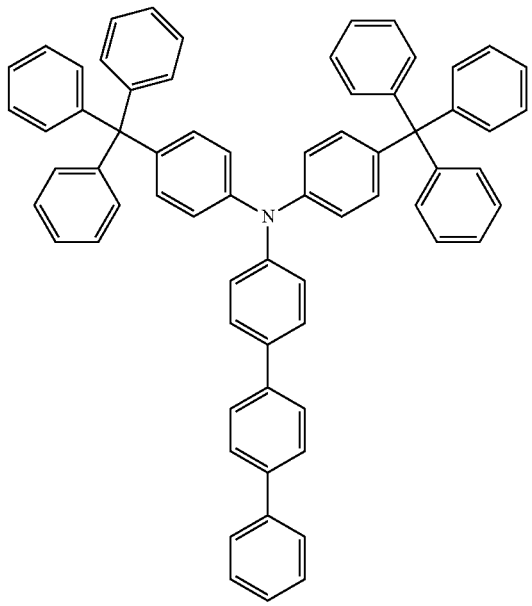

Comparative Example 4

An organic EL device was produced in the same manner as in Example 22 except that the comparative compound-1 was used as a hole transporting material instead of the aromatic amine derivative (H1).

The luminescent color of the resultant organic EL device was observed. Further, the current efficiency, driving voltage, and half lifetime of light emission when the device was driven with a DC constant current at an initial luminance of 5,000 cd/m² and room temperature were measured. Table 1 shows the results.

Comparative Example 5

An organic EL device was produced in the same manner as in Example 23 except that the comparative compound-1 was used as a hole transporting material instead of the aromatic amine derivative (H1).

The luminescent color of the resultant organic EL device was observed. Further, the current efficiency, driving voltage, and half lifetime of light emission when the device was driven with a DC constant current at an initial luminance of 5,000 cd/m² and room temperature were measured. Table 1 shows the results.

Comparative Example 6

An organic EL device was produced in the same manner as in Example 24 except that the comparative compound-1 was used as a hole transporting material instead of the aromatic amine derivative (H1).

The luminescent color of the resultant organic EL device was observed. Further, the current efficiency, driving voltage, and half lifetime of light emission when the device was driven with a DC constant current at an initial luminance of 5,000 cd/m² and room temperature were measured. Table 1 shows the results.

TABLE 1

| | | Hole transporting material | Lumi- nescent color | Current efficiency (cd/A) | Driving voltage (V) | Half lifetime (Hour) |
|---|---|---|---|---|---|---|
| Example | 1 | H1 | Blue | 6.8 | 7.0 | 420 |
| | 2 | H2 | Blue | 7.0 | 7.0 | 400 |
| | 3 | H3 | Blue | 7.1 | 7.0 | 380 |
| | 4 | H4 | Blue | 6.8 | 6.8 | 430 |
| | 5 | H5 | Blue | 7.0 | 6.8 | 400 |
| | 6 | H10 | Blue | 6.3 | 6.7 | 400 |
| | 7 | H11 | Blue | 6.5 | 6.6 | 370 |
| | 8 | H12 | Blue | 6.8 | 7.1 | 420 |
| | 9 | H13 | Blue | 6.9 | 7.1 | 400 |
| | 10 | H14 | Blue | 6.8 | 6.7 | 400 |
| | 11 | H15 | Blue | 6.8 | 6.8 | 370 |
| | 12 | H19 | Blue | 6.7 | 7.0 | 400 |
| | 13 | H20 | Blue | 6.9 | 7.0 | 390 |
| | 14 | H21 | Blue | 7.0 | 7.0 | 370 |
| | 15 | H22 | Blue | 6.7 | 6.8 | 420 |
| | 16 | H23 | Blue | 6.9 | 6.8 | 400 |
| | 17 | H28 | Blue | 6.6 | 6.6 | 370 |
| | 18 | H29 | Blue | 6.5 | 6.5 | 340 |
| | 19 | H30 | Blue | 6.5 | 6.5 | 340 |
| | 20 | H31 | Blue | 6.6 | 6.6 | 360 |
| | 21 | H32 | Blue | 6.5 | 6.5 | 340 |
| | 22 | H1 | Blue | 7.0 | 7.1 | 410 |
| | 23 | H1 | Blue | 6.9 | 6.7 | 400 |
| | 24 | H1 | Blue | 6.9 | 6.7 | 330 |
| Comparative Example | 1 | Comparative compound 1 | Blue | 5.0 | 7.3 | 190 |
| | 2 | Comparative compound 2 | Blue | 5.2 | 7.5 | 150 |
| | 3 | Comparative compound 3 | Blue | 4.8 | 7.3 | 140 |
| | 4 | Comparative compound 1 | Blue | 5.2 | 7.4 | 150 |
| | 5 | Comparative compound 1 | Blue | 5.1 | 6.9 | 180 |
| | 6 | Comparative compound 1 | Blue | 5.1 | 6.9 | 100 |

As can be seen from Table 1, an organic EL device using the aromatic amine derivative of the present invention can be driven at a low voltage, can obtain high current efficiency, and has a device lifetime extended several-fold as compared with a known organic EL device using an aromatic amine derivative.

INDUSTRIAL APPLICABILITY

The utilization of the aromatic amine derivative of the present invention as a material for an organic EL device (especially a hole transporting material) provides the following organic EL device. The organic EL device has high luminous efficiency and a long lifetime, and is driven at a reduced voltage. Accordingly, the organic EL device of the present invention can be utilized in, for example, flat luminous bodies such as the flat panel display of a wall television, light sources for the backlights, meters, and the like of a copying machine, a printer, and a liquid crystal display, display boards, and identification lamps.

In addition, the aromatic amine derivative of the present invention is useful not only in the field of an organic EL device but also in the fields of, for example, an electrophotographic photosensitive member, a photoelectric converter, a solar cell, and an image sensor.

The invention claimed is:

1. An aromatic amine derivative, having a formula (I):

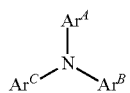

wherein $Ar^A$ has formula (II-1):

$$-L^a\text{\textemdash}(Ar^a)_n \qquad \text{II-1}$$

wherein:
$L^a$ is a substituted or unsubstituted aromatic ring having 6 to 25 ring carbon atoms;
$Ar^a$ is a substituted or unsubstituted aryl group having 6 to 25 ring carbon atoms; and
n is 2 or 3, and a plurality of $Ar^a$'s may be identical to or different from each other,
$Ar^B$ has a formula (III):

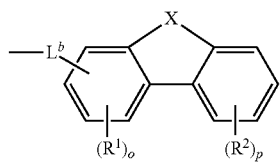

wherein:
$L^b$ is a single bond, a substituted or unsubstituted arylene group having 6 to 25 ring carbon atoms, or a substituted or unsubstituted heteroarylene group having 5 to 25 ring atoms;
$R^1$ and $R^2$ each independently are selected from the group consisting of an alkyl group having 1 to 15 carbon atoms, an alkenyl group having 2 to 15 carbon atoms, a cycloalkyl group having 3 to 15 ring carbon atoms, an aryl group having 6 to 25 ring carbon atoms, a trialkylsilyl group comprising alkyl groups each having 1 to 15 carbon atoms, a triarylsilyl group comprising aryl groups each having 6 to 25 ring carbon atoms, an alkylarylsilyl group comprising an alkyl group having 1 to 15 carbon atoms and an aryl group having 6 to 25 ring carbon atoms, a carbazolyl group, a halogen atom, and a cyano group;
o is an integer of 0 to 3, p is an integer of 0 to 4, and a plurality of $R^1$'s or $R^2$'s adjacent to each other, or $R^1$ and $R^2$ may be bonded to each other to form a ring; and
X is an oxygen atom or a sulfur atom, and
$Ar^C$ is a substituted or unsubstituted aryl group having 6 to 50 ring carbon atoms, or a substituted or unsubstituted heteroaryl group having 5 to 25 ring atoms, or has the formula (II-1) or (III),
with the proviso that the substituents on the substituted groups are selected from an alkyl group having 1 to 15 carbon atoms, a cycloalkyl group having 3 to 15 ring carbon atoms, a trialkylsilyl group formed of alkyl groups each having 1 to 15 carbon atoms, a triarylsilyl group each formed of aryl groups each having 6 to 25 ring carbon atoms, an alkylarylsilyl group each formed of an alkyl group having 1 to 15 carbon atoms, an aryl group having 6 to 25 ring carbon atoms, halogen atoms, and a cyano group.

2. The aromatic amine derivative of claim 1, wherein $Ar^A$ has the formula (II-1), and $L^a$ is a benzene ring, a biphenyl ring, a terphenyl ring, a quaterphenyl ring, a naphthalene ring, or a phenanthrene ring.

3. The aromatic amine derivative of claim 1, wherein $Ar^a$ is a phenyl group.

4. The aromatic amine derivative of claim 1, wherein $Ar^B$ has one of the following formulae:

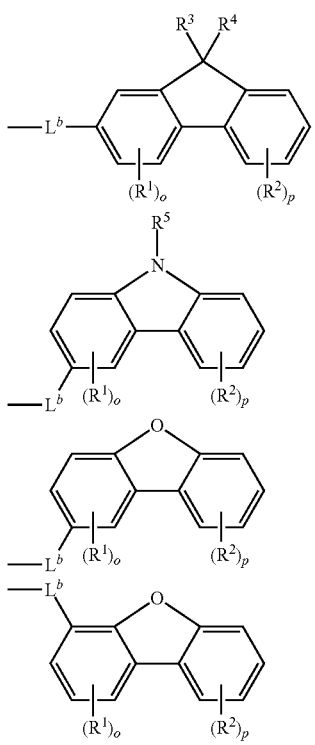

where $L^b$, $R^1$, $R^2$, o, and p are as defined in the formula (III).

5. The aromatic amine derivative of claim 1, wherein $L^b$ is a single bond, a phenylene group, a naphthylene group, a biphenyldiyl group, a terphenyldiyl group, or a phenanthrylene group.

6. The aromatic amine derivative of claim 1, wherein $Ar^C$ has the formula (II-1.

7. The aromatic amine derivative of claim 1, wherein $Ar^C$ has the formula (III).

8. An organic electroluminescence device, comprising an organic thin-film layer between an anode and a cathode, wherein the organic thin-film layer comprises the aromatic amine derivative of claim 1.

9. The organic electroluminescence device of claim 8, wherein the organic thin-film layer is a hole transporting layer comprising the aromatic amine derivative.

10. The organic electroluminescence device of claim 9, further comprising an electron transporting layer comprising a nitrogen-comprising heterocyclic derivative having a formula selected from formulae (1) to (3):

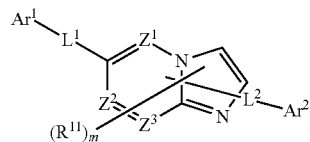

(1)

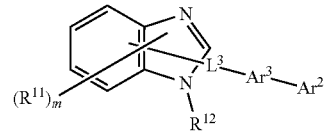

(2)

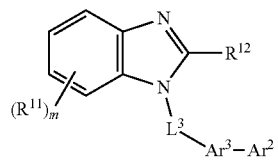

(3)

wherein:

$Z^1$, $Z^2$, and $Z^3$ each independently are a nitrogen atom or a carbon atom;

$R^{11}$ and $R^{12}$ each independently are selected from the group consisting of a substituted or unsubstituted aryl group having 6 to 60 ring carbon atoms, a substituted or unsubstituted heteroaryl group having 5 to 60 ring atoms, an alkyl group having 1 to 20 carbon atoms, an alkyl group having 1 to 20 carbon atoms and substituted with a halogen atom, and an alkoxy group having 1 to 20 carbon atoms;

m is an integer of 0 to 5, and a plurality of $R^{11}$'s may be identical to or different from each other and may bond to each other to form a substituted or unsubstituted aromatic hydrocarbon ring;

$Ar^1$ is a substituted or unsubstituted aryl group having 6 to 60 ring carbon atoms, or a substituted or unsubstituted heteroaryl group having 5 to 60 ring atoms;

$Ar^2$ is a hydrogen atom, an alkyl group having 1 to 20 carbon atoms, an alkyl group having 1 to 20 carbon atoms and substituted with a halogen atom, an alkoxy group having 1 to 20 carbon atoms, a substituted or unsubstituted aryl group having 6 to 60 ring carbon atoms, or a substituted or unsubstituted heteroaryl group having 5 to 60 ring atoms;

$Ar^3$ is a substituted or unsubstituted arylene group having 6 to 60 ring carbon atoms, or a substituted or unsubstituted heteroarylene group having 5 to 60 ring atoms; and $L^1$, $L^2$, and $L^3$ each independently represent a single bond, a substituted or unsubstituted arylene group having 6 to 60 ring carbon atoms, a substituted or unsubstituted heterofused ring group having 9 to 60 ring atoms, or a substituted or unsubstituted fluorenylene group.

11. The aromatic amine derivative of claim 1, wherein $Ar^A$ has the formula (II-1) and $L^a$ is a benzene ring or a biphenyl ring.

12. The aromatic amine derivative of claim 11, wherein two meta positions on the benzene ring, or two meta positions on one benzene ring of the biphenyl ring, are each substituted with $Ar^a$.

13. The aromatic amine derivative of claim 1, wherein $Ar^4$ has the formula (II-1) and n is 2.

14. The aromatic amine derivative of claim 1, wherein $Ar^4$ has a formula:

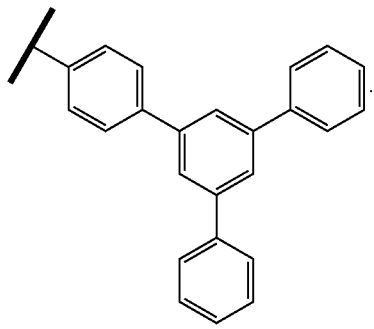

15. The organic electroluminescence device of claim 9, further comprising a hole injecting layer comprising a compound having a formula (A):

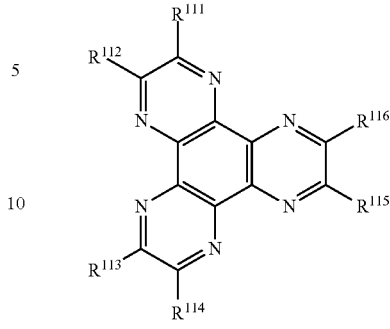 (A)

wherein $R^{111}$ to $R^{116}$ each independently are selected from the group consisting of a cyano group, —$CONH_2$, a carboxyl group, and —$COOR^{117}$ where $R^{117}$ is an alkyl group having 1 to 20 carbon atoms; or wherein at least one pair selected from the group consisting of $R^{111}$ and $R^{112}$, $R^{113}$ and $R^{114}$, and $R^{115}$ and $R^{116}$, bonds to form a group represented by —CO—O—CO—.

* * * * *